US012799194B2

(12) United States Patent
Basore et al.

(10) Patent No.: US 12,799,194 B2
(45) Date of Patent: Nov. 17, 2026

(54) COMPOSITIONS AND METHODS FOR INHIBITING VIRAL RECOGNITION SITES

(71) Applicant: Washington University, St. Louis, MO (US)

(72) Inventors: Katherine Basore, St. Louis, MO (US); Michael Diamond, St. Louis, MO (US); Hongming Ma, St. Louis, MO (US); Natasha Kafai, St. Louis, MO (US); Arthur Kim, St. Louis, MO (US); Larissa Thackray, St. Louis, MO (US); Daved Fremont, St. Louis, MO (US)

(73) Assignee: Washington University, St. Louis, MO (US)

( * ) Notice: Subject to any disclaimer, the term of this patent is extended or adjusted under 35 U.S.C. 154(b) by 869 days.

(21) Appl. No.: 17/922,319

(22) PCT Filed: Apr. 29, 2021

(86) PCT No.: PCT/US2021/029967

§ 371 (c)(1),
(2) Date: Oct. 28, 2022

(87) PCT Pub. No.: WO2021/222623

PCT Pub. Date: Nov. 4, 2021

(65) Prior Publication Data

US 2023/0183338 A1 Jun. 15, 2023

Related U.S. Application Data

(60) Provisional application No. 63/088,680, filed on Oct. 7, 2020, provisional application No. 63/017,399, filed on Apr. 29, 2020.

(51) Int. Cl.

| | |
|---|---|
| ***C07K 16/28*** | (2006.01) |
| ***A61K 38/00*** | (2006.01) |
| ***C07K 14/005*** | (2006.01) |
| ***C07K 14/705*** | (2006.01) |
| ***C12N 7/00*** | (2006.01) |

(52) U.S. Cl.

CPC ............ *C07K 16/28* (2013.01); *C07K 14/005* (2013.01); *C07K 14/705* (2013.01); *C12N 7/00* (2013.01); *A61K 38/00* (2013.01); *C07K 2317/76* (2013.01); *C07K 2319/00* (2013.01); *C07K 2319/30* (2013.01); *C07K 2319/43* (2013.01); *C07K 2319/60* (2013.01); *C12N 2770/36122* (2013.01)

(58) Field of Classification Search

CPC .. C07K 16/28; C07K 14/005; C07K 2317/76; C07K 2319/30; C07K 14/705; C07K 2319/00; C07K 2319/43; C07K 2319/60; C12N 7/00; C12N 2770/36122; A61K 38/00

See application file for complete search history.

(56) References Cited

U.S. PATENT DOCUMENTS

| | | | | |
|---|---|---|---|---|
| 9,738,704 | B2 * | 8/2017 | Warter ............. | G01N 33/56983 |
| 2024/0124553 | A1 | 4/2024 | Diamond et al. | |
| 2025/0109199 | A1 | 4/2025 | Diamond et al. | |

FOREIGN PATENT DOCUMENTS

| | | | | |
|---|---|---|---|---|
| EP | 2374816 B1 * | 9/2016 | ......... | C07K 16/1081 |

OTHER PUBLICATIONS

Felix J, Savvides SN. Mechanisms of immunomodulation by mammalian and viral decoy receptors: insights from structures. Nat Rev Immunol. Feb. 2017;17(2):112-129. (Year: 2017).*
Zhang, R., Kim, A.S., Fox, J.M. et al. Mxra8 is a receptor for multiple arthritogenic alphaviruses. Nature 557, 570â574 (2018) (Year: 2018).*
Basore, K., Ma, H., Kafai, N.M. et al. Structure of Venezuelan equine encephalitis virus in complex with the LDLRAD3 receptor. Nature 598, 672â676 (2021). (Year: 2021).*
Ma, H., Kim, A.S., Kafai, N.M. et al. LDLRAD3 is a receptor for Venezuelan equine encephalitis virus. Nature 588, 308â314 (2020). (Year: 2020).*
Hummer et al. Advances in computational structure-based antibody design. Curr Opin Struct Biol. Jun. 2022;74:102379 (Year: 2022).*
Rabia et al. Understanding and overcoming trade-offs between antibody affinity, specificity, stability and solubility. Biochem Eng J. Sep. 15, 2018;137:365-374 (Year: 2018).*
International Search Report and Written Opinion for Application No. PCT/US2021/029967, mailed on Oct. 14, 2021, 13 pages.
Ma H., et al., "LDLRAD3 is a Receptor for Venezuelan Equine Encephalitis Virus," Nature, Dec. 2020 [Epub. Nov. 18, 2020], vol. 588, No. 7837, 39 pages.
Zhang R., et al., "Mxra8 is a Receptor for Multiple Arthritogenic Alphaviruses," Nature, 2018, vol. 557, No. 7706, 34 pages.

* cited by examiner

*Primary Examiner* — Joanne Hama
*Assistant Examiner* — Emmanuel Led Youtchom Pendie
(74) *Attorney, Agent, or Firm* — Polsinelli PC

(57) ABSTRACT

Compositions and methods for treating a viral infection may comprise use of a viral recognition-site inhibiting agent composition. A viral recognition-site inhibiting agent composition of the present disclosure may substantially inhibit, reduce, or block virus bind to the LDLRAD3 host receptor and reduces the infectivity of a virus for a host cell. A method of treating a viral infection may comprise administering a composition comprising a viral recognition-site inhibiting agent of the present disclosure, to a subject and reducing the infectivity of the virus for a host cell of the subject. The compositions may be administered via intranasal or systemic administration to treat or prevent a viral infection, for example an alphavirus infection.

12 Claims, 54 Drawing Sheets
(52 of 54 Drawing Sheet(s) Filed in Color)
Specification includes a Sequence Listing.

FIG. 2A
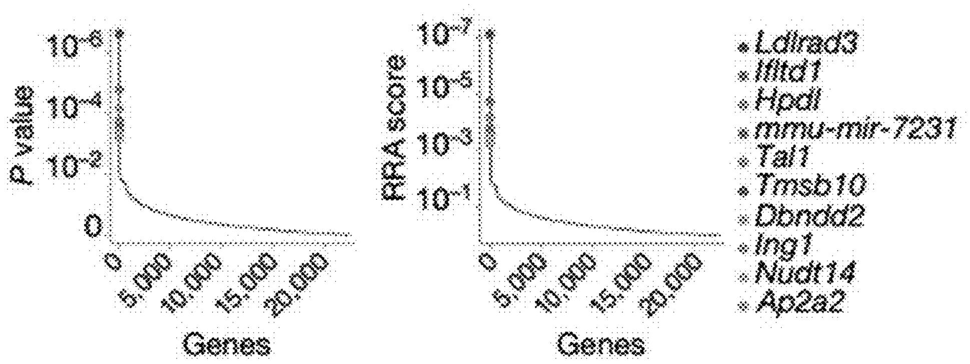
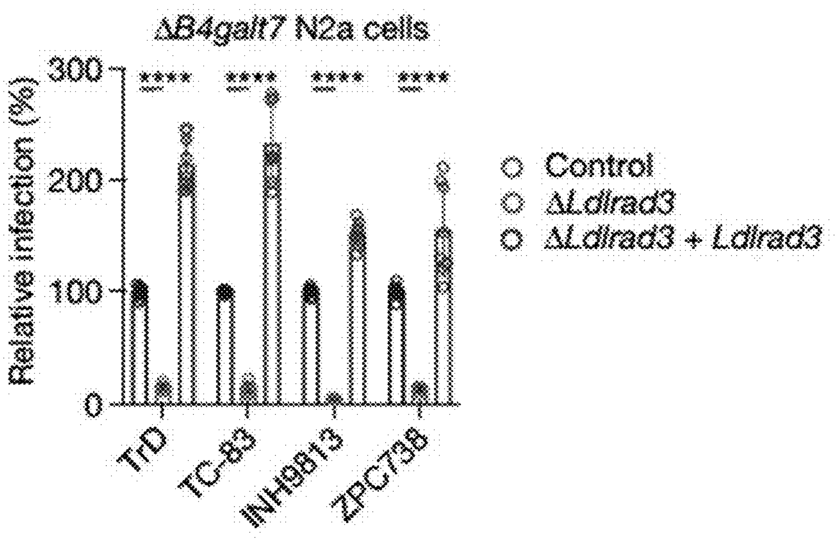
FIG. 2B

N2a cells

*Ldlrad3* CTCGGAGAACCAGCTTGTGTACTACCCCAGCATCACGTACGCCATCATCGGCAGCTCTGTCATCTTCGTGCTGGTGGTGGCCCTGCTCGCACTGGTCCTGCATCATCAGCGAAAG
Δ19 CTCGGAGAACCAGCTTGTGTACTACCCCA-------------------CGGCAGCTCTGTCATCTTCGTGCTGGTGGTGGCCCTGCTCGCACTGGTCCTGCATCATCAGCGAAAG 11.4%
Δ58 CTCGGAGAACCAGCTTGTGTACTACCCCA----------------------------------------------------------CGCACTGGTCCTGCATCATCAGCGAAAG 88.6%

BV2 cells

*Ldlrad3* CAGGCAGCGGGCAGGTGTTTGTGACCTCGGAGAACCAGCTTGTGTACTACCCCAGCATCACGTACGCCAT-CATCGGCAGCTCTGTCATCTTCGTGCTGGTGGTGGCCCTGCTCGCACTGGT
+1 CAGGCAGCGGGCAGGTGTTTGTGACCTCGGAGAACCAGCTTGTGTACTACCCCAGCATCACGTACGCCATTCATCGGCAGCTCTGTCATCTTCGTGCTGGTGGTGGCCCTGCTCGCACTGGT 25.6%
Δ2 CAGGCAGCGGGCAGGTGTTTGTGACCTCGGAGAACCAGCTTGTGTACTACCCCAGCATCACGTACGCC---CATCGGCAGCTCTGTCATCTTCGTGCTGGTGGTGGCCCTGCTCGCACTGGT 24.0%
Δ64 CAGGCAGCGGGCAGGTGTTTGTGACCTCG--------------------------------------------------------------------TGCTGGTGGTGGCCCTGCTCGCACTGGT 50.4%

FIG. 3D

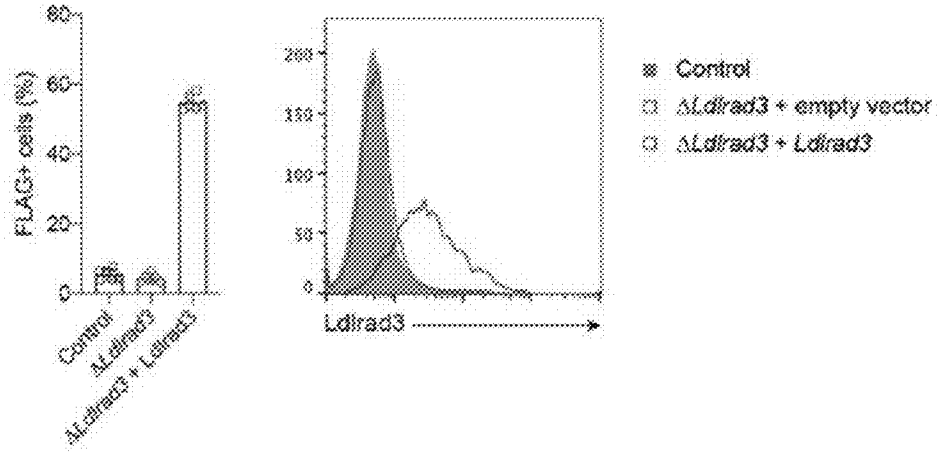

FIG. 3E

SH-SY5Y clone #1

```
Ldlrad3 TCTCCTGATGTCTTGCTGTTTCTTTTTCTTCCTGCAGCCAAGGCTAAGTCGA-AATGTGGCCCAACCTTCTTCCCCTGTGCCAGCGGCATCCATTGCATCA
     +1 TCTCCTGATGTCTTGCTGTTTCTTTTTCTTCCTGCAGCCAAGGCTAAGTCGAAAATGTGGCCCAACCTTCTTCCCCTGTGCCAGCGGCATCCATTGCATCA 50.0%
     Δ8 TCTCCTGATGTCTTGCTGTTTCTTTTTCTTCCTGCAGCCAAGGCTAA---------GTGGCCCAACCTTCTTCCCCTGTGCCAGCGGCATCCATTGCATCA 50.0%
```

SH-SY5Y clone #2

```
Ldlrad3 TCCACCGCCCCGCTACCACTGCAAGAACGGCCTCTG-----------------TATTGACAAGAGCTTCATCTGCGATGGACAGAATAACTGTCAAG
    +17 TCCACCGCCCCGCTACCACTGCAAGAACGGCCTCTGACAAGAGCTCTGACAAGCACTGACAAGAGCTTCATCTGCGATGGACAGAATAACTGTCAAG 93.2%
     Δ8 TCCACCGCCCCGCTACCACTGCAAGAAC-------------------------TATTGACAAGAGCTTCATCTGCGATGGACAGAATAACTGTCAAG 3.4%
    Δ12 TCCACCGCCCCGCTACCACTGCAAGAACGGCCT----------------------------GAGCTTCATCTGCGATGGACAGAATAACTGTCAAG 3.4%
```

FIG. 3F

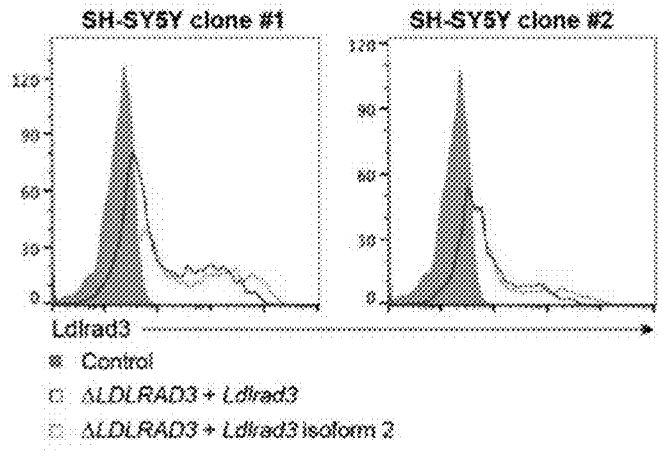

FIG. 3G

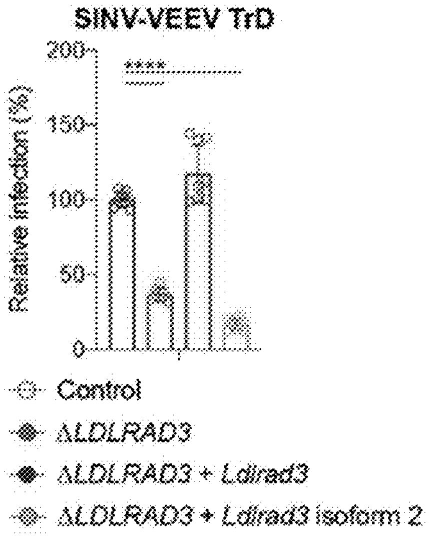

FIG. 3H

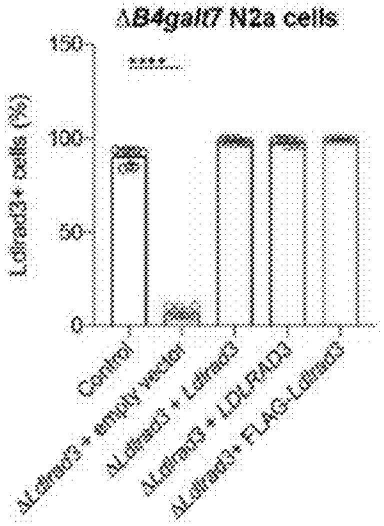

FIG. 3I

FIG. 8A
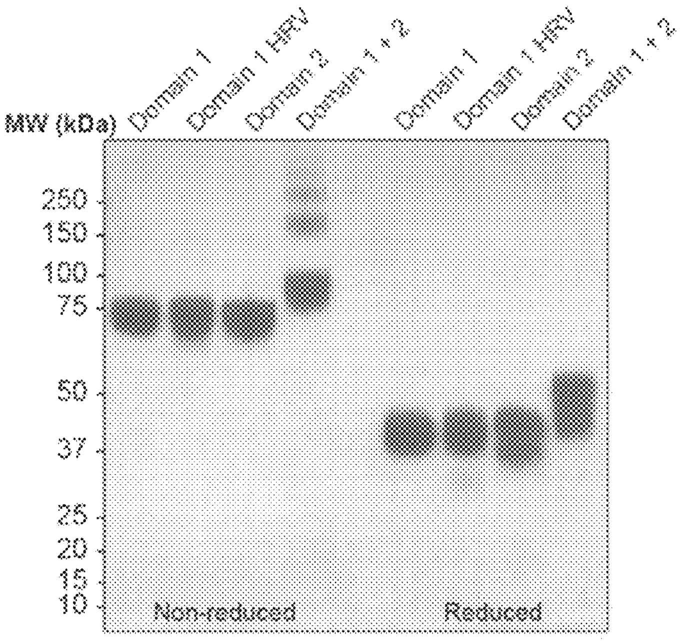
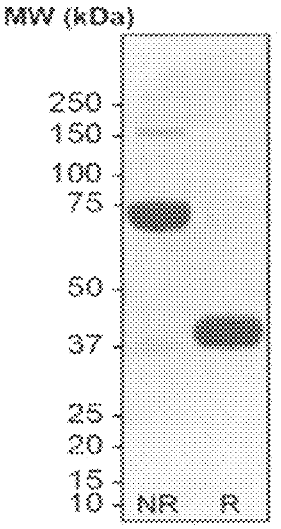
FIG. 8B
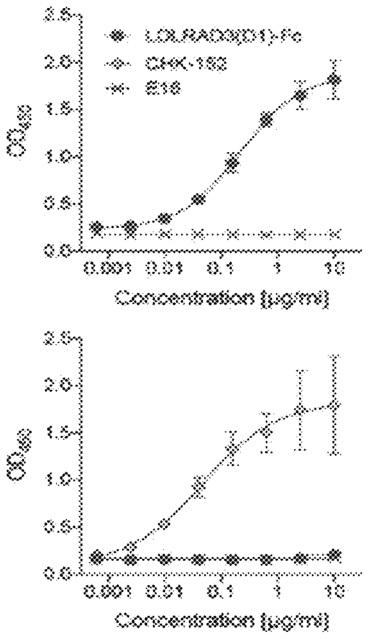
FIG. 8C

SEQUENCE LISTING

```
<160> NUMBER OF SEQ ID NOS: 78

<210> SEQ ID NO 1
<211> LENGTH: 177
<212> TYPE: PRT
<213> ORGANISM: Mus musculus

<400> SEQUENCE: 1

Gln Leu Leu Pro Gly Asn Asn Phe Thr Asn Glu Cys Asn Ile Pro Gly
1               5                   10                  15

Asn Phe Met Cys Ser Asn Gly Arg Cys Ile Pro Gly Ala Trp Gln Cys
            20                  25                  30

Asp Gly Leu Pro Asp Cys Phe Asp Lys Ser Asp Glu Lys Glu Cys Pro
        35                  40                  45

Lys Ala Lys Ser Lys Cys Gly Pro Thr Phe Phe Pro Cys Ala Ser Gly
    50                  55                  60

Ile His Cys Ile Ile Gly Arg Phe Arg Cys Asn Gly Phe Glu Asp Cys
65                  70                  75                  80

Pro Asp Gly Ser Asp Glu Glu Asn Cys Thr Ala Asn Pro Leu Leu Cys
                85                  90                  95

Ser Thr Ala Arg Tyr His Cys Arg Asn Gly Leu Cys Ile Asp Lys Ser
            100                 105                 110

Phe Ile Cys Asp Gly Gln Asn Asn Cys Gln Asp Asn Ser Asp Glu Glu
        115                 120                 125

Ser Cys Glu Ser Ser Leu Glu Pro Gly Ser Gly Gln Val Phe Val Thr
```

```
    130                 135                 140

Ser Glu Asn Gln Leu Val Tyr Tyr Pro Ser Ile Thr Tyr Ala Ile Ile
145                 150                 155                 160

Gly Ser Ser Val Ile Phe Val Leu Val Val Ala Leu Leu Ala Leu Val
                165                 170                 175

Leu


<210> SEQ ID NO 2
<211> LENGTH: 146
<212> TYPE: PRT
<213> ORGANISM: Mus musculus

<400> SEQUENCE: 2

Gln Leu Leu Pro Gly Asn Asn Phe Thr Asn Glu Cys Asn Ile Pro Ala
1               5                   10                  15

Pro Lys Ala Lys Ser Lys Cys Gly Pro Thr Phe Phe Pro Cys Ala Ser
            20                  25                  30

Gly Ile His Cys Ile Ile Gly Arg Phe Arg Cys Asn Gly Phe Glu Asp
        35                  40                  45

Cys Pro Asp Gly Ser Asp Glu Glu Asn Cys Thr Ala Asn Pro Leu Leu
    50                  55                  60

Cys Ser Thr Ala Arg Tyr His Cys Arg Asn Gly Leu Cys Ile Asp Lys
65                  70                  75                  80

Ser Phe Ile Cys Asp Gly Gln Asn Asn Cys Gln Asp Asn Ser Asp Glu
                85                  90                  95

Glu Ser Cys Glu Ser Ser Leu Glu Pro Gly Ser Gly Gln Val Phe Val
            100                 105                 110

Thr Ser Glu Asn Gln Leu Val Tyr Tyr Pro Ser Ile Thr Tyr Ala Ile
        115                 120                 125

Ile Gly Ser Ser Val Ile Phe Val Leu Val Val Ala Leu Leu Ala Leu
    130                 135                 140

Val Leu
145


<210> SEQ ID NO 3
<211> LENGTH: 176
<212> TYPE: PRT
<213> ORGANISM: Homo sapiens

<400> SEQUENCE: 3

Gln Leu Leu Pro Gly Asn Asn Phe Thr Asn Glu Cys Asn Ile Pro Gly
1               5                   10                  15

Asn Phe Met Cys Ser Asn Gly Arg Cys Ile Pro Gly Ala Trp Gln Cys
            20                  25                  30

Asp Gly Leu Pro Asp Cys Phe Asp Lys Ser Asp Glu Lys Glu Cys Pro
        35                  40                  45

Lys Ala Lys Ser Lys Cys Gly Pro Thr Phe Phe Pro Cys Ser Gly Ile
    50                  55                  60

His Cys Ile Ile Gly Arg Phe Arg Cys Asn Gly Phe Glu Asp Cys Pro
65                  70                  75                  80

Asp Gly Ser Asp Glu Glu Asn Cys Thr Ala Asn Pro Leu Leu Cys Ser
                85                  90                  95

Thr Ala Arg Tyr His Cys Lys Asn Gly Leu Cys Ile Asp Lys Ser Phe
            100                 105                 110

Ile Cys Asp Gly Gln Asn Asn Cys Gln Asp Asn Ser Asp Glu Glu Ser
        115                 120                 125
```

```
Cys Glu Ser Ser Gln Glu Pro Gly Ser Gly Gln Val Phe Val Thr Ser
    130                 135                 140

Glu Asn Gln Leu Val Tyr Tyr Pro Ser Ile Thr Tyr Ala Ile Ile Gly
145                 150                 155                 160

Ser Ser Val Ile Phe Val Leu Val Val Ala Leu Leu Ala Leu Val Leu
                165                 170                 175


<210> SEQ ID NO 4
<211> LENGTH: 176
<212> TYPE: PRT
<213> ORGANISM: Macaca mulatta

<400> SEQUENCE: 4

Gln Leu Leu Pro Gly Asn Asn Phe Thr Asn Glu Cys Asn Ile Pro Gly
1               5                   10                  15

Asn Phe Met Cys Ser Asn Gly Arg Cys Ile Pro Gly Ala Trp Gln Cys
            20                  25                  30

Asp Gly Leu Pro Asp Cys Phe Asp Lys Ser Asp Glu Lys Glu Cys Pro
        35                  40                  45

Lys Ala Lys Ser Lys Cys Gly Pro Thr Phe Phe Pro Cys Ser Gly Ile
    50                  55                  60

His Cys Ile Ile Gly Arg Phe Arg Cys Asn Gly Phe Glu Asp Cys Pro
65                  70                  75                  80

Asp Gly Ser Asp Glu Glu Asn Cys Thr Ala Asn Pro Leu Leu Cys Ser
                85                  90                  95

Thr Ala Arg Tyr His Cys Lys Asn Gly Leu Cys Ile Asp Lys Ser Phe
            100                 105                 110

Ile Cys Asp Gly Gln Asn Asn Cys Gln Asp Asn Ser Asp Glu Glu Ser
        115                 120                 125

Cys Glu Ser Ser Gln Glu Pro Gly Ser Gly Gln Val Phe Val Thr Ser
    130                 135                 140

Glu Asn Gln Leu Val Tyr Tyr Pro Ser Ile Thr Tyr Ala Ile Ile Gly
145                 150                 155                 160

Ser Ser Val Ile Phe Val Leu Val Val Ala Leu Leu Ala Leu Val Leu
                165                 170                 175


<210> SEQ ID NO 5
<211> LENGTH: 177
<212> TYPE: PRT
<213> ORGANISM: Bos taurus

<400> SEQUENCE: 5

Gln Leu Leu Pro Gly Asn Asn Phe Thr Asn Glu Cys Asn Ile Pro Gly
1               5                   10                  15

Asn Phe Met Cys Ser Asn Gly Arg Cys Ile Pro Gly Ala Trp Gln Cys
            20                  25                  30

Asp Gly Leu Pro Asp Cys Phe Asp Lys Ser Asp Glu Lys Glu Cys Pro
        35                  40                  45

Lys Ala Lys Ser Lys Cys Gly Pro Thr Phe Phe Pro Cys Ala Ser Gly
    50                  55                  60

Val His Cys Ile Ile Gly Arg Phe Arg Cys Asn Gly Phe Glu Asp Cys
65                  70                  75                  80

Pro Asp Gly Ser Asp Glu Glu Asn Cys Thr Ala Asn Pro Leu Leu Cys
                85                  90                  95

Ser Thr Ala Arg Tyr His Cys Lys Asn Gly Leu Cys Ile Asp Lys Ser
            100                 105                 110
```

```
Phe Ile Cys Asp Gly Gln Asn Asn Cys Gln Asp Asn Ser Asp Glu Glu
        115                 120                 125

Ser Cys Glu Ser Ser Gln Glu Pro Gly Ser Gly Gln Val Phe Val Thr
    130                 135                 140

Ser Glu Asn Gln Leu Val Tyr Tyr Pro Ser Ile Thr Tyr Ala Ile Ile
145                 150                 155                 160

Gly Ser Ser Val Ile Phe Val Leu Val Val Ala Leu Leu Ala Leu Val
                165                 170                 175

Leu


<210> SEQ ID NO 6
<211> LENGTH: 176
<212> TYPE: PRT
<213> ORGANISM: Equus caballus

<400> SEQUENCE: 6

Gln Leu Leu Pro Gly Asn Asn Phe Thr Asn Glu Cys Asn Ile Pro Gly
1               5                   10                  15

Asn Phe Met Cys Ser Asn Gly Arg Cys Ile Pro Gly Ala Trp Gln Cys
            20                  25                  30

Asp Gly Leu Pro Asp Cys Phe Asp Lys Ser Asp Glu Lys Glu Cys Pro
        35                  40                  45

Lys Ala Lys Ser Lys Cys Gly Pro Thr Phe Phe Pro Cys Ser Gly Ile
    50                  55                  60

His Cys Ile Ile Gly Arg Phe Gln Cys Asn Gly Phe Glu Asp Cys Pro
65                  70                  75                  80

Asp Gly Ser Asp Glu Glu Asn Cys Thr Ala Asn Pro Leu Leu Cys Ser
                85                  90                  95

Thr Ala Arg Tyr His Cys Lys Asn Gly Leu Cys Ile Asp Lys Ser Phe
            100                 105                 110

Ile Cys Asp Gly Gln Asn Asn Cys Gln Asp Asn Ser Asp Glu Glu Ser
        115                 120                 125

Cys Glu Ser Ser Gln Glu Pro Gly Ser Gly Gln Val Phe Val Thr Ser
    130                 135                 140

Glu Asn Gln Leu Val Tyr Tyr Pro Ser Ile Thr Tyr Ala Ile Ile Gly
145                 150                 155                 160

Ser Ser Val Ile Phe Val Leu Val Val Ala Leu Leu Ala Leu Val Leu
                165                 170                 175


<210> SEQ ID NO 7
<211> LENGTH: 177
<212> TYPE: PRT
<213> ORGANISM: Canis familiaris

<400> SEQUENCE: 7

Gln Leu Leu Pro Gly Asn Asn Phe Thr Asn Glu Cys Asn Ile Pro Gly
1               5                   10                  15

Asn Phe Met Cys Gly Asn Gly Arg Cys Val Pro Gly Ala Trp Gln Cys
            20                  25                  30

Asp Gly Leu Pro Asp Cys Phe Asp Gly Ser Asp Glu Lys Glu Cys Pro
        35                  40                  45

Lys Ala Lys Ser Lys Cys Gly Pro Thr Phe Phe Pro Cys Ala Ser Gly
    50                  55                  60

Val His Cys Ile Ile Gly Arg Phe Arg Cys Asn Gly Phe Glu Asp Cys
65                  70                  75                  80
```

```
Pro Asp Gly Ser Asp Glu Glu Asn Cys Thr Ala Asn Pro Leu Leu Cys
                85                  90                  95

Ser Thr Ala Arg Tyr His Cys Lys Asn Gly Leu Cys Ile Asp Lys Ser
            100                 105                 110

Phe Ile Cys Asp Gly Gln Asn Asn Cys Gln Asp Asn Ser Asp Glu Glu
        115                 120                 125

Ser Cys Glu Ser Ser Gln Glu Pro Gly Ser Gly Gln Val Phe Val Thr
    130                 135                 140

Ser Glu Asn Gln Leu Val Tyr Tyr Pro Ser Ile Thr Tyr Ala Ile Ile
145                 150                 155                 160

Gly Ser Ser Val Ile Phe Val Leu Val Val Ala Leu Leu Ala Leu Val
                165                 170                 175

Leu


<210> SEQ ID NO 8
<211> LENGTH: 177
<212> TYPE: PRT
<213> ORGANISM: Gallus gallus

<400> SEQUENCE: 8

Gln Leu Leu Pro Gly Asn Asn Phe Thr Asn Glu Cys Asn Ile Pro Gly
1               5                   10                  15

Asn Phe Met Cys Ser Asn Gly Arg Cys Ile Pro Gly Ala Trp Gln Cys
            20                  25                  30

Asp Gly Leu Pro Asp Cys Phe Asp Asp Ser Asp Glu Lys Glu Cys Pro
        35                  40                  45

Lys Ala Lys Ser Lys Cys Gly Ala Thr Phe Phe Pro Cys Ala Ser Gly
    50                  55                  60

Ile His Cys Ile Ile Gly Arg Phe Arg Cys Asn Gly Phe Glu Asp Cys
65                  70                  75                  80

Pro Asp Gly Ser Asp Glu Glu Asn Cys Thr Ala Asn Pro Leu Leu Cys
                85                  90                  95

Ser Thr Ala Arg Phe His Cys Lys Asn Gly Leu Cys Ile Asp Lys Ser
            100                 105                 110

Phe Val Cys Asp Ser Gln Asn Asn Cys Gln Asp Asn Ser Asp Glu Glu
        115                 120                 125

Ser Cys Glu Ser Pro Gln Glu Ala Gly Ser Gly Gln Asp Tyr Val Thr
    130                 135                 140

Ser Glu Asn Gln Leu Leu Tyr Tyr Pro Ser Ile Thr Tyr Ala Ile Ile
145                 150                 155                 160

Gly Ser Ser Val Ile Phe Val Leu Val Val Ala Phe Leu Ala Leu Val
                165                 170                 175

Leu


<210> SEQ ID NO 9
<211> LENGTH: 104
<212> TYPE: DNA
<213> ORGANISM: Homo sapiens

<400> SEQUENCE: 9

gtgtttgtga cctcggagaa ccagcttgtg tactacccca gcatcacgta cgccatcatc      60

ggcagctctg tcatcttcgt gctggtggtg gccctgctcg cact                      104


<210> SEQ ID NO 10
<211> LENGTH: 105
<212> TYPE: DNA
```

<213> ORGANISM: Artificial Sequence
<220> FEATURE:
<223> OTHER INFORMATION: Synthesized

<400> SEQUENCE: 10
gtgtttgtga cctcggagaa ccagcttgtg tactacccca gcatcacgta cgccatccat 60
cggcagctct gtcatcttcg tgctggtggt ggccctgctc gcact 105

<210> SEQ ID NO 11
<211> LENGTH: 94
<212> TYPE: DNA
<213> ORGANISM: Artificial Sequence
<220> FEATURE:
<223> OTHER INFORMATION: Synthesized

<400> SEQUENCE: 11
gtgtttgtga cctcggagaa ccagcttgtg tactacccca gcatcacatc ggcagctctg 60
tcatcttcgt gctggtggtg gccctgctcg cact 94

<210> SEQ ID NO 12
<211> LENGTH: 98
<212> TYPE: DNA
<213> ORGANISM: Homo sapiens

<400> SEQUENCE: 12
tctctctctc acagagagcc agctgctccc tgggaacaac ttcaccaacg agtgcaacat 60
cccaggtaac ttcatgtgca gcaacgggcg gtgcatcc 98

<210> SEQ ID NO 13
<211> LENGTH: 99
<212> TYPE: DNA
<213> ORGANISM: Artificial Sequence
<220> FEATURE:
<223> OTHER INFORMATION: Synthesized

<400> SEQUENCE: 13
tctctctctc acagagagcc agctgctccc tgggaacaac ttcaccaacg agtgcaacat 60
tcccaggtaa cttcatgtgc agcaacgggc ggtgcatcc 99

<210> SEQ ID NO 14
<211> LENGTH: 106
<212> TYPE: DNA
<213> ORGANISM: Artificial Sequence
<220> FEATURE:
<223> OTHER INFORMATION: Synthesized

<400> SEQUENCE: 14
tctctctctc acagagagcc agctgctccc tgggaacaac ttcaccaacg agtaacttca 60
tgtaagttcc caggtaactt catgtgcagc aacgggcggt gcatcc 106

<210> SEQ ID NO 15
<211> LENGTH: 87
<212> TYPE: DNA
<213> ORGANISM: Artificial Sequence
<220> FEATURE:
<223> OTHER INFORMATION: Synthesized

<400> SEQUENCE: 15
tctctctctc acagagagcc agctgctccc tgggaacaac ttcaccaatg ccaggtaact 60
tcatgtgcag caacgggcgg tgcatcc 87

<210> SEQ ID NO 16
<211> LENGTH: 115
<212> TYPE: DNA
<213> ORGANISM: Homo sapiens

<400> SEQUENCE: 16
ctcggagaac cagcttgtgt actaccccag catcacgtac gccatcatcg gcagctctgt 60
catcttcgtg ctggtggtgg ccctgctcgc actggtcctg catcatcagc gaaag 115

<210> SEQ ID NO 17
<211> LENGTH: 96
<212> TYPE: DNA
<213> ORGANISM: Artificial Sequence
<220> FEATURE:
<223> OTHER INFORMATION: Synthesized

<400> SEQUENCE: 17
ctcggagaac cagcttgtgt actaccccac ggcagctctg tcatcttcgt gctggtggtg 60
gccctgctcg cactggtcct gcatcatcag cgaaag 96

<210> SEQ ID NO 18
<211> LENGTH: 57
<212> TYPE: DNA
<213> ORGANISM: Artificial Sequence
<220> FEATURE:
<223> OTHER INFORMATION: Synthesized

<400> SEQUENCE: 18
ctcggagaac cagcttgtgt actaccccac gcactggtcc tgcatcatca gcgaaag 57

<210> SEQ ID NO 19
<211> LENGTH: 121
<212> TYPE: DNA
<213> ORGANISM: Homo sapiens

<400> SEQUENCE: 19
caggcagcgg gcaggtgttt gtgacctcgg agaaccagct tgtgtactac cccagcatca 60
cgtacgccat catcggcagc tctgtcatct tcgtgctggt gctggccctg ctcgcactgg 120
t 121

<210> SEQ ID NO 20
<211> LENGTH: 122
<212> TYPE: DNA
<213> ORGANISM: Artificial Sequence
<220> FEATURE:
<223> OTHER INFORMATION: Synthesized

<400> SEQUENCE: 20
caggcagcgg gcaggtgttt gtgacctcgg agaaccagct tgtgtactac cccagcatca 60
cgtacgccat tcatcggcag ctctgtcatc ttcgtgctgg tgctggccct gctcgcactg 120
gt 122

<210> SEQ ID NO 21
<211> LENGTH: 119
<212> TYPE: DNA
<213> ORGANISM: Artificial Sequence
<220> FEATURE:
<223> OTHER INFORMATION: Synthesized

<400> SEQUENCE: 21
caggcagcgg gcaggtgttt gtgacctcgg agaaccagct tgtgtactac cccagcatca 60
cgtacgccca tcggcagctc tgtcatcttc gtgctggtgg tggccctgct cgcactggt 119

<210> SEQ ID NO 22
<211> LENGTH: 57
<212> TYPE: DNA
<213> ORGANISM: Artificial Sequence
<220> FEATURE:
<223> OTHER INFORMATION: Synthesized

<400> SEQUENCE: 22
caggcagcgg gcaggtgttt gtgacctcgt gctggtggtg gccctgctcg cactggt 57

<210> SEQ ID NO 23
<211> LENGTH: 100
<212> TYPE: DNA
<213> ORGANISM: Homo sapiens

<400> SEQUENCE: 23
tctcctgatg tcttgctgtt tctttttctt cctgcagcca aggctaagtc gaaatgtggc 60
ccaaccttct tcccctgtgc cagcggcatc cattgcatca 100

<210> SEQ ID NO 24
<211> LENGTH: 101
<212> TYPE: DNA
<213> ORGANISM: Artificial Sequence
<220> FEATURE:
<223> OTHER INFORMATION: Synthesized

<400> SEQUENCE: 24
tctcctgatg tcttgctgtt tctttttctt cctgcagcca aggctaagtc gaaaatgtgg 60
cccaaccttc ttcccctgtg ccagcggcat ccattgcatc a 101

<210> SEQ ID NO 25
<211> LENGTH: 92
<212> TYPE: DNA
<213> ORGANISM: Artificial Sequence
<220> FEATURE:
<223> OTHER INFORMATION: Synthesized

<400> SEQUENCE: 25
tctcctgatg tcttgctgtt tctttttctt cctgcagcca aggctaagtg gcccaacctt 60
cttcccctgt gccagcggca tccattgcat ca 92

<210> SEQ ID NO 26
<211> LENGTH: 79
<212> TYPE: DNA
<213> ORGANISM: Homo sapiens

<400> SEQUENCE: 26
tccaccgccc gctaccactg caagaacggc ctctgtattg acaagagctt catctgcgat 60
ggacagaata actgtcaag 79

<210> SEQ ID NO 27
<211> LENGTH: 96
<212> TYPE: DNA
<213> ORGANISM: Artificial Sequence
<220> FEATURE:
<223> OTHER INFORMATION: Synthesized

<400> SEQUENCE: 27
tccaccgccc gctaccactg caagaacggc ctctgacaag agctctgaca agcactgaca 60
agagcttcat ctgcgatgga cagaataact gtcaag 96

<210> SEQ ID NO 28
<211> LENGTH: 71
<212> TYPE: DNA
<213> ORGANISM: Artificial Sequence
<220> FEATURE:
<223> OTHER INFORMATION: Synthesized

<400> SEQUENCE: 28
tccaccgccc gctaccactg caagaactat tgacaagagc ttcatctgcg atggacagaa 60
taactgtcaa g 71

<210> SEQ ID NO 29
<211> LENGTH: 67
<212> TYPE: DNA
<213> ORGANISM: Artificial Sequence
<220> FEATURE:
<223> OTHER INFORMATION: Synthesized

<400> SEQUENCE: 29
tccaccgccc gctaccactg caagaacggc ctgagcttca tctgcgatgg acagaataac 60
tgtcaag 67

<210> SEQ ID NO 30
<211> LENGTH: 23
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (21)..(21)
<223> OTHER INFORMATION: n is a, c, g, or t

<400> SEQUENCE: 30
cagcaacggg cggtgcatcc ngg 23

<210> SEQ ID NO 31
<211> LENGTH: 23
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (21)..(21)
<223> OTHER INFORMATION: n is a, c, g, or t

<400> SEQUENCE: 31
cgtcacactg ccaggcgccc ngg 23

<210> SEQ ID NO 32
<211> LENGTH: 48
<212> TYPE: PRT
<213> ORGANISM: Homo sapiens

<400> SEQUENCE: 32

Ser Gln Leu Leu Pro Gly Asn Asn Phe Thr Asn Glu Cys Asn Ile Pro
1 5 10 15

Gly Asn Phe Met Cys Ser Asn Gly Arg Cys Ile Pro Gly Ala Trp Gln
20 25 30

Cys Asp Gly Leu Pro Asp Cys Phe Asp Lys Ser Asp Glu Lys Glu Cys
35 40 45

```
<210> SEQ ID NO 33
<211> LENGTH: 40
<212> TYPE: PRT
<213> ORGANISM: Artificial Sequence
<220> FEATURE:
<223> OTHER INFORMATION: Synthesized

<400> SEQUENCE: 33

Ser Gln Leu Leu Pro Gly Asn Asn Phe Thr Asn Glu Cys Asn Ile Pro
1               5                   10                  15

Gly Asn Phe Met Cys Ser Asn Gly Arg Leu Ala Val Arg Ala Ala Leu
            20                  25                  30

Leu Arg Gln Glu Arg Glu Gly Met
        35                  40


<210> SEQ ID NO 34
<211> LENGTH: 41
<212> TYPE: PRT
<213> ORGANISM: Artificial Sequence
<220> FEATURE:
<223> OTHER INFORMATION: Synthesized

<400> SEQUENCE: 34

Ser Gln Leu Leu Pro Gly Asn Asn Phe Thr Asn Glu Cys Asn Ile Pro
1               5                   10                  15

Gly Asn Phe Met Cys Ser Asn Gly Arg Cys Leu Ala Val Arg Ala Ala
            20                  25                  30

Leu Leu Arg Gln Glu Arg Glu Gly Met
        35                  40


<210> SEQ ID NO 35
<211> LENGTH: 147
<212> TYPE: DNA
<213> ORGANISM: Homo sapiens

<400> SEQUENCE: 35

agagccagct gctccctggg aacaacttca ccaacgagtg caacatccca ggtaacttca     60

tgtgcagcaa cgggcggtgc atcccgggcg cctggcagtg tgacgggctg cctgactgct    120

tcgacaagag tgacgagaag gaatgcc                                        147


<210> SEQ ID NO 36
<211> LENGTH: 132
<212> TYPE: DNA
<213> ORGANISM: Artificial Sequence
<220> FEATURE:
<223> OTHER INFORMATION: Synthesized

<400> SEQUENCE: 36

gagccagctg ctccctggga acaacttcac caacgagtgc aacatcccag gtaacttcat     60

gtgcagcaac gggcgcctgg cagtgtgacg ggctgcctga ctgcttcgac aagagtgacg    120

agaaggaatg cc                                                        132


<210> SEQ ID NO 37
<211> LENGTH: 136
<212> TYPE: DNA
<213> ORGANISM: Artificial Sequence
<220> FEATURE:
<223> OTHER INFORMATION: Synthesized

<400> SEQUENCE: 37

agagccagct gctccctggg aacaacttca ccaacgagtg caacatccca ggtaacttca     60
```

tgtgcagcaa cgggcggtgc ctggcagtgt gacgggctgc ctgactgctt cgacaagagt 120
gacgagaagg aatgcc 136

<210> SEQ ID NO 38
<211> LENGTH: 20
<212> TYPE: DNA
<213> ORGANISM: Artificial Sequence
<220> FEATURE:
<223> OTHER INFORMATION: Synthesized

<400> SEQUENCE: 38
tgcagcaacg ggcggtgcat 20

<210> SEQ ID NO 39
<211> LENGTH: 19
<212> TYPE: DNA
<213> ORGANISM: Artificial Sequence
<220> FEATURE:
<223> OTHER INFORMATION: Synthesized

<400> SEQUENCE: 39
agcccgtcac actgccagg 19

<210> SEQ ID NO 40
<211> LENGTH: 20
<212> TYPE: DNA
<213> ORGANISM: Artificial Sequence
<220> FEATURE:
<223> OTHER INFORMATION: Synthesized

<400> SEQUENCE: 40
ccgatgatac agtggatgcc 20

<210> SEQ ID NO 41
<211> LENGTH: 20
<212> TYPE: DNA
<213> ORGANISM: Artificial Sequence
<220> FEATURE:
<223> OTHER INFORMATION: Synthesized

<400> SEQUENCE: 41
accaacgagt gcaacatccc 20

<210> SEQ ID NO 42
<211> LENGTH: 20
<212> TYPE: DNA
<213> ORGANISM: Artificial Sequence
<220> FEATURE:
<223> OTHER INFORMATION: Synthesized

<400> SEQUENCE: 42
agcatcacgt acgccatcat 20

<210> SEQ ID NO 43
<211> LENGTH: 20
<212> TYPE: DNA
<213> ORGANISM: Artificial Sequence
<220> FEATURE:
<223> OTHER INFORMATION: Synthesized

<400> SEQUENCE: 43
gaagttcgag ggcgacaccc 20

<210> SEQ ID NO 44
<211> LENGTH: 22

<212> TYPE: DNA
<213> ORGANISM: Artificial Sequence
<220> FEATURE:
<223> OTHER INFORMATION: Synthesized

<400> SEQUENCE: 44
atctatgtgc tcaaccaggt gg 22

<210> SEQ ID NO 45
<211> LENGTH: 20
<212> TYPE: DNA
<213> ORGANISM: Artificial Sequence
<220> FEATURE:
<223> OTHER INFORMATION: Synthesized

<400> SEQUENCE: 45
gccaaggcta agtcgaaatg 20

<210> SEQ ID NO 46
<211> LENGTH: 20
<212> TYPE: DNA
<213> ORGANISM: Artificial Sequence
<220> FEATURE:
<223> OTHER INFORMATION: Synthesized

<400> SEQUENCE: 46
tgaagctctt gtcaatacag 20

<210> SEQ ID NO 47
<211> LENGTH: 20
<212> TYPE: DNA
<213> ORGANISM: Artificial Sequence
<220> FEATURE:
<223> OTHER INFORMATION: Synthesized

<400> SEQUENCE: 47
acaaatgaat gtaatattcc 20

<210> SEQ ID NO 48
<211> LENGTH: 20
<212> TYPE: DNA
<213> ORGANISM: Artificial Sequence
<220> FEATURE:
<223> OTHER INFORMATION: Synthesized

<400> SEQUENCE: 48
tctattactt atgctattat 20

<210> SEQ ID NO 49
<211> LENGTH: 114
<212> TYPE: DNA
<213> ORGANISM: Artificial Sequence
<220> FEATURE:
<223> OTHER INFORMATION: Synthesized

<400> SEQUENCE: 49
ctggcgcccc ccgccggcac caccgacgcc gcgcacccgg ggcggtccgt ggtccccgcg 60
ttgcttcctc tgctggccgg gaccctgctg ctgctggaga cggccactgc tccc 114

<210> SEQ ID NO 50
<211> LENGTH: 21
<212> TYPE: DNA
<213> ORGANISM: Artificial Sequence
<220> FEATURE:
<223> OTHER INFORMATION: Synthesized

<400> SEQUENCE: 50
aagatcatcg acgcagtcat c 21

<210> SEQ ID NO 51
<211> LENGTH: 21
<212> TYPE: DNA
<213> ORGANISM: Artificial Sequence
<220> FEATURE:
<223> OTHER INFORMATION: Synthesized

<400> SEQUENCE: 51
gctgtggaag taaccgaatc t 21

<210> SEQ ID NO 52
<211> LENGTH: 20
<212> TYPE: DNA
<213> ORGANISM: Artificial Sequence
<220> FEATURE:
<223> OTHER INFORMATION: Synthesized

<400> SEQUENCE: 52
gcccagaaca tcatccctgc 20

<210> SEQ ID NO 53
<211> LENGTH: 21
<212> TYPE: DNA
<213> ORGANISM: Artificial Sequence
<220> FEATURE:
<223> OTHER INFORMATION: Synthesized

<400> SEQUENCE: 53
ccgttcagct ctgggatgac c 21

<210> SEQ ID NO 54
<211> LENGTH: 5
<212> TYPE: PRT
<213> ORGANISM: Artificial Sequence
<220> FEATURE:
<223> OTHER INFORMATION: Synthesized

<400> SEQUENCE: 54

Gly Gly Gly Gly Ser
1 5

<210> SEQ ID NO 55
<211> LENGTH: 23
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (21)..(21)
<223> OTHER INFORMATION: n is a, c, g, or t

<400> SEQUENCE: 55
cagcaacggg cggtgcatcc ngg 23

<210> SEQ ID NO 56
<211> LENGTH: 23
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (21)..(21)

<223> OTHER INFORMATION: n is a, c, g, or t

<400> SEQUENCE: 56
cgtcacactg ccaggcgccc ngg 23

<210> SEQ ID NO 57
<211> LENGTH: 20
<212> TYPE: DNA
<213> ORGANISM: Artificial Sequence
<220> FEATURE:
<223> OTHER INFORMATION: Synthesized

<400> SEQUENCE: 57
caagtcgagg cagacattca 20

<210> SEQ ID NO 58
<211> LENGTH: 22
<212> TYPE: DNA
<213> ORGANISM: Artificial Sequence
<220> FEATURE:
<223> OTHER INFORMATION: Synthesized

<400> SEQUENCE: 58
cagggtgtca aggatggata aa 22

<210> SEQ ID NO 59
<211> LENGTH: 20
<212> TYPE: DNA
<213> ORGANISM: Artificial Sequence
<220> FEATURE:
<223> OTHER INFORMATION: Synthesized

<400> SEQUENCE: 59
tgcagcaacg ggcggtgcat 20

<210> SEQ ID NO 60
<211> LENGTH: 20
<212> TYPE: DNA
<213> ORGANISM: Artificial Sequence
<220> FEATURE:
<223> OTHER INFORMATION: Synthesized

<400> SEQUENCE: 60
ccgatgatac agtggatgcc 20

<210> SEQ ID NO 61
<211> LENGTH: 423
<212> TYPE: PRT
<213> ORGANISM: Venezuelan equine encephalitis virus

<400> SEQUENCE: 61

Ser Thr Glu Glu Leu Phe Asn Glu Tyr Lys Leu Thr Pro Pro Tyr Met
1 5 10 15

Ala Arg Cys Ile Pro Cys Ala Val Gly Ser Cys His Ser Pro Ile Ala
20 25 30

Ile Glu Ala Val Lys Ser Asp Gly His Asp Gly Tyr Val Arg Leu Gln
35 40 45

Thr Ser Ser Gln Tyr Gly Leu Asp Ser Ser Gly Asn Leu Lys Gly Arg
50 55 60

Thr Met Arg Tyr Asp Met His Gly Thr Ile Lys Glu Ile Pro Leu His
65 70 75 80

Gln Val Ser Leu Tyr Thr Ser Arg Pro Cys His Ile Val Asp Gly His
85 90 95

```
Gly Tyr Phe Leu Leu Ala Arg Cys Pro Ala Gly Asp Ser Ile Thr Met
            100                 105                 110

Glu Phe Lys Lys Asp Ser Val Arg His Ser Cys Ser Val Pro Tyr Glu
        115                 120                 125

Val Lys Phe Asn Pro Val Gly Arg Glu Leu Tyr Thr His Pro Pro Glu
    130                 135                 140

His Gly Val Glu Gln Ala Cys Gln Val Tyr Ala His Asp Ala Gln Asn
145                 150                 155                 160

Arg Gly Ala Tyr Val Glu Met His Leu Pro Gly Ser Glu Val Asp Ser
                165                 170                 175

Ser Leu Val Ser Leu Ser Gly Ser Ser Val Thr Val Thr Pro Pro Asp
            180                 185                 190

Gly Thr Ser Ala Leu Val Glu Cys Glu Cys Gly Gly Thr Lys Ile Ser
        195                 200                 205

Glu Thr Ile Asn Lys Thr Lys Gln Phe Ser Gln Cys Thr Lys Lys Glu
    210                 215                 220

Gln Cys Arg Ala Tyr Arg Leu Gln Asn Asp Lys Trp Val Tyr Asn Ser
225                 230                 235                 240

Asp Lys Leu Pro Lys Ala Ala Gly Ala Thr Leu Lys Gly Lys Leu His
                245                 250                 255

Val Pro Phe Leu Leu Ala Asp Gly Lys Cys Thr Val Pro Leu Ala Pro
            260                 265                 270

Glu Pro Met Ile Thr Phe Gly Phe Arg Ser Val Ser Leu Lys Leu His
        275                 280                 285

Pro Lys Asn Pro Thr Tyr Leu Ile Thr Arg Gln Leu Ala Asp Glu Pro
    290                 295                 300

His Tyr Thr His Glu Leu Ile Ser Glu Pro Ala Val Arg Asn Phe Thr
305                 310                 315                 320

Val Thr Glu Lys Gly Trp Glu Phe Val Trp Gly Asn His Pro Pro Lys
                325                 330                 335

Arg Phe Trp Ala Gln Glu Thr Ala Pro Gly Asn Pro His Gly Leu Pro
            340                 345                 350

His Glu Val Ile Thr His Tyr Tyr His Arg Tyr Pro Met Ser Thr Ile
        355                 360                 365

Leu Gly Leu Ser Ile Cys Ala Ala Ile Ala Thr Val Ser Val Ala Ala
    370                 375                 380

Ser Thr Trp Leu Phe Cys Arg Ser Arg Val Ala Cys Leu Thr Pro Tyr
385                 390                 395                 400

Arg Leu Thr Pro Asn Ala Arg Ile Pro Phe Cys Leu Ala Val Leu Cys
                405                 410                 415

Cys Ala Arg Thr Ala Arg Ala
            420
```

<210> SEQ ID NO 62
<211> LENGTH: 424
<212> TYPE: PRT
<213> ORGANISM: Venezuelan equine encephalitis virus

<400> SEQUENCE: 62

```
Ser Thr Glu Glu Leu Phe Lys Glu Tyr Lys Leu Thr Pro Pro Tyr Met
1               5                   10                  15

Ala Arg Cys Ile Pro Cys Ala Val Gly Ser Cys His Ser Pro Ile Ala
            20                  25                  30

Ile Glu Ala Val Lys Ser Asp Gly His Asp Gly Tyr Val Arg Leu Gln
```

```
        35                  40                  45

Thr Ser Ser Gln Tyr Gly Leu Asp Ser Ser Gly Asn Leu Lys Gly Arg
    50                  55                  60

Thr Met Arg Tyr Asp Met His Gly Thr Ile Lys Glu Ile Pro Leu His
65                  70                  75                  80

Gln Val Ser Leu Tyr Thr Ser Arg Pro Cys His Ile Val Asp Gly His
                85                  90                  95

Gly Tyr Phe Leu Leu Ala Arg Cys Pro Ala Gly Asp Ser Ile Thr Met
            100                 105                 110

Glu Phe Lys Lys Asp Ser Val Thr Arg His Ser Cys Ser Val Pro Tyr
        115                 120                 125

Glu Val Lys Phe Asn Pro Val Gly Arg Glu Leu Tyr Thr His Pro Pro
    130                 135                 140

Glu His Gly Val Glu Gln Ala Cys Gln Val Tyr Ala His Asp Ala Gln
145                 150                 155                 160

Asn Arg Gly Ala Tyr Val Glu Met His Leu Pro Gly Ser Glu Val Asp
                165                 170                 175

Ser Ser Leu Val Ser Leu Ser Gly Ser Ser Val Thr Val Thr Pro Pro
            180                 185                 190

Val Gly Thr Ser Ala Leu Val Glu Cys Glu Cys Gly Gly Thr Lys Ile
        195                 200                 205

Ser Glu Thr Ile Asn Lys Thr Lys Gln Phe Ser Gln Cys Thr Lys Lys
    210                 215                 220

Glu Gln Cys Arg Ala Tyr Arg Leu Gln Asn Asp Lys Trp Val Tyr Asn
225                 230                 235                 240

Ser Asp Lys Leu Pro Lys Ala Ala Gly Ala Thr Leu Lys Gly Lys Leu
                245                 250                 255

His Val Pro Phe Leu Leu Ala Asp Gly Lys Cys Thr Val Pro Leu Ala
            260                 265                 270

Pro Glu Pro Met Ile Thr Phe Gly Phe Arg Ser Val Ser Leu Lys Leu
        275                 280                 285

His Pro Lys Asn Pro Thr Tyr Leu Thr Thr Arg Gln Leu Ala Asp Glu
    290                 295                 300

Pro His Tyr Thr His Glu Leu Ile Ser Glu Pro Ala Val Arg Asn Phe
305                 310                 315                 320

Thr Val Thr Glu Lys Gly Trp Glu Phe Val Trp Gly Asn His Pro Pro
                325                 330                 335

Lys Arg Phe Trp Ala Gln Glu Thr Ala Pro Gly Asn Pro His Gly Leu
            340                 345                 350

Pro His Glu Val Ile Thr His Tyr Tyr His Arg Tyr Pro Met Ser Thr
        355                 360                 365

Ile Leu Gly Leu Ser Ile Cys Ala Ala Ile Ala Thr Val Ser Val Ala
    370                 375                 380

Ala Ser Thr Trp Leu Phe Cys Arg Ser Arg Val Ala Cys Leu Thr Pro
385                 390                 395                 400

Tyr Arg Leu Thr Pro Asn Ala Arg Ile Pro Phe Cys Leu Ala Val Leu
                405                 410                 415

Cys Cys Ala Arg Thr Ala Arg Ala
            420
```

<210> SEQ ID NO 63
<211> LENGTH: 424
<212> TYPE: PRT
<213> ORGANISM: Venezuelan equine encephalitis virus

<400> SEQUENCE: 63

Ser Thr Lys Glu Leu Phe Lys Glu Tyr Lys Leu Thr Pro Pro Tyr Met
1               5                   10                  15

Ala Arg Cys Ile Pro Cys Ala Val Gly Ser Cys His Ser Pro Ile Ala
            20                  25                  30

Ile Glu Ala Val Lys Ser Asp Gly His Asp Gly Tyr Val Arg Leu Gln
        35                  40                  45

Thr Ser Ser Gln Tyr Gly Leu Asp Ser Ser Gly Asn Leu Lys Gly Arg
    50                  55                  60

Thr Met Arg Tyr Asp Met His Gly Thr Ile Glu Glu Ile Pro Leu His
65                  70                  75                  80

Gln Val Ser Leu Tyr Thr Ser Arg Pro Cys His Ile Val Asp Gly His
                85                  90                  95

Gly Tyr Phe Leu Leu Ala Arg Cys Pro Ala Gly Asp Ser Ile Thr Met
            100                 105                 110

Glu Phe Lys Lys Gly Ser Val Thr Arg His Ser Cys Ser Val Pro Tyr
        115                 120                 125

Glu Val Lys Phe Asn Pro Val Gly Arg Glu Leu Tyr Thr His Pro Pro
    130                 135                 140

Glu His Gly Ala Glu Gln Ala Cys Gln Val Tyr Ala His Asp Ala Gln
145                 150                 155                 160

Asn Arg Gly Ala Tyr Val Glu Met His Leu Pro Gly Ser Glu Val Asp
                165                 170                 175

Ser Ser Leu Ile Ser Leu Ser Gly Ser Ser Val Thr Val Thr Pro Pro
            180                 185                 190

Val Gly Thr Ser Ala Leu Val Glu Cys Lys Cys Gly Gly Thr Lys Ile
        195                 200                 205

Ser Glu Thr Ile Asn Lys Ala Lys Gln Phe Ser Gln Cys Thr Lys Lys
    210                 215                 220

Glu Gln Cys Arg Ala Tyr Arg Leu Gln Asn Asp Lys Trp Val Tyr Asn
225                 230                 235                 240

Ser Asp Lys Leu Pro Lys Ala Ala Gly Ala Thr Leu Lys Gly Lys Leu
                245                 250                 255

His Val Pro Phe Leu Leu Ala Asp Gly Lys Cys Thr Val Pro Leu Ala
            260                 265                 270

Pro Glu Pro Met Ile Thr Phe Gly Phe Arg Ser Val Ser Leu Lys Leu
        275                 280                 285

His Pro Lys Asn Pro Thr Tyr Leu Thr Thr Arg Gln Leu Ala Asp Glu
    290                 295                 300

Pro His Tyr Thr His Glu Leu Ile Ser Glu Pro Ala Val Arg Asn Phe
305                 310                 315                 320

Thr Val Thr Glu Lys Gly Trp Glu Phe Val Trp Gly Asn His Pro Pro
                325                 330                 335

Lys Arg Phe Trp Ala Gln Glu Thr Ala Pro Gly Asn Pro His Gly Leu
            340                 345                 350

Pro His Glu Val Ile Thr His Tyr Tyr His Arg Tyr Pro Met Ser Thr
        355                 360                 365

Ile Leu Gly Leu Ser Ile Cys Ala Ala Ile Val Thr Val Ser Val Ala
    370                 375                 380

Ala Ser Thr Trp Leu Phe Cys Lys Ser Arg Val Ser Cys Leu Thr Pro
385                 390                 395                 400

Tyr Arg Leu Thr Pro Asn Ala Arg Met Pro Leu Cys Leu Ala Val Leu 405 410 415

Cys Cys Ala Arg Thr Ala Arg Ala
420

<210> SEQ ID NO 64
<211> LENGTH: 424
<212> TYPE: PRT
<213> ORGANISM: Venezuelan equine encephalitis virus

<400> SEQUENCE: 64

Ser Thr Glu Glu Leu Phe Lys Glu Tyr Lys Leu Thr Pro Pro Tyr Met
1 5 10 15

Ala Arg Cys Ile Pro Cys Ala Val Gly Ser Cys His Ser Pro Ile Ala
20 25 30

Ile Glu Ala Val Lys Ser Asp Gly His Asp Gly Tyr Val Arg Leu Gln
35 40 45

Thr Ser Ser Gln Tyr Gly Leu Asp Ser Ser Gly Asn Leu Lys Gly Arg
50 55 60

Thr Met Arg Tyr Asp Met His Gly Thr Ile Glu Glu Ile Pro Leu His
65 70 75 80

Gln Val Ser Leu Tyr Thr Ser Arg Pro Cys His Ile Val Asp Gly His
85 90 95

Gly Tyr Phe Leu Leu Ala Arg Cys Pro Ala Gly Asp Ser Ile Thr Met
100 105 110

Glu Phe Lys Lys Asn Ser Val Thr Arg His Ser Cys Ser Val Pro Tyr
115 120 125

Glu Val Lys Phe Asn Pro Val Gly Arg Glu Leu Tyr Thr His Pro Pro
130 135 140

Glu His Gly Ala Glu Gln Ala Cys Gln Val Tyr Ala His Asp Ala Gln
145 150 155 160

Asn Arg Gly Ala Tyr Val Glu Met His Leu Pro Gly Ser Glu Val Asp
165 170 175

Ser Ser Leu Val Ser Leu Ser Gly Ser Ser Val Thr Val Thr Pro Pro
180 185 190

Ala Gly Thr Ser Ala Leu Val Glu Cys Glu Cys Gly Gly Thr Lys Ile
195 200 205

Ser Glu Thr Ile Asn Thr Ala Lys Gln Phe Ser Gln Cys Thr Lys Lys
210 215 220

Glu Gln Cys Arg Ala Tyr Arg Leu Gln Asn Asp Lys Trp Val Tyr Asn
225 230 235 240

Ser Asp Lys Leu Pro Lys Ala Ala Gly Ala Thr Leu Lys Gly Lys Leu
245 250 255

His Val Pro Phe Leu Leu Ala Asp Gly Lys Cys Thr Val Pro Leu Ala
260 265 270

Pro Glu Pro Met Ile Thr Phe Gly Phe Arg Ser Val Ser Leu Lys Leu
275 280 285

His Pro Lys Asn Pro Thr Tyr Leu Thr Thr Arg Gln Leu Ala Asp Glu
290 295 300

Pro His Tyr Thr His Glu Leu Ile Ser Glu Pro Ala Val Arg Asn Phe
305 310 315 320

Thr Val Thr Glu Lys Gly Trp Glu Phe Val Trp Gly Asn His Pro Pro
325 330 335

Lys Arg Phe Trp Ala Gln Glu Thr Ala Pro Gly Asn Pro His Gly Leu
340 345 350

```
Pro His Glu Val Ile Thr His Tyr Tyr His Arg Tyr Pro Met Ser Thr
        355                 360                 365

Ile Leu Gly Leu Ser Ile Cys Ala Ala Ile Val Thr Val Ser Val Ala
    370                 375                 380

Ala Ser Thr Trp Leu Phe Cys Lys Ser Arg Val Ser Cys Leu Thr Pro
385                 390                 395                 400

Tyr Arg Leu Thr Pro Asn Ala Arg Met Pro Leu Cys Leu Ala Val Leu
                405                 410                 415

Cys Cys Ala Arg Thr Ala Arg Ala
            420


<210> SEQ ID NO 65
<211> LENGTH: 420
<212> TYPE: PRT
<213> ORGANISM: Venezuelan equine encephalitis virus

<400> SEQUENCE: 65

Asp Leu Asp Thr His Phe Thr Gln Tyr Lys Leu Ala Arg Pro Tyr Ile
1               5                   10                  15

Ala Asp Cys Pro Asn Cys Gly His Ser Arg Cys Asp Ser Pro Ile Ala
            20                  25                  30

Ile Glu Val Arg Gly Asp Ala His Ala Gly Val Ile Arg Ile Gln Thr
        35                  40                  45

Ser Ala Met Phe Gly Leu Lys Thr Asp Gly Val Asp Leu Ala Tyr Met
    50                  55                  60

Ser Phe Met Asn Gly Lys Thr Gln Lys Ser Ile Lys Ile Asp Asn Leu
65                  70                  75                  80

His Val Arg Thr Ser Ala Pro Cys Ser Leu Val Ser His His Gly Tyr
                85                  90                  95

Tyr Ile Leu Ala Gln Cys Pro Pro Gly Asp Thr Val Thr Val Gly Phe
            100                 105                 110

His Asp Gly Pro Asn Arg His Thr Cys Thr Val Ala His Lys Val Glu
        115                 120                 125

Phe Arg Pro Val Gly Arg Glu Lys Tyr Arg His Pro Pro Glu His Gly
    130                 135                 140

Val Glu Leu Pro Cys Asn Arg Tyr Thr His Lys Arg Ala Asp Gln Gly
145                 150                 155                 160

His Tyr Val Glu Met His Gln Pro Gly Leu Val Ala Asp His Ser Leu
                165                 170                 175

Leu Ser Ile His Ser Ala Lys Val Lys Ile Thr Val Pro Ser Gly Ala
            180                 185                 190

Gln Val Lys Tyr Tyr Cys Lys Cys Pro Asp Val Arg Glu Gly Ile Thr
        195                 200                 205

Ser Ser Asp His Thr Thr Thr Cys Thr Asp Val Lys Gln Cys Arg Ala
    210                 215                 220

Tyr Leu Ile Asp Asn Lys Lys Glu Trp Val Tyr Asn Ser Gly Arg Leu
225                 230                 235                 240

Pro Arg Gly Glu Gly Asp Thr Phe Lys Gly Lys Leu His Val Pro Phe
                245                 250                 255

Val Pro Val Lys Ala Lys Cys Ile Ala Thr Leu Ala Pro Glu Pro Leu
            260                 265                 270

Val Glu His Lys His Arg Thr Leu Ile Leu His Leu His Pro Asp His
        275                 280                 285

Pro Thr Leu Leu Thr Thr Arg Ser Leu Gly Ser Asp Ala Asn Pro Thr
    290                 295                 300
```

Arg Gln Trp Ile Glu Arg Pro Thr Thr Val Asn Phe Thr Val Thr Gly
305 310 315 320

Glu Gly Leu Glu Tyr Thr Trp Gly Asn His Pro Pro Lys Arg Val Trp
325 330 335

Ala Gln Glu Ser Gly Glu Gly Asn Pro His Gly Trp Pro His Glu Val
340 345 350

Val Val Tyr Tyr Tyr Asn Arg Tyr Pro Leu Thr Thr Ile Ile Gly Leu
355 360 365

Cys Thr Cys Val Ala Ile Ile Met Val Ser Cys Val Thr Ser Val Trp
370 375 380

Leu Leu Cys Arg Thr Arg Asn Leu Cys Ile Thr Pro Tyr Lys Leu Ala
385 390 395 400

Pro Asn Ala Gln Val Pro Ile Leu Leu Ala Leu Leu Cys Cys Ile Lys
405 410 415

Pro Thr Arg Ala
420

<210> SEQ ID NO 66
<211> LENGTH: 423
<212> TYPE: PRT
<213> ORGANISM: Western equine encephalomyelitis virus

<400> SEQUENCE: 66

Ser Ile Thr Asp Asp Phe Thr Leu Thr Ser Pro Tyr Leu Gly Phe Cys
1 5 10 15

Pro Tyr Cys Arg His Ser Ala Pro Cys Phe Ser Pro Ile Lys Ile Glu
20 25 30

Asn Val Trp Asp Glu Ser Asp Asp Gly Ser Ile Arg Ile Gln Val Ser
35 40 45

Ala Gln Phe Gly Tyr Asn Gln Ala Gly Thr Ala Asp Val Thr Lys Phe
50 55 60

Arg Tyr Met Ser Tyr Asp His Asp His Asp Ile Lys Glu Asp Ser Met
65 70 75 80

Glu Lys Leu Ala Ile Ser Thr Ser Gly Pro Cys Arg Arg Leu Gly His
85 90 95

Lys Gly Tyr Phe Leu Leu Ala Gln Cys Pro Pro Gly Asp Ser Val Thr
100 105 110

Val Ser Ile Thr Ser Gly Ala Ser Glu Asn Ser Cys Thr Val Glu Lys
115 120 125

Lys Ile Arg Arg Lys Phe Val Gly Arg Glu Glu Tyr Leu Phe Pro Pro
130 135 140

Val His Gly Lys Leu Val Lys Cys His Val Tyr Asp His Leu Lys Glu
145 150 155 160

Thr Ser Ala Gly Tyr Ile Thr Met His Arg Pro Gly Pro His Ala Tyr
165 170 175

Lys Ser Tyr Leu Glu Glu Ala Ser Gly Glu Val Tyr Ile Lys Pro Pro
180 185 190

Ser Gly Lys Asn Val Thr Tyr Glu Cys Lys Cys Gly Asp Tyr Ser Thr
195 200 205

Gly Ile Val Ser Thr Arg Thr Lys Met Asn Gly Cys Thr Lys Ala Lys
210 215 220

Gln Cys Ile Ala Tyr Lys Arg Asp Gln Thr Lys Trp Val Phe Asn Ser
225 230 235 240

Pro Asp Leu Ile Arg His Thr Asp His Ser Val Gln Gly Lys Leu His

```
                245                 250                 255

Ile Pro Phe Arg Leu Thr Pro Thr Val Cys Pro Val Pro Leu Ala His
            260                 265                 270

Thr Pro Thr Val Thr Lys Trp Phe Lys Gly Ile Thr Leu His Leu Thr
        275                 280                 285

Ala Thr Arg Pro Thr Leu Leu Thr Thr Arg Lys Leu Gly Leu Arg Ala
    290                 295                 300

Asp Ala Thr Ala Glu Trp Ile Thr Gly Thr Thr Ser Arg Asn Phe Ser
305                 310                 315                 320

Val Gly Arg Glu Gly Leu Glu Tyr Val Trp Gly Asn His Glu Pro Val
                325                 330                 335

Arg Val Trp Ala Gln Glu Ser Ala Pro Gly Asp Pro His Gly Trp Pro
            340                 345                 350

His Glu Ile Ile Ile His Tyr Tyr His Arg His Pro Val Tyr Thr Val
        355                 360                 365

Ile Val Leu Cys Gly Val Ala Leu Ala Ile Leu Val Gly Thr Ala Ser
    370                 375                 380

Ser Ala Ala Cys Ile Ala Lys Ala Arg Arg Asp Cys Leu Thr Pro Tyr
385                 390                 395                 400

Ala Leu Ala Pro Asn Ala Thr Val Pro Thr Ala Leu Ala Val Leu Cys
                405                 410                 415

Cys Ile Arg Pro Thr Asn Ala
            420


<210> SEQ ID NO 67
<211> LENGTH: 424
<212> TYPE: PRT
<213> ORGANISM: Sindbis virus

<400> SEQUENCE: 67

Ser Val Thr Asp Asp Phe Thr Leu Thr Ser Pro Tyr Leu Gly Thr Cys
1               5                   10                  15

Ser Tyr Cys His His Thr Glu Pro Cys Phe Ser Pro Ile Lys Ile Glu
            20                  25                  30

Gln Val Trp Asp Glu Ala Asp Asp Asn Thr Ile Arg Ile Gln Thr Ser
        35                  40                  45

Ala Gln Phe Gly Tyr Asp Gln Ser Gly Ala Ala Ser Ser Asn Lys Tyr
    50                  55                  60

Arg Tyr Met Ser Leu Glu Gln Asp His Thr Val Lys Glu Gly Thr Met
65                  70                  75                  80

Asp Asp Ile Lys Ile Ser Thr Ser Gly Pro Cys Arg Arg Leu Ser Tyr
                85                  90                  95

Lys Gly Tyr Phe Leu Leu Ala Lys Cys Pro Pro Gly Asp Ser Val Thr
            100                 105                 110

Val Ser Ile Ile Ala Ser Ser Asn Ser Ala Thr Ser Cys Thr Met Ala
        115                 120                 125

Arg Lys Ile Lys Pro Lys Phe Val Gly Arg Glu Lys Tyr Asp Leu Pro
    130                 135                 140

Pro Val His Gly Lys Lys Ile Pro Cys Thr Val Tyr Asp Arg Leu Lys
145                 150                 155                 160

Glu Thr Thr Ala Gly Tyr Ile Thr Met His Arg Pro Gly Pro His Ala
                165                 170                 175

Tyr Thr Ser Tyr Leu Glu Glu Ser Ser Gly Lys Val Tyr Ala Lys Pro
            180                 185                 190
```

```
Pro Ser Gly Lys Asn Ile Thr Tyr Glu Cys Lys Cys Gly Asp Tyr Lys
        195                 200                 205

Thr Gly Thr Val Thr Thr Arg Thr Glu Ile Thr Gly Cys Thr Ala Ile
    210                 215                 220

Lys Gln Cys Val Ala Tyr Lys Ser Asp Gln Thr Lys Trp Val Phe Asn
225                 230                 235                 240

Ser Pro Asp Leu Ile Arg His Ala Asp His Thr Ala Gln Cys Lys Leu
                245                 250                 255

His Leu Pro Phe Lys Leu Ile Pro Ser Thr Cys Met Val Pro Val Ala
            260                 265                 270

His Ala Pro Asn Val Val His Gly Glu Lys His Ile Ser Leu Gln Leu
        275                 280                 285

Asp Thr Asp His Leu Thr Leu Leu Thr Thr Arg Arg Leu Gly Ala Asn
    290                 295                 300

Pro Glu Pro Thr Thr Glu Trp Ile Ile Gly Lys Thr Val Arg Asn Phe
305                 310                 315                 320

Thr Val Asp Arg Asp Gly Leu Glu Tyr Ile Trp Gly Asn His Glu Pro
                325                 330                 335

Val Arg Val Tyr Ala Gln Glu Ser Ala Pro Gly Asp Pro His Gly Trp
            340                 345                 350

Pro His Glu Ile Val Gln His Tyr Tyr His Arg His Pro Val Tyr Thr
        355                 360                 365

Ile Leu Ala Val Ala Ser Ala Ala Val Ala Met Met Ile Gly Val Thr
    370                 375                 380

Val Ala Ala Leu Cys Ala Cys Lys Ala Arg Arg Glu Cys Leu Thr Pro
385                 390                 395                 400

Tyr Ala Leu Ala Pro Asn Ala Val Ile Pro Thr Ser Leu Ala Leu Leu
                405                 410                 415

Cys Cys Val Arg Ser Ala Asn Ala
            420
```

<210> SEQ ID NO 68
<211> LENGTH: 422
<212> TYPE: PRT
<213> ORGANISM: Chikungunya virus

<400> SEQUENCE: 68

```
Ser Thr Lys Asp Asn Phe Asn Val Thr Lys Ala Thr Arg Pro Tyr Leu
1               5                   10                  15

Ala His Cys Pro Asp Cys Cys Glu Gly His Ser Cys His Ser Pro Ile
            20                  25                  30

Ala Leu Glu Arg Ile Arg Asn Glu Ala Thr Asp Cys Thr Leu Lys Ile
        35                  40                  45

Gln Val Ser Leu Gln Ile Cys Ile Lys Thr Asp Asp Ser His Asp Trp
    50                  55                  60

Thr Lys Leu Arg Tyr Met Asp Ser His Thr Pro Ala Asp Ala Glu Arg
65                  70                  75                  80

Ala Gly Leu Leu Val Arg Thr Ser Ala Pro Cys Thr Ile Thr Gly Thr
                85                  90                  95

Met Met His Phe Ile Leu Ala Arg Cys Pro Lys Gly Glu Thr Leu Thr
            100                 105                 110

Val Gly Phe Thr Asp Ser Arg Lys Ile Ser His Thr Cys Thr His Pro
        115                 120                 125

Phe His His Glu Pro Pro Val Ile Gly Arg Glu Arg Phe His Ser Arg
    130                 135                 140
```

Pro Gln His Gly Lys Glu Leu Pro Cys Ser Thr Tyr Val Gln Ser Thr
145 150 155 160

Ala Ala Thr Ala Glu Glu Ile Glu Val His Met Pro Pro Asp Thr Pro
165 170 175

Asp Arg Thr Leu Met Thr Gln Gln Ser Gly Asn Val Lys Ile Thr Val
180 185 190

Asn Gly Gln Thr Val Arg Tyr Lys Cys Asn Cys Gly Gly Ser Asn Glu
195 200 205

Gly Leu Thr Thr Thr Asp Lys Val Ile Asn Asn Cys Lys Ile Asp Gln
210 215 220

Cys His Ala Ala Val Thr Asn His Lys Asn Trp Gln Tyr Asn Ser Pro
225 230 235 240

Leu Val Pro Arg Asn Ala Glu Leu Gly Asp Arg Lys Gly Lys Ile His
245 250 255

Ile Pro Phe Pro Leu Ala Asn Val Thr Cys Arg Val Pro Lys Ala Arg
260 265 270

Asn Pro Thr Val Thr Tyr Gly Lys Asn Gln Val Thr Met Leu Leu Tyr
275 280 285

Pro Asp His Pro Thr Leu Leu Ser Tyr Arg Asn Met Gly Gln Glu Pro
290 295 300

Asn Tyr His Glu Glu Trp Val Thr His Lys Lys Glu Val Thr Leu Thr
305 310 315 320

Val Pro Thr Glu Gly Leu Glu Val Thr Trp Gly Asn Asn Glu Pro Tyr
325 330 335

Lys Tyr Trp Pro Gln Met Ser Thr Asn Gly Thr Ala His Gly His Pro
340 345 350

His Glu Ile Ile Leu Tyr Tyr Tyr Glu Leu Tyr Pro Thr Met Thr Val
355 360 365

Val Ile Val Ser Val Ala Ser Phe Val Leu Leu Ser Met Val Gly Thr
370 375 380

Ala Val Gly Met Cys Val Cys Ala Arg Arg Arg Cys Ile Thr Pro Tyr
385 390 395 400

Glu Leu Thr Pro Gly Ala Thr Val Pro Phe Leu Leu Ser Leu Cys Cys
405 410 415

Val Arg Thr Thr Lys Ala
420

<210> SEQ ID NO 69
<211> LENGTH: 441
<212> TYPE: PRT
<213> ORGANISM: Venezuelan equine encephalitis virus

<400> SEQUENCE: 69

Tyr Glu His Ala Thr Thr Met Pro Ser Gln Ala Gly Ile Ser Tyr Asn
1 5 10 15

Thr Ile Val Asn Arg Ala Gly Tyr Ala Pro Leu Pro Ile Ser Ile Thr
20 25 30

Pro Thr Lys Ile Lys Leu Ile Pro Thr Val Asn Leu Glu Tyr Val Thr
35 40 45

Cys His Tyr Lys Thr Gly Met Asp Ser Pro Ala Ile Lys Cys Cys Gly
50 55 60

Ser Gln Glu Cys Thr Pro Thr Tyr Arg Pro Asp Glu Gln Cys Lys Val
65 70 75 80

Phe Thr Gly Val Tyr Pro Phe Met Trp Gly Gly Ala Tyr Cys Phe Cys

```
                85                  90                  95

Asp Thr Glu Asn Thr Gln Val Ser Lys Ala Tyr Val Met Lys Ser Asp
            100                 105                 110

Asp Cys Leu Ala Asp His Ala Glu Ala Tyr Lys Ala His Thr Ala Ser
        115                 120                 125

Val Gln Ala Phe Leu Asn Ile Thr Val Gly Glu His Ser Ile Val Thr
    130                 135                 140

Thr Tyr Val Asn Gly Glu Thr Pro Val Asn Phe Asn Gly Val Lys Ile
145                 150                 155                 160

Thr Ala Gly Pro Leu Ser Thr Ala Trp Thr Pro Phe Asp Arg Lys Ile
                165                 170                 175

Val Gln Tyr Ala Gly Glu Ile Tyr Asn Tyr Asp Phe Pro Glu Tyr Gly
            180                 185                 190

Ala Gly Gln Pro Gly Ala Phe Gly Asp Ile Gln Ser Arg Thr Val Ser
        195                 200                 205

Ser Ser Asp Leu Tyr Ala Asn Thr Asn Leu Val Leu Gln Arg Pro Lys
    210                 215                 220

Ala Gly Ala Ile His Val Pro Tyr Thr Gln Ala Pro Ser Gly Phe Glu
225                 230                 235                 240

Gln Trp Lys Lys Asp Lys Ala Pro Ser Leu Lys Phe Thr Ala Pro Phe
                245                 250                 255

Gly Cys Glu Ile Tyr Thr Asn Pro Ile Arg Ala Glu Asn Cys Ala Val
            260                 265                 270

Gly Ser Ile Pro Leu Ala Phe Asp Ile Pro Asp Ala Leu Phe Thr Arg
        275                 280                 285

Val Ser Glu Thr Pro Thr Leu Ser Ala Ala Glu Cys Thr Leu Asn Glu
    290                 295                 300

Cys Val Tyr Ser Ser Asp Phe Gly Gly Ile Ala Thr Val Lys Tyr Ser
305                 310                 315                 320

Ala Ser Lys Ser Gly Lys Cys Ala Val His Val Pro Ser Gly Thr Ala
                325                 330                 335

Thr Leu Lys Glu Ala Ala Val Glu Leu Thr Glu Gln Gly Ser Ala Thr
            340                 345                 350

Ile His Phe Ser Thr Ala Asn Ile His Pro Glu Phe Arg Leu Gln Ile
        355                 360                 365

Cys Thr Ser Tyr Val Thr Cys Lys Gly Asp Cys His Pro Pro Lys Asp
    370                 375                 380

His Ile Val Thr His Pro Gln Tyr His Ala Gln Thr Phe Thr Ala Ala
385                 390                 395                 400

Val Ser Lys Thr Ala Trp Thr Trp Leu Thr Ser Leu Leu Gly Gly Ser
                405                 410                 415

Ala Val Ile Ile Ile Ile Gly Leu Val Leu Ala Thr Ile Val Ala Met
            420                 425                 430

Tyr Val Leu Thr Asn Gln Lys His Asn
        435                 440


<210> SEQ ID NO 70
<211> LENGTH: 441
<212> TYPE: PRT
<213> ORGANISM: Venezuelan equine encephalitis virus

<400> SEQUENCE: 70

Tyr Glu His Ala Thr Thr Met Pro Ser Gln Ala Gly Ile Ser Tyr Asn
1               5                   10                  15
```

```
Thr Ile Val Asn Arg Ala Gly Tyr Ala Pro Leu Pro Ile Ser Ile Thr
            20                  25                  30

Pro Thr Lys Ile Lys Leu Ile Pro Thr Val Asn Leu Glu Tyr Val Thr
        35                  40                  45

Cys His Tyr Lys Thr Gly Met Asp Ser Pro Ala Ile Lys Cys Cys Gly
    50                  55                  60

Ser Gln Glu Cys Thr Pro Thr Tyr Arg Pro Asp Glu Gln Cys Lys Val
65                  70                  75                  80

Phe Thr Gly Val Tyr Pro Phe Met Trp Gly Gly Ala Tyr Cys Phe Cys
                85                  90                  95

Asp Thr Glu Asn Thr Gln Val Ser Lys Ala Tyr Val Met Lys Ser Asp
            100                 105                 110

Asp Cys Leu Ala Asp His Ala Glu Ala Tyr Lys Ala His Thr Ala Ser
        115                 120                 125

Val Gln Ala Phe Leu Asn Ile Thr Val Gly Glu His Ser Ile Val Thr
    130                 135                 140

Thr Tyr Val Asn Gly Glu Thr Pro Val Asn Phe Asn Gly Val Lys Leu
145                 150                 155                 160

Thr Ala Gly Pro Leu Ser Thr Ala Trp Thr Pro Phe Asp Arg Lys Ile
                165                 170                 175

Val Gln Tyr Ala Gly Glu Ile Tyr Asn Tyr Asp Phe Pro Glu Tyr Gly
            180                 185                 190

Ala Gly Gln Pro Gly Ala Phe Gly Asp Ile Gln Ser Arg Thr Val Ser
        195                 200                 205

Ser Ser Asp Leu Tyr Ala Asn Thr Asn Leu Val Leu Gln Arg Pro Lys
    210                 215                 220

Ala Gly Ala Ile His Val Pro Tyr Thr Gln Ala Pro Ser Gly Phe Glu
225                 230                 235                 240

Gln Trp Lys Lys Asp Lys Ala Pro Ser Leu Lys Phe Thr Ala Pro Phe
                245                 250                 255

Gly Cys Glu Ile Tyr Thr Asn Pro Ile Arg Ala Glu Asn Cys Ala Val
            260                 265                 270

Gly Ser Ile Pro Leu Ala Phe Asp Ile Pro Asp Ala Leu Phe Thr Arg
        275                 280                 285

Val Ser Glu Thr Pro Thr Leu Ser Ala Ala Glu Cys Thr Leu Asn Glu
    290                 295                 300

Cys Val Tyr Ser Ser Asp Phe Gly Gly Ile Ala Thr Val Lys Tyr Ser
305                 310                 315                 320

Ala Ser Lys Ser Gly Lys Cys Ala Val His Val Pro Ser Gly Thr Ala
                325                 330                 335

Thr Leu Lys Glu Ala Ala Val Glu Leu Thr Glu Gln Gly Ser Ala Thr
            340                 345                 350

Ile His Phe Ser Thr Ala Asn Ile His Pro Glu Phe Arg Leu Gln Ile
        355                 360                 365

Cys Thr Ser Tyr Val Thr Cys Lys Gly Asp Cys His Pro Pro Lys Asp
    370                 375                 380

His Ile Val Thr His Pro Gln Tyr His Ala Gln Thr Phe Thr Ala Ala
385                 390                 395                 400

Val Ser Lys Thr Ala Trp Thr Trp Leu Thr Ser Leu Leu Gly Gly Ser
                405                 410                 415

Ala Val Ile Ile Ile Ile Gly Leu Val Leu Ala Thr Ile Val Ala Met
            420                 425                 430

Tyr Val Leu Thr Asn Gln Lys His Asn
```

435 440

<210> SEQ ID NO 71
<211> LENGTH: 441
<212> TYPE: PRT
<213> ORGANISM: Venezuelan equine encephalitis virus

<400> SEQUENCE: 71

Tyr Glu His Ala Thr Thr Met Pro Ser Gln Ala Gly Ile Ser Tyr Asn
1 5 10 15

Thr Ile Val Asn Arg Ala Gly Tyr Ala Pro Leu Pro Ile Ser Ile Thr
20 25 30

Pro Thr Lys Ile Lys Leu Ile Pro Thr Val Asn Leu Glu Tyr Val Thr
35 40 45

Cys His Tyr Lys Thr Gly Met Asp Ser Pro Ala Ile Lys Cys Cys Gly
50 55 60

Ser Gln Glu Cys Thr Pro Thr Asn Arg Pro Asp Glu Gln Cys Lys Val
65 70 75 80

Phe Thr Gly Val Tyr Pro Phe Met Trp Gly Gly Ala Tyr Cys Phe Cys
85 90 95

Asp Thr Glu Asn Thr Gln Val Ser Lys Ala Tyr Val Met Lys Ser Asp
100 105 110

Asp Cys Leu Ala Asp His Ala Glu Ala Tyr Lys Ala His Thr Ala Ser
115 120 125

Val Gln Ala Phe Leu Asn Ile Thr Val Gly Glu His Ser Ile Val Thr
130 135 140

Thr Tyr Val Asn Gly Glu Thr Pro Val Asn Phe Asn Gly Val Lys Leu
145 150 155 160

Thr Ala Gly Pro Leu Ser Thr Ala Trp Thr Pro Phe Asp Arg Lys Ile
165 170 175

Val Gln Tyr Ala Gly Glu Ile Tyr Asn Tyr Asp Phe Pro Glu Tyr Gly
180 185 190

Ala Gly Gln Pro Gly Ala Phe Gly Asp Ile Gln Ser Arg Thr Val Ser
195 200 205

Ser Ser Asp Leu Tyr Ala Asn Thr Asn Leu Val Leu Gln Arg Pro Lys
210 215 220

Ala Gly Ala Ile His Val Pro Tyr Thr Gln Ala Pro Ser Gly Phe Glu
225 230 235 240

Gln Trp Lys Lys Asp Lys Ala Pro Ser Leu Lys Phe Thr Ala Pro Phe
245 250 255

Gly Cys Glu Ile Tyr Thr Asn Pro Ile Arg Ala Glu Asn Cys Ala Val
260 265 270

Gly Ser Ile Pro Leu Ala Phe Asp Ile Pro Asp Ala Leu Phe Thr Arg
275 280 285

Val Ser Glu Thr Pro Thr Leu Ser Ala Ala Glu Cys Thr Leu Asn Glu
290 295 300

Cys Val Tyr Ser Ser Asp Phe Gly Gly Ile Ala Thr Val Lys Tyr Ser
305 310 315 320

Ala Ser Lys Ser Gly Lys Cys Ala Val His Val Pro Ser Gly Thr Ala
325 330 335

Thr Leu Lys Glu Ala Ala Val Glu Leu Thr Glu Gln Gly Ser Ala Thr
340 345 350

Ile His Phe Ser Thr Ala Asn Ile His Pro Glu Phe Arg Leu Gln Ile
355 360 365

Cys Thr Ser Tyr Val Thr Cys Lys Gly Asp Cys His Pro Pro Lys Asp
370 375 380

His Ile Val Thr His Pro Gln Tyr His Ala Gln Thr Phe Thr Ala Ala
385 390 395 400

Val Ser Lys Thr Ala Trp Thr Trp Leu Thr Ser Leu Leu Gly Gly Ser
405 410 415

Ala Val Ile Ile Ile Ile Gly Leu Val Leu Ala Thr Ile Val Ala Met
420 425 430

Tyr Val Leu Thr Asn Gln Lys His Asn
435 440

<210> SEQ ID NO 72
<211> LENGTH: 441
<212> TYPE: PRT
<213> ORGANISM: Venezuelan equine encephalitis virus

<400> SEQUENCE: 72

Tyr Glu His Ala Thr Thr Met Pro Ser Gln Ala Gly Ile Ser Tyr Asn
1 5 10 15

Thr Ile Val Asn Arg Ala Gly Tyr Ala Pro Leu Pro Ile Ser Ile Thr
20 25 30

Pro Thr Lys Ile Lys Leu Ile Pro Thr Val Asn Leu Glu Tyr Val Thr
35 40 45

Cys His Tyr Lys Thr Gly Met Asp Ser Pro Ala Ile Lys Cys Cys Gly
50 55 60

Ser Gln Glu Cys Thr Pro Thr Tyr Arg Pro Asp Glu Gln Cys Lys Val
65 70 75 80

Phe Thr Gly Val Tyr Pro Phe Met Trp Gly Gly Ala Tyr Cys Phe Cys
85 90 95

Asp Thr Glu Asn Thr Gln Val Ser Lys Ala Tyr Val Met Lys Ser Asp
100 105 110

Asp Cys Leu Ala Asp His Ala Glu Ala Tyr Lys Ala His Thr Ala Ser
115 120 125

Val Gln Ala Phe Leu Asn Ile Thr Val Gly Glu His Ser Ile Val Thr
130 135 140

Thr Tyr Val Asn Gly Glu Thr Pro Val Asn Phe Asn Gly Val Lys Leu
145 150 155 160

Thr Ala Gly Pro Leu Ser Thr Ala Trp Thr Pro Phe Asp Arg Lys Ile
165 170 175

Val Gln Tyr Ala Gly Glu Ile Tyr Asn Tyr Asp Phe Pro Glu Tyr Gly
180 185 190

Ala Gly Gln Pro Gly Ala Phe Gly Asp Ile Gln Ser Arg Thr Val Ser
195 200 205

Ser Ser Asp Leu Tyr Ala Asn Thr Asn Leu Val Leu Gln Arg Pro Lys
210 215 220

Ala Gly Ala Ile His Val Pro Tyr Thr Gln Ala Pro Ser Gly Phe Glu
225 230 235 240

Gln Trp Lys Lys Asp Lys Ala Pro Ser Leu Lys Phe Thr Ala Pro Phe
245 250 255

Gly Cys Glu Ile Tyr Thr Asn Pro Ile Arg Ala Glu Asn Cys Ala Val
260 265 270

Gly Ser Ile Pro Leu Ala Phe Asp Ile Pro Asp Ala Leu Phe Thr Arg
275 280 285

Val Ser Glu Thr Pro Thr Leu Ser Ala Ala Glu Cys Thr Leu Asn Glu
290 295 300

```
Cys Val Tyr Ser Ser Asp Phe Gly Gly Ile Ala Thr Val Lys Tyr Ser
305                 310                 315                 320

Ala Ser Lys Ser Gly Lys Cys Ala Val His Val Pro Ser Gly Thr Ala
                325                 330                 335

Thr Leu Lys Glu Ala Ala Val Glu Leu Thr Glu Gln Gly Ser Val Thr
            340                 345                 350

Ile His Phe Ser Thr Ala Asn Ile His Pro Glu Phe Arg Leu Gln Ile
        355                 360                 365

Cys Thr Ser Tyr Val Thr Cys Lys Gly Asp Cys His Pro Pro Lys Asp
    370                 375                 380

His Ile Val Thr His Pro Gln Tyr His Ala Gln Thr Phe Thr Ala Ala
385                 390                 395                 400

Val Ser Lys Thr Ala Trp Thr Trp Leu Thr Ser Leu Leu Gly Gly Ser
                405                 410                 415

Ala Val Ile Ile Ile Ile Gly Leu Val Leu Ala Thr Ile Val Ala Met
            420                 425                 430

Tyr Val Leu Thr Asn Gln Lys His Asn
        435                 440
```

<210> SEQ ID NO 73
<211> LENGTH: 441
<212> TYPE: PRT
<213> ORGANISM: Venezuelan equine encephalitis virus

<400> SEQUENCE: 73

```
Tyr Glu His Thr Ala Val Met Pro Asn Lys Val Gly Ile Pro Tyr Lys
1               5                   10                  15

Ala Leu Val Glu Arg Pro Gly Tyr Ala Pro Val His Leu Gln Ile Gln
            20                  25                  30

Leu Val Asn Thr Arg Ile Ile Pro Ser Thr Asn Leu Glu Tyr Ile Thr
        35                  40                  45

Cys Lys Tyr Lys Thr Lys Val Pro Ser Pro Val Val Lys Cys Cys Gly
    50                  55                  60

Ala Thr Gln Cys Thr Ser Lys Pro His Pro Asp Tyr Gln Cys Gln Val
65                  70                  75                  80

Phe Thr Gly Val Tyr Pro Phe Met Trp Gly Gly Ala Tyr Cys Phe Cys
                85                  90                  95

Asp Thr Glu Asn Thr Gln Met Ser Glu Ala Tyr Val Glu Arg Ser Glu
            100                 105                 110

Glu Cys Ser Ile Asp His Ala Lys Ala Tyr Lys Val His Thr Gly Thr
        115                 120                 125

Val Gln Ala Met Val Asn Ile Thr Tyr Gly Ser Val Ser Trp Arg Ser
    130                 135                 140

Ala Asp Val Tyr Val Asn Gly Glu Thr Pro Ala Lys Ile Gly Asp Ala
145                 150                 155                 160

Lys Leu Ile Ile Gly Pro Leu Ser Ser Ala Trp Ser Pro Phe Asp Asn
                165                 170                 175

Lys Val Val Val Tyr Gly His Glu Val Tyr Asn Tyr Asp Phe Pro Glu
            180                 185                 190

Tyr Gly Thr Gly Lys Ala Gly Ser Phe Gly Asp Leu Gln Ser Arg Thr
        195                 200                 205

Ser Thr Ser Asn Asp Leu Tyr Ala Asn Thr Asn Leu Lys Leu Gln Arg
    210                 215                 220

Pro Gln Ala Gly Ile Val His Tyr Pro Phe Thr Gln Ala Pro Ser Gly
```

```
225                 230                 235                 240

Phe Glu Arg Trp Lys Arg Asp Lys Gly Ala Pro Leu Asn Asp Val Ala
                245                 250                 255

Pro Phe Gly Cys Ser Ile Ala Leu Glu Pro Leu Arg Ala Glu Asn Cys
            260                 265                 270

Ala Val Gly Ser Ile Pro Ile Ser Ile Asp Ile Pro Asp Ala Ala Phe
        275                 280                 285

Thr Arg Ile Ser Glu Thr Pro Thr Val Ser Asp Leu Glu Cys Lys Ile
    290                 295                 300

Thr Glu Cys Thr Tyr Ala Ser Asp Phe Gly Gly Ile Ala Thr Val Ala
305                 310                 315                 320

Tyr Lys Ser Ser Lys Ala Gly Asn Cys Pro Ile His Ser Pro Ser Gly
                325                 330                 335

Val Ala Val Ile Lys Glu Asn Asp Val Thr Leu Ala Glu Ser Gly Ser
            340                 345                 350

Phe Thr Phe His Phe Ser Thr Ala Asn Ile His Pro Ala Phe Lys Leu
        355                 360                 365

Gln Val Cys Thr Ser Ala Val Thr Cys Lys Gly Asp Cys Lys Pro Pro
    370                 375                 380

Lys Asp His Ile Val Asp Tyr Pro Ala Gln His Thr Glu Ser Phe Thr
385                 390                 395                 400

Ser Ala Ile Ser Ala Thr Ala Trp Ser Trp Leu Lys Val Leu Val Gly
                405                 410                 415

Gly Thr Ser Ala Phe Ile Val Leu Gly Leu Ile Ala Thr Ala Val Val
            420                 425                 430

Ala Leu Val Leu Phe Phe His Arg His
        435                 440


<210> SEQ ID NO 74
<211> LENGTH: 439
<212> TYPE: PRT
<213> ORGANISM: Venezuelan equine encephalitis virus

<400> SEQUENCE: 74

Phe Glu His Ala Thr Thr Val Pro Asn Val Pro Gly Ile Pro Tyr Lys
1               5                   10                  15

Ala Leu Val Glu Arg Ala Gly Tyr Ala Pro Leu Asn Leu Glu Ile Thr
            20                  25                  30

Val Val Ser Ser Glu Leu Thr Pro Ser Thr Asn Lys Glu Tyr Val Thr
        35                  40                  45

Cys Lys Phe His Thr Val Val Pro Ser Pro Gln Val Lys Cys Cys Gly
    50                  55                  60

Ser Leu Glu Cys Lys Ala Ser Ser Lys Ala Asp Tyr Thr Cys Arg Val
65                  70                  75                  80

Phe Cys Cys Val Tyr Pro Phe Met Trp Cys Cys Ala Gln Cys Phe Cys
                85                  90                  95

Asp Ser Glu Asn Thr Gln Leu Ser Glu Ala Tyr Val Glu Phe Ala Pro
            100                 105                 110

Asp Cys Thr Ile Asp His Ala Val Ala Leu Lys Val His Thr Ala Ala
        115                 120                 125

Leu Lys Val Gly Leu Arg Ile Val Tyr Cys Asn Thr Thr Ala Arg Leu
    130                 135                 140

Asp Thr Phe Val Asn Gly Val Thr Pro Gly Ser Ser Arg Asp Leu Lys
145                 150                 155                 160
```

```
Val Ile Ala Gly Pro Ile Ser Ala Ala Phe Ser Pro Phe Asp His Lys
                165                 170                 175

Val Val Ile Arg Lys Gly Leu Val Tyr Asn Tyr Asp Phe Pro Glu Tyr
            180                 185                 190

Gly Ala Met Asn Pro Gly Ala Phe Gly Asp Ile Gln Ala Ser Ser Leu
        195                 200                 205

Asp Ala Thr Asp Ile Val Ala Arg Thr Asp Ile Arg Leu Leu Lys Pro
    210                 215                 220

Ser Val Lys Asn Ile His Val Pro Tyr Thr Gln Ala Val Ser Gly Tyr
225                 230                 235                 240

Glu Met Trp Lys Asn Asn Ser Gly Arg Pro Leu Gln Glu Thr Ala Pro
                245                 250                 255

Phe Gly Cys Lys Ile Glu Val Glu Pro Leu Arg Ala Thr Asn Cys Ala
            260                 265                 270

Tyr Gly His Ile Pro Ile Ser Ile Asp Ile Pro Asp Ala Ala Phe Val
        275                 280                 285

Arg Ser Ser Glu Ser Pro Thr Ile Leu Glu Val Ser Cys Thr Val Ala
    290                 295                 300

Asp Cys Ile Tyr Ser Ala Asp Phe Gly Gly Ser Leu Thr Leu Gln Tyr
305                 310                 315                 320

Lys Ala Asn Arg Glu Gly His Cys Pro Val His Ser His Ser Thr Thr
                325                 330                 335

Ala Val Leu Lys Glu Ala Thr Thr His Val Thr Ala Thr Gly Ser Ile
            340                 345                 350

Thr Leu His Phe Ser Thr Ser Ser Pro Gln Ala Asn Phe Ile Val Ser
        355                 360                 365

Leu Cys Gly Lys Lys Thr Thr Cys Asn Ala Glu Cys Lys Pro Pro Ala
    370                 375                 380

Asp His Ile Ile Gly Glu Pro His Lys Val Asp Gln Glu Phe Gln Ala
385                 390                 395                 400

Ala Val Ser Lys Thr Ser Trp Asn Trp Leu Leu Ala Leu Phe Gly Gly
                405                 410                 415

Ala Ser Ser Leu Ile Val Val Gly Leu Ile Val Leu Val Cys Ser Ser
            420                 425                 430

Met Leu Ile Asn Thr Arg Arg
        435


<210> SEQ ID NO 75
<211> LENGTH: 439
<212> TYPE: PRT
<213> ORGANISM: Sindbis virus

<400> SEQUENCE: 75

Tyr Glu His Ala Thr Thr Val Pro Asn Val Pro Gln Ile Pro Tyr Lys
1               5                   10                  15

Ala Leu Val Glu Arg Ala Gly Tyr Ala Pro Leu Asn Leu Glu Ile Thr
            20                  25                  30

Val Met Ser Ser Glu Val Leu Pro Ser Thr Asn Gln Glu Tyr Ile Thr
        35                  40                  45

Cys Lys Phe Thr Thr Val Val Pro Ser Pro Lys Val Lys Cys Cys Gly
    50                  55                  60

Ser Leu Glu Cys Gln Pro Ala Ala His Ala Asp Tyr Thr Cys Lys Val
65                  70                  75                  80

Phe Gly Gly Val Tyr Pro Phe Met Trp Cys Cys Ala Gln Cys Phe Cys
                85                  90                  95
```

```
Asp Ser Glu Asn Ser Gln Met Ser Glu Ala Tyr Val Glu Leu Ser Ala
            100                 105                 110

Asp Cys Ala Thr Asp His Ala Gln Ala Ile Lys Val His Thr Ala Ala
        115                 120                 125

Ala Met Lys Val Gly Leu Arg Ile Val Tyr Gly Asn Thr Thr Ser Phe
    130                 135                 140

Leu Asp Val Tyr Val Asn Gly Val Thr Pro Gly Thr Ser Lys Asp Leu
145                 150                 155                 160

Lys Val Ile Ala Gly Pro Ile Ser Ala Ser Phe Thr Pro Phe Asp His
                165                 170                 175

Lys Val Val Ile His Arg Gly Leu Val Tyr Asn Thr Asp Phe Pro Glu
            180                 185                 190

Tyr Gly Ala Met Lys Pro Gly Ala Phe Gly Asp Ile Ala Thr Ser Leu
        195                 200                 205

Thr Ser Lys Asp Leu Ile Ala Ser Thr Asp Ile Arg Leu Leu Lys Pro
    210                 215                 220

Ser Ala Lys Asn Val His Val Pro Tyr Thr Gln Ala Ala Ser Gly Phe
225                 230                 235                 240

Glu Met Trp Lys Asn Asn Ser Gly Arg Pro Leu Gln Glu Thr Ala Pro
                245                 250                 255

Phe Gly Cys Lys Ile Ala Val Asn Pro Leu Arg Ala Val Asp Cys Ser
            260                 265                 270

Tyr Gly Asn Ile Pro Ile Ser Ile Asp Ile Pro Asn Ala Ala Phe Ile
        275                 280                 285

Arg Thr Ser Asp Ala Pro Leu Val Ser Thr Val Lys Cys Asp Val Ser
    290                 295                 300

Glu Cys Thr Tyr Ser Ala Asp Phe Gly Gly Met Ala Thr Leu Gln Tyr
305                 310                 315                 320

Val Ser Asp Arg Glu Cys Gln Cys Pro Val His Ser His Ser Ser Thr
                325                 330                 335

Ala Thr Leu Gln Glu Ser Thr Val His Val Leu Glu Lys Gly Ala Val
            340                 345                 350

Thr Val His Phe Ser Thr Ala Ser Pro Gln Ala Asn Phe Ile Val Ser
        355                 360                 365

Leu Cys Gly Lys Lys Thr Thr Cys Asn Ala Glu Cys Lys Pro Pro Ala
    370                 375                 380

Asp His Ile Val Ser Thr Pro His Lys Asn Asp Gln Glu Phe Gln Ala
385                 390                 395                 400

Ala Ile Ser Lys Thr Ser Trp Ser Trp Leu Phe Ala Leu Phe Gly Gly
                405                 410                 415

Ala Ser Ser Leu Leu Ile Ile Gly Leu Met Ile Phe Ala Cys Ser Met
            420                 425                 430

Met Leu Thr Ser Thr Arg Arg
        435


<210> SEQ ID NO 76
<211> LENGTH: 439
<212> TYPE: PRT
<213> ORGANISM: Chikungunya virus

<400> SEQUENCE: 76

Tyr Glu His Val Thr Val Ile Pro Asn Thr Val Gly Val Pro Tyr Lys
1               5                   10                  15

Thr Leu Val Asn Arg Pro Gly Tyr Ser Pro Met Val Leu Glu Met Glu
```

```
            20                  25                  30

Leu Gln Ser Val Thr Leu Glu Pro Thr Leu Ser Leu Asp Tyr Ile Thr
        35                  40                  45

Cys Glu Tyr Lys Thr Val Ile Pro Ser Pro Tyr Val Lys Cys Cys Gly
    50                  55                  60

Thr Ala Glu Cys Lys Asp Lys Ser Leu Pro Asp Tyr Ser Cys Lys Val
65                  70                  75                  80

Phe Thr Gly Val Thr Pro Phe Met Trp Gly Gly Ala Tyr Cys Phe Cys
                85                  90                  95

Asp Ala Glu Asn Thr Gln Leu Ser Glu Ala His Val Glu Lys Ser Glu
            100                 105                 110

Ser Cys Lys Thr Glu Phe Ala Ser Ala Tyr Arg Ala His Thr Ala Ser
        115                 120                 125

Ala Ser Ala Lys Leu Arg Val Leu Tyr Gln Gly Asn Asn Ile Thr Val
    130                 135                 140

Ala Ala Tyr Ala Asn Gly Asp His Ala Val Thr Val Lys Asp Ala Lys
145                 150                 155                 160

Phe Val Val Gly Pro Met Ser Ser Ala Trp Thr Pro Phe Asp Asn Lys
                165                 170                 175

Ile Val Val Tyr Lys Gly Asp Val Tyr Asn Met Asp Tyr Pro Pro Phe
            180                 185                 190

Gly Ala Gly Arg Pro Gly Gln Phe Gly Asp Ile Gln Ser Arg Thr Pro
        195                 200                 205

Glu Ser Lys Asp Val Tyr Ala Asn Thr Gln Leu Val Leu Gln Arg Pro
    210                 215                 220

Ala Ala Gly Thr Val His Val Pro Tyr Ser Gln Ala Pro Ser Gly Phe
225                 230                 235                 240

Lys Tyr Trp Leu Lys Glu Arg Gly Ala Ser Leu Gln His Thr Ala Pro
                245                 250                 255

Phe Gly Cys Gln Ile Ala Thr Asn Pro Val Arg Ala Val Asn Cys Ala
            260                 265                 270

Val Gly Asn Ile Pro Ile Ser Ile Asp Ile Pro Asp Ala Ala Phe Thr
        275                 280                 285

Arg Val Val Asp Ala Pro Ser Val Thr Asp Met Ser Cys Glu Val Pro
    290                 295                 300

Ala Cys Thr His Ser Ser Asp Phe Gly Gly Val Ala Ile Ile Lys Tyr
305                 310                 315                 320

Thr Ala Ser Lys Lys Gly Lys Cys Ala Val His Ser Met Thr Asn Ala
                325                 330                 335

Val Thr Ile Arg Glu Ala Asp Val Glu Val Glu Gly Asn Ser Gln Leu
            340                 345                 350

Gln Ile Ser Phe Ser Thr Ala Leu Ala Ser Ala Glu Phe Arg Val Gln
        355                 360                 365

Val Cys Ser Thr Gln Val His Cys Ala Ala Ala Cys His Pro Pro Lys
    370                 375                 380

Asp His Ile Val Asn Tyr Pro Ala Ser His Thr Thr Leu Gly Val Gln
385                 390                 395                 400

Asp Ile Ser Thr Thr Ala Met Ser Trp Val Gln Lys Ile Thr Gly Gly
                405                 410                 415

Val Gly Leu Ile Val Ala Val Ala Ala Leu Ile Leu Ile Val Val Leu
            420                 425                 430

Cys Val Ser Phe Ser Arg His
        435
```

<210> SEQ ID NO 77
<211> LENGTH: 37
<212> TYPE: PRT
<213> ORGANISM: Homo sapiens

<400> SEQUENCE: 77

Glu Cys Ile Pro Gly Asn Phe Met Cys Ser Asn Gly Arg Cys Ile Pro
1 5 10 15

Gly Ala Trp Gln Cys Asp Gly Leu Pro Asp Cys Phe Asp Lys Ser Asp
20 25 30

Glu Lys Glu Cys Pro
35

<210> SEQ ID NO 78
<211> LENGTH: 345
<212> TYPE: PRT
<213> ORGANISM: Homo sapiens

<400> SEQUENCE: 78

Met Trp Leu Leu Gly Pro Leu Cys Leu Leu Leu Ser Ser Ala Ala Glu
1 5 10 15

Ser Gln Leu Leu Pro Gly Asn Asn Phe Thr Asn Glu Cys Asn Ile Pro
20 25 30

Gly Asn Phe Met Cys Ser Asn Gly Arg Cys Ile Pro Gly Ala Trp Gln
35 40 45

Cys Asp Gly Leu Pro Asp Cys Phe Asp Lys Ser Asp Glu Lys Glu Cys
50 55 60

Pro Lys Ala Lys Ser Lys Cys Gly Pro Thr Phe Phe Pro Cys Ala Ser
65 70 75 80

Gly Ile His Cys Ile Ile Gly Arg Phe Arg Cys Asn Gly Phe Glu Asp
85 90 95

Cys Pro Asp Gly Ser Asp Glu Glu Asn Cys Thr Ala Asn Pro Leu Leu
100 105 110

Cys Ser Thr Ala Arg Tyr His Cys Lys Asn Gly Leu Cys Ile Asp Lys
115 120 125

Ser Phe Ile Cys Asp Gly Gln Asn Asn Cys Gln Asp Asn Ser Asp Glu
130 135 140

Glu Ser Cys Glu Ser Ser Gln Glu Pro Gly Ser Gly Gln Val Phe Val
145 150 155 160

Thr Ser Glu Asn Gln Leu Val Tyr Tyr Pro Ser Ile Thr Tyr Ala Ile
165 170 175

Ile Gly Ser Ser Val Ile Phe Val Leu Val Val Ala Leu Leu Ala Leu
180 185 190

Val Leu His His Gln Arg Lys Arg Asn Asn Leu Met Thr Leu Pro Val
195 200 205

His Arg Leu Gln His Pro Val Leu Leu Ser Arg Leu Val Val Leu Asp
210 215 220

His Pro His His Cys Asn Val Thr Tyr Asn Val Asn Asn Gly Ile Gln
225 230 235 240

Tyr Val Ala Ser Gln Ala Glu Gln Asn Ala Ser Glu Val Gly Ser Pro
245 250 255

Pro Ser Tyr Ser Glu Ala Leu Leu Asp Gln Arg Pro Ala Trp Tyr Asp
260 265 270

Leu Pro Pro Pro Pro Tyr Ser Ser Asp Thr Glu Ser Leu Asn Gln Ala
275 280 285

-continued

| | | | | | | | | | | | | | | | |
|---|---|---|---|---|---|---|---|---|---|---|---|---|---|---|---|
| Asp | Leu | Pro | Pro | Tyr | Arg | Ser | Arg | Ser | Gly | Ser | Ala | Asn | Ser | Ala | Ser |
| | 290 | | | | | 295 | | | | | 300 | | | | |
| Ser | Gln | Ala | Ala | Ser | Ser | Leu | Leu | Ser | Val | Glu | Asp | Thr | Ser | His | Ser |
| 305 | | | | | 310 | | | | | 315 | | | | | 320 |
| Pro | Gly | Gln | Pro | Gly | Pro | Gln | Glu | Gly | Thr | Ala | Glu | Pro | Arg | Asp | Ser |
| | | | | 325 | | | | | 330 | | | | | 335 | |
| Glu | Pro | Ser | Gln | Gly | Thr | Glu | Glu | Val | | | | | | | |
| | | | 340 | | | | | 345 | | | | | | | |

COMPOSITIONS AND METHODS FOR INHIBITING VIRAL RECOGNITION SITES

GOVERNMENT SUPPORT

This invention was made with government support under AI142790 awarded by the National Institutes of Health. The government has certain rights in the invention.

FIELD OF THE TECHNOLOGY

The present disclosure encompasses compositions for enhanced therapy for respiratory viral infections and methods of use thereof. In particular, the disclosure relates to compositions and methods to improve the local delivery to the lung while reducing systemic side effects of therapeutic agents for treating respiratory viruses, such as coronaviruses.

REFERENCE TO SEQUENCE LISTING

This application contains a Sequence Listing that has been submitted in ASCII format via EFS-Web and is hereby incorporated by reference in its entirety. The ASCII copy, created on Apr. 29, 2021, is named 686540_ST25.txt, and is 89,040 bytes in size.

BACKGROUND

Viral infections are responsible for hundreds of thousands of deaths each year. However, treatment options are limited for many viruses. Additionally, carriers of a virus may be asymptomatic, leading to high transmission rates from infected but asymptomatic individuals. There is a need for improved therapeutics to treat viral infections in both symptomatic and asymptomatic individuals. Furthermore, people such as healthcare workers who are in contact with infected individuals are at high-risk of infection. There is a need for therapeutics to prevent viral infections in at-risk individuals and other members of the population.

SUMMARY

Among the various aspects of the present disclosure provides compositions and methods for the prevention or treatment of a viral infection in a subject.

An aspect of the present disclosure provides for a method of treating a subject having, suspected of having, or at risk for contracting a virus, comprising administering a pharmaceutical composition comprising a viral recognition-site inhibiting agent in an amount sufficient to substantially inhibit, reduce, or block a viral infection, wherein the viral recognition site is a LDLRAD3 recognition site. In some embodiments, the viral infection is an alphavirus infection. In some embodiments, the alphavirus is an alphavirus capable of binding a LDLRAD3 receptor on a cell. In some embodiments, the alphavirus infection is a neurotropic alphavirus infection. In some embodiments, the alphavirus infection is an encephalitic alphavirus infection. In some embodiments, the encephalitic alphaviruses is a Venezuelan equine encephalitis virus (VEEV), Eastern equine encephalitis virus (EEEV), or Western equine encephalitis virus (WEEV). In some embodiments, the viral recognition-site inhibiting agent is a LDLRAD3 receptor decoy. In some embodiments, the viral recognition-site inhibiting agent is a LDLRAD3(D1)-Fc fusion protein or functional fragment of variant thereof.

Another aspect of the present disclosure if a LDLRAD3 fusion protein comprising D1, D2, and/or D3 LDLRAD3 domain linked to an Fc region (e.g., IgG2b Fc domain) or a functional fragment or variant thereof. In some embodiments, the LDLRAD3 fusion protein is a LDLRAD3-D1 human IgG1 fusion protein.

Another aspect of the disclosure provides an isolated antibody or antigen-binding fragment thereof that specifically binds LDLRAD3, wherein the antibody or antigen-binding fragment prevents binding of the virus to the LDLRAD3 receptor on a cell While multiple embodiments are disclosed, still other embodiments of the present disclosure will become apparent to those skilled in the art from the following detailed description, which shows and describes illustrative embodiments of the invention.

BRIEF DESCRIPTION OF THE FIGURES

The application file contains at least one drawing executed in color. Copies of this patent or patent application publication with color drawing(s) will be provided by the Office upon request and payment of the necessary fee.

Those of skill in the art will understand that the drawings, described below, are for illustrative purposes only. The drawings are not intended to limit the scope of the present teachings in any way.

FIG. 1A shows ΔB4galt7 N2a cells were transfected separately with two half libraries containing 130,209 sgRNAs, puromycin selected, and then inoculated with SINV-VEEV-GFP (TrD strain) at an MOI of 1. After 24 h, GFP-negative cells were sorted, expanded in the presence of anti-VEEV mAbs (VEEV-57, VEEV-67, and VEEV-68 [2 μg/ml]), and re-inoculated with SINVVEEV-GFP. The infection and sorting process were repeated twice. Genomic DNA from GFPnegative cells was sequenced for sgRNA abundance. FIG. 1B is a representative flow cytometry histogram of parental N2a (gray) and ΔB4galt7 N2a (red) cells stained for heparan sulfate (HS) surface expression using R1732, a rodent herpesvirus immune evasion protein that binds to HS. FIG. 1C shows a schematic diagram of chimeric SINV-VEEV virus. The chimera contains the non-structural genes from SINV (strain TR339), structural genes from VEEV (IAB strain TrD, IC strain INH9813, or ID strain ZPC738), and an eGFP gene (green) between the capsid and E3 protein. The insertion of GFP has minimal effects on virus infection and replication. FIG. 1D shows a sequence alignment of mouse (*Mus musculus*)(SEQ ID NO: 1), mouse Δ32 N-terminus isoform (SEQ ID NO: 2), human (*Homo sapiens* (SEQ ID NO: 3), rhesus macaque (*Macaca* mulatta)(SEQ ID NO: 4), cattle (*Bos taurus*) (SEQ ID NO: 5), horse (*Equus caballus*) (SEQ ID NO: 6), dog (*Canis lupus familiaris*) (SEQ ID NO: 7), and chicken (*Gallus gallus*)(SEQ ID NO: 8) Ldlrad3 ectodomain using ESPript. Red boxes indicate conserved residues between orthologs. The predicted domains based on sequence similarity to other related proteins and the transmembrane domain are indicated below the sequence.

FIG. 2A-2N show LDLRAD3 is required for efficient VEEV infection in cells. FIG. 2A shows enriched genes on the basis of top P values (top) or robust rank aggregation (RRA) scores (bottom) in the SINV-VEEV-selected population. FIG. 2B shows ΔB4galt7 (control), ΔB4galt7 ΔLdlrad3 (ΔLdlrad3) and Ldlrad3-complemented ΔB4galt7 ΔLdlrad3 (ΔLdlrad3+Ldlrad3) N2a cells were inoculated with SINV-VEEV-GFP (TrD (IAB), INH9813 (IC), and ZPC738 (ID)) or VEEV TC-83 (IAB), and infection assessed through GFP expression or E2 antigen staining. TrD, TC-83 and INH9813, n=9; ZPC738, n=8. FIG. 2G n=9. FIG. 2H shows ΔB4galt7, ΔB4galt7 ΔLdlrad3 and Ldlrad3-complemented ΔB4galt7 ΔLdlrad3 N2a cells were inoculated with SINV-EEEV or SINV-WEEV FIG. 2G, SINV (strains AR86, TR339, Toto1101 or Girdwood) FIG. 2H, MAW FIG. 2I or VSV FIG. 2J and infection assessed via GFP expression or viral antigen staining. FIG. 2I shows ΔB4galt7, ΔB4galt7 ΔLdlrad3 and Ldlrad3-complemented ΔB4galt7 ΔLdlrad3 N2a cells were inoculated with SINV-EEEV or SINV-WEEV FIG. 2G, SINV (strains AR86, TR339, Toto1101 or Girdwood) FIG. 2H, MAW FIG. 2I or VSV FIG. 2J and infection assessed via GFP expression or viral antigen staining. FIG. 2J shows ΔB4galt7, ΔB4galt7 ΔLdlrad3 and Ldlrad3-complemented ΔB4galt7 ΔLdlrad3 N2a cells were inoculated with SINV-EEEV or SINV-WEEV FIG. 2G, SINV (strains AR86, TR339, Toto1101 or Girdwood) FIG. 2H, MAW FIG. 2I or VSV FIG. 2J and infection assessed via GFP expression or viral antigen staining. FIG. 2N shows multistep growth curves of control (black) and ΔLDLRAD3 (red) B4GALT7$^{+/+}$ human SH-SY5Y cells inoculated with SINV-VEEV (TrD). n=9: two-way analysis of variance (ANOVA) with Dunnett's post-test, **P<0.0001. One-way (FIG. 2E, FIG. 2F, FIG. 2L, FIG. 2M) or two-way (FIG. 2B, FIG. 2C, FIG. 2N) ANOVA with Dunnett's post-test, P<0.0001; NS, not significant. FIG. 2D Two-way ANOVA with Dunnett's post-test: +++P<0.001; ** or ++++P<0.0001; NS, not significant. Black text indicates a comparison between ΔB4galt7 and ΔB4galt7 ΔLdlrad3 N2a cells (INH9813, 12 h, P=0.8935; ZPC738, 12 h, P=0.0553). Blue plus signs indicate a comparison between Ldlrad3-complemented ΔB4galt7 ΔLdlrad3 and ΔB4galt7 ΔLdlrad3 N2a cells (INH9813, 12 h, P=0.8541; 24 h, P=0.0003; ZPC738, 12 h, P=0.6690). Mean±s.d. of 3 experiments (FIG. 2B, FIG. 2D, FIG. 2E, FIG. 2F (VEEV), FIG. 2G-2J, FIG. 2L-2N); 2 experiments (FIG. 2F, EEEV); 3-6 experiments (FIG. 2C).

FIG. 3A-3I show Gene editing of LDLRAD3 expression. FIG. 3A shows parental and gene-edited ΔB4galt7 N2a (top) and BV2 (bottom) cells were subjected to next-generation sequencing to confirm gene editing of Ldlrad3. Sequences were aligned to the Ldlrad3 gene to identify nucleotide insertions or deletions (indels). Allele frequency is indicated next to each sequence (SEQ ID NO: 9, SEQ ID NO: 10, SEQ ID NO: 11, SEQ ID NO: 12, SEQ ID NO: 13, SEQ ID NO: 14, and SEQ ID NO: 15). FIG. 3B shows viability of ΔB4galt7 (control, black), ΔB4galt7 ΔLdlrad3 (red) and Ldlrad3-complemented ΔB4galt7 ΔLdlrad3 (blue) N2a (left) and BV2 (right) cells as determined by Cell-Titer Glo assay. Mean±s.d. of three to six experiments (N2a: n=12; BV2: control, n=17; ΔLdlrad3+vector, n=17; ΔLdlrad3+Ldlrad3, n=9). FIG. 3C shows anti-Flag staining of ΔB4galt7 N2a cells (control, black) and lentivirus-complemented ΔB4galt7 ΔLdlrad3 N2a cells with empty vector (red) or Ldlrad3 cDNA (blue) containing an N-terminal Flag-tag sequence (left). Schematic of the Flag-tagged LDLRAD3 protein (bottom) indicating the signal peptide (orange), Flag tag (red), GGS linker (grey) and LDLRAD3 coding region (blue). Cells were stained with an anti-Flag monoclonal antibody and analyzed by flow cytometry. Mean±s.d. of two experiments (n=6). Representative flow cytometry histograms (right) showing LDLRAD3 surface expression of empty vector (red) and Ldlrad3 (blue)-complemented ΔLdlrad3 cells. FIG. 3D shows next-generation sequencing confirmation of Ldlrad3 gene editing in N2a (top) and BV2 (bottom) cells retaining heparin sulfate biosynthetic capacity. Allele frequency is indicated next to each sequence (SEQ ID NO: 16, SEQ ID NO: 17, SEQ ID NO: 18, SEQ ID NO: 19, SEQ ID NO: 20, SEQ ID NO: 21, and SEQ ID NO: 22). FIG. 3E shows B4galt7$^{+/+}$ (control, black), B4galt7$^{+/+}$ ΔLdlrad3 (red) and B4galt7$^{+/+}$ΔLdlrad3 complemented with Ldlrad3 cDNA (blue) N2a cells were analyzed for surface expression of LDLRAD3 by flow cytometry using an anti-Flag monoclonal antibody. Mean±s.d. of two experiments (n=6). Representative flow cytometry histograms (right) showing LDLRAD3 surface expression of empty vector (red) and Ldlrad3 (blue)-complemented ΔLdlrad3 cells. FIG. 3F shows next-generation sequencing of LDLRAD3 gene editing in two independent SH-SY5Y cell lines. Allele frequency is indicated next to each sequence (SEQ ID NO: 23, SEQ ID NO: 24, SEQ ID NO: 25, SEQ ID NO: 26, SEQ ID NO: 27, SEQ ID NO: 28, and SEQ ID NO: 29). FIG. 3G shows two clonal ΔLDLRAD3 SH-SY5Y cell populations were complemented with full-length Ldlrad3 or truncated Ldlrad3 isoform (N-terminal 32 amino acid deletion, isoform 2) cDNA containing an N-terminal Flag-tag sequence, stained with an anti-Flag monoclonal antibody and analyzed by flow cytometry. Representative flow cytometry histograms are shown. FIG. 3H shows a second clonal population of ΔLDLRAD3 SH-SY5Y (red) cells were complemented with full-length Ldlrad3 (blue) or the truncated Ldlrad3 isoform (orange), inoculated with SINV-VEEV-GFP (TrD) and infection was assessed by flow cytometry. Mean±s.d. of three experiments (n=9; one-way ANOVA with Dunnett's post-test: **P<0.0001). FIG. 3I shows ΔB4galt7 (control, black), ΔB4galt7 ΔLdlrad3 (red), Ldlrad3-complemented ΔB4galt7 ΔLdlrad3 (blue), LDLRAD3-complemented ΔB4galt7 ΔLdlrad3 (light blue) and N-terminal Flag-tagged Ldlrad3-complemented B4galt7 ΔLdlrad3 (teal) N2a cells were analyzed for LDLRAD3 cell surface expression with anti-LDLRAD3 polyclonal serum. Mean±s.d. of three experiments (n=9; one-way ANOVA with Dunnett's post-test: **P<0.0001).

FIG. 4A shows representative flow cytometry histograms of LDLRAD3 surface expression using anti-LDLRAD3 polyclonal serum (left) and contour plots of SINV-VEEV-GFP infection (right) of Jurkat cells. FIG. 4B shows LDLRAD3-complemented Jurkat cells were assessed for LDLRAD3 surface expression (left) and infection by SINV-VEEV-GFP (TrD) (middle and right). Representative flow cytometry histograms and contour plots are shown. Mean±s.d. of three experiments (n=9; Mann-Whitney test: **P<0.0001). FIG. 4C shows representative flow cytometry histograms of LDLRAD3 surface expression using anti-LDLRAD3 polyclonal serum (left) and contour plots of SINV-VEEV-GFP infection (right) of Raji cells. FIG. 4D shows LDLRAD3-complemented Raji cells were assessed for LDLRAD3 surface expression (left) and infection by SINV-VEEV-GFP (TrD) (middle and right). Representative flow cytometry histograms are shown. Mean±s.d. of three experiments (n=9; Mann-Whitney test: **P<0.0001).

FIG. 5A show representative flow cytometry histograms of LDLRAD3 surface expression using anti-LDLRAD3 polyclonal serum. FIG. 5B show contour plots of SINV-VEEV-GFP infection of 293T, 3T3, A549, HAP1, HeLa, hCMEC/D3, HT1080, Huh7.5, K562, LADMAC, MRC-5 and U2OS cells. The population of infected cells are indicated for each cell line. Data are representative of two or three experiments.

FIG. 6A shows control and ΔLDLRAD3 or ΔLdlrad3 293T, 3T3, HeLa and hCMEC/D3 cells were assessed for LDLRAD3 surface expression (left) and SINV-VEEV-GFP (TrD) infection via GFP expression by flow cytometry (right). Two independent Ldlrad3 or LDLRAD3 gene-edited cell lines were generated (sgRNAs no. 1 and no. 2) and evaluated. Mean±s.d. of three experiments (LDLRAD3 surface expression, n=6; VEEV infection, n=9; one-way ANOVA with Dunnett's post-test: **P<0.0001). FIG. 6**B shows primary cell lines (CADMEC, HDF, HPBM and HPBT) were assessed for LDLRAD3 surface expression using anti-LDLRAD3 polyclonal serum (left) (red). Cells were inoculated with SINV-VEEV-GFP (TrD) and assessed for infection via GFP expression by flow cytometry (right) (orange). The population of infected cells are indicated for each cell line. Data are representative of two or three experiments.

FIG. 7A shows SINV-VEEV TrD was incubated with ΔB4galt7 (control), ΔB4galt7 ΔLdlrad3 (ΔLdlrad3) and Ldlrad3-complemented ΔB4galt7 ΔLdlrad3 (ΔLdlrad3+Ldlrad3) N2a cells at 4° C. Bound virions were quantified as relative FFU equivalents by measuring viral RNA (vRNA) levels via qRT-PCR. FIG. 7B shows after removal of unbound virus, the temperature was increased to 37° C. to allow internalization. Intracellular RNA (VEEV and Gapdh) levels were measured by qRT-PCR. Mean±s.d. of 3 experiments (n=9). FIG. 7C is a schematic (left) of wild-type Ldlrad3 (control), ΔLdlrad3, ΔLdlrad3+LDLRAD3-GPI, and ΔLdlrad3+LDLRAD3(ΔCD) constructs. Complemented ΔB4galt7 N2a cells were inoculated with SINV-VEEV-GFP, and infection was measured by flow cytometry (right). Mean±s.d. of 3 experiments (n=9). FIG. 7D shows complementation of ΔB4galt7 ΔLdlrad3 clonal cells with wild-type Ldlrad3 or LDLRAD3-GPI, and effects of treatment with phosphatidylinositol-specific phospholipase C (PI-PLC). Cells were incubated with 0, 0.1 or 1 U ml-1 PI-PLC (concentration is denoted by wedges beneath the x-axis throughout) and analyzed for LDLRAD3 surface expression (left) or inoculated with SINV-VEEV-GFP (right). Representative flow cytometry histograms of surface expression of LDLRAD3 or VEEV infection are shown. Isotype-control monoclonal antibody or uninfected cells are included as black, unfilled histogram plots. Mean±s.d. of 3 experiments (n=9). FIG. 7E shows blockade of SINV-VEEV-GFP (left) or SINV-EEEV-GFP (right) infection with serial dilutions of naive or anti-LDLRAD3 polyclonal mouse serum (no serum, 1:12,800, 1:3,200, 1:800, 1:200 and 1:50 dilutions) in ΔB4galt7 N2a cells. SINV-VEEV, n=7; SINV-EEEV, n=6. Mean±s.d. of 3 experiments. FIG. 7F shows blockade of SINV-VEEV-GFP with naive or anti-LDLRAD3 polyclonal mouse serum (1:1,000 dilution) in primary human dermal microvascular endothelial cells (CADMEC) and fibroblasts (HDF). Mean±s.d. of 3 experiments (n=9; Mann-Whitney test: **P<0.0001). a-d, One-way ANOVA with Dunnett's post-test: P=0.0019; ****P<0.0001; NS, not significant (P>0.9999).

FIG. 8A-8I shows expression and characterization of recombinant LDLRAD3-Fc, VEEV structural proteins and domain-truncated forms of LDLRAD3 proteins. FIG. 8A shows coomassie-stained SDS-PAGE under non-reducing (NR) and reducing (R) conditions of mouse LDLRAD3 domain variants (D1, D1-HRV, D2 and D1+D2) fused to mouse IgG2b Fc domain. FIG. 8B shows coomassie-stained SDS-PAGE under non-reducing (NR) and reducing (R) conditions of mouse LDLRAD3 (D1) fused to human IgG1 Fc domain. Data are representative of two experiments. FIG. 8C shows binding of human LDLRAD3(D1)-Fc, CHIKV positive control (humanized CHK-152 (CHK-152)), or negative control (humanized E16 (E16)) to VEEV (top) or CHIKV (bottom) VLPs by ELISA. Mean±s.d. of two experiments (n=8). FIG. 8D shows silver-stained SDS-PAGE of LDLRAD3(D1-HRV)-Fc ((−)HRV protease) and HRV 3C protease-digested LDLRAD3(D1) ((+)HRV protease) under non-reducing conditions. Data are representative of three experiments. FIG. 8E shows coomassie-stained SDS-PAGE of baculovirus-generated VEEV p62-E1 under non-reducing and reducing conditions. Data are representative of two experiments. FIG. 8F shows binding of LDLRAD3(D1) (2,000 nM starting concentration, twofold dilutions) to CHIKV p62-E1 by surface plasmon resonance. LDLRAD3 (D1) does not bind appreciably to CHIKV p62-E1. Cartoon diagram (inset) and sensograms of HRV-cleaved monovalent LDLRAD3(D1) (purple) binding to CHIKV p62-E1 (E3, yellow; E2, cyan; E1, grey). Data are representative of three experiments. FIG. 8G shows ΔLdlrad3 ΔB4galt7 N2a cells were complemented with either full-length Ldlrad3 (black), Ldlrad3 domain truncations D1+D2 (cyan), D2+D3 (purple) or an Ldlrad3 isoform that lacks 32 N-terminal residues (orange). Cells were assessed for LDLRAD3 surface expression by N-terminal Flag-tag staining FIG. 8G and SINV-VEEV-GFP (TrD) infection FIG. 8H by flow cytometry analysis. The population of infected cells are indicated for each cell line. Data are representative of three experiments. FIG. 8H shows ΔLdlrad3 ΔB4galt7 N2a cells were complemented with either full-length Ldlrad3 (black), Ldlrad3 domain truncations D1+D2 (cyan), D2+D3 (purple) or an Ldlrad3 isoform that lacks 32 N-terminal residues (orange). Cells were assessed for LDLRAD3 surface expression by N-terminal Flag-tag staining FIG. 8G and SINV-VEEV-GFP (TrD) infection FIG. 8H by flow cytometry analysis. The population of infected cells are indicated for each cell line. Data are representative of three experiments. FIG. 8I shows ΔB4galt7 ΔLdlrad3 N2a cells were complemented with either empty vector (red) or LDLRAD3 D1 truncation (blue), inoculated with SINV-VEEV-GFP, and infection was assessed by flow cytometry (left). A representative flow cytometry plot of LDLRAD3(D1)-complemented ΔB4galt7 ΔLdlrad3 N2a cells infected with SINV-VEEV-GFP (TrD) infection is shown. Mean±s.d. of three experiments (n=9; one-way ANOVA with Dunnett's post-test: **P<0.0001). Flow cytometry histogram of LDLRAD3(D1) surface expression as assessed by N-terminal Flag-tag staining and flow cytometry analysis (middle). Data are representative of two experiments. SINV-VEEV-GFP (TrD) infection of ΔB4galt7 (control, black), ΔB4galt7 ΔLdlrad3 (red) and Ldlrad3(D1)-complemented ΔB4galt7 ΔLdlrad3 (blue) cells was normalized for Flag-positive cells (right). Mean±s.d. of three experiments (n=9; one-way ANOVA with Dunnett's post-test: P<0.0001). For gel source data, see FIG. 1**.

FIG. 9A shows a schematic of the ectodomain of LDLRAD3 (left) and LDLRAD3(D1)-Fc (right). FIG. 9B shows binding of LDLRAD3-Fc domain variants, VEEV positive control (3B4C-4), CHIKV positive control (CHK-152) or negative control (H77.39) to VEEV (left) or CHIKV (right) virus-like particles (VLPs) by enzyme-linked immunosorbent assay (ELISA). VEEV: LDLRAD3(D1)-Fc, n=10; LDLRAD3 (D1-HRV)-Fc and LDLRAD3(D1+D2)-Fc, n=8; LDLRAD3(D2)-Fc and 3B4C-4, n=6; H77.39, n=4. CHIKV: LDLRAD3(D1)-Fc, LDLRAD3(D1-HRV)-Fc, LDLRAD3 (D2)-Fc, LDLRAD3(D1+D2)-Fc, CHK-152 and H77.39, n=4. Mean±s.d. of 2-3 experiments. OD450, optical density at 450 nm. FIG. 9C shows binding of human LDLRAD3 (D1) human IgG1 fusion protein (10 μg ml-1) to VEEV or CHIKV VLPs by ELISA. Mean±s.d. of 2 experiments (n=8). FIG. 9D is a cartoon diagram (inset), sensograms and binding parameters of HRV-cleaved monovalent LDLRAD3 (D1) (purple) binding to VEEV p62-E1 (E3, yellow; E2, cyan; E1, grey). A 1:1 binding model (red traces) was used to fit experimental curves. Right, representative response curve for steady-state analysis, in which binding is plotted versus LDLRAD3(D1) concentration. Inset, linear Scatchard plot. Mean±s.e.m. of 3 experiments. RU, response unit. FIG. 9E shows ΔB4galt7 ΔLdlrad3 N2a cells were complemented with full-length LDLRAD3 (control), empty vector (ΔLdlrad3), LDLRAD3(D1+D2) or LDLRAD3(D2+D3), and inoculated with SINV-VEEV-GFP. Infection data at 7.5 h after infection are the mean±s.d. of 3 experiments (n=9). FIG. 9F shows full-length (WT) Ldlrad3 or a Ldlrad3 truncated isoform (Ldlrad3Δ32) was introduced into ΔB4galt7 ΔLdlrad3 N2a cells and inoculated with SINV-VEEV-GFP. Infection data at 7.5 h after infection are the mean±s.d. of 3 experiments (n=8). FIG. 9G shows inhibition of SINV-VEEV-GFP and SINV-EEEV-GFP infection with LDLRAD3(D1)-Fc or isotype control IgG (0, 0.1, 1, 10 and 100 μg ml$^{-1}$) in ΔLdlrad3 and ΔB4galt7 ΔLdlrad3 N2a cells. Mean±s.d. of 3 experiments (n=9). FIG. 9H shows blockade of SINV-VEEV-GFP with LDLRAD3(D1)-Fc or isotype control IgG (1 μg ml$^{-1}$) in human dermal microvascular endothelial cells (CADMEC) and fibroblasts (HDF). Mean±s.d. of 3 experiments (n=9). FIG. 9I shows dose-dependent inhibition of SINV-VEEV-GFP with LDLRAD3-Fc domain variants (D1, D1-HRV, D2 and D1+D2) or isotype control IgG (0, 0.1, 1, 10 and 100 μg ml$^{-1}$). LDLRAD3(D1-HRV)-Fc and isotype, n=9; LDLRAD3(D1)-Fc, LDLRAD3(D2)-Fc and LDLRAD3(D1+D2)-Fc, n=6. Mean±s.d. of 3 experiments. FIG. 9J shows competition binding analysis of LDLRAD3(D1)-Fc and anti-VEEV monoclonal antibodies by ELISA. LDLRAD3(D1)-Fc did not bind to VEEV VLPs incubated with either 3B4C-4 or 1A4A-1, which indicates epitope competition. Isotype and 3B4C-4, n=8; 1A4A-1, n=6. Mean±s.d. of 2-3 experiments. e, One-way ANOVA with Dunnett's post-test: **P<0.0001; f, h, Mann-Whitney test: P=0.0002; ****P<0.0001.

FIG. 10A shows two hundred and fifty μg of LDLRAD3 (D1)-Fc was injected 6 h before intraperitoneal inoculation with SINV-VEEV TrD. FIG. 10B shows two hundred and fifty μg of isotype control monoclonal antibody JEV-13 was injected 6 h before intraperitoneal inoculation with SINV-VEEV TrD. FIG. 10C shows two hundred and fifty μg of isotype control monoclonal antibody JEV-13 was injected 24 h after intraperitoneal inoculation with SINV-VEEV TrD. Survival data are from 2-3 experiments (a, n=15; c, n=10). At 4 days post-infection (dpi), serum and tissues were assessed for viral RNA levels (b). Three experiments (n=15). Bars indicate median values and dashed lines indicate the limit of detection (LOD). d-f, FIG. 10D shows six-week-old CD-1 mice were administered 200 μg LDLRAD3(D1)-Fc or isotype-control monoclonal antibody JEV-13 via intraperitoneal route 6 h before subcutaneous inoculation with VEEV TrD. FIG. 10E shows C57BL/6J mice were administered 250 μg LDLRAD3(D1)-Fc or isotype-control monoclonal antibody JEV-13 via intraperitoneal route 6 h before subcutaneous inoculation with VEEV ZPC738. FIG. 10F shows C57BL/6J mice were administered 250 μg LDLRAD3(D1)-Fc or isotype-control monoclonal antibody JEV-13 via intraperitoneal route 6 h before subcutaneous inoculation with VEEV ZPC738. Survival data are from two experiments (d, JEV-13, n=7; LDLRAD3(D1)-Fc, n=8; e, n=10). At 6 dpi, serum, cells and tissues were assessed for viral RNA levels (f). Bars indicate median values and dashed lines indicate LOD. FIG. 10G shows six-week-old CD-1 mice were administered 200 μg LDLRAD3(D1)-Fc or isotype-control monoclonal antibody via intraperitoneal route 6 h before intracranial inoculation with VEEV TrD. Survival data are from 2 experiments (n=10). FIG. 10H shows in situ hybridization of brain (left) and spinal cord (right) tissues for VEEV RNA (brown). C57BL/6J mice were administered 250 μg isotype-control monoclonal antibody JEV-13 (top) or LDLRAD3(D1)-Fc (bottom) via intraperitoneal route 6 h before subcutaneous inoculation of VEEV ZPC738. Tissues were collected at 6 dpi. Slides were counterstained with Gill's haematoxylin. Scale bars, 2 mm (brain), 500 μm (spinal cord), 200 μm (high-power (10×) magnification insets). Representative images from one experiment (n=5 per group). FIG. 10I shows seven-week-old mice with deletions in Ldlrad3 (FIG. 13B) or wild-type (WT) C57BL/6J mice were inoculated subcutaneously with VEEV TrD. or FIG. 10J shows seven-week-old mice with deletions in Ldlrad3 (FIG. 13B) or wild-type (WT) C57BL/6J mice were inoculated subcutaneously with VEEV ZPC738. Survival data are from two experiments (i, WT, n=12; ΔLdlrad3, n=10; j, WT, n=9; ΔLdlrad3, n=8). a, c-e, g, i, j, log-rank test, **P<0.0001. b, f, Mann-Whitney test, **P<0.0001.

FIG. 11A shows two hundred and fifty μg of LDLRAD3(D1)-Fc or isotype control monoclonal antibody JEV-13 was given 6 h before (a) i.p. inoculation with $10^5$ FFU of SINV-VEEV TrD. FIG. 11B shows two hundred and fifty μg of LDLRAD3(D1)-Fc or isotype control monoclonal antibody JEV-13 was given 24 h after i.p. inoculation with $10^5$ FFU of SINV-VEEV TrD. Mice were monitored for weight change. Mean±s.d. from two or three experiments (a: n=15; b: n=10; two-way ANOVA with Dunnett's post-test: *P<0.05; P<0.01, P<0.0001; n.s., not significant). FIG. 11A one day post infection (dpi), P=0.0271; FIG. 11B 1 dpi, P=0.9978; 2 dpi, P=0.9940; 3 dpi, P=0.0082. FIG. 11**C shows six-week-old C57BL/6J mice were administered 250 μg of LDLRAD3(D1)-Fc or isotype control monoclonal antibody JEV-13 via i.p. route 6 h before subcutaneous inoculation with 102 FFU of VEEV ZPC738. Mice were monitored for weight change. Data are mean±s.d. from two experiments (n=10; two-way ANOVA with Dunnett's post-test for weight change: *P<0.05, *P<0.001, P<0.0001; n.s., not significant). One dpi, P>0.9999; 2 dpi, P=0.05; 8 dpi, P=0.0001. d-f, Six-week-old CD-1 mice were administered 200 μg of LDLRAD3(D1)-Fc or isotype control monoclonal antibody JEV-13 via i.p. route 6 h before subcutaneous (FIG. 11D) or intracranial (FIG. 11**E-F) inoculation with 103 PFU of VEEV TrD. Mice were monitored for weight change (left) and clinical disease (right) was assessed over time (healthy, ruffled fur, hunched posture, seizures, ataxia, moribund or death). Mean±s.d. from two experiments (two-way ANOVA with Dunnett's post-test for weight change: *P<0.05, **P<0.0001; n.s., not significant; d, JEV-13, n=7; LDLRAD3(D1)-Fc, n=8; e, n=10). FIG. 11D shows one dpi, P=0.8267; 2 dpi, P=0.0531; 3 dpi, P=0.032; FIG. 11E shows 1 dpi, P>0.9999; 2 dpi, P=0.2961; 3 dpi, P=0.0482. FIG. 11**F shows at 4.5, 5.5, 8 and 14 dpi, IVIS imaging was used to visual VEEV TrD luciferase infection in CD-1 mice that received LDLRAD3(D1)-Fc or isotype control monoclonal antibody JEV-13 prophylactic treatment and were challenged via intracranial inoculation. Isotype control treated mice became moribund at 4.5 dpi. The total flux (photons $s^{-1}$) in the head region of each mouse was quantified. IVIS images shown are representative images from two experiments (n=10).

FIG. 12A-120 show RNA in situ hybridization and histopathological analysis of VEEV infection in LDLRAD3 (D1)-Fc- or isotype-control-treated mice. FIG. 12A shows six-week-old C57BL/6J mice were administered 250 μg of isotype control monoclonal antibody JEV-13 via intraperitoneal route 6 h before subcutaneous inoculation of $10^2$ FFU of VEEV ZPC738.

FIG. 13A shows a scheme of Ldlrad3 gene locus with two sgRNA targeting guides for a site in exon 2 of both isoforms (SEQ ID NO: 30 and SEQ ID NO: 31). The full-length and truncated Δ32 N terminus residue Ldlrad3 isoforms are coloured red (top) and orange (bottom), respectively. FIG. 13B shows sequencing and alignment of Ldlrad3 sgRNA targeting region in exon 2 (11- and 14-nucleotide frameshift deletions) in gene-edited Ldlrad3 mice. The amino acid residues and the two sgRNA guides used for gene-editing (blue and orange arrows) are indicated above (SEQ ID NO: 32, SEQ ID NO: 33, SEQ ID NO: 34, SEQ ID NO: 35, SEQ ID NO: 36 and SEQ ID NO: 37). FIG. 13C show seven-week-old male and female mice with deletions in Ldlrad3 (Δ11 or Δ14 nucleotides; homozygous or compound heterozygous) or wild-type C57BL/6 mice were inoculated subcutaneously with $10^3$ PFU of VEEV TrD. FIG. 13D show seven-week-old male and female mice with deletions in Ldlrad3 (Δ11 or Δ14 nucleotides; homozygous or compound heterozygous) or wild-type C57BL/6 mice were inoculated subcutaneously with $10^2$ FFU of VEEV ZPC738. Mice were monitored for weight change. Data are from two experiments (VEEV TrD: WT, n=12; ΔLdlrad3, n=10; VEEV ZPC738: WT, n=9; ΔLdlrad3, n=8; two-way ANOVA with Dunnett's post-test: P<0.01, **P<0.0001; n.s., not significant). c, One dpi, P>0.999; 2 dpi, P=0.2136; 3 dpi, P=0.5489; 4 dpi, P=0.0065; 8 dpi, P=0.0014. d, One dpi, P=0.8383; 2 dpi, P=0.001. Clinical disease (right) was assessed over time (healthy, ruffled fur, hunched posture, seizures, ataxia, moribund or death) in mice inoculated with VEEV TrD (c, right).

FIG. 14A-140 show Ldlrad3 mRNA expression in tissues from mice. FIG. 14A shows generation of a TaqMan primer/probe set against the Ldlrad3 gene targeting exons 2 and 3 (SEQ ID NO: 38, SEQ ID NO: 39, and SEQ ID NO: 40).

FIG. 15A shows VEEV VLP alone. FIG. 15B shows VEEV VLP complexed with LDLRAD3 D1. The surfaces are colored by radial distance in Angstroms, and with density of LDLRAD3 colored purple. The white triangle indicates one icosahedral asymmetric unit. The 5-fold (i5), 3-fold (i3), and 2-fold (i2) icosahedral axes of symmetry are indicated with a pentagon, triangles, and an oval, respectively. Trimeric spikes are labeled "i3" if coincident with the i3 axes and "q3" if on a quasi-3-fold axis. Black arrows: directions of icosahedral symmetry axes (i2, i3, q3, and i5). Scale bars: 100 A°.

FIG. 20A shows a comprehensive mutation library was made by mutating single amino acid in domain 1 of Ldlrad3 protein. The amino acids essential for keeping the 3D structure of Ldlrad3 protein, i.e. the Cysteines forming disulfide bond, the amino acids coordinate the calcium, and those forming the hydrophobic core were intact (PMID 9262405). Other amino acids in domain 1 were mutated according to BLOSUM scoring matrix (PMID 1438297, see the table for detail). The mutants were synthesized and cloned into lentivirus vector (Genecscript LLC, USA). ΔB4galt7 ΔLdlrad3 Neuro 2a cell was transduced to express each Ldlrad3 mutant and then subjected to SINV-VEEV (TrD)-GFP infection at MOI 20 for 7.5 h (Top). FIG. 20B shows cells were also stained with an anti-FLAG antibody (D6W5B, Cell Signaling, USA) to measure the expression level of these mutants on cell surface (Bottom). *** The numbering of LDLRAD3 residues between the experimental data and structural studies is off by 17 positions. For example: G16 in the contact table=G33 in the mutagenesis data. M19 in contact table=M36 in mutagenesis data, etc.

FIG. 21A shows the amino acid sequence alignment for E2 (SEQ ID NO: 61, SEQ ID NO: 62, SEQ ID NO: 63, SEQ ID NO: 64, SEQ ID NO: 65, SEQ ID NO: 66, SEQ ID NO: 67, and SEQ ID NO: 68). FIG. 21B shows the amino acid sequence alignment for E2 (SEQ ID NO: 69, SEQ ID NO: 70, SEQ ID NO: 71, SEQ ID NO: 72, SEQ ID NO: 73, SEQ ID NO: 74, SEQ ID NO: 75, and SEQ ID NO: 76). Amino acid sequence alignment of E2 and E1 proteins of VEEV (IAB strain TC-83, AAB02517; IAB strain TrD, AAC19322; IC strain INH9813, AJP13627; ID strain ZPC738, AUV65225), and other alphaviruses (EEEV strain FL93-939, ABL84687; WEEV strain CBA87, ABD98014; SINV strain Girdwood, AUV65223, CHIKV strain 37997, ABX40011. Structure based sequence alignments were performed between alphaviruses that do (group 1, left margin) or do not (groups 2 and 3, left margin) require LDLRAD3 for infection using PROMALS3D with VEEV numbering. The Figure was prepared using ESPript 3.0. Domains are colored (E1: I, light grey; II, medium grey; III, dark grey; fusion loop, orange; E2: A, light cyan; B, medium cyan; C, blue; b-linker, medium cyan) and indicated above the sequence, along with the secondary structure features and nomenclature (PDB: 3J0C; Zhang et al., 2011). Red boxes, 100% conserved; white boxes and red letters; homologous residues within the specific group; white boxes and black letters, non-conserved residues. Purple stars under the alignment indicate contacts between LDLRAD3 D1 and individual E2-E1 heterodimers, as determined by PDBePISA. "Wrapped" denotes contacts to the wrapped E2-E1 heterodimer whose fusion loop is covered by LDLRAD3 D1. "Intraspike" refers to the intraspike heterodimer, which is adjacent to the wrapped heterodimer but within the same trimeric spike.

DETAILED DESCRIPTION

Figure 1A:
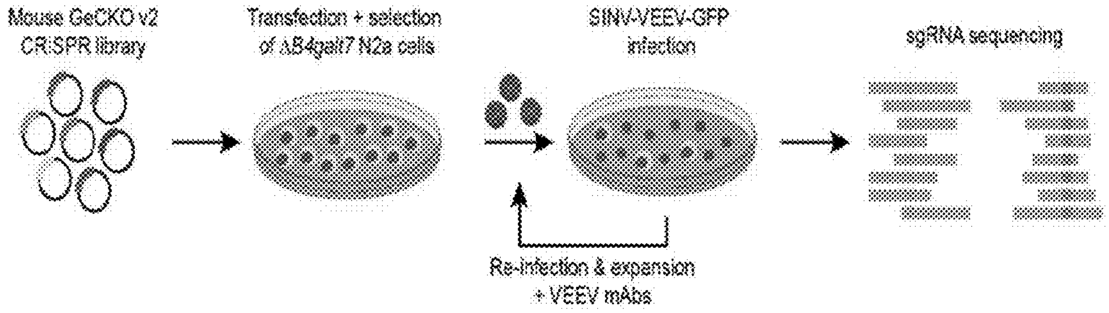
FIG. 1A-1D show CRISPR-Cas9-based screen identifying Ldlrad3 as required factor for VEEV infectivity.

The present disclosure is based, at least in part, on the discovery that Low-density lipoprotein receptor class A domain-containing protein 3 (LDLRAD3) is a receptor for viral infectivity. Venezuelan equine encephalitis virus (VEEV) is a mosquito-transmitted neurotropic alphavirus that causes encephalitis and death in humans. VEEV is a biodefense concern because of its potential for aerosol spread and lack of sufficient countermeasures. The host factors required for VEEV entry and infection had remained poorly characterized. As described herein, a genome-wide CRISPR/Cas9-based screen, identified LDLRAD3, a highly conserved member of the scavenger receptor superfamily, as a receptor for VEEV. Gene editing of mouse Ldlrad3 or human LDLRAD3 results in markedly reduced viral infection of neuronal cells, which is restored upon complementation. LDLRAD3 binds directly to VEEV particles and enhances virus attachment and internalization into cells. Genetic studies indicate that domain 1 (D1) of LDLRAD3 is necessary and sufficient to support VEEV infection, and both anti-Ldlrad3 antibodies and a LDLRAD3(D1)-fusion proteins block VEEV infection. Remarkably, VEEV pathogenesis is abrogated in mice with deletions in Ldlrad3, and administration of LDLRAD3(D1)-Fc abolishes disease caused by multiple VEEV subtypes including highly virulent strains. The present disclosure provides the development of a decoy receptor fusion proteins and therapeutic antibodies which create a strategy for preventing severe VEEV infection and disease in humans.

Alphaviruses are enveloped, positive-sense, single-stranded RNA viruses in the Togaviridae family that are transmitted by arthropods and are responsible for emerging and reemerging diseases in humans. Some alphaviruses (e.g., Chikungunya (CHIKV), Ross River (RRV), Mayaro (MAYV), Semliki Forest (SFV), Sindbis (SINV), and O'nyong-nyong (ONNV)) cause acute inflammatory musculoskeletal and joint-associated syndromes, which can become chronic, whereas others (Eastern (EEEV), Western (WEEV), and Venezuelan (VEEV) equine encephalitis viruses) cause infection in the brain and neurological disease. Although pathogenic alphaviruses are maintained in sylvatic transmission cycles in nature, their insect vectors and reservoir host species vary, which has implications for their geographic range and potential for causing outbreaks in humans.

The alphavirus virion is approximately 70 nanometers in diameter and has T=4 icosahedral symmetry. The spherical virion is comprised of a single approximately 11.4 kb RNA genome encapsidated in a nucleocapsid core and surrounded by a host-derived lipid membrane. The genome encodes 4 nonstructural proteins, nsP1-4, which mediate viral translation, viral replication, and host subversion and evasion and 6 structural proteins, capsid, E3, E2, 6K, transframe (TF), and E1. E1 and E2 are transmembrane proteins that interact to form a heterodimer. Trimers of E1/E2 heterodimers assemble into higher order spikes (80 in total) on the virion surface. The alphavirus E2 protein facilitates receptor engagement, whereas E1 principally mediates membrane fusion after viral entry. The carboxyl terminus of E2 also interacts with the capsid core, which stabilizes the virion. The 6K protein is thought to promote glycoprotein maturation, spike assembly, and act as a viroporin. The 6K gene produces 2 proteins, 6K and TF, the latter of which also contributes to virus particle assembly. The TF product associates with E1/E2 and is detected on the virion surface, albeit at lower stoichiometric levels than other structural proteins. TF also inhibits type I interferon (IFN) responses in cultured cells and in vivo through a mechanism dependent upon palmitoylation of the protein.

The E2 glycoprotein is translated in the infected cell in conjunction with E3 as a polyprotein termed p62, also called PE2. P62 co-translationally associates with E1 within the endoplasmic reticulum (ER), an interaction that is required for proper folding of E1. Subsequently, p62 is processed into the mature E2 and E3 proteins by furin-like proteases in the trans-Golgi network. After furin cleavage, E3 remains associated with E2 at acidic pH to stabilize the heterodimer and prevent premature fusion within secretory vesicles. For most alphaviruses, E3 dissociates from the virion in the neutral pH environment of the extracellular space. This coordinated binding and dissociation of E3 ensures the generation of a fusion-competent, infectious particle. Indeed, when the furin cleavage site of p62 is mutagenized, the resultant virion is less infectious and requires a lower pH to initiate fusion. Moreover, structural analysis of immature CHIKV virus-like particles containing mutations in the furin cleavage site showed that E3 stabilizes domain B of E2 and prevents exposure of the fusion peptide on E1. However, for some alphaviruses (e.g., VEEV, SFV, and CHIKV), E3 may not fully dissociate from E2, which may depend in part on the pH of the medium in which the virus is produced. Although the functional significance of retained E3 on the virion remains uncertain, it could impact receptor binding.

E2 is comprised of 3 principal ectodomains, A, B, and C. A subdomain D within E2 also was identified in the VEEV crystal structure, seen in SINV, and contains key residues for SFV budding. This subdomain has also been referred to as the E2 stem region. Domain B is positioned furthest from the lipid bilayer, domain C is membrane proximal, and domain A is located between domains B and C. E2 also contains a β-ribbon motif that connects domains A and B. E1 is a class II fusion protein that has 3 ectodomains, DI, DII, and DIII. The hydrophobic fusion loop (FL) is located in DII. E1 also contains a stem region that connects DIII to the transmembrane domain of the protein. DIII adopts an immunoglobulin-like fold and is connected to DI through a linker region of approximately 28 amino acids.

Upon exposure to low pH in solution or in endosomes, E1 dissociates from E2, which exposes the hydrophobic FL. Subsequently, E1 forms a homotrimer, which triggers membrane fusion and enables nucleocapsid penetration into the cytosol. A computational study predicted that highly conserved histidine residues across 13 different alphavirus species located at the E1/E2 interface mediate the dissociation of E2 from E1. This model is consistent with structural and biochemical analyses suggesting that conserved histidine residues stabilize E1/E2 interactions. A recently reported 3.5 Å resolution cryo-electron microscopy (cryo-EM) structure of SINV corroborated observations from prior analyses and provided new insights into the features governing the dissociation of E2 from E1. In addition to the role of conserved histidine residues, this study identified a novel hydrophobic pocket formed by E2 subdomain D and the E2 and E1 transmembrane helices. Decreases in pH might disrupt this hydrophobic pocket, which, along with changes in hydrogen bonding between the conserved histidine residues, could destabilize E1/E2 interactions and promote E1 homotrimerization and membrane fusion.

The E1 DI and DII subdomains fold into a hairpin-like structure following trimerization. Domain DIII packs against DI and DII and participates in a "fold-back" mechanism that brings the viral envelope and target membranes in proximity. E1-mediated membrane fusion is dynamic, with several intermediates described. E1 initially engages the target membrane as 3 individual monomers, while E2 is still complexed as a trimer. Using truncated forms of SFV E1 in vitro, a stable E1 trimer was shown to consist of only DI and DII at low pH (pH 5.7) in the absence of DIII or hairpin formation. Thus, E1 trimerization likely occurs prior to the fold-back of DIII. Accordingly, exogenously expressed DIII can inhibit membrane fusion by acting as a dominant negative.

Disclosed herein are compositions, methods, and treatment plans for treating an individual who is at risk of having a viral infection, has mild symptoms of a viral infection, or has severe symptoms of a viral infection. A composition of the present disclosure comprising a viral recognition-site inhibiting agent in an amount sufficient to substantially treat, prevent, or reduce the infectivity of a respiratory viral infection. The viral recognition-site inhibiting agent according to the disclosure blocks or reduces viral binding to LDLRAD3. A treatment plan may comprise administering a composition (e.g., a composition comprising a viral recognition-site inhibiting agent of the disclosure) to an individual at risk of having a viral infection or who has a viral infection, thereby preventing or treating the viral infection. In some embodiments, a viral infection may be prevented by reducing the amount of virus capable of binding to a host cell or tissue. For example, a composition of the present disclosure may comprise a viral recognition-site inhibiting agent binds to the virus or LDLRAD3 thereby disrupting interactions between a viral surface proteins and host cell proteins that activate or enhance insertion of the viral genetic material into the host cell. In some embodiments, a host viral decoy receptor or fragment thereof binds to the virus. In some embodiments, a viral infection may be prevented by disrupting interactions between a viral surface proteins and host cell proteins that activate or enhance insertion of the viral genetic material into the host cell. For example, interactions between an alphavirus E2-E1 domain, and a host cell LDLRAD3 receptor.

A composition of the present disclosure may be formulated as a pharmaceutical composition and administered for treating or preventing a viral infection (e.g., an alphavirus infection such as VEEV). The compositions of the present disclosure (e.g., compositions comprising a viral recognition-site inhibiting agent) may be administered to a subject who may be at risk of contracting a viral infection (e.g., VEEV). For example, the compositions of the present disclosure may be administered to individuals in high risk environments (e.g., healthcare workers), individuals who have been or who are suspected to have been exposed to a virus (e.g., VEEV), or individuals who have tested positive for a viral infection. A composition of the present disclosure may be administered to an individual who is displaying symptoms of an infection (e.g., a VEEV infection) or who is asymptomatic at the time of administration.

In some embodiments, the methods and compositions provided herein may prevent or reduce the infectivity of a viral infection by preventing internalization of a virus into a cell of the subject or by preventing internalization of a viral genome into a cell of the subject. In some embodiments, a composition provided herein may disrupt or prevent an interaction between a viral surface protein (e.g., E1 domain, E2 domain, or E2-E1 heterodimer) and a host receptor protein (e.g., LDLRAD3). For example, a composition as described herein may block internalization of an alphavirus into a cell of a subject by blocking or disrupting interactions between an alphavirus E2-E1 heterodimer and a host receptor LDLRAD3 protein or sequestering the virus in vivo allowing for the virus bound to viral recognition-site inhibiting agent to be eliminated by immune cells. Administering a viral recognition-site inhibiting agent composition to a subject at risk for a viral infection may reduce the risk of alphavirus infection in the subject. A composition to treat or prevent a viral infection may comprise a viral recognition-site inhibiting agent composition. In some embodiments, the viral recognition-site inhibiting agent composition may comprise a LDLRAD3 fusion protein. In some embodiments, the viral recognition-site inhibiting agent composition may comprise one or more antibodies or antigen-binding fragments. In some embodiments, the viral recognition-site inhibiting agent composition may comprise a small molecule.

Discussed below are components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to a number of molecules of the compound are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Various aspects of the invention are described in further detail in the following sections.

I. Compositions

A composition of the present disclosure may comprise one or more active agents. In some embodiments, an active agent may be an agent to prevent, treat, or reduce the infectivity of a viral infection. In some embodiments, treating a viral infection may comprise reducing the infectivity of the virus. In some embodiments, preventing a viral infection may comprise reducing the infectivity of the virus. A composition of the present disclosure may comprise an active agent to prevent a viral infection, an active agent to treat a viral infection, an active agent to reduce the infectivity of a viral infection, or a combination thereof. A composition of the disclosure may further comprise a pharmaceutically acceptable excipient, carrier, or diluent. Further, a composition of the disclosure may contain preserving agents, solubilizing agents, stabilizing agents, wetting agents, emulsifiers, sweeteners, colorants, odorants, salts (substances of the present invention may themselves be provided in the form of a pharmaceutically acceptable salt), buffers, coating agents, or antioxidants.

The present disclosure relates to compositions comprising a viral recognition-site inhibiting agent and methods of using viral recognition-site inhibiting agent composition to treat or prevent a respiratory viral infection. A viral recognition-site inhibiting agent composition of the disclosure may comprise an LDLRAD3-fusion protein that is specifically delivered to cells susceptible to infection by the virus. In another aspect, a viral recognition-site inhibiting agent composition of the disclosure may comprise a neutralizing antibody or antigen-binding fragment which specifically binds to LDLRAD3 or an alphavirus E2-E1 heterodimer and disrupts alphavirus attachment and entry of host cells susceptible to infection by the virus.

Other aspects of the invention are described in further detail below.

a) A Viral Recognition-Site Inhibiting Agent

Figure 20A:
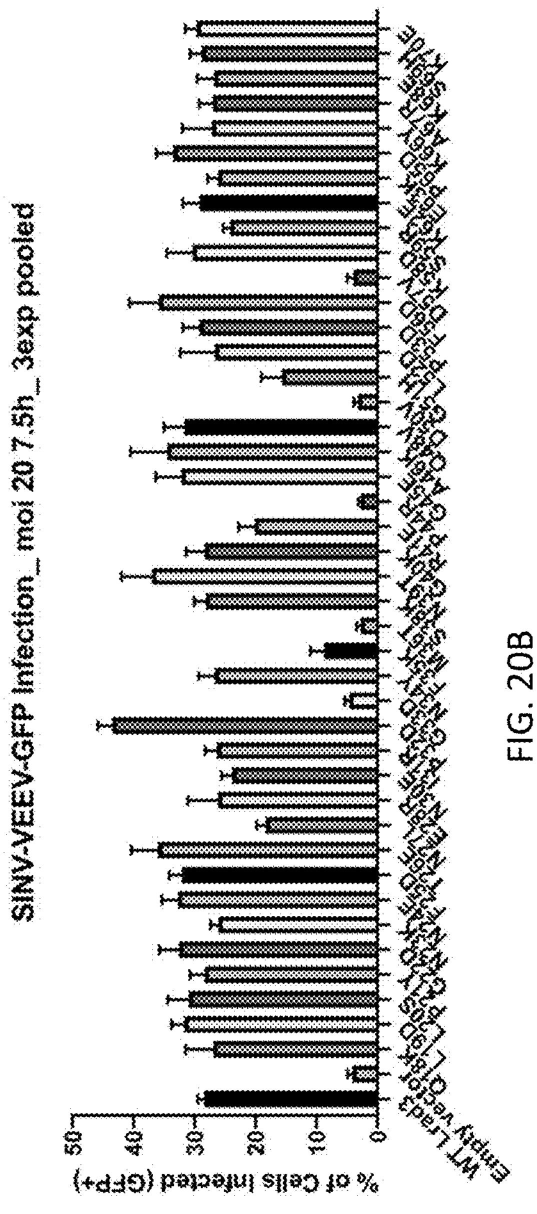
FIG. 20A-20B shows VEEV E2 mutagenesis supports atomic model.
Figure 20B:
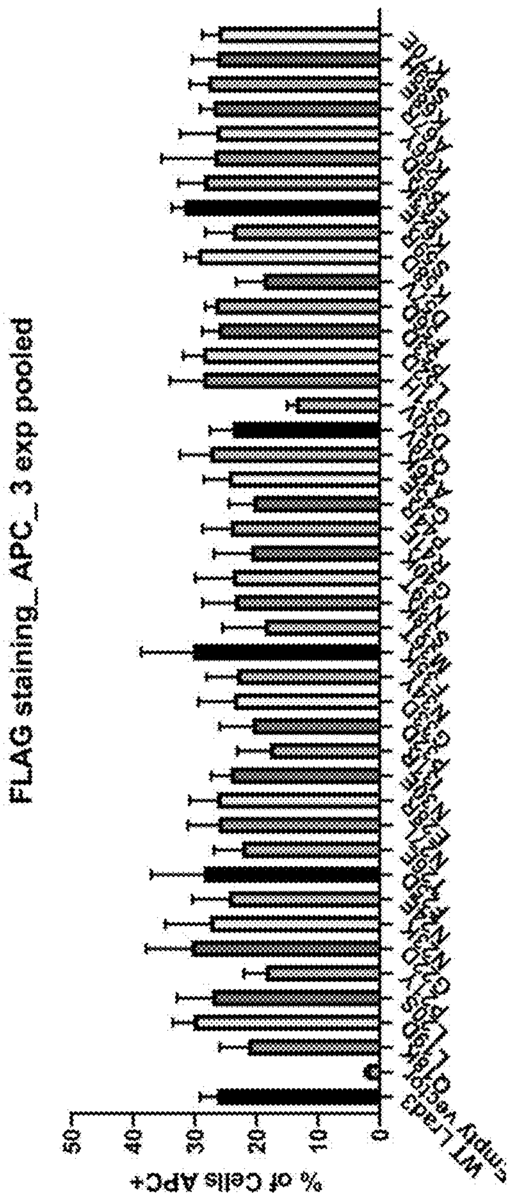
Figure 21B:
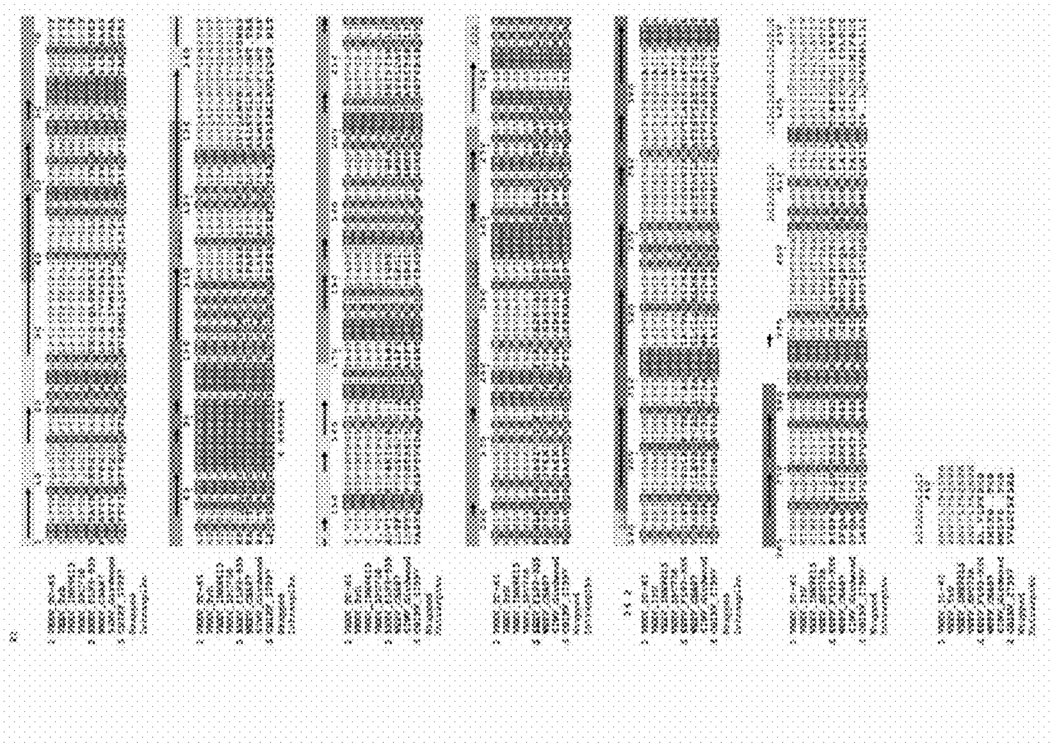
FIG. 21A-21B show conserved and unique alphavirus E1 and E2 glycoprotein contacts made by LDLRAD3.
Figure 21A:
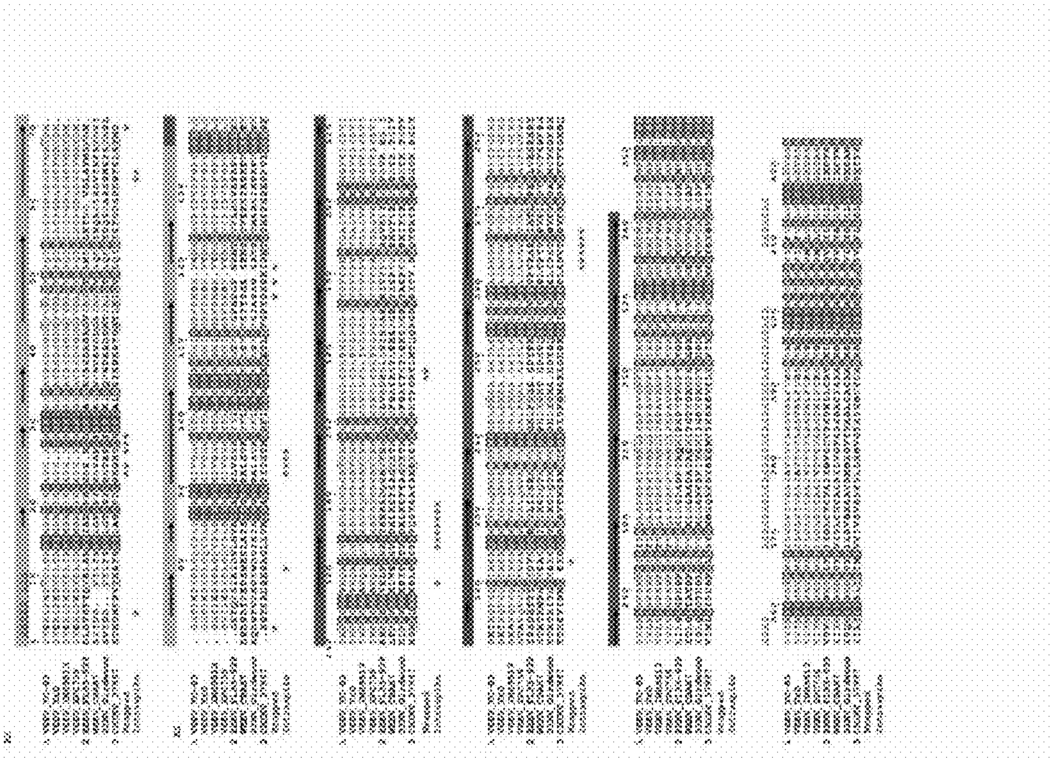
Figure 22:
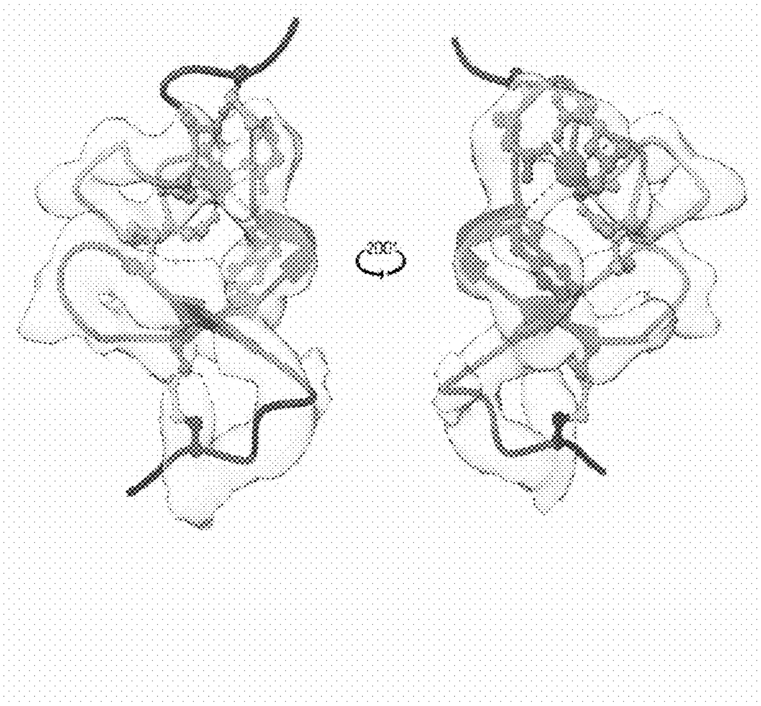
FIG. 22 shows a refined model of LDLRAD3 D1 in its electron density map, with the N to C terminus in a rainbow spectrum of blue to red. Shown as balls and sticks are the cysteine residues and the acidic residues responsible for calcium ion coordination. The disulfide bonds and calcium ion are colored yellow and green, respectively.

As used herein, the term "viral recognition-site inhibiting agent" refers to a composition which disrupts viral (e.g., alphavirus) attachment and/or entry of host cells susceptible to infection by the virus. For example, as shown herein a VEEV infection depends on host cell LDLRAD3 domain 1 binding. As shown in FIGS. 16-20 LDLRAD3 D1 specifically binds to the VEEV E2-E1 heterodimer ectodomains, moreover, critical residues that mediate binding are shown in FIG. 20 and Table 3. Thus, a viral recognition-site inhibiting agent according to the disclosure blocks or reduces these interactions between the viral proteins and host viral receptor. As described herein, a viral recognition-site inhibiting agent (e.g., antibodies, fusion proteins, small molecules) can reduce or prevent viral infection by preventing or reducing binding of the virus to LDLRAD3. In some embodiments, a viral recognition-site inhibiting agent can be a decoy LDLRAD3 or a LDLRAD3-binding inhibiting agent. A viral recognition-site inhibiting agent can be any agent that can inhibit the binding of a virus onto the LDLRAD3 receptor on a cell.

(i) Viral Decoy Receptor

In an aspect, the present disclosure encompasses a composition comprising viral recognition-site inhibiting agent, wherein the viral recognition-site inhibiting agent comprises at least one viral decoy receptor. More specifically, the viral decoy receptor includes polypeptides which bind to viral surface polypeptides (e.g. E1 or E2 domains of an alphavirus). As used herein, the term "viral decoy receptor," refers to a receptor that binds to a viral polypeptide such that internalization of the virus (e.g., an alphavirus) into a cell of a subject is blocked or disrupted or such that the virus is sequestered in vivo allowing for the virus bound to the viral decoy receptor to be eliminated by immune cells. A viral decoy receptor according to the disclosure may correspond to soluble versions of their native cellular counterparts. In some embodiments, the present disclosure provides a Low-density lipoprotein receptor class A domain-containing protein 3 (LDLRAD3) (exemplary sequences can be found at GenBank NM_001290784 and NP_00127713) viral decoy receptor. In some embodiments, the viral decoy receptor polypeptide disclosed herein binds to a virus and inhibits or reduces infectivity of the virus. Unless otherwise indicated, "polypeptide" shall include a protein, protein domain, or peptide, and any fragment thereof.

The terms "LDLRAD3" or "Low-density lipoprotein receptor class A domain-containing protein 3" as used herein, refers to the full length LDLRAD3 polypeptide, which is 345 amino acids in length. The amino acid sequence of full length LDLRAD3 is provided as SEQ ID NO: 78 (MWLLGPLCLLLSSAAESQLLPGNNFTNECN IPGNFMCSNGRCIPGAWQCDGLPDCFDKSDEKE-CPKAKSKCGPTFFPCAS GIHCIIGRFRC-NGFEDCPDGSDEENCTANPLLCSTARYHCKNGL-CIDKSF ICDGQNNCQD NSDEESCESSQEPGSGQVFVTSENQLVYYPSI-TYAIIGSS VIFVLWALLALVLHHQRKRNNLMTLPVHR LQHPVLLSRLWLDHPHHCN VTYNVNNGIQY-VASQAEQNASEVGSPPSYSEALLDQRPAWYDLPPP-PYSS DTESLNQADLP-PYRSRSGSANSASSQAASSLLSVEDTSHSPGQPGPQE-GT AEPRDSEPSQGTEEV).

The term "LDLRAD3 ectodomain", as used herein, refers to an extracellular portion of a LDLRAD3 protein, or a plurality of LDLRAD3 proteins, that comprise(s) two or more amino acids of ectodomain of LDLRAD3 (e.g., amino acids 1-173 of full length LDLRAD3, etc.)

The terms "LDL-receptor class A domain 1" or "LDLRAD3 D1" or "LDLRAD3(D1)-fusion", as used herein, refers to a LDLRAD3 protein, or a plurality of LDLRAD3 proteins, that comprise(s) two or more amino acids of domain 1 of LDLRAD3 (e.g., amino acids 28-65 of full length LDLRAD3, etc.)

The terms "LDL-receptor class A domain 2" or "LDLRAD3 D2", as used herein, refers to a LDLRAD3 protein, or a plurality of LDLRAD3 proteins, that comprise(s) two or more amino acids of domain 2 of LDLRAD3 (e.g., amino acids 70-108 of full length LDLRAD3, etc.)

The terms "LDL-receptor class A domain 3" or "LDLRAD3 D3", as used herein, refers to a LDLRAD3 protein, or a plurality of LDLRAD3 proteins, that comprise(s) two or more amino acids of domain 3 of LDLRAD3 (e.g., amino acids 112-148 of full length LDLRAD3, etc.)

According to an aspect of the present disclosure, a viral decoy receptor may be encoded by LDLRAD3, wherein the viral decoy receptor comprises an LDLRAD3 ectodomain polypeptide or its functional homologues, including derivatives and fragments. For example, a viral decoy receptor according to the disclosure may comprises a LDL-receptor class A domain 1 polypeptide and/or a LDL-receptor class A domain 2 polypeptide and/or a LDL-receptor class A domain 3 polypeptide. Suitable examples of a LDLRAD3 ectodomain polypeptide include, but are not limited to, LDLRAD3 ectodomain polypeptides isolated from *Mus musculus* (SEQ ID NO: 1), *Homo sapiens* (SEQ ID NO: 3), *Macaca mulatta* (SEQ ID NO: 4), *Bos taurus* (SEQ ID NO: 5), *Equus caballus* (SEQ ID NO: 6), *Canis lupus familiaris* (SEQ ID NO: 7), and *Gallus gallus* (SEQ ID NO: 8). In a preferred embodiments, a viral decoy receptor according to the disclosure may comprises a LDL-receptor class A domain 1 polypeptide. In an exemplary embodiment, a LDL-receptor class A domain 1 polypeptide includes amino acids 18-80 with reference to SEQ ID NO: 3.

Homologues of LDLRAD3 polypeptides can be obtained, for example by mutation of an LDLRAD3-encoding nucleotide sequence, respectively, and expression from the mutated sequence and/or by use or derivation from related gene sequences. Alternatively, homologues can be obtained, for example by identifying gene sequences homologous to LDLRAD3 by screening databases containing either protein sequences or nucleotide sequences encoding proteins, for example using homology-based search algorithms such as those commonly known and referred to as BLAST, FASTA, and Smith-Waterman. A local sequence alignment program, e.g., BLAST, can be used to search a database of sequences to find similar sequences, and the summary Expectation value (E-value) used to measure the sequence base similarity. As a protein hit with the best E-value for a particular organism may not necessarily be an ortholog or the only ortholog, a reciprocal query is used in the present invention to filter hit sequences with significant E-values for ortholog identification. The reciprocal query entails search of the significant hits against a database of amino acid sequences from the base organism that are similar to the sequence of the query protein. A hit is a likely ortholog, when the reciprocal query's best hit is the query protein itself or a protein encoded by a duplicated gene after speciation. An acceptable level of homology over the whole sequence is at least about 20%, for example 30% homology, 40% homology, 50% homology, 60% homology, 70% homology, 80% homology, 90% homology or greater. The homology of a functional fragment of a LDLRAD3 polypeptide may be at least 10% homology. A "homologous" amino acid sequence is meant an amino acid sequence that differs from a reference amino acid sequence, only by one or more (e.g., 1, 2, 3, 4 or 5) conservative amino acid substitutions, or by one or more (e.g., 1, 2, 3, 4 or 5) non-conservative amino acid substitutions, deletions, or additions located at positions at which they do not adversely affect the activity of the polypeptide. In some embodiments, such a sequence is at least 75%, 80%, 85%, 90%, or 95% or greater identical to a reference amino acid sequence.

Homologous amino acid sequences include peptide sequences that are identical or substantially identical to a reference amino acid sequence. By "amino acid sequence substantially identical" is meant a sequence that is at least 90%, preferably 95%, more preferably 97%, and most preferably 99% identical to an amino acid sequence of reference and that preferably differs from the sequence of reference, if at all, by a majority of conservative amino acid substitutions.

Conservative amino acid substitutions typically include substitutions among amino acids of the same class. These classes include, for example, (a) amino acids having uncharged polar side chains, such as asparagine, glutamine, serine, threonine, and tyrosine; (b) amino acids having basic side chains, such as lysine, arginine, and histidine; (c) amino acids having acidic side chains, such as aspartic acid and glutamic acid; and (d) amino acids having nonpolar side chains, such as glycine, alanine, valine, leucine, isoleucine, proline, phenylalanine, methionine, tryptophan, and cysteine.

According to another aspect of the invention, the viral decoy receptors may be mutated to modulate their virus binding properties. As disclosed herein, specific regions of LDLRAD3 are essential for binding to chemokines. For example, amino acids 11-45 with reference to SEQ ID NO:3 are shown to be important for viral binding (e.g., E28, C29, N30, I31, P32, G33, N34, M36, S38, N39, G40, R41, C42, I43, P44, G45, A46, W47, D50, G51, L52, D53, C54, F55, D56 and K57 with reference to full length LDLRAD3). In some embodiments, when these viral binding regions are mutated, the binding of a virus to the viral decoy receptor may be reduced. In alternative embodiments, mutation of viral binding regions may increase the binding of a virus to the decoy receptor. The viral binding properties of a viral decoy receptor may be measured using assays described herein, for example those discussed in the examples.

In an aspect, a LDLRAD3 viral decoy receptor of the disclosure may comprise the amino acid sequence set forth in SEQ ID NO: 3 (QLLPGNNFTNECNIPGNFMCSNGRCIPGAWQCDGLPDCFDKSDEKECPKAKSKCGP TFFPCSGIHCIIGRFRCNGFEDCPDGSDEENCTANPLLCSTARYHCKNGLCIDKSFICD GQNNCQDNSDEESCESSQEPGSGQVFVTSENQLVYYPSITYAIIGSSVIFVLVVALLAL VL). In another aspect, a LDLRAD3 viral decoy receptor decoy receptor of the disclosure may comprise an amino acid sequence with 80% sequence identity, 81% sequence identity, 82% sequence identity, 83% sequence identity, 84% sequence identity, 85% sequence identity, 86% sequence identity, 87% sequence identity, 88% sequence identity, 89% sequence identity, 90% sequence identity, 91% sequence identity, 92% sequence identity, 93% sequence identity, 94% sequence identity, 95% sequence identity, 96% sequence identity, 97% sequence identity, 98% sequence identity, 99% sequence identity to SEQ ID NO: 3.

In still another aspect, a LDLRAD3 viral decoy receptor of the disclosure may comprise the amino acid sequence set forth in SEQ ID NO: 77 (ECNIPGNFMCSNGRCIPGAWQCDGLPDCFDKSDEKECP). In another aspect, a LDLRAD3 viral decoy receptor of the disclosure may comprise an amino acid sequence with 80% sequence identity, 81% sequence identity, 82% sequence identity, 83% sequence identity, 84% sequence identity, 85% sequence identity, 86% sequence identity, 87% sequence identity, 88% sequence identity, 89% sequence identity, 90% sequence identity, 91% sequence identity, 92% sequence identity, 93% sequence identity, 94% sequence identity, 95% sequence identity, 96% sequence identity, 97% sequence identity, 98% sequence identity, 99% sequence identity to SEQ ID NO: 77.

In another aspect, a LDLRAD3 viral decoy receptor of the disclosure may comprise an amino acid sequence with 80% sequence identity, 81% sequence identity, 82% sequence identity, 83% sequence identity, 84% sequence identity, 85% sequence identity, 86% sequence identity, 87% sequence identity, 88% sequence identity, 89% sequence identity, 90% sequence identity, 91% sequence identity, 92% sequence identity, 93% sequence identity, 94% sequence identity, 95% sequence identity, 96% sequence identity, 97% sequence identity, 98% sequence identity, 99% sequence identity to SEQ ID NO: 1, 2, 4, 5, 6, 7, 8, or 78.

In an aspect of the disclosure, a LDLRAD3 viral decoy receptor as described herein may be a fusion protein. In some embodiments, a LDLRAD3 viral decoy receptor fusion protein may comprise a LDLRAD3 polypeptide described herein linked to an Fc region. An Fc fragment comprises the heavy chain constant region of an antibody. Heavy chains are classified as gamma, mu, alpha, delta, or epsilon, and define the antibody's isotype as IgG, IgM, IgA, IgD and IgE, respectively. In a specific embodiment, the Fc fragment is an IgG Fc fragment. There are four IgG subclasses (IgG1, 2, 3, and 4) in humans. Each of the four IgG subclasses may be used as a targeting moiety of the invention. Non-limiting examples of suitable target receptors include the Fc receptors: FcRy, FcRa, FcRs, and FcRμ. In a specific embodiment, the Fc region is an IgG2b Fc domain. Fc receptors are cell-surface receptors that recognize the Fc region of an antibody. In an exemplary embodiment, the LDLRAD3 viral decoy receptor fusion is a LDLRAD3(D1)-Fc fusion protein.

The LDLRAD3 viral decoy receptor according to the disclosure may optionally comprise further functional domains such that they provide improved pharmacokinetics, for example, by increasing the availability or in vivo half-life. For example, LDLRAD3 viral decoy receptor according to the disclosure may optionally comprise an in non-limiting examples, a PEGylation or modified glycosylation domain. In some embodiments, the optional domain may be least one tag. In non-limiting examples the at least one tag is a StrepTag, a polyhistidine tag, an antibody epitope (e.g., derived from myc), and the like or a combination thereof. The additional domain or at least one tag can be located at the N-terminus, the C-terminus, or in an internal location of the protein. The additional domain or tag maybe attached to a LDLRAD3 viral decoy receptor by a linker domain, where the linker domain optionally comprises an enzymatic cleavage site for the release of the LDLRAD3 viral decoy receptor.

Another aspect of the present disclosure provides nucleic acids encoding the LDLRAD3 viral decoy receptors described herein. The nucleic acid can be DNA or RNA. In one embodiment the DNA can be present in a vector. The nucleic acid sequences which encode the reporter molecule of the invention can be operatively linked to expression control sequences. "Operatively linked" refers to a juxtaposition wherein the components so described are in a relationship permitting them to function in their intended manner. An expression control sequence operatively linked to a coding sequence is achieved under conditions compatible with the expression control sequences. As used herein, the expression control sequences refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, and maintenance of the correct reading frame of that gene to permit proper translation of the mRNA, and stop codons. The term “control sequences” is intended to include, at a minimum, components whose presence can influence expression, and can also include additional components whose presence is advantageous, for example, leader sequences and fusion partner sequences. Expression control sequences can include a promoter.

By “promoter” is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see e.g., Bitter et al., Methods in Enzymology 153:516-544, 1987). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

In some embodiments, the nucleic acid sequences encoding a LDLRAD3 viral decoy receptor of the invention may be inserted into a recombinant expression vector. The term “recombinant expression vector” refers to a plasmid, virus or other vehicle known in the art that has been manipulated by insertion or incorporation of the nucleic acid sequences encoding the fusion peptides of the invention. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg, et al., Gene 56:125, 1987), the pMSXND expression vector for expression in mammalian cells (Lee and Nathans, J. Biol. Chem. 263:3521, 1988), baculovirus derived vectors for expression in insect cells, cauliflower mosaic virus, CaMV; tobacco mosaic virus, TMV. The nucleic acid sequences encoding a viral decoy receptor as described herein can also include a localization sequence to direct the indicator to particular cellular sites by fusion to appropriate organellar targeting signals or localized host proteins. A polynucleotide encoding a localization sequence, or signal sequence, can be used as a repressor and thus can be ligated or fused at the 5' terminus of a polynucleotide encoding the reporter polypeptide such that the signal peptide is located at the amino terminal end of the resulting fusion polynucleotide/polypeptide. The construction of expression vectors and the expression of genes in transfected cells involve the use of molecular cloning techniques also well known in the art. Sambrook et al., Molecular Cloning—A Laboratory Manual, Cold Spring Harbor Laboratory, Cold Spring Harbor, N.Y., 1989, and Current Protocols in Molecular Biolo-gy, M. Ausubel et al., eds., (Current Protocols, a joint venture between Greene Publish-ing Associates, Inc. and John Wiley & Sons, Inc., most recent Supplement). These methods include in vitro recombinant DNA techniques, synthetic techniques and in vivo recombination/genetic recombination. (See, for example, the techniques described in Maniatis, et al., Molecular Cloning A Laboratory Manual, Cold Spring Harbor Labora-tory, N.Y., 1989).

Depending on the vector utilized, any of a number of suitable transcription and translation elements, including constitutive and inducible promoters, transcription enhancer elements, transcription terminators, etc. may be used in the expression vector (see, e.g., Bitter, et al., Methods in Enzymology 153:516-544, 1987). These elements are well known to one of skill in the art.

By “transformation” is meant a permanent genetic change induce in a cell following incorporation of new DNA (i.e., DNA exogenous to the cell). Where the cell is a mammalian cell, the permanent genetic change is generally achieved by introduction of the DNA into the genome of the cell.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$) method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be co-transfected with DNA sequences encoding the reporter molecules of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the pro-tein. (Eukaryotic Viral Vectors, Cold Spring Harbor Laboratory, Gluzman ed., 1982). Preferably, a eukaryotic host is utilized as the host cell as described herein. The eukaryotic cell may be a yeast cell (e.g., *Saccharomyces cerevisiae*), or may be a mammalian cell. In one embodiment, the mammalian cell is a human cell.

Eukaryotic systems, and preferably mammalian expression systems, allow for proper post-translational modifications of expressed mammalian proteins to occur. Eukaryotic cells which possess the cellular machinery for proper processing of the primary transcript, glycosylation, phosphorylation, and, advantageously secretion of the gene product should be used as host cells for the expression of fluorescent indicator. Such host cell lines may include but are not limited to CHO, VERO, BHK, HeLa, COS, MDCK, Jurkat, HEK-293, and W138. In one embodiment, the eukaryotic cell is a human cell.

Mammalian cell systems which utilize recombinant viruses or viral elements to direct expression may be engineered. For example, when using adenovirus expression vectors, the nucleic acid sequences encoding a viral decoy receptor of the invention may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the fluorescent indicator in infected hosts (e.g., see Logan & Shenk, Proc. Natl. Acad. Sci. USA, 81:3655-3659, 1984). Alternatively, the vaccinia virus 7.5K promoter may be used. (e.g., see, Mackett, et al., Proc. Natl. Acad. Sci. USA, 79:7415-7419, 1982; Mackett, et al., J. Virol. 49:857-864, 1984; Panicali, et al., Proc. Natl. Acad. Sci. USA 79:4927-4931, 1982). Of particular interest are vectors based on bovine papilloma virus which have the ability to replicate as extrachromosomal elements (Sarver, et al., Mol. Cell. Biol. 1:486, 1981). Shortly after entry of this DNA into mouse cells, the plasmid replicates to about 100 to 200 copies per cell. Transcription of the inserted cDNA does not require integration of the plasmid into the host's chromosome, thereby yielding a high level of expression. These vectors can be used for stable expression by including a selectable marker in the plasmid, such as the neo gene. Alternatively, the retroviral genome can be modified for use as a vector capable of introducing and directing the expression of the fluorescent indicator gene in host cells (Cone & Mulligan, Proc. Natl. Acad. Sci. USA, 81:6349-6353, 1984). High level expression may also be achieved using inducible promoters, including, but not limited to, the metallothionine IIA promoter and heat shock promoters.

For long-term, high-yield production of recombinant proteins, stable expression may be preferred. Rather than using expression vectors which contain viral origins of replication, host cells can be transformed with the cDNA encoding a viral decoy receptor of the invention controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1-2 days in an enriched media, and then are switched to a selective media. A number of selection systems may be used, including but not limited to the herpes simplex virus thymidine kinase (Wigler, et al., Cell, 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy, et al., Cell, 22:817, 1980) genes can be employed in tk-, hgprt- or aprt-cells respectively. Also, antimetabolite resistance can be used as the basis of selection for dhfr, which confers resistance to methotrexate (Wigler, et al., Proc. Natl. Acad. Sci. USA, 77:3567, 1980; O'Hare, et al., Proc. Natl. Acad Sci. USA, 8:1527, 1981); gpt, which confers resistance to mycophenolic acid (Mulligan & Berg, Proc. Natl. Acad. Sci. USA, 78:2072, 1981; neo, which confers resistance to the aminoglycoside G-418 (Colberre-Garapin, et al, J. Mol. Biol 150:1, 1981); and hygro, which confers resistance to hygromycin (Santerre, et al., Gene 30: 147, 1984) genes. Recently, additional selectable genes have been de-scribed, namely trpB, which allows cells to utilize indole in place of tryptophan; hisD, which allows cells to utilize histinol in place of histidine (Hartman & Mulligan, Proc. Natl. Acad. Sci. USA 85:8047, 1988); and ODC (ornithine decarboxylase) which con-fers resistance to the omithine decarboxylase inhibitor, 2-(difluoromethyl)-DL-omithine, DFMO (McConlogue L., In: Current Communications in Molecular Biology, Cold Spring Harbor Laboratory, ed., 1987).

A LDLRAD3 viral decoy receptor as described herein can be produced by expression of nucleic acid encoding the protein in prokaryotes. These include but are not limited to microorganisms such as bacteria transformed with recombinant bacteriophage DNA, plasmid DNA or cosmid DNA expression vectors encoding a viral decoy receptor. The constructs can also be expressed in *E. coli* in large scale. Purification from bacteria is simplified when the sequences include tags for one-step purification by nickel-chelate chromatography. The construct can also contain a tag to simplify isolation of the fluorescent indicator. For example, a polyhistidine tag of, e.g., six histidine residues, can be incorporated at the amino terminal end of the fluorescent protein. The polyhistidine tag allows convenient isolation of the protein in a single step by nickel-chelate chromatography. The viral decoy receptor of the disclosure can also be engineered to contain a cleavage site to aid in protein recovery.

Techniques for the isolation and purification of either microbially or eukaryotically expressed polypeptides of the invention may be by any conventional means such as, for example, preparative chromatographic separations and immunological separations such as those involving the use of monoclonal or polyclonal antibodies or antigen.

(ii) Neutralizing Antibodies or Antigen-Binding Fragment

In an aspect, the present disclosure encompasses a composition comprising viral recognition-site inhibiting agent, wherein the viral recognition-site inhibiting agent comprises at least one neutralizing antibody or antigen-binding fragment. As shown herein, anti-LDLRAD3 antibodies are useful for reducing the infectivity of a virus (e.g., an alphavirus). As an example, the antibody specifically binds to and blocks the viral recognition binding site, wherein the antibody prevents binding of the virus to the LDLRAD3 receptor on a cell.

In an exemplary embodiment, the neutralizing antibody or antigen-binding fragment of the disclosure specifically bind LDLRAD3. For example, a neutralizing antibody according to the disclosure includes anti-LDLRAD3-D1 antibody which specifically binds to any combination of LDLRAD3 or LDLRAD3-D1. Furthermore, the anti-LDLRAD3 antibody can be a murine antibody, a humanized murine antibody, or a human antibody. As discussed above, the structure function relationship between infectivity of VEEV and the host receptor LDLRAD3 has been described herein. FIGS. 16-20 show LDLRAD3 D1 specifically binds to the VEEV E2-E1 hetero-dimer ectodomains, and identifies critical residues that mediate binding (see, e.g., FIG. 20 and Table 3). Thus, a neutralizing antibody or antigen-binding fragment of the disclosure specifically binds LDLRAD3 and sterically prevents viral binding to the host receptor. For example, a neutralizing antibody or antigen-binding fragment of the disclosure specifically binds LDLRAD3 within amino acids 11-45 with reference to SEQ ID NO:3 (e.g., E28, C29, N30, I31, P32, G33, N34, M36, S38, N39, G40, R41, C42, I43, P44, G45, A46, W47, D50, G51, L52, D53, C54, F55, D56 and K57 with reference to full length LDLRAD3). For example, a neutralizing antibody or antigen-binding fragment of the disclosure may specifically bind LDLRAD3 D1 such that the interaction between an alphavirus (e.g., VEEV)

E2-E1 polypeptide residues V24, G25, S26, C27, H28, M70, H71, K116, S118 or V119 are sterically unable to interact with LDLRAD3 D1 residues C29, N34, N39, R41, C42, I43, P44, W47, L52, D54 or F56. In another aspect, a neutralizing antibody or antigen-binding fragment of the disclosure may specifically bind LDLRAD3 D1 such that the interaction between an alphavirus (e.g., VEEV) E2 polypeptide residues S176, S177, or K223 are sterically unable to interact with LDLRAD3 D1 residues S38, D57, or K62. In another aspect, a neutralizing antibody or antigen-binding fragment of the disclosure may specifically bind LDLRAD3 D1 such that the interaction between an alphavirus (e.g., VEEV) E1 polypeptide residues Y85, F87, M88, W89, G90, G91, or A92 are sterically unable to interact with LDLRAD3 D1 residues M36, S38, N39, G40, R41, C56, F58 or D57. In another aspect, a neutralizing antibody or antigen-binding fragment of the disclosure may specifically bind LDLRAD3 D1 such that the interaction between an alphavirus (e.g., VEEV) E2 polypeptide residues L5, G63, R64, L79, 192, V93, D94 or G95 are sterically unable to interact with LDLRAD3 D1 residues C42, I45, P46, G47, A48, W47, D50, G51, or L52. In another aspect, a neutralizing antibody or antigen-binding fragment of the disclosure may specifically bind LDLRAD3 D1 such that the interaction between an alphavirus (e.g., VEEV) E2 polypeptide residues E148, V153, Y154, A155, H156, D157, A158, Q159, A262, D263, G264, K265, C266 or T267 are sterically unable to interact with LDLRAD3 D1 residues E28, C29, N30, I31, P32, G33, or N34.

In another aspect, a neutralizing antibody or antigen-binding fragment of the disclosure may specifically bind a viral surface protein such as an alphavirus E1 polypeptide, E2 polypeptide or E2/E1 heterodomain polypeptide. In one embodiment, a neutralizing antibody or antigen-binding fragment of the disclosure may specifically binds domain A of an alphavirus (e.g., VEEV) E2 polypeptide. For example, a neutralizing antibody or antigen-binding fragment of the disclosure may specifically bind domain A of an alphavirus (e.g., VEEV) E2 polypeptide such that the interaction between E2-E1 residues V24, G25, S26, C27, H28, M70, H71, K116, S118 or V119 are sterically unable to interact with LDLRAD3 D1 residues C29, N34, N39, R41, C42, I43, P44, W47, L52, D54 or F56. In another aspect, a neutralizing antibody or antigen-binding fragment of the disclosure may specifically bind domain B of an alphavirus (e.g., VEEV) E2 polypeptide such that the interaction between E2-E1 residues S176, S177, or K223 are sterically unable to interact with LDLRAD3 D1 residues S38, D57, or K62. In another aspect, a neutralizing antibody or antigen-binding fragment of the disclosure may specifically bind the fusion loop of an alphavirus (e.g., VEEV) E1 polypeptide such that the interaction between E2-E1 residues Y85, F87, M88, W89, G90, G91, or A92 are sterically unable to interact with LDLRAD3 D1 residues M36, S38, N39, G40, R41, C56, F58 or D57. In another aspect, a neutralizing antibody or antigen-binding fragment of the disclosure may specifically bind domain A of an alphavirus (e.g., VEEV) E2 polypeptide such that the interaction between E2-E1 residues L5, G63, R64, L79, 192, V93, D94 or G95 are sterically unable to interact with LDLRAD3 D1 residues C42, I45, P46, G47, A48, W47, D50, G51, or L52. In another aspect, a neutralizing antibody or antigen-binding fragment of the disclosure may specifically bind the β-linker of an alphavirus (e.g., VEEV) E2 polypeptide such that the interaction between E2-E1 residues E148, V153, Y154, A155, H156, D157, A158, Q159, A262, D263, G264, K265, C266 or T267 are sterically unable to interact with LDLRAD3 D1 residues E28, C29, N30, I31, P32, G33, or N34.

The phrase "specifically binds" herein means antigen binding proteins bind to an epitope with an affinity constant or affinity of interaction (KD) of less than 300 nM, less than 250 nM, less than 200 nM, less than 150 nM, less than 100 nM, less than 75 nM, less than 50 nM, less than 25 nM, less than 20 nM, less than 15 nM, less than 10 nM, less than 5 nM, or less than 1 nM.

The term "antigen binding protein" refers to any form of antibody or fragment thereof that exhibits the desired biological activity. Thus, it is used in the broadest sense and specifically covers monoclonal antibodies (including full length monoclonal antibodies), polyclonal antibodies, multispecific antibodies (e.g. bispecific antibodies), and antibody fragments so long as they exhibit the desired biological activity, for example, specifically binding LDLRAD3.

The term "antibody" includes the term "monoclonal antibody". The term "monoclonal antibody" refers to an antibody that is derived from a single copy or clone, including e.g., any eukaryotic, prokaryotic, or phage clone. Monoclonal antibodies are obtained from a population of substantially homogeneous antibodies, i.e., the individual antibodies comprising the population are identical except for possible naturally occurring mutations or post-translational modification that may be present in minor amounts. Monoclonal antibodies are highly specific, being directed against a single antigenic epitope. "Monoclonal antibody" is not limited to antibodies produced through hybridoma technology. Monoclonal antibodies can be produced using e.g., hybridoma techniques well known in the art, as well as recombinant technologies, phage display technologies, synthetic technologies or combinations of such technologies and other technologies readily known in the art. Furthermore, the monoclonal antibody may be labeled with a detectable label, immobilized on a solid phase and/or conjugated with a heterologous compound (e.g., an enzyme or toxin) according to methods known in the art.

The term "fragment thereof" encompasses a fragment or a derivative of an antibody that still substantially retain its biological activity. Therefore, the term "antibody fragment" or "fragment thereof" refers to a portion of a full length antibody, generally the antigen binding or variable region thereof. Examples of an immunologically effective fragment thereof include Fab, Fab', F(ab')2 and Fv fragments, diabodies, linear antibodies, single-chain molecules, and multispecific antibodies formed from antibody fragments. In some embodiments, the antibody fragments as disclosed herein include, in non-limiting examples, fusions to a Fc domain, a cytokine, a toxin, or an enzyme. In some contexts herein, fragments will be mentioned specifically for emphasis; nevertheless, it will be understood that regardless of whether fragments are specified, the term "antibody" includes such fragments.

Also included within the definition "antibody" for example are single chain forms, generally designated Fv, regions, of antibodies with this specificity. These scFvs are comprised of the heavy and light chain variable regions connected by a linker. In most instances, but not all, the linker may be a peptide. A linker peptide is preferably from about 10 to 25 amino acids in length. Preferably, a linker peptide is rich in glycine, as well as serine or threonine. scFvs can be used to facilitate phage display or can be used for flow cytometry, immunohistochemistry, or as targeting domains. Methods of making and using scFvs are known in the art. In a preferred embodiment, the scFvs of the present disclosure are conjugated to a human constant domain. In some embodi-ments, the heavy constant domain is derived from an IgG domain, such as IgG1, IgG2, IgG3, or IgG4. In other embodiments, the heavy chain constant domain may be derived from IgA, IgM, or IgE.

The basic antibody structural unit of an antibody useful herein comprises a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acid sequences primarily responsible for antigen recognition. The carboxy-terminal portion of each chain defines a constant region primarily responsible for effector function.

Light chains are classified as gamma, mu, alpha, and lambda. Heavy chains are classified as gamma, mu, alpha, delta, or epsilon, and define the antibody's isotype as IgG, IgM, IgA, IgD and IgE, respectively. Within light and heavy chains, the variable and constant regions are joined by a "J" region of about 12 or more amino acid sequences, with the heavy chain also including a "D" region of about 10 more amino acid sequences.

The variable regions of each light/heavy chain pair form the antibody binding site. Thus, an intact antibody has two binding sites, although recombinant versions can be of higher valency. The chains exhibit the same general structure of relatively conserved framework regions (FR) joined by three hypervariable regions, also called complementarity determining regions (hereinafter referred to as "CDRs"). The CDRs from the two chains are aligned by the framework regions, enabling binding to a specific epitope. From N-terminal to C-terminal, both light and heavy chains comprise the domains FR1, CDR1, FR2, CDR2, FR3, CDR3 and FR4 respectively. The assignment of amino acid sequences to each domain is in accordance with known conventions (See, Kabat "Sequences of Proteins of Immunological Interest" National Institutes of Health, Bethesda, Md., 1987 and 1991; Chothia, et al, J. Mol. Bio. (1987) 196:901-917; Chothia, et al., Nature (1989) 342:878-883). For example, Kabat, Chothia, combinations thereof, or other known methods of determining CDRs may be used.

In an aspect, antibodies of the invention are generated with appropriate specificity by immunization of mammals, forming hybridomas from the antibody-producing cells of said mammals or otherwise immortalizing them, and culturing the hybridomas or immortalized cells to assess them for the appropriate specificity. In the present case, such antibodies may be generated by immunizing a human, rabbit, rat or mouse, for example, with a peptide representing an epitope encompassing a region of the LDLRAD3 protein coding sequences or an appropriate subregion thereof. Materials for recombinant manipulation may be obtained by retrieving the nucleotide sequences encoding the desired antibody from the hybridoma or other cell that produces it. These nucleotide sequences may then be manipulated and isolated, characterized, purified and recovered to provide them in humanized form, if desired.

In an aspect, the disclosure provides a method of generating anti-LDLRAD3 and bodies for use within the methods of the disclosure comprising immunizing a Ldlrad3$^{-/-}$ animal with an isolated LDLRAD3 protein and optionally further administering an isolated LDLRAD3(D1)-Fc protein and isolating the antibodies from the immunized animals serum. The disclosure also contemplates a compositions comprising antibodies generated using the preceding method. Methods for generating an Ldlrad3$^{-/-}$ animal are described herein, including in the examples.

As used herein "humanized antibody" includes an anti-LDLRAD3 antibody that is composed partially or fully of amino acid sequences derived from a human antibody germline by altering the sequence of an antibody having non-human complementarity determining regions ("CDR"). The simplest such alteration may consist simply of substituting the constant region of a human antibody for the murine constant region, thus resulting in a human/murine chimera which may have sufficiently low immunogenicity to be acceptable for pharmaceutical use. Preferably, however, the variable region of the antibody and even the CDR is also humanized by techniques that are by now well known in the art. The framework regions of the variable regions are substituted by the corresponding human framework regions leaving the non-human CDR substantially intact, or even replacing the CDR with sequences derived from a human genome. CDRs may also be randomly mutated such that binding activity and affinity for GRP78 is maintained or enhanced in the context of fully human germline framework regions or framework regions that are substantially human. Substantially human frameworks have at least 90%, 95%, or 99% sequence identity with a known human framework sequence. Fully useful human antibodies are produced in genetically modified mice whose immune systems have been altered to correspond to human immune systems. As mentioned above, it is sufficient for use in the methods of this discovery, to employ an immunologically specific fragment of the antibody, including fragments representing single chain forms.

Further, as used herein the term "humanized antibody" refers to an anti-LDLRAD3 antibody comprising a human framework, at least one CDR from a nonhuman antibody, and in which any constant region present is substantially identical to a human immunoglobulin constant region, i.e., at least about 85-90%, preferably at least 95% identical. Hence, all parts of a humanized antibody, except possibly the CDRs, are substantially identical to corresponding pairs of one or more native human immuno-globulin sequences.

If desired, the design of humanized immunoglobulins may be carried out as follows. When an amino acid sequence falls under the following category, the framework amino acid sequence of a human immunoglobulin to be used (acceptor immunoglobulin) is replaced by a framework amino acid sequence from a CDR-providing nonhuman immunoglobulin (donor immunoglobulin): (a) the amino acid sequence in the human framework region of the acceptor immunoglobulin is unusual for human immuno-globulin at that position, whereas the corresponding amino acid sequence in the donor immunoglobulin is typical for human immunoglobulin at that position; (b) the position of the amino acid sequence is immediately adjacent to one of the CDRs; or (c) any side chain atom of a framework amino acid sequence is within about 5-6 angstroms (center-to-center) of any atom of a CDR amino acid sequence in a three dimensional immuno-globulin model (Queen, et al., op. cit., and Co, ct al, Proc. Natl. Acad. Sci. USA (1991) 88:2869). When each of the amino acid sequences in the human framework region of the acceptor immunoglobulin and a corresponding amino acid sequence in the donor immunoglobulin is unusual for human immunoglobulin at that position, such an amino acid sequence is replaced by an amino acid sequence typical for human immunoglobulin at that position.

(iii) Additional Viral Recognition-Site Inhibiting Agents

The present disclosure, also provides an aptamer composition which specifically binds to the viral recognition site of LDLRAD3 thereby preventing or reducing viral infectivity. As used herein, the term "aptamer" refers to a polynucleotide, generally a RNA or DNA that has a useful biological activity in terms of biochemical activity, molecular recognition or binding attributes. Usually, an aptamer has a molecular activity such as binging to a target molecule at a specific epitope (region). It is generally accepted that an aptamer, which is specific in it binding to a polypeptide, may be synthesized and/or identified by in vitro evolution methods. Means for preparing and characterizing aptamers, including by in vitro evolution methods, are well known in the art. See, for instance U.S. Pat. No. 7,939,313, herein incorporated by reference in its entirety. An aptamer or small molecule can be prepared to target specific amino acid residues disclosed herein as critical for VEEV binding to LDLRAD3 (see, e.g., FIG. 20 and Table 3).

As another example, the LDLRAD3-binding inhibiting agent can be an inhibitory protein that binds to the LDLRAD3 on a cell. For example, the LDLRAD3 inhibiting agent can be a viral protein, which has been shown to bind to LDLRAD3. For example, an alphavirus E1 or E2 or E2-E1 heterodimer polypeptide.

As another example, LDLRAD3-binding inhibiting agent can be a short hairpin RNA (shRNA) or a short interfering RNA (siRNA) which specifically targets LDLRAD3 mRNA and reduces expression of the LDLRAD3 protein.

As another example, LDLRAD3-binding inhibiting agent can be an sgRNA targeting LDLRAD3 for use in CRISPR. Methods for making and using CRISPR to target LDLRAD3 are described herein including in the Examples. As described herein, mouse Ldlrad3 or human LDLRAD3 signals can be modulated (e.g., reduced, eliminated, or enhanced) using genome editing. Processes for genome editing are well known; see e.g. Aldi 2018 Nature Communications 9(1911). Except as otherwise noted herein, therefore, the process of the present disclosure can be carried out in accordance with such processes.

For example, genome editing can comprise CRISPR/Cas9, CRISPR-Cpf1, TALEN, or ZNFs. Adequate blockage of LDLRAD3-virus binding by genome editing can result in protection from autoimmune or inflammatory diseases.

As an example, clustered regularly interspaced short palindromic repeats (CRISPR)/CRISPR-associated (Cas) systems are a new class of genome-editing tools that target desired genomic sites in mammalian cells. Recently published type II CRISPR/Cas systems use Cas9 nuclease that is targeted to a genomic site by complexing with a synthetic guide RNA that hybridizes to a 20-nucleotide DNA sequence and immediately preceding an NGG motif recognized by Cas9 (thus, a (N)20NGG target DNA sequence). This results in a double-strand break three nucleotides upstream of the NGG motif. The double-strand break instigates either non-homologous end-joining, which is error-prone and conducive to frameshift mutations that knock out gene alleles, or homology-directed repair, which can be exploited with the use of an exogenously introduced double-strand or single-strand DNA repair template to knock in or correct a mutation in the genome. Thus, genomic editing, for example, using CRISPR/Cas systems could be useful tools for therapeutic applications for treating or preventing viral infections to target cells by the removal of LDLRAD3.

For example, the methods as described herein can comprise a method for altering a target polynucleotide sequence in a cell comprising contacting the polynucleotide sequence with a clustered regularly interspaced short palindromic repeats-associated (Cas) protein.

Methods for preparing a LDLRAD3-binding inhibiting agent (e.g., an agent capable of inhibiting LDLRAD3 binding by a virus) can comprise construction of a protein/Ab scaffold containing the natural LDLRAD3 receptor as a viral infection neutralizing agent; developing inhibitors of the LDLRAD3 receptor "down-stream"; or developing inhibitors of the LDLRAD3 production "up-stream".

Inhibiting LDLRAD3-binding can be performed by genetically modifying LDLRAD3 in a subject or genetically modifying a subject to reduce or prevent expression of the LDLRAD3 gene, such as through the use of CRISPR-Cas9 or analogous technologies, wherein, such modification reduces or prevents a viral infection.

Also provided are methods for screening compositions for treating or preventing a viral infection according to the present disclosure.

The subject methods find use in the screening of a variety of different candidate molecules (e.g., potentially therapeutic candidate molecules). Candidate substances for screening according to the methods described herein include, but are not limited to, fractions of tissues or cells, nucleic acids, polypeptides, siRNAs, antisense molecules, aptamers, ribozymes, triple helix compounds, antibodies, and small (e.g., less than about 2000 mw, or less than about 1000 mw, or less than about 800 mw) organic molecules or inorganic molecules including but not limited to salts or metals.

Candidate molecules encompass numerous chemical classes, for example, organic molecules, such as small organic compounds having a molecular weight of more than 50 and less than about 2,500 Daltons. Candidate molecules can comprise functional groups necessary for structural interaction with proteins, particularly hydrogen bonding, and typically include at least an amine, carbonyl, hydroxyl, or carboxyl group, and usually at least two of the functional chemical groups. The candidate molecules can comprise cyclical carbon or heterocyclic structures and/or aromatic or polyaromatic structures substituted with one or more of the above functional groups.

A candidate molecule can be a compound in a library database of compounds. One of skill in the art will be generally familiar with, for example, numerous databases for commercially available compounds for screening (see e.g., ZINC database, UCSF, with 2.7 million compounds over 12 distinct subsets of molecules; Irwin and Shoichet (2005) J Chem Inf Model 45, 177-182). One of skill in the art will also be familiar with a variety of search engines to identify commercial sources or desirable compounds and classes of compounds for further testing (see e.g., ZINC database; eMolecules.com; and electronic libraries of commercial compounds provided by vendors, for example: ChemBridge, Princeton BioMolecular, Ambinter SARL, Enamine, ASDI, Life Chemicals etc.).

Candidate molecules for screening according to the methods described herein include both lead-like compounds and drug-like compounds. A lead-like compound is generally understood to have a relatively smaller scaffold-like structure (e.g., molecular weight of about 150 to about 350 kD) with relatively fewer features (e.g., less than about 3 hydrogen donors and/or less than about 6 hydrogen acceptors; hydrophobicity character x log P of about −2 to about 4) (see e.g., Angewante (1999) Chemie Int. ed. Engl. 24, 3943-3948). In contrast, a drug-like compound is generally understood to have a relatively larger scaffold (e.g., molecular weight of about 150 to about 500 kD) with relatively more numerous features (e.g., less than about 10 hydrogen acceptors and/or less than about 8 rotatable bonds; hydrophobicity character x log P of less than about 5) (see e.g., Lipinski (2000) J. Pharm. Tox. Methods 44, 235-249). Initial screening can be performed with lead-like compounds.

When designing a lead from spatial orientation data, it can be useful to understand that certain molecular structures are characterized as being "drug-like". Such characterization can be based on a set of empirically recognized qualities derived by comparing similarities across the breadth of known drugs within the pharmacopoeia. While it is not required for drugs to meet all, or even any, of these characterizations, it is far more likely for a drug candidate to meet with clinical success if it is drug-like.

Several of these "drug-like" characteristics have been summarized into the four rules of Lipinski (generally known as the "rules of fives" because of the prevalence of the number 5 among them). While these rules generally relate to oral absorption and are used to predict bioavailability of compound during lead optimization, they can serve as effective guidelines for constructing a lead molecule during rational drug design efforts such as may be accomplished by using the methods of the present disclosure.

The four "rules of five" state that a candidate drug-like compound should have at least three of the following characteristics: (i) a weight less than 500 Daltons; (ii) a log of P less than 5; (iii) no more than 5 hydrogen bond donors (expressed as the sum of OH and NH groups); and (iv) no more than 10 hydrogen bond acceptors (the sum of N and O atoms). Also, drug-like molecules typically have a span (breadth) of between about 8 Å to about 15 Å.

A control sample or a reference sample as described herein can be a sample from a healthy subject. A reference value can be used in place of a control or reference sample, which was previously obtained from a healthy subject or a group of healthy subjects. A control sample or a reference sample can also be a sample with a known amount of a detectable compound or a spiked sample. A control sample can be from a subject being administered a placebo.

Compositions and methods described herein utilizing molecular biology protocols can be according to a variety of standard techniques known to the art (see e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Definitions and methods described herein are provided to better define the present disclosure and to guide those of ordinary skill in the art in the practice of the present disclosure. Unless otherwise noted, terms are to be understood according to conventional usage by those of ordinary skill in the relevant art.

In some embodiments, numbers expressing quantities of ingredients, properties such as molecular weight, reaction conditions, and so forth, used to describe and claim certain embodiments of the present disclosure are to be understood as being modified in some instances by the term "about." In some embodiments, the term "about" is used to indicate that a value includes the standard deviation of the mean for the device or method being employed to determine the value. In some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the present disclosure are approximations, the numerical values set forth in the specific examples are reported as precisely as practicable. The numerical values presented in some embodiments of the present disclosure may contain certain errors necessarily resulting from the standard deviation found in their respective testing measurements. The recitation of ranges of values herein is merely intended to serve as a shorthand method of referring individually to each separate value falling within the range. Unless otherwise indicated herein, each individual value is incorporated into the specification as if it were individually recited herein. The recitation of discrete values is understood to include ranges between each value.

b) Components of the Composition

The present disclosure also provides pharmaceutical compositions. The pharmaceutical composition comprises a viral recognition-site inhibiting agent composition of the present disclosure, as an active ingredient, and at least one pharmaceutically acceptable excipient.

The pharmaceutically acceptable excipient may be a diluent, a binder, a filler, a buffering agent, a pH modifying agent, a disintegrant, a dispersant, a preservative, a lubricant, taste-masking agent, a flavoring agent, or a coloring agent. The amount and types of excipients utilized to form pharmaceutical compositions may be selected according to known principles of pharmaceutical science.

In each of the embodiments described herein, a composition of the invention may optionally comprise one or more additional drug or therapeutically active agent in addition to the nanoparticle composition of the present disclosure. Thus, in addition to the therapies described herein, one may also provide to the subject other therapies known to be efficacious for treatment of a viral infection. In some embodiments, the secondary agent is selected from a corticosteroid, a non-steroidal anti-inflammatory drug (NSAID), an intravenous immunoglobulin, a kinase inhibitor, a fusion or recombinant protein, a monoclonal antibody, or a combination thereof. In some embodiments, agents suitable for combination therapy include but are not limited to inhaled bronchodilators and inhaled steroids.

(i) Diluent

In one embodiment, the excipient may be a diluent. The diluent may be compressible (i.e., plastically deformable) or abrasively brittle. Non-limiting examples of suitable compressible diluents include microcrystalline cellulose (MCC), cellulose derivatives, cellulose powder, cellulose esters (i.e., acetate and butyrate mixed esters), ethyl cellulose, methyl cellulose, hydroxypropyl cellulose, hydroxypropyl methylcellulose, sodium carboxymethylcellulose, corn starch, phosphated corn starch, pregelatinized corn starch, rice starch, potato starch, tapioca starch, starch-lactose, starch-calcium carbonate, sodium starch glycolate, glucose, fructose, lactose, lactose monohydrate, sucrose, xylose, lactitol, mannitol, malitol, sorbitol, xylitol, maltodextrin, and trehalose. Non-limiting examples of suitable abrasively brittle diluents include dibasic calcium phosphate (anhydrous or dihydrate), calcium phosphate tribasic, calcium carbonate, and magnesium carbonate.

(ii) Binder

In another embodiment, the excipient may be a binder. Suitable binders include, but are not limited to, starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, $C_{12}$-$C_{18}$ fatty acid alcohol, polyethylene glycol, polyols, saccharides, oligosaccharides, polypeptides, oligopeptides, and combinations thereof.

(iii) Filler

In another embodiment, the excipient may be a filler. Suitable fillers include, but are not limited to, carbohydrates, inorganic compounds, and polyvinylpyrrolidone. By way of non-limiting example, the filler may be calcium sulfate, both di- and tri-basic, starch, calcium carbonate, magnesium carbonate, microcrystalline cellulose, dibasic calcium phosphate, magnesium carbonate, magnesium oxide, calcium silicate, talc, modified starches, lactose, sucrose, mannitol, or sorbitol.

(iv) Buffering Agent

In still another embodiment, the excipient may be a buffering agent. Representative examples of suitable buffering agents include, but are not limited to, phosphates, carbonates, citrates, tris buffers, and buffered saline salts (e.g., Tris buffered saline or phosphate buffered saline).

(v) pH Modifier

In various embodiments, the excipient may be a pH modifier. By way of non-limiting example, the pH modifying agent may be sodium carbonate, sodium bicarbonate, sodium citrate, citric acid, or phosphoric acid.

(vi) Disintegrant

In a further embodiment, the excipient may be a disintegrant. The disintegrant may be non-effervescent or effervescent. Suitable examples of non-effervescent disintegrants include, but are not limited to, starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Non-limiting examples of suitable effervescent disintegrants include sodium bicarbonate in combination with citric acid and sodium bicarbonate in combination with tartaric acid.

(vii) Dispersant

In yet another embodiment, the excipient may be a dispersant or dispersing enhancing agent. Suitable dispersants may include, but are not limited to, starch, alginic acid, polyvinylpyrrolidones, guar gum, kaolin, bentonite, purified wood cellulose, sodium starch glycolate, isoamorphous silicate, and microcrystalline cellulose.

(viii) Excipient

In another alternate embodiment, the excipient may be a preservative. Non-limiting examples of suitable preservatives include antioxidants, such as BHA, BHT, vitamin A, vitamin C, vitamin E, or retinyl palmitate, citric acid, sodium citrate; chelators such as EDTA or EGTA; and antimicrobials, such as parabens, chlorobutanol, or phenol.

(ix) Lubricant

In a further embodiment, the excipient may be a lubricant. Non-limiting examples of suitable lubricants include minerals such as talc or silica; and fats such as vegetable stearin, magnesium stearate, or stearic acid.

(x) Taste-Masking Agent

In yet another embodiment, the excipient may be a taste-masking agent. Taste-masking materials include cellulose ethers; polyethylene glycols; polyvinyl alcohol; polyvinyl alcohol and polyethylene glycol copolymers; monoglycerides or triglycerides; acrylic polymers; mixtures of acrylic polymers with cellulose ethers; cellulose acetate phthalate; and combinations thereof.

(xi) Flavoring Agent

In an alternate embodiment, the excipient may be a flavoring agent. Flavoring agents may be chosen from synthetic flavor oils and flavoring aromatics and/or natural oils, extracts from plants, leaves, flowers, fruits, and combinations thereof.

(xii) Coloring Agent

In still a further embodiment, the excipient may be a coloring agent. Suitable color additives include, but are not limited to, food, drug and cosmetic colors (FD&C), drug and cosmetic colors (D&C), or external drug and cosmetic colors (Ext. D&C).

The weight fraction of the excipient or combination of excipients in the composition may be about 99% or less, about 97% or less, about 95% or less, about 90% or less, about 85% or less, about 80% or less, about 75% or less, about 70% or less, about 65% or less, about 60% or less, about 55% or less, about 50% or less, about 45% or less, about 40% or less, about 35% or less, about 30% or less, about 25% or less, about 20% or less, about 15% or less, about 10% or less, about 5% or less, about 2%, or about 1% or less of the total weight of the composition.

The agents and compositions described herein can be formulated by any conventional manner using one or more pharmaceutically acceptable carriers or excipients as described in, for example, Remington's Pharmaceutical Sciences (A. R. Gennaro, Ed.), 21st edition, ISBN: 0781746736 (2005), incorporated herein by reference in its entirety. Such formulations will contain a therapeutically effective amount of a biologically active agent described herein, which can be in purified form, together with a suitable amount of carrier so as to provide the form for proper administration to the subject.

The term "formulation" refers to preparing a drug in a form suitable for administration to a subject, such as a human. Thus, a "formulation" can include pharmaceutically acceptable excipients, including diluents or carriers.

The term "pharmaceutically acceptable" as used herein can describe substances or components that do not cause unacceptable losses of pharmacological activity or unacceptable adverse side effects. Examples of pharmaceutically acceptable ingredients can be those having monographs in United States Pharmacopeia (USP 29) and National Formulary (NF 24), United States Pharmacopeial Convention, Inc, Rockville, Maryland, 2005 ("USP/NF"), or a more recent edition, and the components listed in the continuously updated Inactive Ingredient Search online database of the FDA. Other useful components that are not described in the USP/NF, etc. may also be used.

The term "pharmaceutically acceptable excipient," as used herein, can include any and all solvents, dispersion media, coatings, antibacterial and antifungal agents, isotonic, or absorption delaying agents. The use of such media and agents for pharmaceutical active substances is well known in the art (see generally Remington's Pharmaceutical Sciences (A. R. Gennaro, Ed.), 21st edition, ISBN: 0781746736 (2005)). Except insofar as any conventional media or agent is incompatible with an active ingredient, its use in the therapeutic compositions is contemplated. Supplementary active ingredients can also be incorporated into the compositions.

A "stable" formulation or composition can refer to a composition having sufficient stability to allow storage at a convenient temperature, such as between about 0° C. and about 60° C., for a commercially reasonable period of time, such as at least about one day, at least about one week, at least about one month, at least about three months, at least about six months, at least about one year, or at least about two years.

The formulation should suit the mode of administration. The agents of use with the current disclosure can be formulated by known methods for administration to a subject using several routes which include, but are not limited to, parenteral, pulmonary, oral, topical, intradermal, intramuscular, intraperitoneal, intravenous, subcutaneous, intranasal, epidural, ophthalmic, buccal, and rectal. The individual agents may also be administered in combination with one or more additional agents or together with other biologically active or biologically inert agents. Such biologically active or inert agents may be in fluid or mechanical communication with the agent(s) or attached to the agent(s) by ionic, covalent, Van der Waals, hydrophobic, hydrophilic or other physical forces.

c) Administration (i) Dosage Forms

The composition can be formulated into various dosage forms and administered by a number of different means that will deliver a therapeutically effective amount of the active ingredient. Such compositions can be administered orally (e.g. inhalation), or parenterally in dosage unit formulations containing conventional nontoxic pharmaceutically acceptable carriers, adjuvants, and vehicles as desired. Topical administration may also involve the use of transdermal administration such as transdermal patches or iontophoresis devices. The term parenteral as used herein includes subcutaneous, intravenous, intramuscular, intra-articular, or intrasternal injection, or infusion techniques. Formulation of drugs is discussed in, for example, Gennaro, A. R., Remington's Pharmaceutical Sciences, Mack Publishing Co., Easton, Pa. (18th ed, 1995), and Liberman, H. A. and Lachman, L., Eds., Pharmaceutical Dosage Forms, Marcel Dekker Inc., New York, N.Y. (1980). In a specific embodiment, a composition may be a food supplement or a composition may be a cosmetic.

For parenteral administration (including subcutaneous, intraocular, intradermal, intravenous, intramuscular, intra-articular and intraperitoneal), the preparation may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules, and tablets.

Generally, a safe and effective amount of a nanoparticle composition is administered, for example, that amount that would cause the desired therapeutic effect in a subject while minimizing undesired side effects. In various embodiments, an effective amount of a nanoparticle composition described herein can substantially reduce viral infectivity in a subject suffering from a viral infection. In some embodiments, an effective amount is an amount capable of treating a respiratory viral infection. In some embodiments, an effective amount is an amount capable of treating one or more symptoms associated with a respiratory viral infection.

For topical (e.g., transdermal or transmucosal) administration, penetrants appropriate to the barrier to be permeated are generally included in the preparation. Pharmaceutical compositions adapted for topical administration may be formulated as ointments, creams, suspensions, lotions, powders, solutions, pastes, gels, sprays, aerosols, or oils. In some embodiments, the pharmaceutical composition is applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles, and mouth washes. Transmucosal administration may be accomplished through the use of nasal sprays, aerosol sprays, tablets, or suppositories, and transdermal administration may be via ointments, salves, gels, patches, or creams as generally known in the art.

In certain embodiments, a composition comprising at least one a viral recognition-site inhibiting agent is encapsulated in a suitable vehicle to either aid in the delivery of the compound to target cells, to increase the stability of the composition, or to minimize potential toxicity of the composition. As will be appreciated by a skilled artisan, a variety of vehicles are suitable for delivering a composition of the present invention. Non-limiting examples of suitable structured fluid delivery systems may include nanoparticles, liposomes, microemulsions, micelles, dendrimers, and other phospholipid-containing systems. Methods of incorporating compositions into delivery vehicles are known in the art.

In one alternative embodiment, a liposome delivery vehicle may be utilized. Liposomes, depending upon the embodiment, are suitable for delivery of at least one a viral recognition-site inhibiting agent in view of their structural and chemical properties. Generally speaking, liposomes are spherical vesicles with a phospholipid bilayer membrane. The lipid bilayer of a liposome may fuse with other bilayers (e.g., the cell membrane), thus delivering the contents of the liposome to cells. In this manner, at least one a viral recognition-site inhibiting agent may be selectively delivered to a cell by encapsulation in a liposome that fuses with the targeted cell's membrane.

Liposomes may be comprised of a variety of different types of phospholipids having varying hydrocarbon chain lengths. Phospholipids generally comprise two fatty acids linked through glycerol phosphate to one of a variety of polar groups. Suitable phospholipids include phosphatidic acid (PA), phosphatidylserine (PS), phosphatidyl-inositol (PI), phosphatidylglycerol (PG), diphosphatidylglycerol (DPG), phosphatidyl-choline (PC), and phosphatidylethanolamine (PE). The fatty acid chains comprising the phospholipids may range from about 6 to about 26 carbon atoms in length, and the lipid chains may be saturated or unsaturated. Suitable fatty acid chains include (corn-mon name presented in parentheses) n-dodecanoate (laurate), n-tretradecanoate (myristate), n-hexadecanoate (palmitate), n-octadecanoate (stearate), n-eicosanoate (arachidate), n-docosanoate (behenate), n-tetracosanoate (lignocerate), cis-9-hexadecenoate (palmitoleate), cis-9-octadecanoate (oleate), cis,cis-9,12-octadecandienoate (linoleate), all cis-9, 12, 15-octadecatrienoate (linolenate), and all cis-5,8,11,14-eicosatetraenoate (arachidonate). The two fatty acid chains of a phospho-lipid may be identical or different. Acceptable phospholipids include dioleoyl PS, di-oleoyl PC, distearoyl PS, distearoyl PC, dimyristoyl PS, dimyristoyl PC, dipalmitoyl PG, stearoyl, oleoyl PS, palmitoyl, linolenyl PS, and the like.

The phospholipids may come from any natural source, and, as such, may comprise a mixture of phospholipids. For example, egg yolk is rich in PC, PG, and PE, soy beans contains PC, PE, PI, and PA, and animal brain or spinal cord is enriched in PS. Phospholipids may come from synthetic sources too. Mixtures of phospholipids having a varied ratio of individual phospholipids may be used. Mixtures of different phospholipids may result in liposome compositions having advantageous activity or stability of activity properties. The above mentioned phospholipids may be mixed, in optimal ratios with cationic lipids, such as N-(1-(2,3-dioleolyoxy)propyl)-N,N,N-trimethyl ammonium chloride, 1,1'-dioctadecyl-3,3,3',3'-tetramethylindocarbocyanine perchloarate, 3,3'-deheptyloxacarbocyanine iodide, 1,1'-dedodecyl-3,3,3',3'-tetramethylindocarbocya-nine perchloarate, 1,1'-dioleyl-3,3,3',3'-tetramethylindo carbocyanine methanesul-fonate, N-4-(delinoleylaminostyryl)-N-methylpyridinium iodide, or 1,1,-dilinoleyl-3,3,3',3'-tetramethylindocarbocyanine perchloarate.

Liposomes may optionally comprise sphingolipids, in which spingosine is the structural counterpart of glycerol and one of the one fatty acids of a phosphoglyceride, or cholesterol, a major component of animal cell membranes. Liposomes may optionally contain pegylated lipids, which are lipids covalently linked to polymers of polyeth-ylene glycol (PEG). PEGs may range in size from about 500 to about 10,000 daltons.

Liposomes may further comprise a suitable solvent. The solvent may be an or-ganic solvent or an inorganic solvent. Suitable solvents include, but are not limited to, dimethylsulfoxide (DMSO), methylpyrrolidone, N-methylpyrrolidone, acetronitrile, alco-hols, dimethylformamide, tetrahydrofuran, or combinations thereof.

Liposomes carrying at least a viral recognition-site inhibiting agent may be prepared by any known method of preparing liposomes for drug delivery, such as, for example, de-tailed in U.S. Pat. Nos. 4,241,046; 4,394,448; 4,529,561; 4,755,388; 4,828,837; 4,925,661; 4,954,345; 4,957,735; 5,043,164; 5,064,655; 5,077,211; and 5,264,618, the disclosures of which are hereby incorporated by reference in their entirety. For exam-ple, liposomes may be prepared by sonicating lipids in an aqueous solution, solvent injection, lipid hydration, reverse evaporation, or freeze drying by repeated freezing and thawing. In a preferred embodiment the liposomes are formed by sonication. The liposomes may be multilamellar, which have many layers like an onion, or unilamellar. The liposomes may be large or small. Continued high-shear sonication tends to form smaller unilamellar liposomes.

As would be apparent to one of ordinary skill, all of the parameters that govern liposome formation may be varied. These parameters include, but are not limited to, temperature, pH, concentration of a viral recognition-site inhibiting agent, concentration and composition of lipid, concentration of multivalent cations, rate of mixing, presence of and concentration of solvent.

In another embodiment, a composition of the invention may be delivered to a cell as a microemulsion. Microemulsions are generally clear, thermodynamically stable solutions comprising an aqueous solution, a surfactant, and "oil." The "oil" in this case, is the supercritical fluid phase. The surfactant rests at the oil-water interface. Any of a variety of surfactants are suitable for use in microemulsion formulations including those described herein or otherwise known in the art. The aqueous microdomains suitable for use in the invention generally will have characteristic structural dimensions from about 5 nm to about 100 nm. Aggregates of this size are poor scatters of visible light and hence, these solutions are optically clear. As will be appreciated by a skilled artisan, microemulsions can and will have a multitude of different microscopic structures including sphere, rod, or disc shaped aggregates. In one embodiment, the structure may be micelles, which are the simplest microemulsion structures that are generally spherical or cylindrical objects. Micelles are like drops of oil in water, and re-verse micelles are like drops of water in oil. In an alternative embodiment, the micro-emulsion structure is the lamellae. It comprises consecutive layers of water and oil separated by layers of surfactant. The "oil" of microemulsions optimally comprises phospholipids. Any of the phospholipids detailed above for liposomes are suitable for embodiments directed to microemulsions. At least one a viral recognition-site inhibiting agent may be encapsulated in a microemulsion by any method generally known in the art.

In yet another embodiment, at least one a viral recognition-site inhibiting agent may be delivered in a dendritic macromolecule, or a dendrimer. Generally speaking, a dendrimer is a branched tree-like molecule, in which each branch is an interlinked chain of molecules that divides into two new branches (molecules) after a certain length. This branching continues until the branches (molecules) become so densely packed that the canopy forms a globe. Generally, the properties of dendrimers are determined by the functional groups at their surface. For example, hydrophilic end groups, such as carboxyl groups, would typically make a water-soluble dendrimer. Alternatively, phospholipids may be incorporated in the surface of a dendrimer to facilitate absorption across the skin. Any of the phospholipids detailed for use in liposome embodiments are suitable for use in dendrimer embodiments. Any method generally known in the art may be utilized to make dendrimers and to encapsulate compositions of the invention therein. For example, dendrimers may be produced by an iterative sequence of reaction steps, in which each additional iteration leads to a higher order dendrimer. Consequently, they have a regular, highly branched 3D structure, with nearly uniform size and shape. Furthermore, the final size of a dendrimer is typically controlled by the number of iterative steps used during synthesis. A variety of dendrimer sizes are suitable for use in the invention. Generally, the size of dendrimers may range from about 1 nm to about 100 nm.

The amount of a composition described herein that can be combined with a pharmaceutically acceptable carrier to produce a single dosage form will vary depending upon the host treated and the particular mode of administration. It will be appreciated by those skilled in the art that the unit content of agent contained in an individual dose of each dosage form need not in itself constitute a therapeutically effective amount, as the necessary therapeutically effective amount could be reached by administration of a number of individual doses.

The concentration of the composition of the present disclosure in the fluid pharmaceutical formulations can vary widely, i.e., from less than about 0.05% usually or at least about 2-10% to as much as 30 to 50% by weight and will be selected primarily by fluid volumes, viscosities, etc., in accordance with the particular mode of administration selected. For example, the concentration may be increased to lower the fluid load associated with treatment. The amount of nanoparticle pharmaceutical composition administered will depend upon the particular therapeutic entity entrapped inside the nanoparticle, the type of nanoparticle being used, and the judgment of the clinician. Generally the amount of nanoparticle pharmaceutical composition administered will be sufficient to deliver a therapeutically effective dose of the particular therapeutic entity.

The quantity of a pharmaceutical composition necessary to deliver a therapeutically effective dose can be determined by routine in vitro and in vivo methods, common in the art of drug testing. See, for example, D. B. Budman, A. H. Calvert, E. K. Rowinsky (editors). Handbook of Anticancer Drug Development, LWW, 2003. Therapeutically effective dosages for various therapeutic entities are well known to those of skill in the art; and according to the present disclosure a therapeutic entity delivered via the pharmaceutical liposome composition of the present invention provides at least the same, or 2-fold, 4-fold, or 10-fold higher activity than the activity obtained by administering the same amount of the therapeutic entity in its routine non-liposome formulation. Typically the dosages for the nanoparticle pharmaceutical composition of the present disclosure range between about 0.005 and about 500 mg of the therapeutic entity per kilogram of body weight, most often, between about 0.1 and about 100 mg therapeutic entity/kg of body weight.

Toxicity and therapeutic efficacy of compositions described herein can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$, where larger therapeutic indices are generally understood in the art to be optimal.

The specific therapeutically effective dose level for any particular subject will depend upon a variety of factors including the disorder being treated and the severity of the disorder; activity of the specific compound employed; the specific composition employed; the age, body weight, general health, sex and diet of the subject; the time of administration; the route of administration; the rate of excretion of the composition employed; the duration of the treatment; drugs used in combination or coincidental with the specific compound employed; and like factors well known in the medical arts (see e.g., Koda-Kimble et al. (2004) Applied Therapeutics: The Clinical Use of Drugs, Lippincott Williams & Wilkins, ISBN 0781748453; Winter (2003) Basic Clinical Pharmacokinetics, 4th ed., Lippincott Williams & Wilkins, ISBN 0781741475; Sharqel (2004) Applied Biopharmaceutics & Pharmacokinetics, McGraw-Hill/Appleton & Lange, ISBN 0071375503). For example, it is well within the skill of the art to start doses of the composition at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose. It will be understood, however, that the total daily usage of the compounds and compositions of the present disclosure will be decided by an attending physician within the scope of sound medical judgment.

Administration of a composition of the disclosure can occur as a single event or over a time course of treatment. For example, one or more of a nanoparticle composition can be administered daily, weekly, bi-weekly, or monthly. For treatment of acute conditions, the time course of treatment will usually be at least several days. Certain conditions could extend treatment from several days to several weeks. For example, treatment could extend over one week, two weeks, or three weeks. For more chronic conditions, treatment could extend from several weeks to several months or even a year or more.

Treatment in accord with the methods described herein can be performed prior to, concurrent with, or after conventional treatment modalities for an alphavirus (e.g., VEEV). A viral recognition-site inhibiting agent can be administered simultaneously or sequentially with another agent, such as an antibiotic, an anti-inflammatory, or another agent. For example, a viral recognition-site inhibiting agent can be administered simultaneously with another agent, such as an antiviral, an antibiotic, or an anti-inflammatory. Simultaneous administration can occur through administration of separate compositions, each containing one or more of a viral recognition-site inhibiting agent, an antiviral, an antibiotic, an anti-inflammatory, or another agent. Simultaneous administration can occur through administration of one composition containing two or more of a viral recognition-site inhibiting agent, an antiviral, an antibiotic, an anti-inflammatory, or another agent. A viral recognition-site inhibiting agent can be administered sequentially with an antiviral, an antibiotic, an anti-inflammatory, or another agent. For example, a viral recognition-site inhibiting agent can be administered before or after administration of an antiviral, an antibiotic, an anti-inflammatory, or another agent.

The present disclosure encompasses pharmaceutical compositions comprising compounds as disclosed above, so as to facilitate administration and promote stability of the active agent. For example, a compound of this disclosure may be admixed with at least one pharmaceutically acceptable carrier or excipient resulting in a pharmaceutical composition which is capably and effectively administered (given) to a living subject, such as to a suitable subject (i.e. "a subject in need of treatment" or "a subject in need thereof"). For the purposes of the aspects and embodiments of the invention, the subject may be a human or any other animal.

II. Methods

The present disclosure encompasses methods to treat, prevent, or reduce the infectivity of a virus in a subject in need thereof. In some embodiments, the methods prevent or reduce the infectivity of a viral infection by preventing internalization of a virus into a cell of the subject or by preventing internalization of a viral genome into a cell of the subject. In some embodiments, administration of a composition provided herein, for instance those described in Section I which is incorporated by reference in to this section in its entirety, may disrupt or prevent an interaction between a viral surface protein (e.g., E1 or E2) and a host receptor protein (e.g., LDLRAD3). For example, administration of a viral recognition-site inhibiting agent composition may block internalization of an alphavirus (e.g., VEEV) into a cell of a subject by blocking or disrupting interactions between an alphavirus E1 or E2 or E2/E1 heterodimer protein and a host LDLRAD3 receptor protein and/or by sequestering the virus in vivo allowing for the virus bound to the viral recognition-site inhibiting agent composition to be eliminated by the subject's immune cells. In addition, administering a viral recognition-site inhibiting agent composition to a subject at risk for a viral infection may reduce the risk of coronavirus infection in the subject.

In some embodiments, the method include preventing or reducing neuronal injury in a subject infected with an alphavirus by administering to the subject a viral recognition-site inhibiting agent composition according to the disclosure. In some embodiments, the method include preventing or reducing a hemorrhage in the central nervous system of a subject infected with an alphavirus by administering to the subject a viral recognition-site inhibiting agent composition according to the disclosure.

In some embodiments, the present disclosure provides methods to treat, prevent, or reduce the infectivity of a virus by reducing expression of an endogenous LDLRAD3 protein in cells which are susceptible to infection by the virus. Compositions and method of making the same useful for reducing expression of LDLRAD3 are described herein. As used herein, the phrase "cells susceptible to infection by a virus" refers to cells that express a receptor which allows the virus to infect the cell.

In other embodiments, the present disclosure provides methods to treat, prevent, or reduce the infectivity of a viral infection. In some embodiments, the viral infection may be an Adenoviridae, Alloherpesviridae, Asfarviridae, Herpesviridae, Iridoviridae, Malacoherpesviridae, Papillomaviridae, Polyomaviridae, Poxviridae, Birnaviridae, Picobirnaviridae, Reoviridae, Retroviridae, Hepadnaviridae, Parvoviridae, Anelloviridae, Circoviridae, Coronaviridae, Bunyaviridae, Flaviviridae, Orthomyxoviridae, Caliciviridae, Togaviridae, Arenaviridae, Arteriviridae, Astroviridae, Bornaviridae, Filoviridae, Hepeviridae, Paramyxoviridae, Picornaviridae, or Rhabdoviridae infection. In some embodiments, the viral infection may be an alphavirus infection. In some embodiments, the alphavirus is an alphavirus capable of binding a LDLRAD3 receptor on a cell. In some embodiments, the alphavirus is a virus capable of binding domain 1 (D1) of LDLRAD3. In some embodiments, the alphavirus infection is a neurotropic alphavirus infection. In some embodiments, the alphavirus infection is an encephalitic alphavirus infection. In some embodiments, the encephalitic alphaviruses is a Venezuelan equine encephalitis virus (VEEV), Eastern equine encephalitis virus (EEEV), or Western equine encephalitis virus (WEEV). A subject at risk for an alphavirus infection may come in contact with a carrier of the alphavirus infection, thereby unknowingly contracting the alphavirus infection.

In some embodiments, the compositions, methods, or treatment regiments disclosed herein may treat or prevent a VEEV infection. A VEEV infection may depend on host cell LDLRAD3. In some embodiments, a VEEV infection may be blocked (e.g., prevented, treated, or slowed) by a composition of the disclosure.

Generally, the methods as described herein comprise administration of a therapeutically effective amount of a nanoparticle composition of the disclosure to a subject. The methods described herein are generally performed on a subject in need thereof. A subject may be a rodent, a human, a livestock animal, a companion animal, or a zoological animal. In one embodiment, the subject may be a rodent, e.g. a mouse, a rat, a guinea pig, etc. In another embodiment, the subject may be a livestock animal. Non-limiting examples of suitable livestock animals may include pigs, cows, horses, goats, sheep, llamas and alpacas. In still another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a preferred embodiment, the subject is a human.

III. Kits

Also provided are kits. Such kits can include an agent or composition described herein and, in certain embodiments, instructions for administration. Such kits can facilitate performance of the methods described herein. When supplied as a kit, the different components of the composition can be packaged in separate containers and admixed immediately before use. Components include, but are not limited to compositions and pharmaceutical formulations comprising a viral recognition-site inhibiting agent composition, as described herein. Such packaging of the components separately can, if desired, be presented in a pack or dispenser device which may contain one or more unit dosage forms containing the composition. The pack may, for example, comprise metal or plastic foil such as a blister pack. Such packaging of the components separately can also, in certain instances, permit long-term storage without losing activity of the components.

Kits may also include reagents in separate containers such as, for example, sterile water or saline to be added to a lyophilized active component packaged separately. For example, sealed glass ampules may contain a lyophilized component and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit.

Compositions and methods described herein utilizing molecular biology protocols can be according to a variety of standard techniques known to the art (see, e.g., Sambrook and Russel (2006) Condensed Protocols from Molecular Cloning: A Laboratory Manual, Cold Spring Harbor Laboratory Press, ISBN-10: 0879697717; Ausubel et al. (2002) Short Protocols in Molecular Biology, 5th ed., Current Protocols, ISBN-10: 0471250929; Sambrook and Russel (2001) Molecular Cloning: A Laboratory Manual, 3d ed., Cold Spring Harbor Laboratory Press, ISBN-10: 0879695773; Elhai, J. and Wolk, C. P. 1988. Methods in Enzymology 167, 747-754; Studier (2005) Protein Expr Purif. 41(1), 207-234; Gellissen, ed. (2005) Production of Recombinant Proteins: Novel Microbial and Eukaryotic Expression Systems, Wiley-VCH, ISBN-10: 3527310363; Baneyx (2004) Protein Expression Technologies, Taylor & Francis, ISBN-10: 0954523253).

Specific embodiments disclosed herein may be further limited in the claims using "consisting of" or "consisting essentially of" language, rather than "comprising". When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

As various changes could be made in the above-described materials and methods without departing from the scope of the invention, it is intended that all matter contained in the above description and in the examples given below, shall be interpreted as illustrative and not in a limiting sense.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1: Ldlrad3 is a Receptor for Venezuelan Equine Encephalitis Virus

Alphaviruses are mosquito-transmitted positive-sense RNA viruses that can cause explosive disease outbreaks in humans and animals. Arthritogenic alphaviruses, including chikungunya (CHIKV), Ross River (RRV), O'nyong nyong (ONNV), and Mayaro (MAYV) viruses cause musculoskeletal disease affecting millions of people globally. Encephalitic alphaviruses, including Venezuelan (VEEV), Eastern (EEEV), and Western (WEEV) equine encephalitis viruses, infect the central nervous system and are highly pathogenic, with most strains contained at laboratory Biosafety Level (BSL) 3.

VEEV is widely distributed throughout the Americas. It has an enzootic cycle between mosquitoes and birds or rodents, an epizootic cycle in equids, and is transmitted to humans via mosquito inoculation or an aerosol route. While at least 14 antigenic groups within the VEEV complex are described, only subtypes IAB and IC cause epidemics of severe illness. Despite the potential for morbidity or mortality by VEEV, there are no licensed therapies or vaccines for general use in humans. Only at-risk laboratory workers can obtain a highly reactogenic live-attenuated virus (TC-83) or a formalin-inactivated vaccine that requires frequent boosting.

Figure 1B:
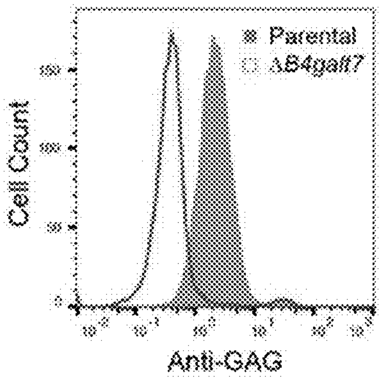
Figure 1C:
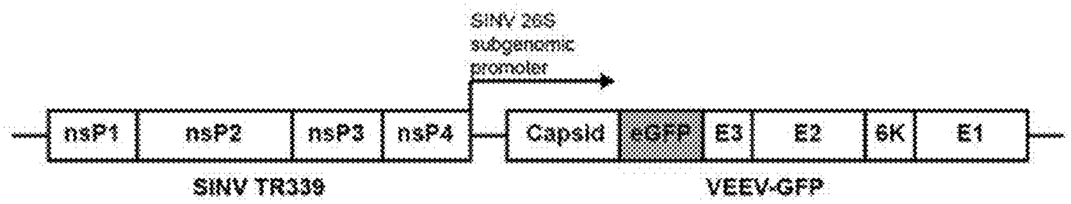
Figure 1D:
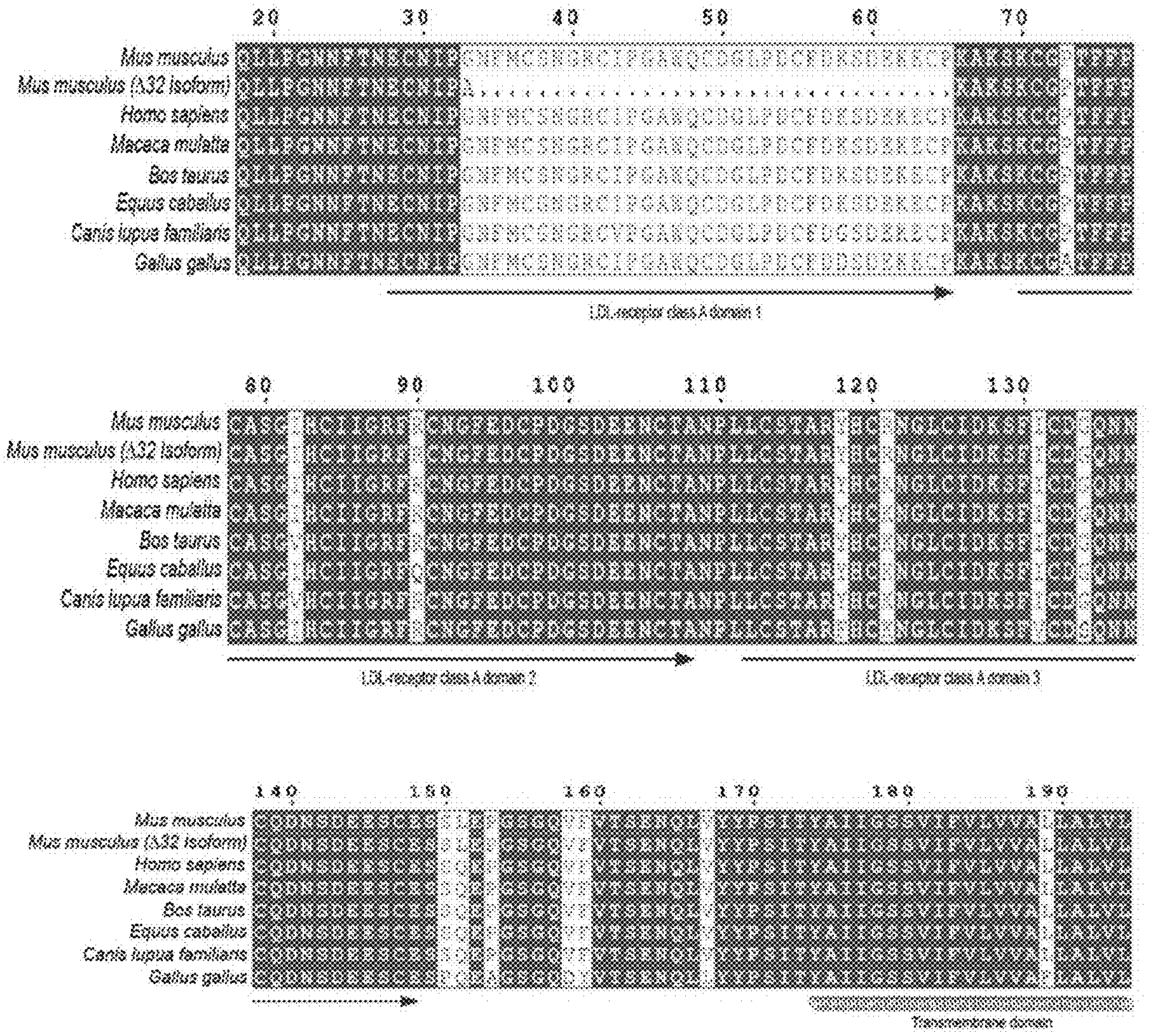

The cell adhesion molecule Mxra8 has been recently identified as a receptor for several arthritogenic alphaviruses. Because expression of Mxra8 did not impact VEEV, WEEV, or EEEV infection, it was hypothesized that separate receptors exist for the encephalitic alphaviruses. For VEEV, no physiologically relevant entry receptor has been established, although a laminin-binding protein reportedly enhances infection of mosquito and human cells. C-type lectins can promote infection of cells by mosquito-derived alphaviruses, and the infection efficiency of cell culture-adapted VEEV strains is increased by binding to heparan sulfate (HS) proteoglycans. To identify a receptor required for VEEV infection, the present example utilized a genome-wide CRISPR/Cas9 screen (FIG. 1A) in neuronal cells, a target cell of VEEV. Because some alphaviruses can attach to cells via engagement of HS11-13, the screen was performed using mouse Neuro2a (termed N2a hereafter) cells that were edited to lack expression of B4galt7 (FIG. 1B), an enzyme required for glycosaminoglycan (GAG) and HS biosynthesis. A library of ΔB4galt7 N2a cells were inoculated with a chimeric SINV-VEEV-GFP that encodes for the non-structural genes of Sindbis (SINV) virus (nsP1, neP2, nsP3 and nsP4), the structural genes of the TrD strain of VEEV (C, E3, E2, 6K, and E1) and green fluorescent protein (GFP) (FIG. 1C) so the screen could be performed at lower biosafety containment level, but with structural proteins from a pathogenic VEEV IAB strain. Under high multiplicity-of-infection (MOI) conditions, virtually all cells expressed GFP by 17 h. The few cells that lacked GFP expression were sorted, propagated in the presence of neutralizing anti-VEEV monoclonal antibodies (mAbs VEEV-57, VEEV-67, and VEEV-68), and then re-inoculated with SINV-VEEV-GFP TrD. After three rounds of infection, genomic DNA from GFP-negative cells was collected, and single-guide (sg)RNAs were sequenced, and analyzed. The top candidate was Ldlrad3 (FIG. 2A) which a conserved plasma membrane protein of the LDL scavenger-receptor family found in mammals, birds, reptiles, amphibians, and fish (FIG. 1D). Available transcriptomic data suggests that Ldlrad3 is expressed in neurons and in epithelial cells of the gastrointestinal tract, myeloid cells, and muscle tissues. Little is known about the function of LDLRAD3, beyond reports suggesting it has roles in modulating amyloid precursor protein function in neurons and promoting activity of E3 ubiquitin ligases.

Figure 2C:
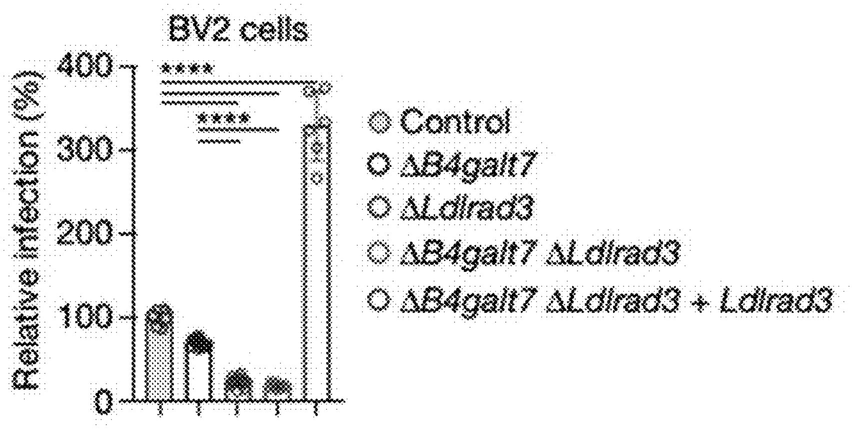
FIG. 2C shows control sgRNA, ΔB4galt7, ΔLdlrad3, ΔB4galt7 ΔLdlrad3 and Ldlrad3-complemented ΔB4galt7 ΔLdlrad3 BV2 cells were inoculated with SINV-VEEV-GFP (TrD), and infection assessed by flow cytometry. Control and ΔLdlrad3, n=18; ΔB4galt7 and ΔB4galt7 ΔLdlrad3, n=12; ΔB4galt7 ΔLdlrad3+Ldlrad3, n=6. FFU, focus-forming units.
Figure 2D:
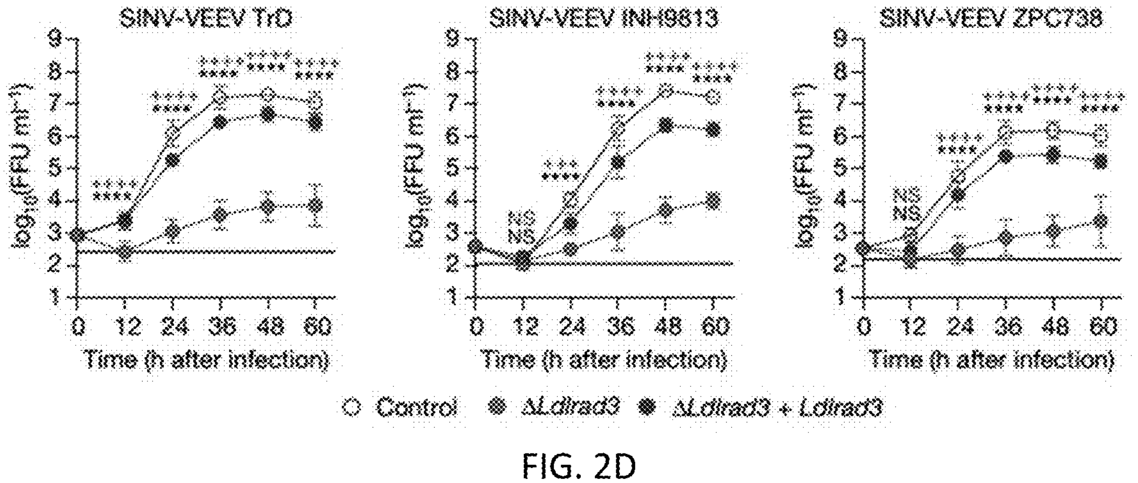
FIG. 2D depicts multistep growth curves of ΔB4galt7, ΔB4galt7 ΔLdlrad3 and Ldlrad3-complemented ΔB4galt7 ΔLdlrad3 N2a cells with SINV-VEEV (TrD, INH9813 and ZPC738). n=9.
Figure 2E:
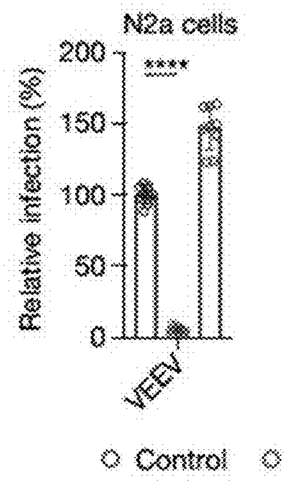
FIG. 2E shows control, ΔLdlrad3 and Ldlrad3-complemented ΔLdlrad3 N2a cells retaining glycosaminoglycan biosynthesis (B4galt7$^{+/+}$) were inoculated with SINV-VEEV-GFP (TrD), and infection assessed by flow cytometry. n=9.
Figure 3A:
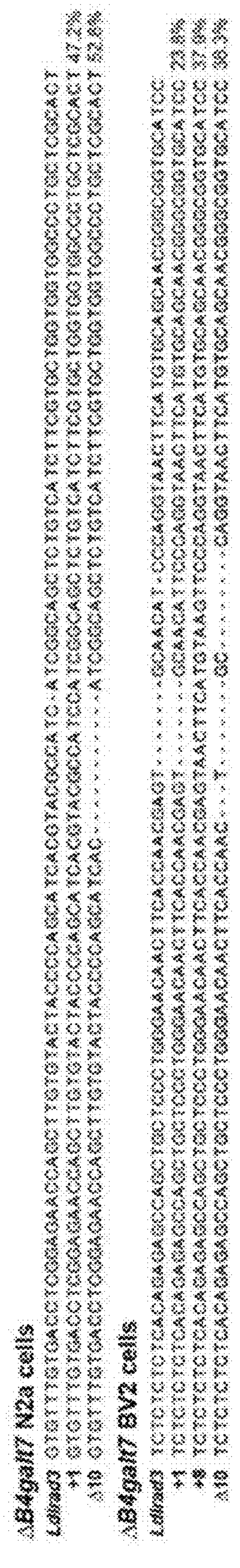
Figure 3B:
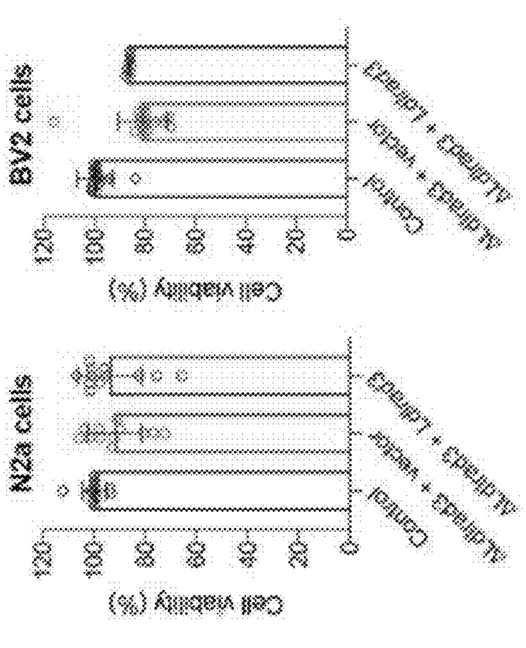
Figure 3C:
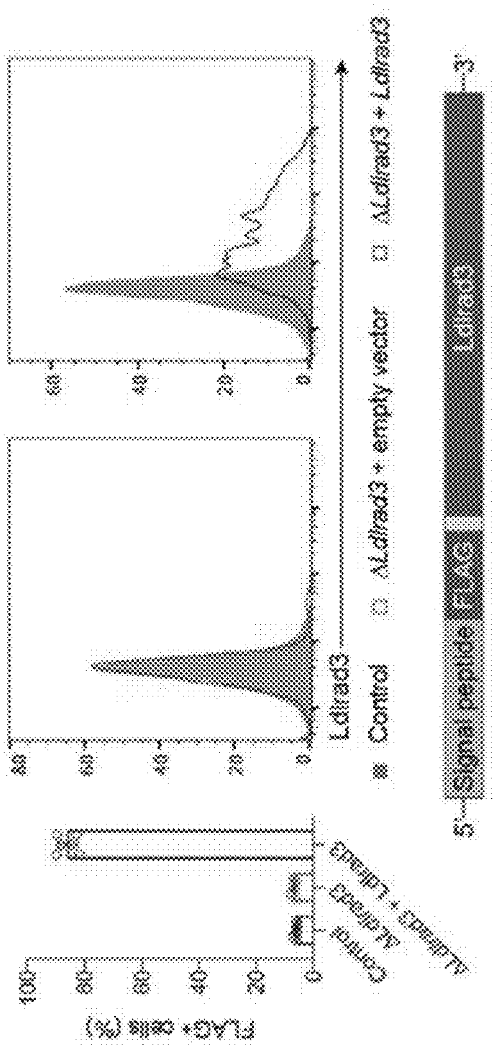

Ldlrad3 was validated using as a key host factor for VEEV two Ldlrad3 sgRNAs in bulk ΔB4galt7 N2a cells, by generating ΔLdlrad3 single-cell clones in ΔB4galt7 N2a cells and BV2 microglial cells, and confirming gene deletion and cell viability (FIG. 3A-3B). Markedly reduced infection with SINV-VEEV-GFP TrD was detected in ΔB4galt7 ΔLdlrad3 cells under single step or multistep growth conditions (FIG. 2B-2D). Complementation with a full-length seed-sequence Ldlrad3 variant restored expression and infectivity (FIG. 2B-2D, FIG. 3C and FIG. 3J). The effect of LDLRAD3 on infection of viruses expressing VEEV structural proteins from epizootic or enzootic strains or using an attenuated VEEV IAB strain (TC-83) was evaluated. Infection of VEEV IAB (TC-83), SINV-VEEV IC (INH9813), and SINV-VEEV ID (ZPC738) subtypes was diminished in ΔB4galt7 ΔLdlrad3 N2a cells and restored in complemented cells (FIG. 2B and FIG. 2D). The importance of LDLRAD3 expression in B4galt7$^{+/+}$ N2a cells with intact glycosaminoglycan expression was also determined. In B4galt7$^{+/+}$ ΔLdlrad3 cells, SINV-VEEV-GFP TrD infection was decreased but restored upon re-introduction of LDLRAD3 (FIG. 2C, FIG. 2E and FIG. 3E).

Figure 2F:
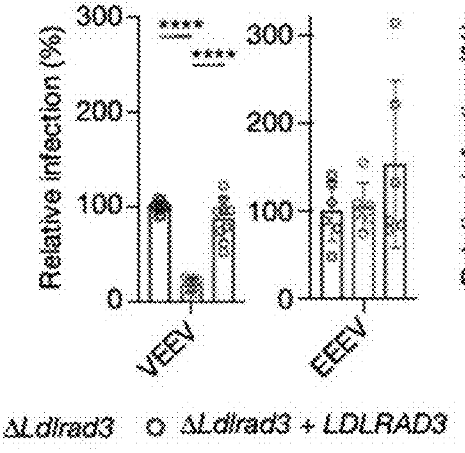
FIG. 2F shows ΔB4galt7, ΔB4galt7 ΔLdlrad3 and Ldlrad3-complemented ΔB4galt7 ΔLdlrad3 N2a cells were inoculated with VEEV TrD-GFP (left) or EEEV FL93-939-GFP (right) and assessed for infection by flow cytometry. EEEV, n=6; VEEV, n=9.
Figure 2G:
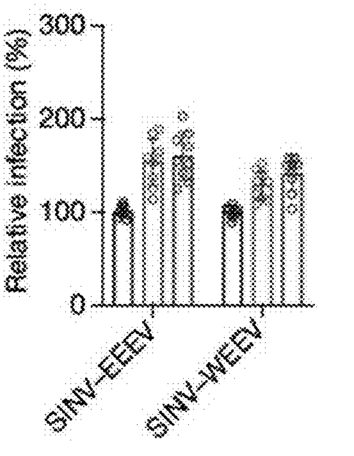
FIG. 2G shows ΔB4galt7, ΔB4galt7 ΔLdlrad3 and Ldlrad3-complemented ΔB4galt7 ΔLdlrad3 N2a cells were inoculated with SINV-EEEV or SINV-WEEV FIG. 2G, SINV (strains AR86, TR339, Toto1101 or Girdwood) FIG. 2H, MAW FIG. 2I or VSV FIG. 2J and infection assessed via GFP expression or viral antigen staining.
Figure 2H:
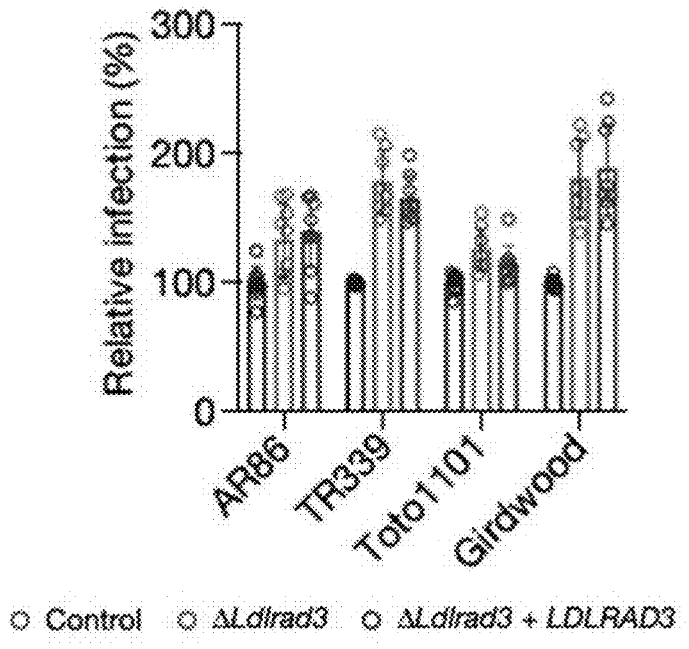
FIG. 2H AR86, Toto1101: n=9; TR339, Girdwood: n=8.
Figure 2I:
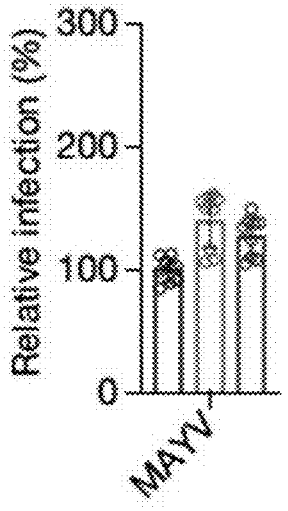
FIG. 2I n=9.
Figure 2J:
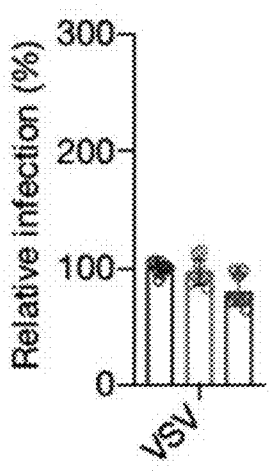
FIG. 2J n=9.
Figure 2K:
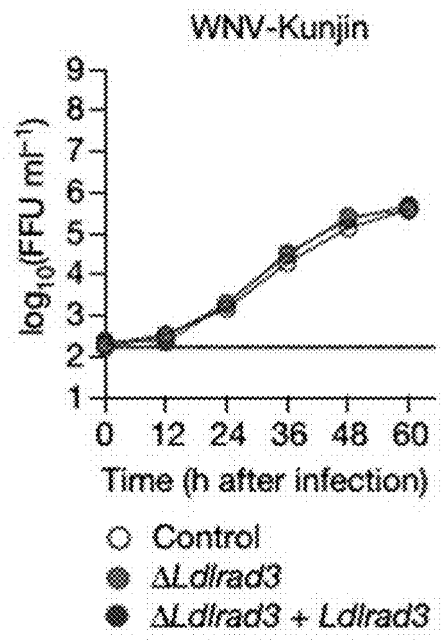
FIG. 2K shows multistep growth curves of ΔB4galt7, ΔB4galt7 ΔLdlrad3 and Ldlrad3-complemented ΔB4galt7 ΔLdlrad3 N2a cells with WNV Kunjin strain. Mean of 2 experiments performed in duplicate.
Figure 2L:
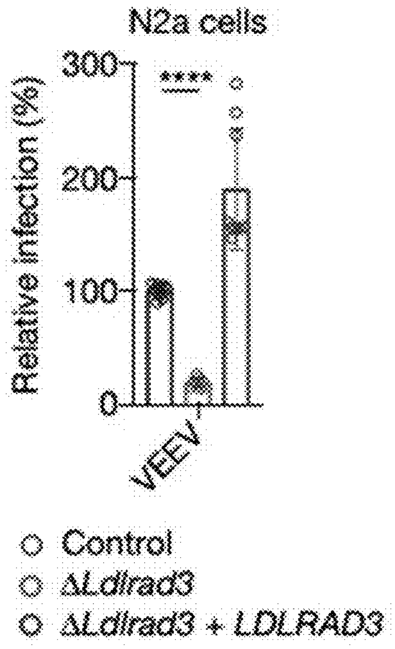
FIG. 2L shows ΔB4galt7, ΔB4galt7 ΔLdlrad3 and human LDLRAD3-complemented ΔB4galt7 ΔLdlrad3 N2a cells were inoculated with SINV-VEEV-GFP (TrD), and infection assessed by flow cytometry. n=9.
Figure 2M:
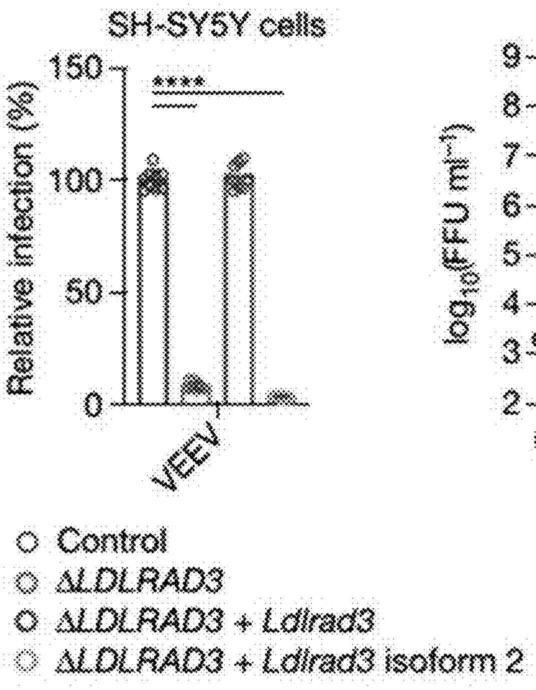
FIG. 2M shows control, ΔLDLRAD3, full-length Ldlrad3-complemented and truncated Ldlrad3-isoform-complemented ΔLDLRAD3 B4GALT7+/+ human SH-SY5Y cells were inoculated with SINV-VEEV-GFP (TrD), and infection assessed by flow cytometry. n=9.
Figure 2N:
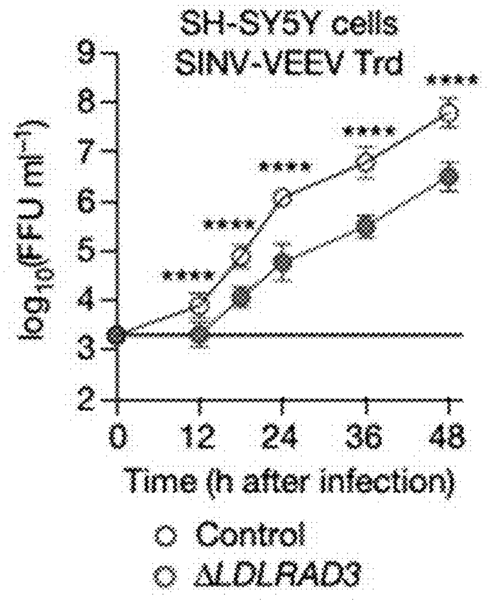

We tested the requirement of LDLRAD3 for infection of other viruses, including pathogenic VEEV TrD and EEEV (FL93-939) strains. Although substantially reduced infection was observed with VEEV TrD when Ldlrad3 was edited, no difference was observed with EEEV (FIG. 2F). This phenotype was confirmed with SINV-EEEV and extended to SINV-WEEV (CBA87 strain) (FIG. 2G). Similarly, no loss of infection by arthritogenic alphaviruses (SINV and MAYV) was observed, an unrelated rhabdovirus (Vesicular stomatitis virus (VSV)), or an unrelated flavivirus (West Nile virus (WNV)) when Ldlrad3 was edited (FIG. 2H-2K). The full-length human isoform of LDLRAD3 is 96% identical to the mouse protein and differs by only three amino acids in the ectodomain (FIG. 1D). Ectopic expression of LDLRAD3 in ΔB4galt7 ΔLdlrad3 N2a cells also increased infection with SINV-VEEV-GFP TrD infection (FIG. 2L and FIG. 3I). Full-length and truncated (Δ32 amino acids) isoforms of Ldlrad3 were also introduced (FIG. 1D and FIG. 3G) into B4GALT7$^{+/+}$ ΔLDLRAD3 human SH-SY5Y neuroblastoma cells that retained glycosaminoglycan expression. A loss of LDLRAD3 expression in SH-SY5Y cells resulted in decreased infection with SINV-VEEV TrD, which was restored by expression of the full-length but not truncated isoform of Ldlrad3 (FIGS. 2M-2N and FIG. 3H).

Figure 4A:
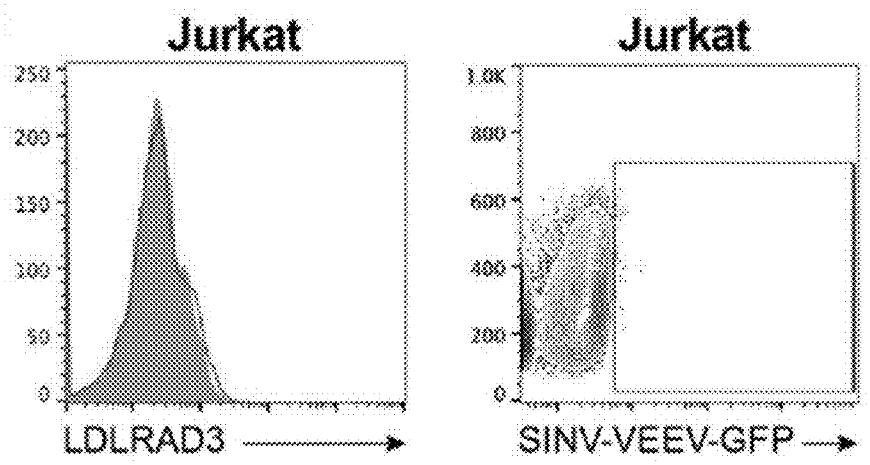
FIG. 4A-4D show surface expression of LDLRAD3 and VEEV infection of human lymphocyte cell lines.
Figure 4B:
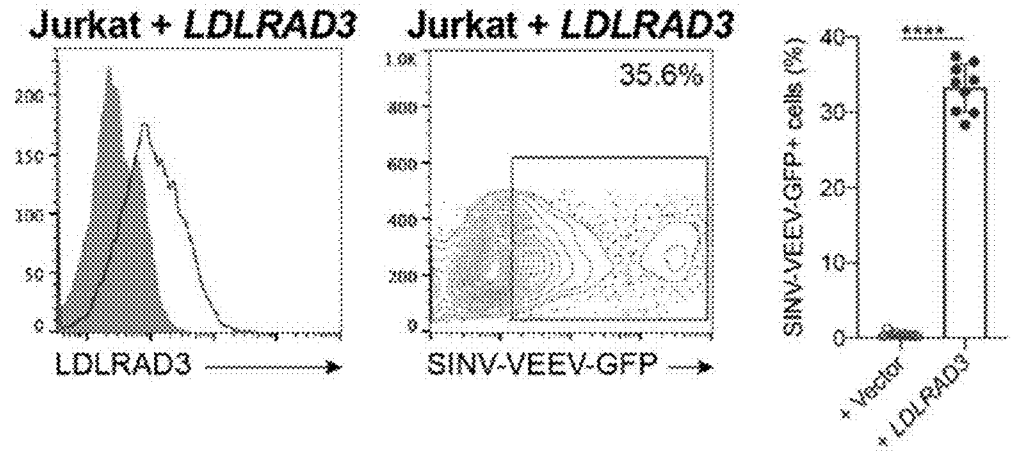
Figure 4C:
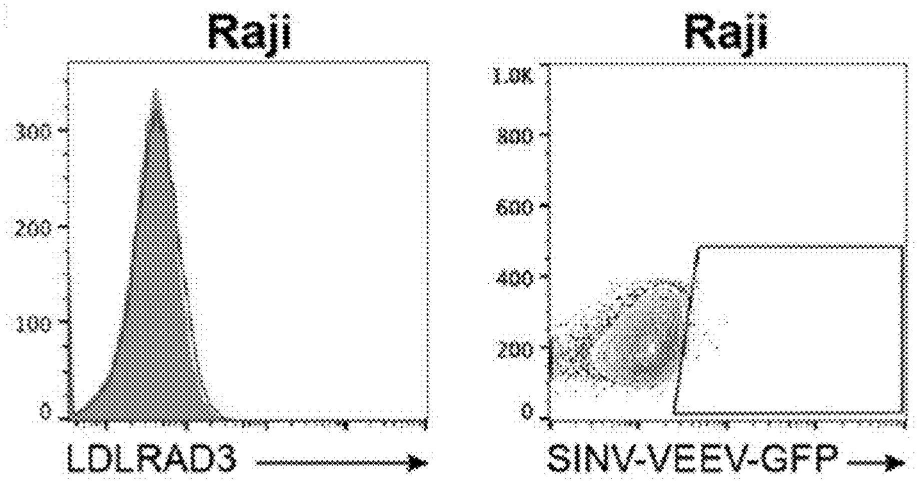
Figure 4D:
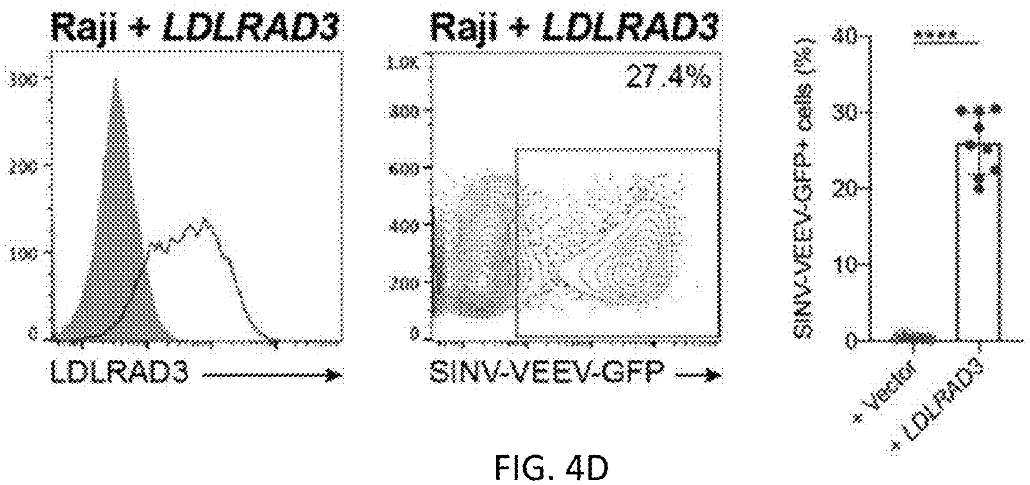
Figure 5A:
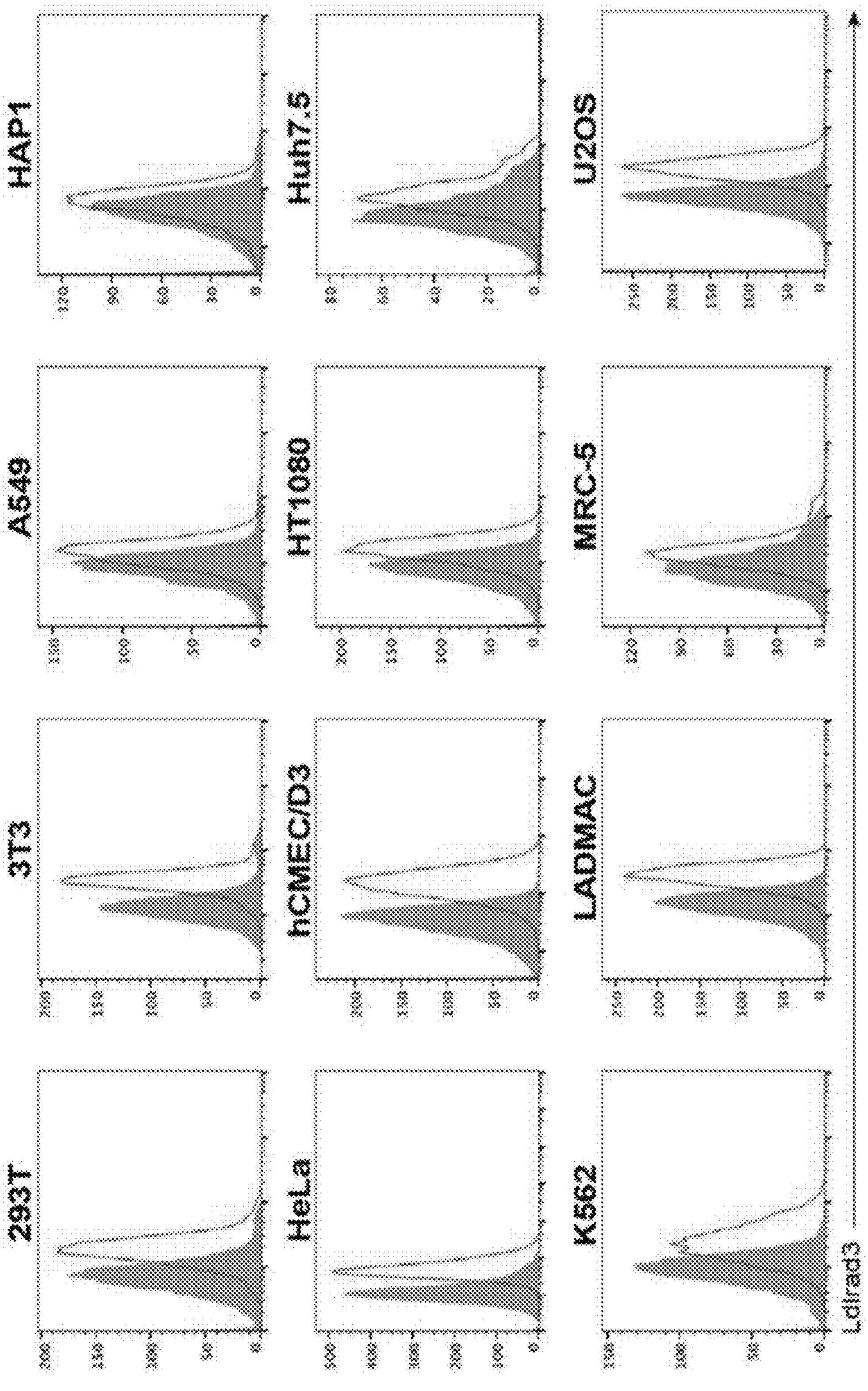
FIG. 5A-5B show surface expression of LDLRAD3 and VEEV infection in different cell lines.
Figure 5B:
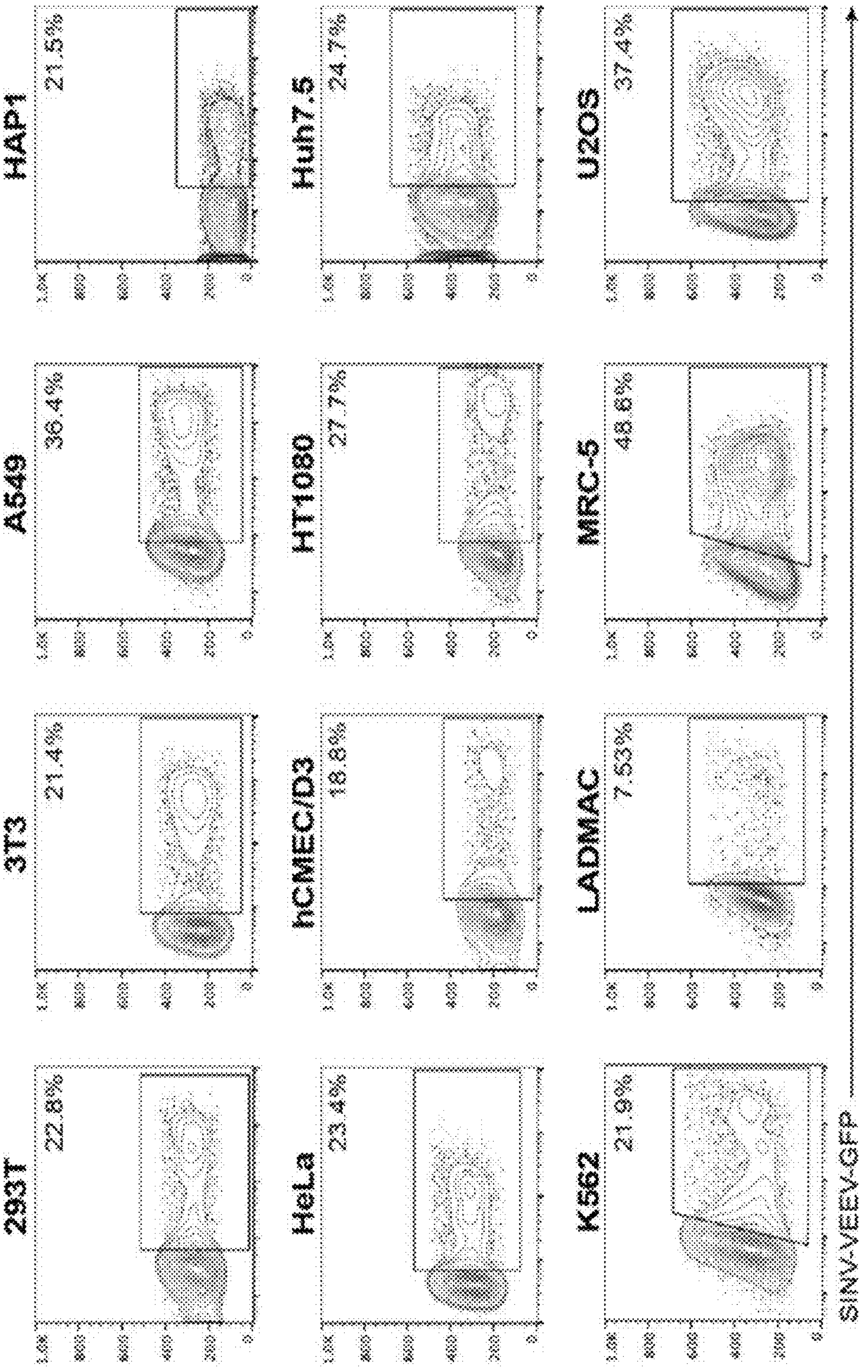
Figure 6A:
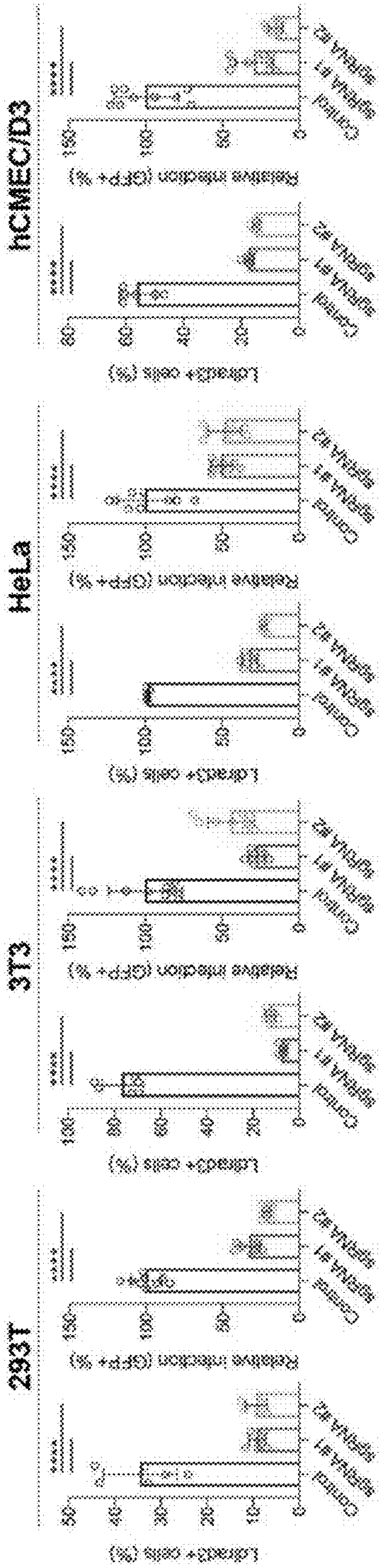
FIG. 6A-6B shows the Assessment of LDLRAD3 surface expression and VEEV infection in gene-edited cell lines and primary cells.
Figure 6B:
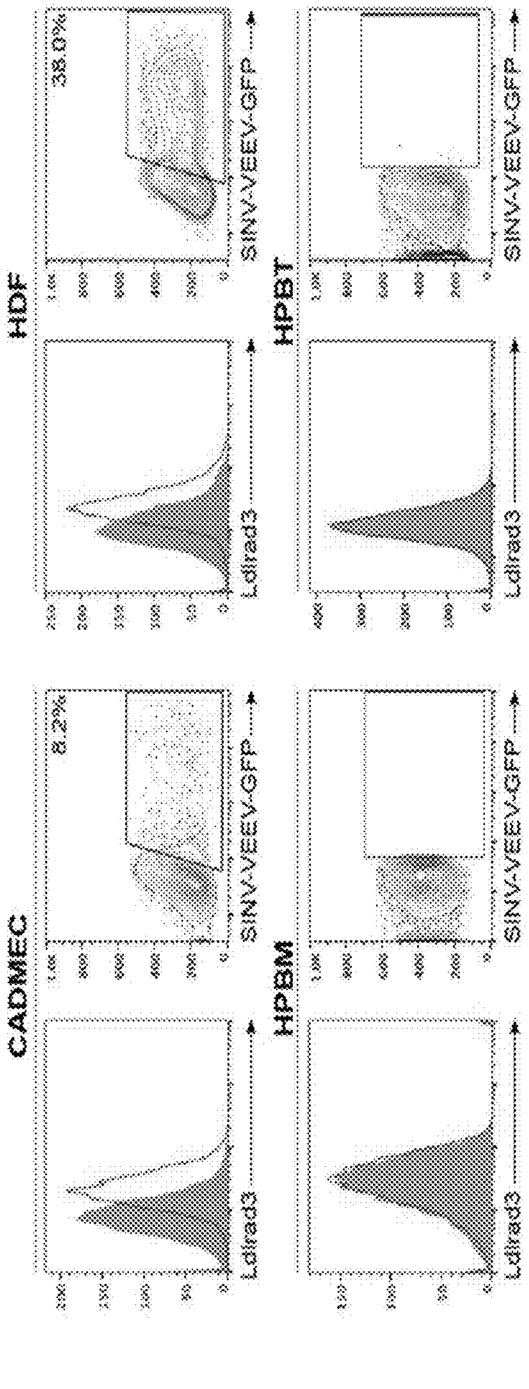

The relationship between LDLRAD3 expression and SINV-VEEV-GFP TrD infectivity was confirmed using a panel of human and mouse cell lines. Two human tumor cell lines (Jurkat and Raji cells) lack surface expression of LDLRAD3 and were resistant to SINV-VEEV-GFP TrD infection (FIG. 4A and FIG. 4C). Ectopic expression of LDLRAD3 resulted in a gain-of-infection phenotype (FIG. 4B and FIG. 4D). Twelve human and mouse cell lines that express LDLRAD3 were permissive for SINV-VEEV-GFP TrD infection (FIG. 5A-5B). When LDLRAD3 expression was reduced in a subset of these cells by gene editing, the level of infection by SINV-VEEV-GFP TrD infection decreased markedly (FIG. 6A). In additional experiments with primary cells, it was observed that human dermal fibroblast—but not peripheral blood monocytes and peripheral blood T cells-express LDLRAD3 and were permissive for infection with SINV-VEEV-GFP TrD (FIG. 6B).

Figure 7A:
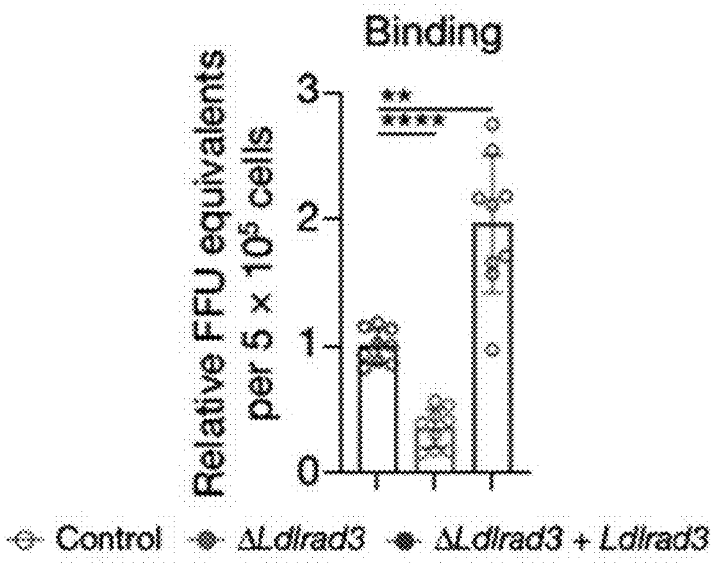
FIG. 7A-7F shows LDLRAD3 modulates VEEV attachment and internalization.
Figure 7B:
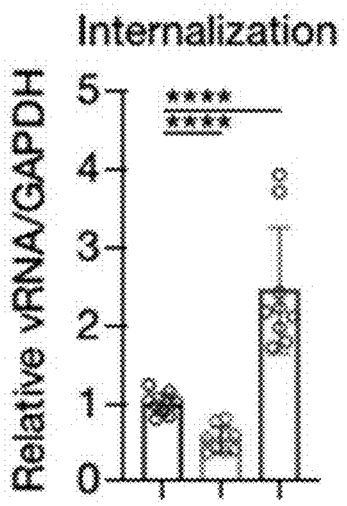

Because of its cell surface expression of LDLRAD3, it was hypothesized that this protein could function in VEEV entry. To test this idea, binding and internalization assays were performed with ΔB4galt7, ΔB4galt7 ΔLdlrad, and Ldlrad3-complemented ΔB4galt7 ΔLdlrad3 N2a cells. SINV-VEEV TrD showed reduced binding at 4° C. to ΔB4galt7 ΔLdlrad3 cells compared to control ΔB4galt7 N2a cells and increased binding to cells that express LDLRAD3 (FIG. 7A). When virus internalization assays were performed at 37° C., less SINV-VEEV TrD RNA was measured in ΔB4galt7 ΔLdlrad3 cells, and increased levels were detected in cells that express LDLRAD3 (FIG. 7B).

Figure 7C:
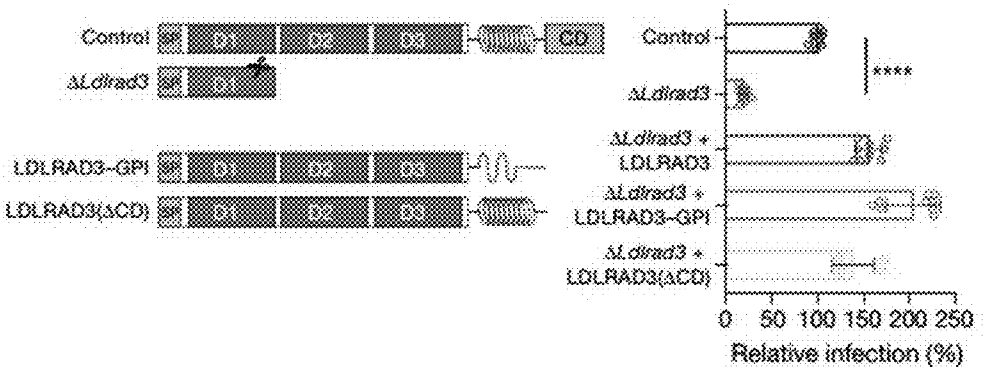
Figure 7D:
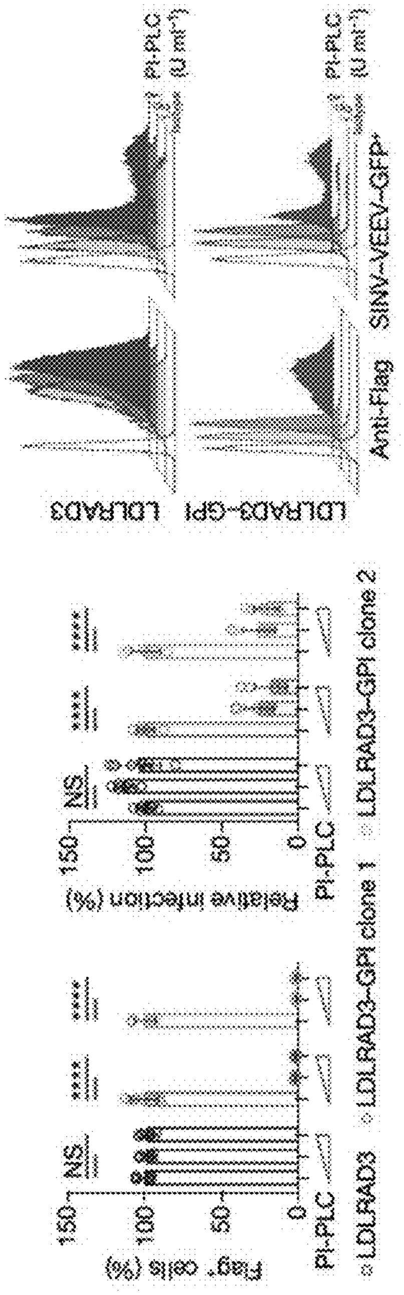
Figure 7E:
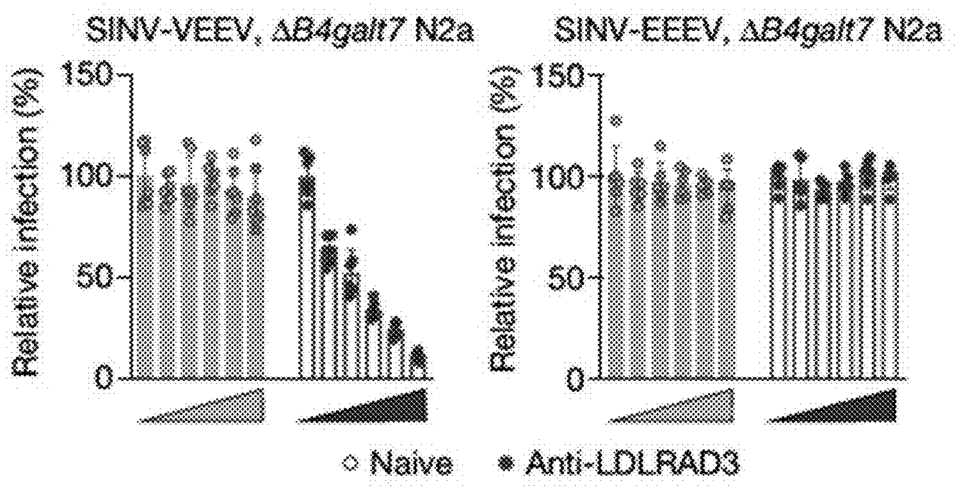
Figure 7F:
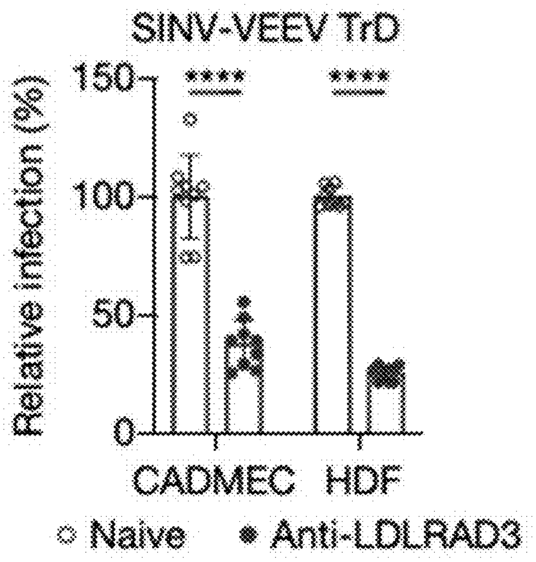

To establish the importance of the LDLRAD3 ectodomain for VEEV interaction, variants with glycophosphatidylinositol (GPI) anchors or that lack a cytoplasmic domain (ΔCD) were engineered for complementation (FIG. 7C). Notably, ΔB4galt7 ΔLdlrad3 cells complemented with LDLRAD3-GPI and LDLRAD(ΔCD) restored infection with SINV-VEEV-GFP TrD. Treatment with phospholipase C of ΔB4galt7 ΔLdlrad3 N2a cells complemented with the GPI-anchored, but not the transmembrane form of LDLRAD3, reduced infection with SINV-VEEV-GFP TrD (FIG. 7D) Moreover, pretreatment of ΔB4galt7 N2a cells with anti-LDLRAD3 immune serum blocked infection with SINV-VEEV-GFP but not SINV-EEEV-GFP TrD (FIG. 7E). Additionally, pre-treatment of primary cells with anti-LDLRAD3 immune serum reduced infection with SINV-VEEV-GFP TrD (FIG. 7F).

Figure 8D:
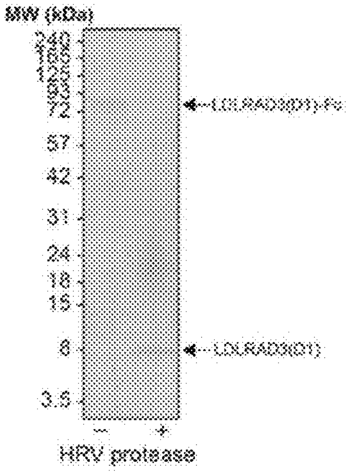
Figure 8E:
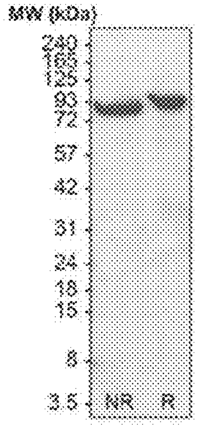
Figure 8F:
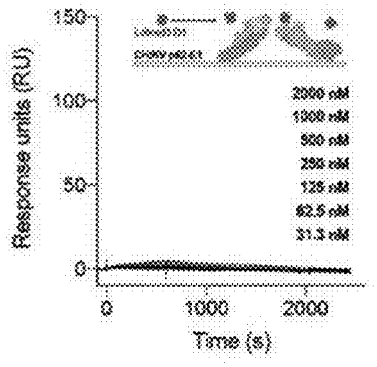
Figure 9A:
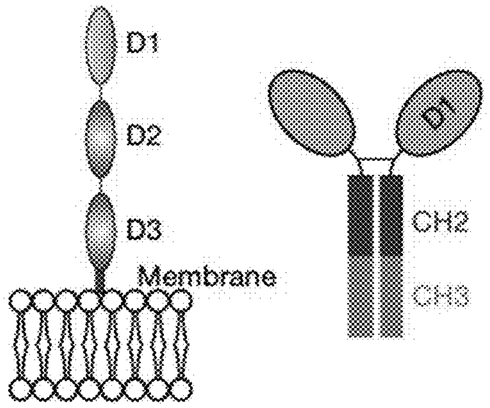
FIG. 9A-9J show direct binding of LDLRAD3 to VEEV.
Figure 9B:
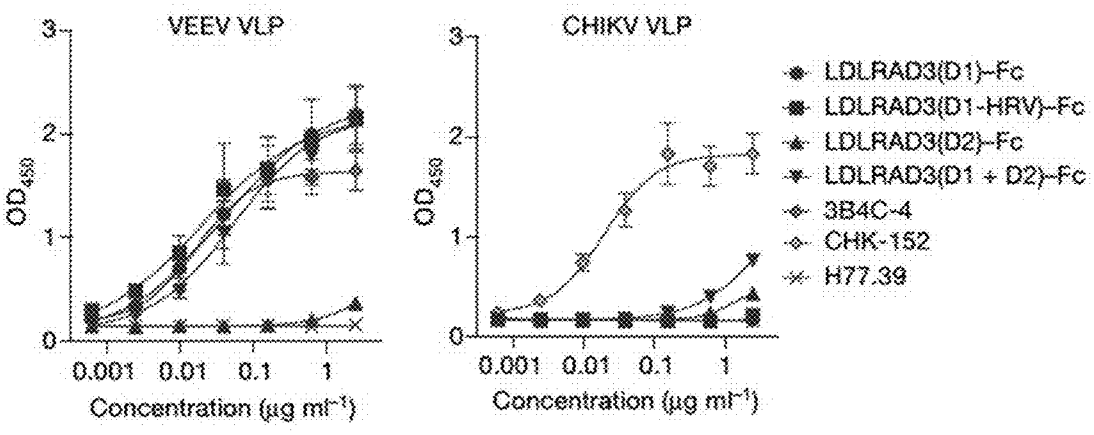
Figure 9C:
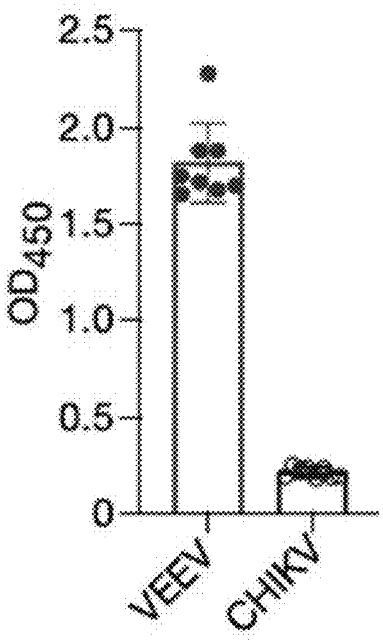
Figure 9D:
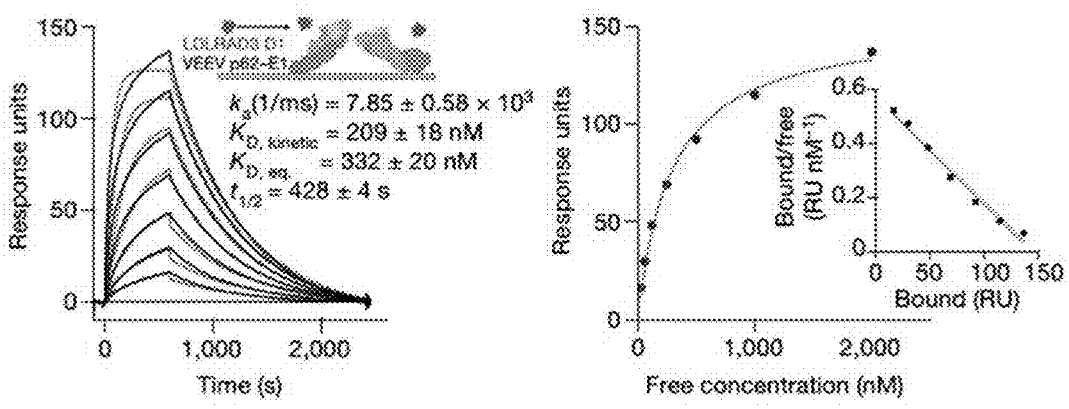

LDLRAD3 has three LDL-receptor class A extracellular domains (FIG. 9A, left panel). Because domain 1 (D1) is predicted to be the most membrane-distal, it was hypothesized it might interact with VEEV. To test this idea, Fc fusion proteins were generated with D1, domain 2 (D2), D1+D2, or a human rhinovirus 3C protease-cleavable D1 variant (D1-HRV) of mouse LDLRAD3 linked to the mouse IgG2b Fc domain (FIG. 9A and FIG. 8A). The LDLRAD3 (D1)-Fc variants and LDLRAD3(D1+D2)-Fc fusion protein bound to VEEV but not to CHIKV virus-like particles (VLPs); however, LDLRAD3-D2-Fc did not bind to VEEV VLPs (FIG. 9B). A similar fusion protein with human LDLRAD3(D1) linked to the human Fc domain of human IgG1 Fc domain also bound to VEEV but not to CHIKV VLPs (FIG. 9C and FIG. 8B-8C). Monovalent LDLRAD3 (D1) was also generated by cleaving the Fc moiety (FIG. 8D) and analyzed binding to purified VEEV p62-E1 (FIG. 8E). A slow association rate, a long half-life, and an affinity of 209 nM was found (FIG. 9D). Monovalent LDLRAD3 (D1) did not bind to CHIKV p62-E1 (FIG. 8F).

Figure 8G:
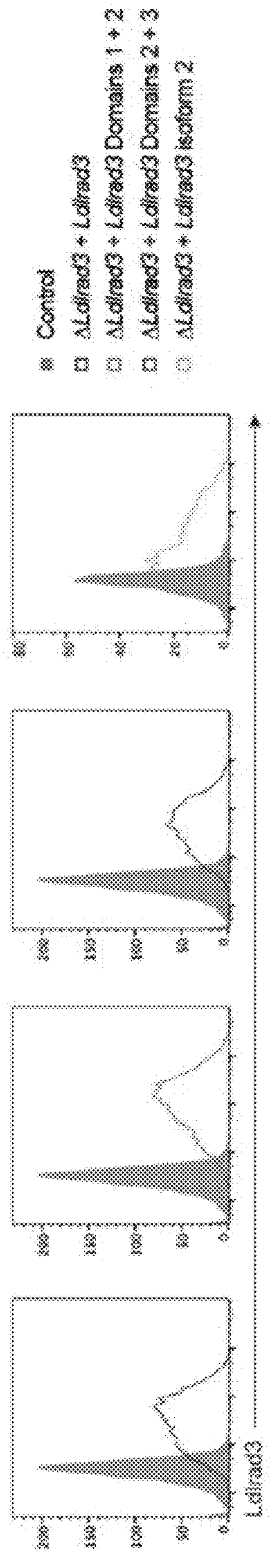
Figure 8H:
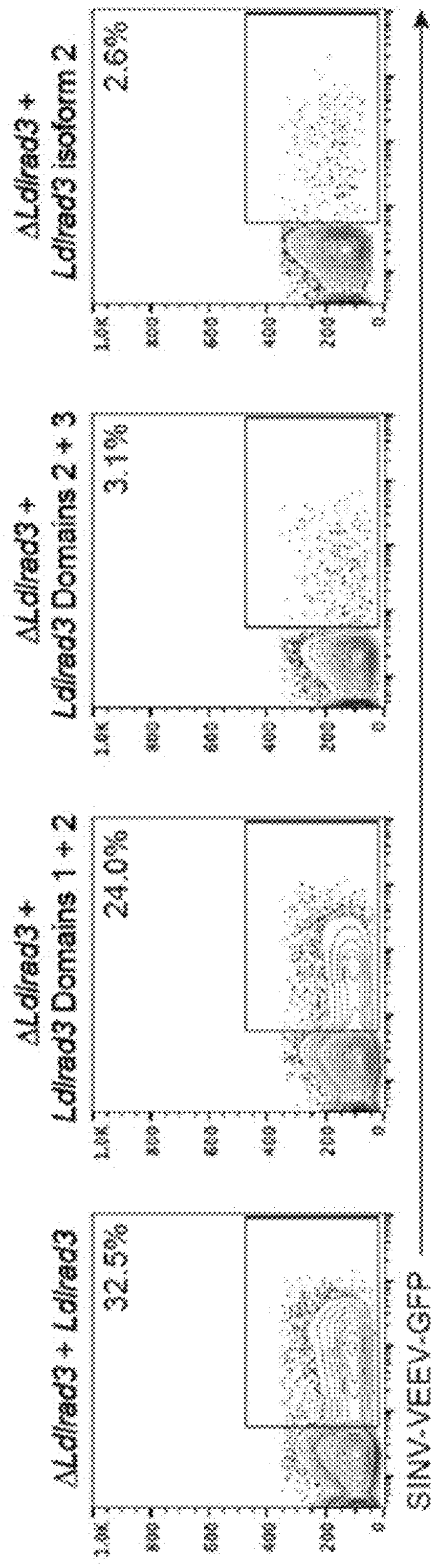
Figure 8I:
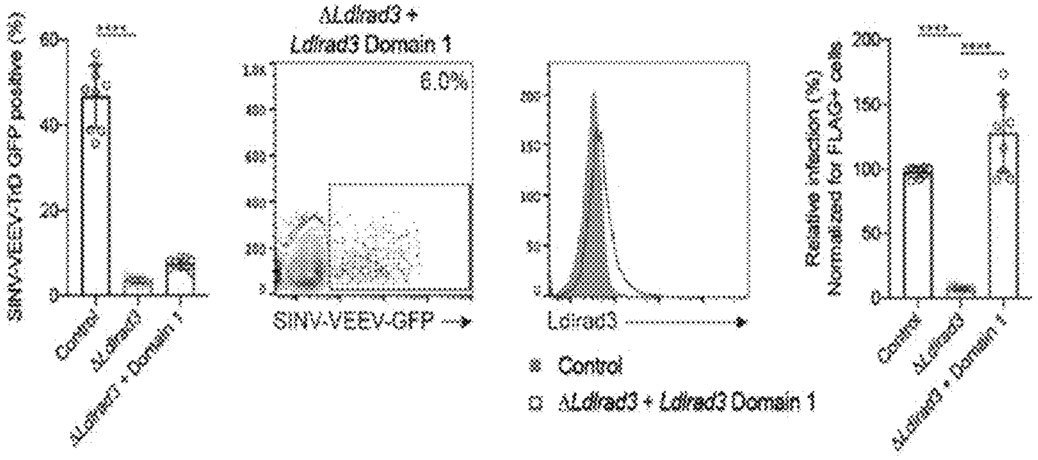
Figure 9E:
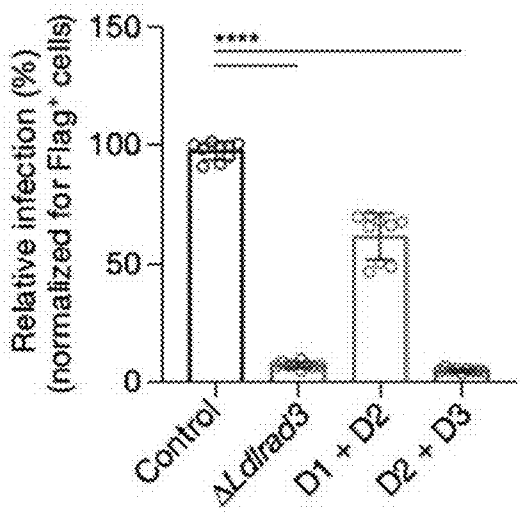
Figure 9F:
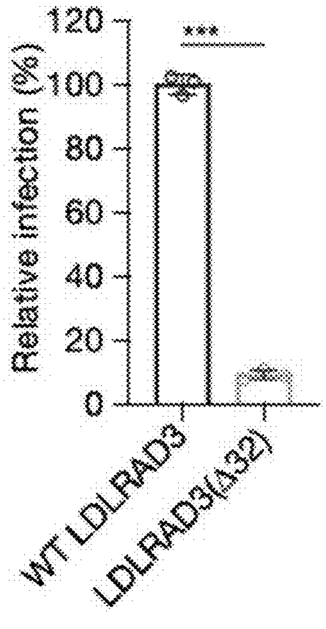

To confirm the importance of D1 of LDLRAD3 for VEEV infection, we complemented ΔB4galt7 ΔLdlrad3 N2a cells with LDLRAD3 truncation mutants that include D1 only, D1 and D2, or D2 and domain 3 (D3). Surface expression of LDLRAD3 variants was confirmed using an N-terminal tag placed downstream of the signal peptide, although the D1-truncated variant was expressed at lower levels (FIG. 8G and FIG. 8I). Whereas D1 and D2 supported infection with SINV-VEEV-GFP TrD, D2 and D3 did not—consistent with a role for D1 in binding VEEV (FIG. 9E and FIG. 8H). Despite being expressed at lower levels, D1 alone still promoted infection with SINV-VEEV-GFP TrD (FIG. 8I). It was also assessed whether the shorter isoform of LDLRAD3 with a 32-amino acid deletion near the N-terminal region (Δ32; FIG. 10) could support infection with SINV-VEEV-GFP TrD. Whereas expression of full-length LDLRAD3 restored infection in ΔB4galt7 ΔLdlrad3 N2a cells, Δ32 LDLRAD3 did not (FIG. 9F).

Figure 9G:
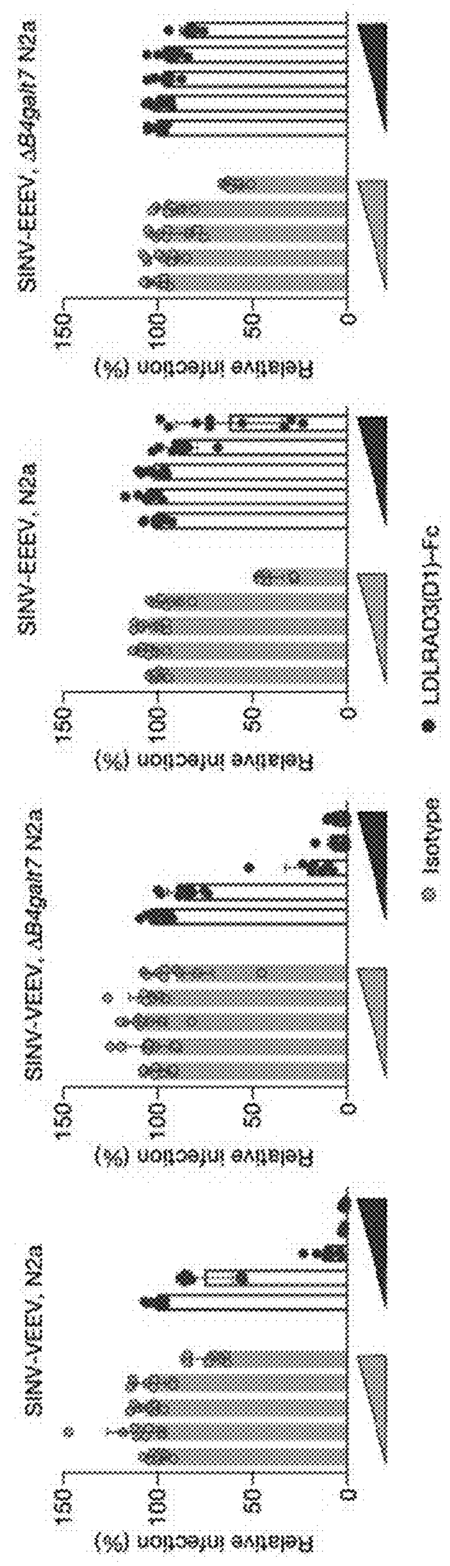
Figure 9H:
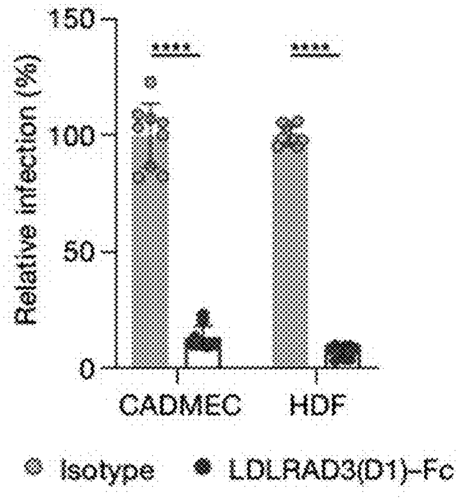
Figure 9I:
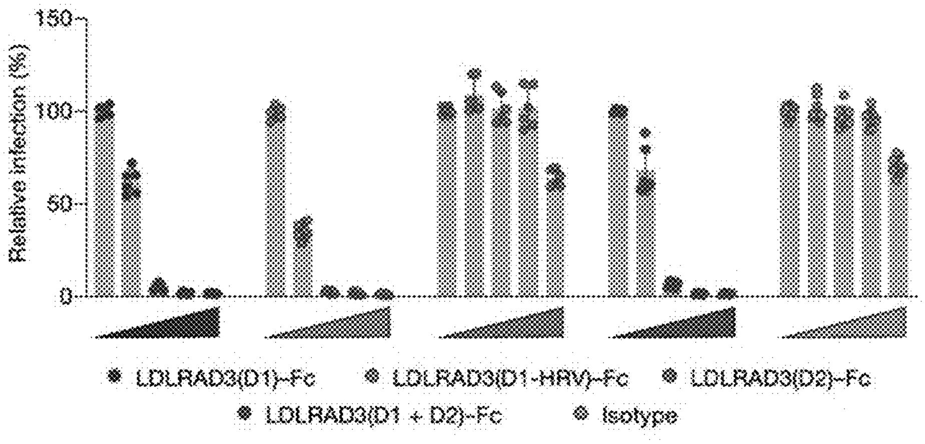
Figure 9J:
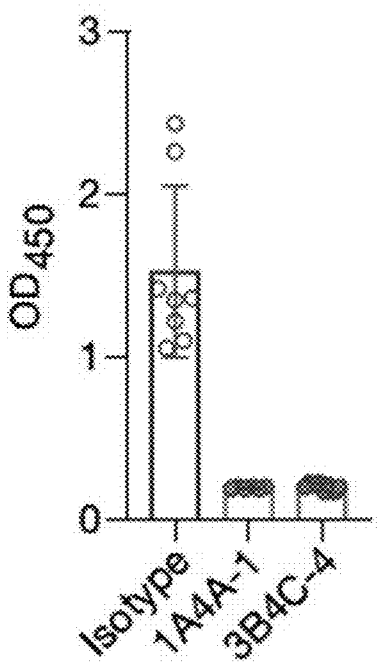

It was evaluated whether the LDLRAD3-D1-Fc protein could directly block infection. SINV-VEEV-GFP TrD was pre-incubated with LDLRAD3(D1)-Fc protein before addition parental or ΔB4galt7 N2a cells. In both cell types, LDLRAD3(D1)-Fc dose-dependently inhibited infection with SINV-VEEV-GFP TrD; no inhibition of SINV-EEEV was observed (FIG. 9G). Consistent with these data, LDLRAD3(D1)-Fc blocked infection of primary cells with SINV-VEEV-GFP TrD (FIG. 9H). LDLRAD3(D1+D2)-Fc, but not LDLRAD3(D2)-Fc, inhibited infection by SINV-VEEV-GFP TrD comparably to LDLRAD3(D1)-Fc (FIG. 9I). We next tested whether anti-VEEV monoclonal antibodies that bound epitopes within the E2 protein altered LDLRAD3(D1)-Fc binding to VEEV. The anti-VEEV mAbs 3B4C-4 and 1A4A-1 inhibited binding of LDLRAD3-Fc to VEEV VLPs (FIG. 9J).

Figure 10A:
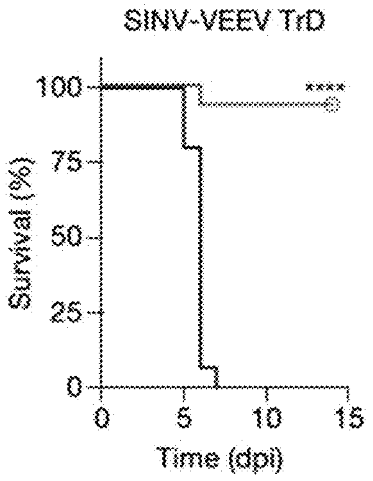
FIG. 10A-10J show LDLRAD3 is required for VEEV pathogenesis in mice. Four-week-old C57BL/6J mice were administered 750 μg of anti-IFNAR1 monoclonal antibody via intraperitoneal (i.p.) route 24 h before virus inoculation.
Figure 10B:
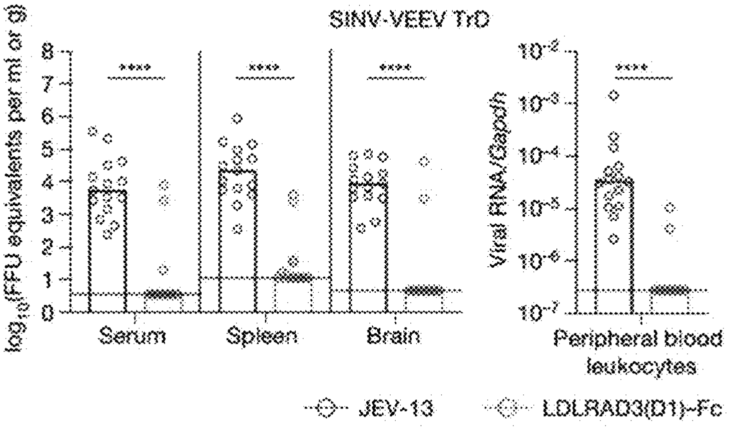
Figure 10C:
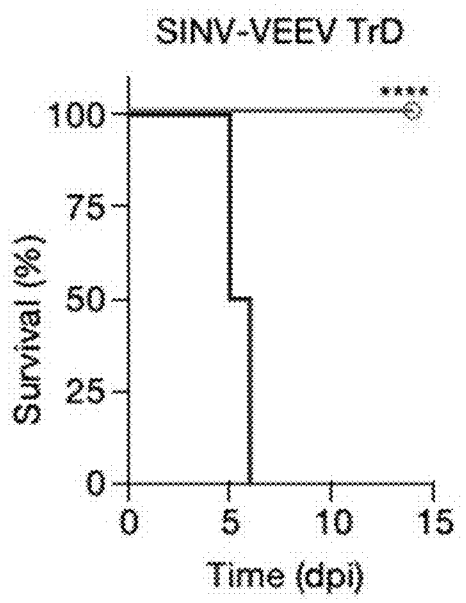
Figure 10D:
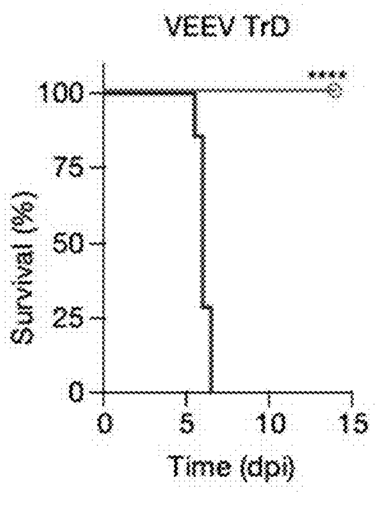
Figure 10E:
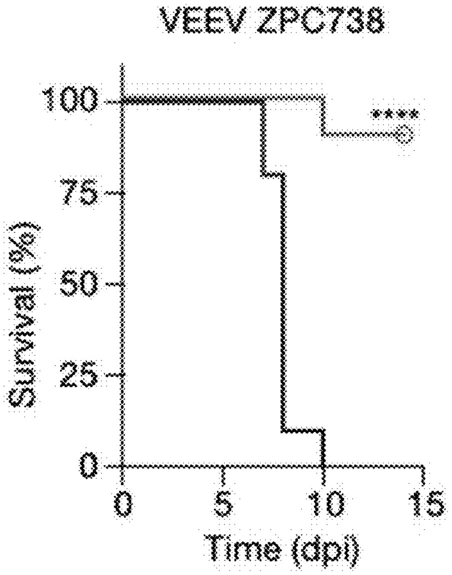
Figure 10F:
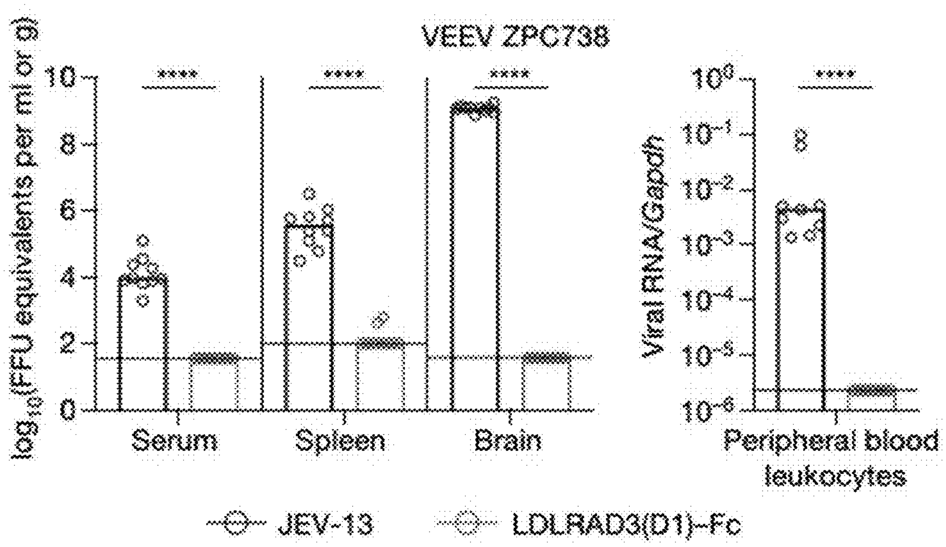
Figure 10G:
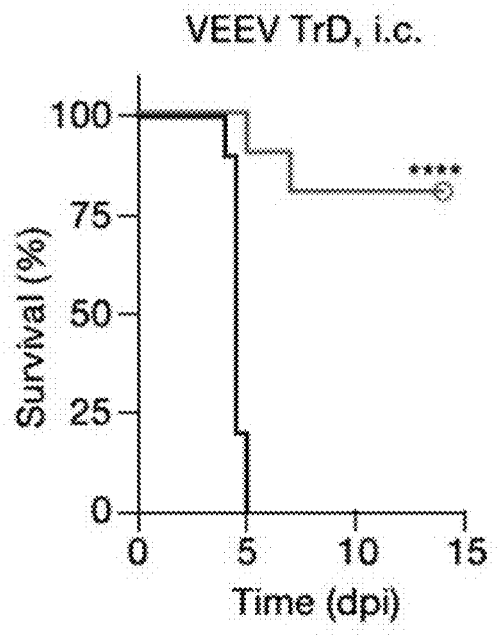
Figure 10H:
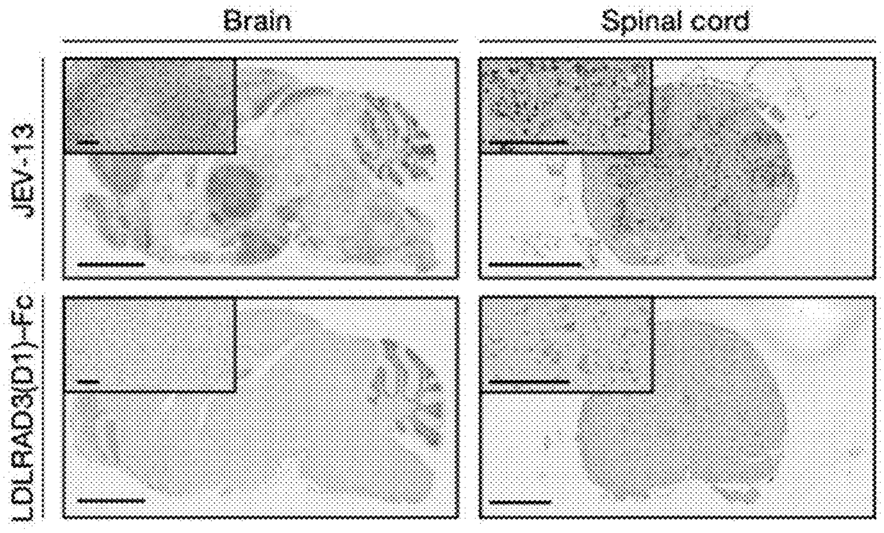
Figure 10I:
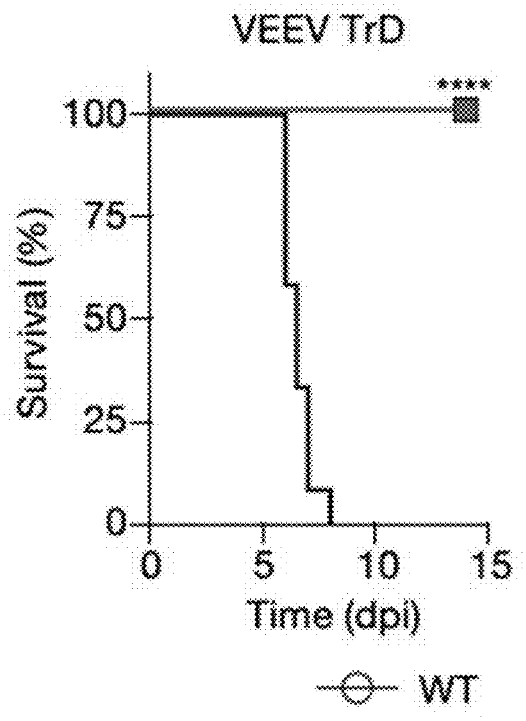
Figure 10J:
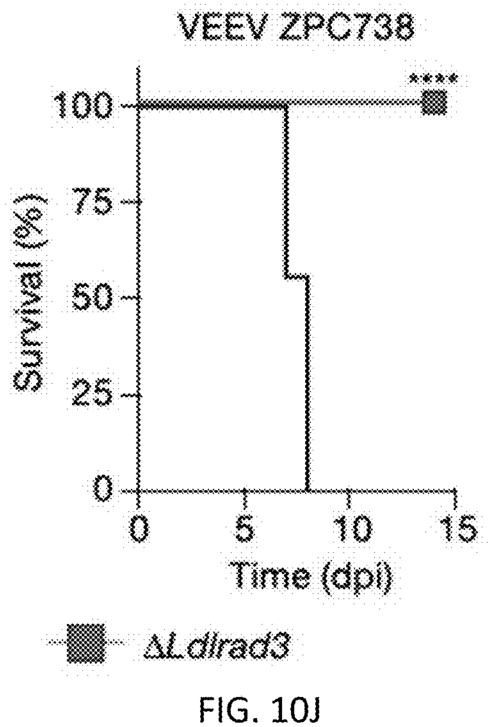
Figure 11A:
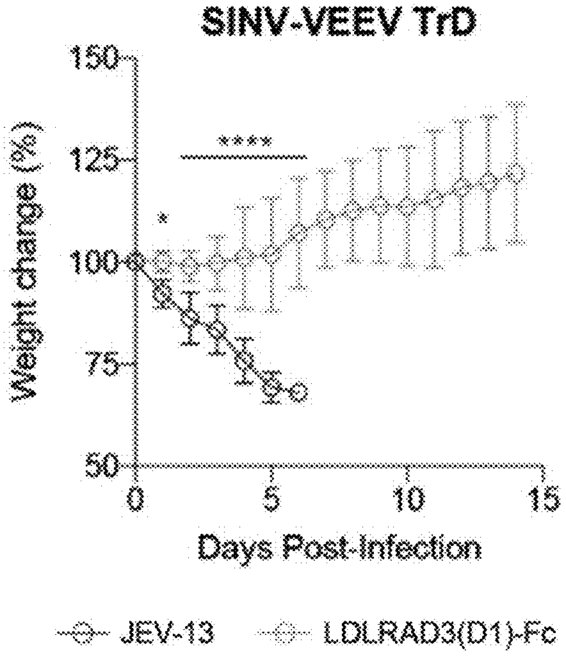
FIG. 11A-11F show weight change and clinical assessment of C57BL/6J and CD-1 mice treated with LDLRAD3 (D1)-Fc. Four-week-old C57BL/6J mice were administered 750 μg of anti-IFNAR1 monoclonal antibody via intraperitoneal (i.p.) route 24 h before virus inoculation.
Figure 11B:
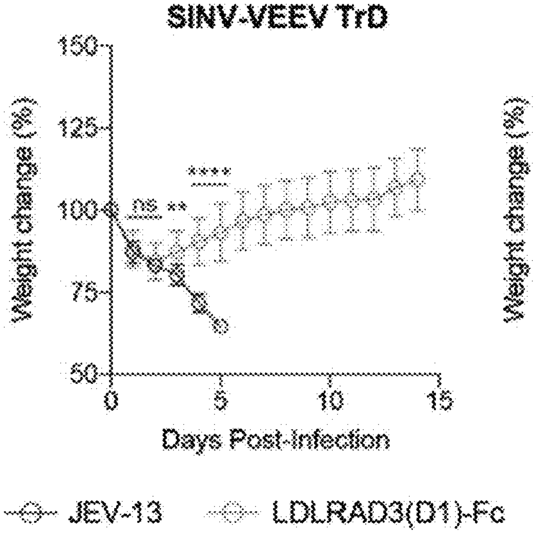
Figure 11C:
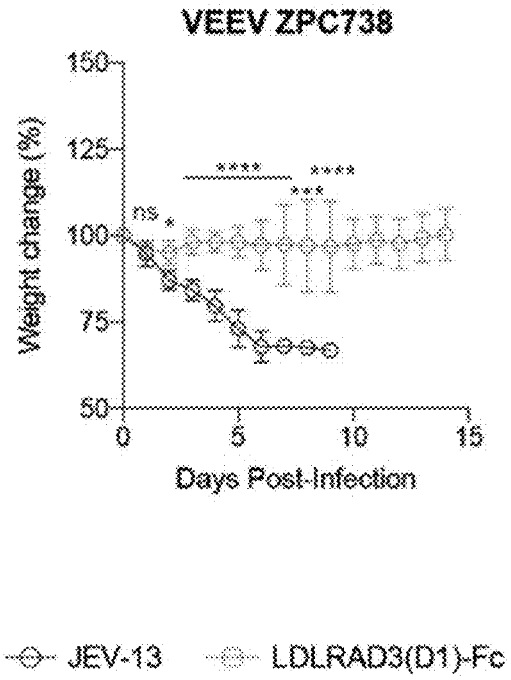
Figure 11D:
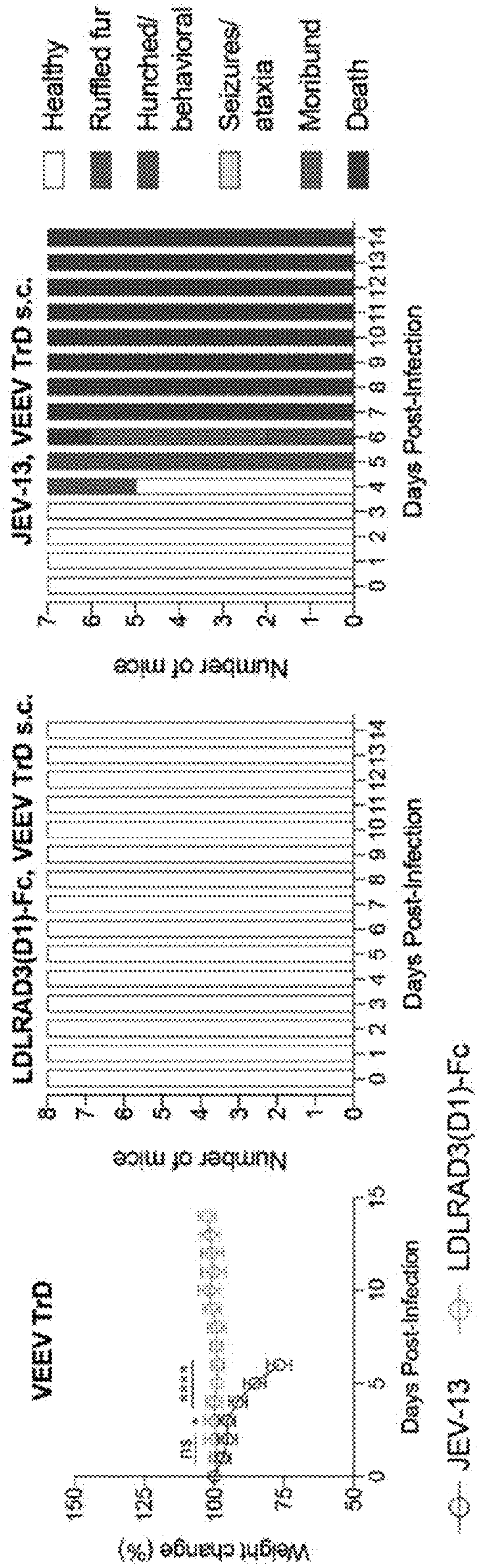
Figure 11E:
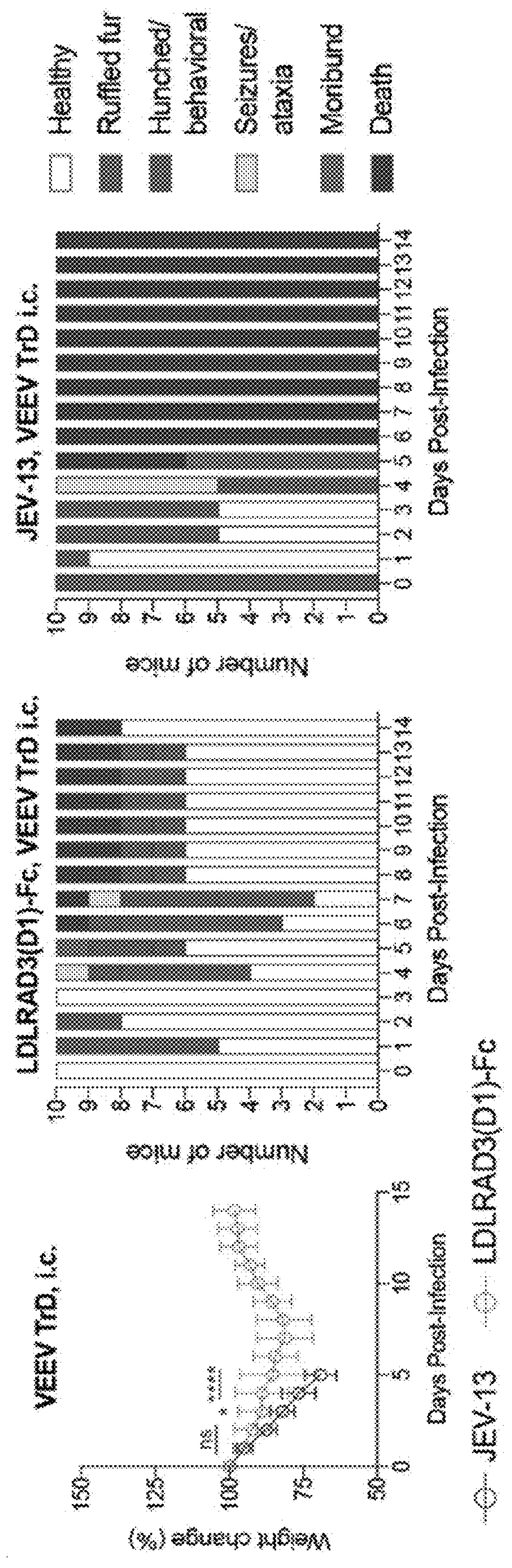
Figure 11F:
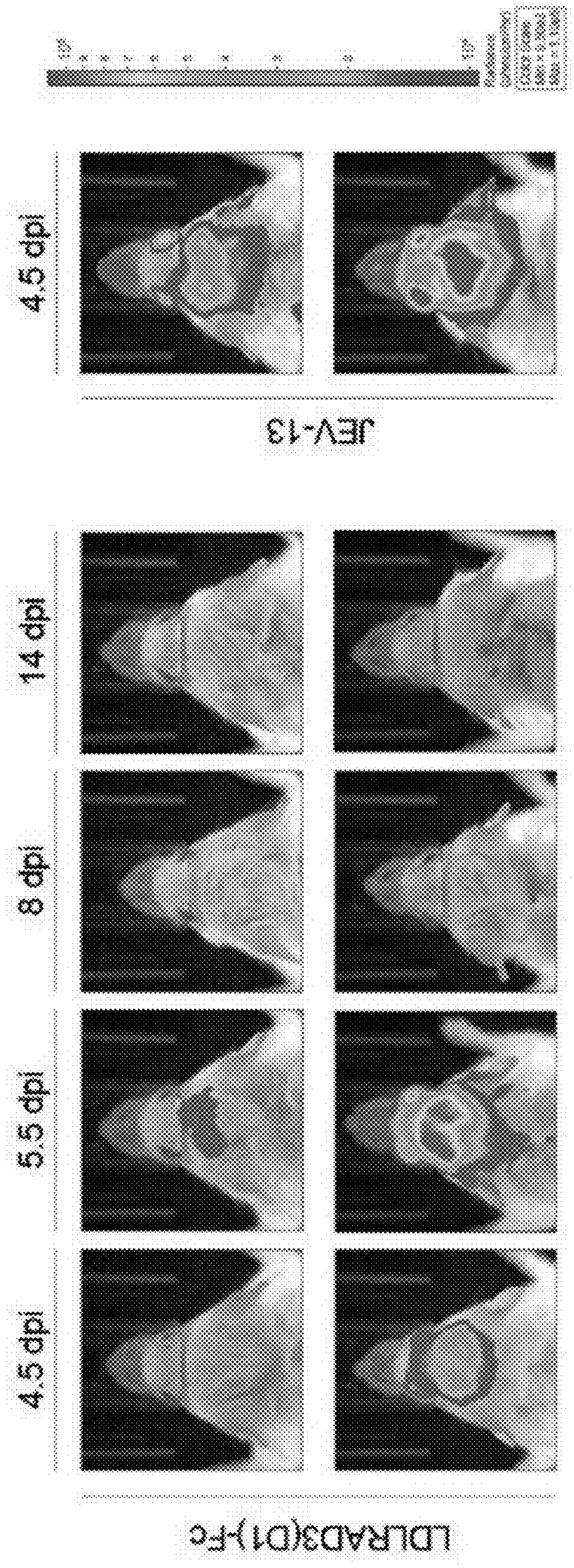
Figure 12A:
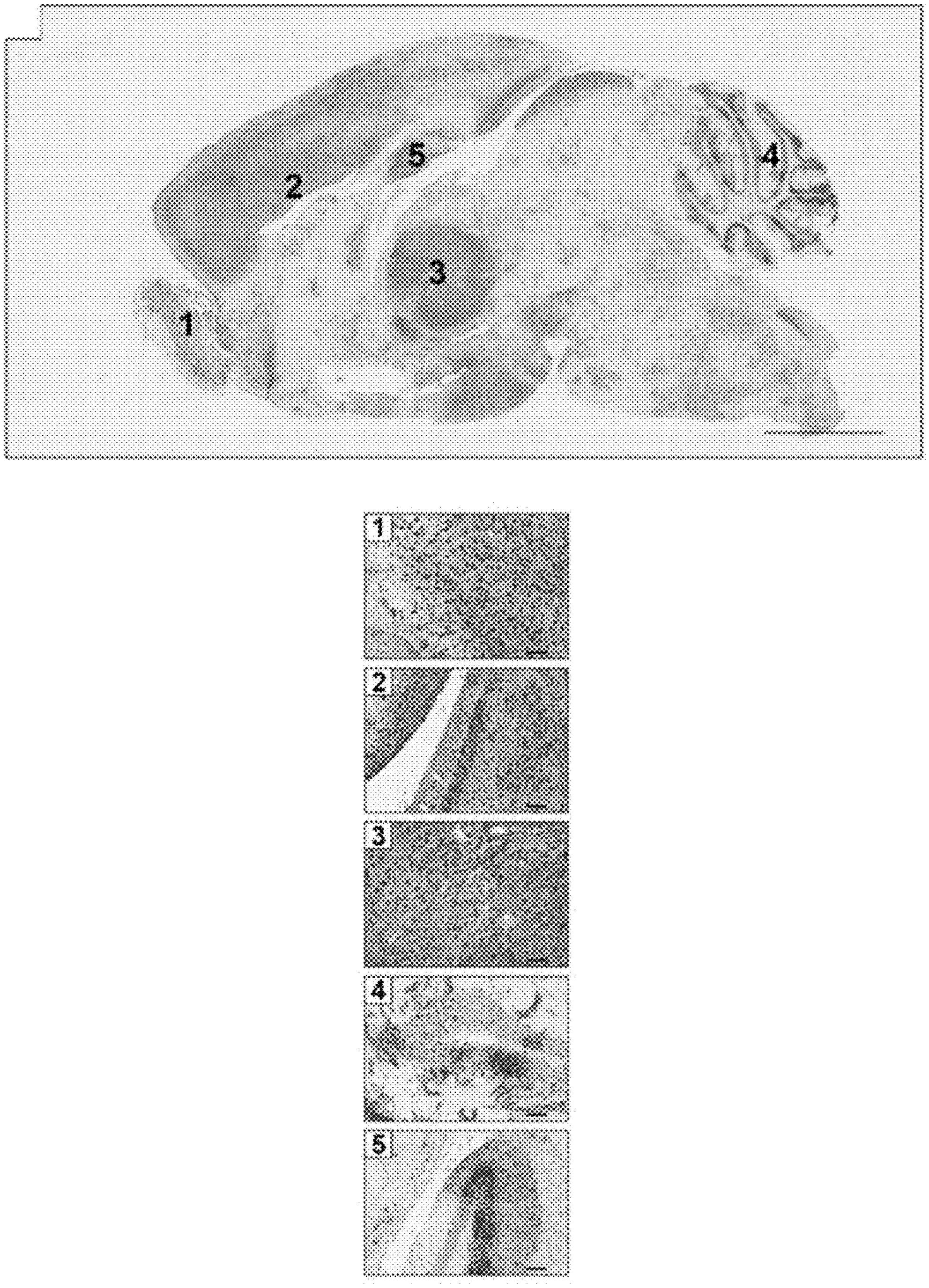
Figure 12B:
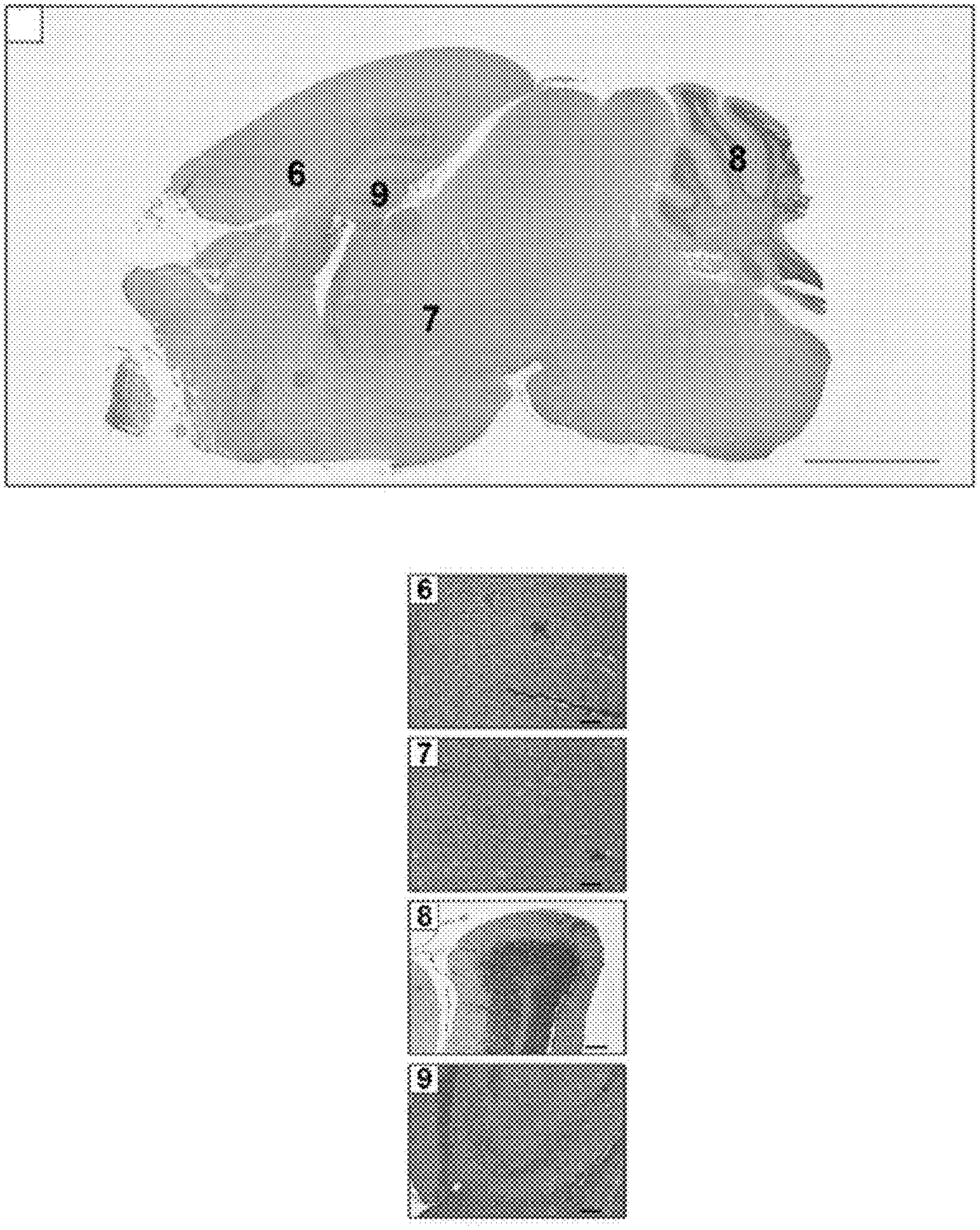
FIG. 12B shows six-week-old C57BL/6J mice were administered 250 μg of isotype control monoclonal antibody JEV-13 via intraperitoneal route 6 h before subcutaneous inoculation of $10^2$ FFU of VEEV ZPC738.
Figure 12C:
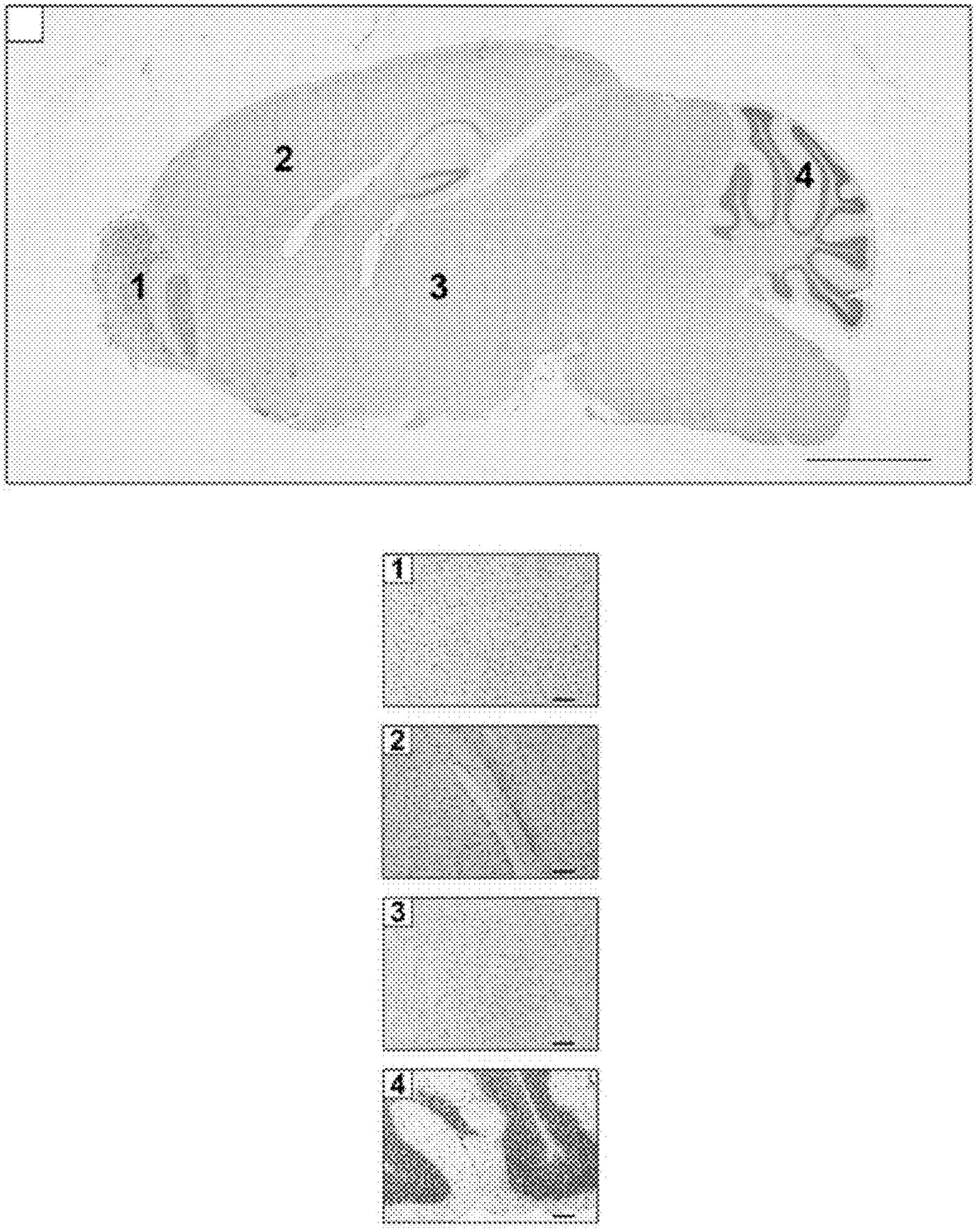
FIG. 12C shows six-week-old C57BL/6J mice were administered 250 μg of LDLRAD3(D1)-Fc via intraperitoneal route 6 h before subcutaneous inoculation of $10^2$ FFU of VEEV ZPC738.
Figure 12D:
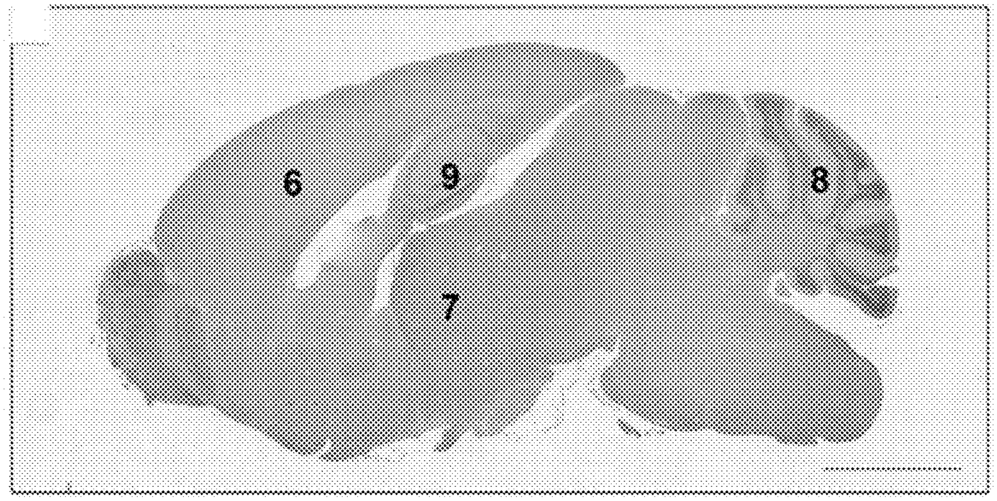
FIG. 12D shows six-week-old C57BL/6J mice were administered 250 μg of LDLRAD3(D1)-Fc via intraperitoneal route 6 h before subcutaneous inoculation of $10^2$ FFU of VEEV ZPC738. Six days post-infection, brain tissues were collected, fixed, paraffin embedded and subjected to RNA in situ hybridization using VEEV ZPC738-specific probes (FIG. 12A, C) and haematoxylin and eosin staining (FIG. 12B, D). Scale bars, 2 mm. Representative high-power (10×) magnification insets of the olfactory bulb (1), cortex/midbrain (2), thalamus (3), cerebellum (4) and hippocampus (5) are shown for isotype control (a, top) or LDLRAD3(D1)-Fc (FIG. 12C, bottom) treated mice. Scale bars, 100 μm. Haematoxylin and eosin staining of brain sections from isotype control-(b) or LDLRAD3(D1)-Fc (d)-treated mice. Scale bars, 2 mm. Representative high-power (10×) magnification insets of the cerebral cortex (6), thalamus (7), cerebellum (8) and hippocampus (9) are shown for isotype control-(b, top) or LDLRAD3(D1)-Fc (d, bottom)-treated mice. Scale bars, 100 μm. Representative images from one experiment (n=5 per group) are shown.
Figure 12D:
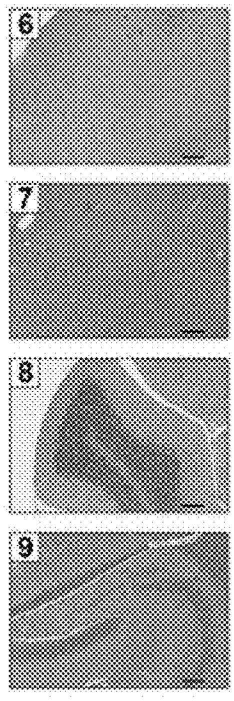

To assess the physiological role of the interaction between LDLRAD3 and VEEV, it was evaluated whether prophylaxis with LDLRAD3(D1)-Fc could diminish infection by SINV-VEEV TrD in immunocompromised mice or by pathogenic VEEV TrD and ZPC738 strains in immunocompetent mice. For infections with SINV-VEEV TrD, C57BL/6J mice were treated one day prior to infection with anti-IFNAR1 mAb, which enables the chimeric virus to overcome innate immune responses. Mice subsequently were administered 250 μg of LDLRAD3(D1)-Fc or an isotype control mAb to the mice 6 h before inoculation with SINV-VEEV TrD. Prophylaxis with LDLRAD3(D1)-Fc protected against weight loss and lethality (FIG. 10A and FIG. 11A). More notably, at 4 days after infection SINV-VEEV TrD viral RNA was largely absent from sites normally targeted by VEEV (including the brain) in mice that were administered LDLRAD3(D1)-Fc, whereas high levels were present in mice treated with the control mAb (FIG. 10B). Administration of LDLRAD3(D1)-Fc at 24 h after infection also protected mice against weight loss and lethality (FIG. 10C and FIG. 11B). Analogously, prophylaxis of C57BL/6J and CD-1 mice with LDLRAD3(D1)-Fc prevented morbidity and mortality by pathogenic VEEV TrD and VEEV ZPC738 strains, respectively (FIGS. 10D-10E and FIGS. 11C-11D), and VEEV ZPC738 viral RNA levels were abrogated in mice treated with LDLRAD3(D1)-Fc (FIGS. 10F-10G and FIG. 12A and FIG. 12C). Histological evaluation of brains infected with VEEV ZPC738 showed neuronal injury and hemorrhage, which was absent in mice treated with LDLRAD3(D1)-Fc (FIG. 12B and FIG. 12D). Remarkably, treatment with LDLRAD3(D1)-Fc via intraperitoneal injection protected mice against intracranial challenge with VEEV TrD (FIG. 10G and FIG. 11E-11F).

Figure 13A:
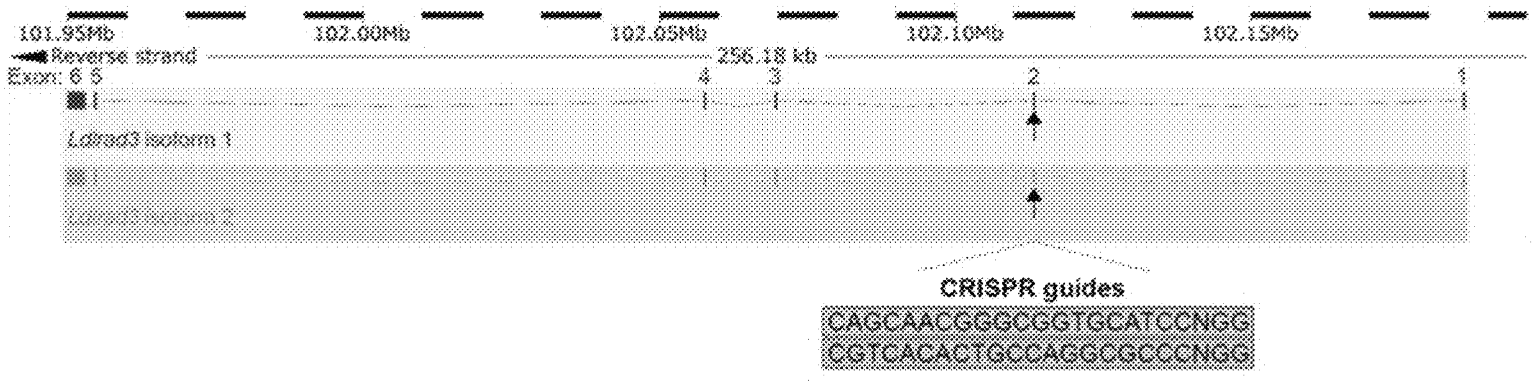
FIG. 13A-13D show generation and clinical assessment of C57BL/6 mice with deletions in Ldlrad3 by CRISPR-Cas9 gene targeting.
Figure 13B:
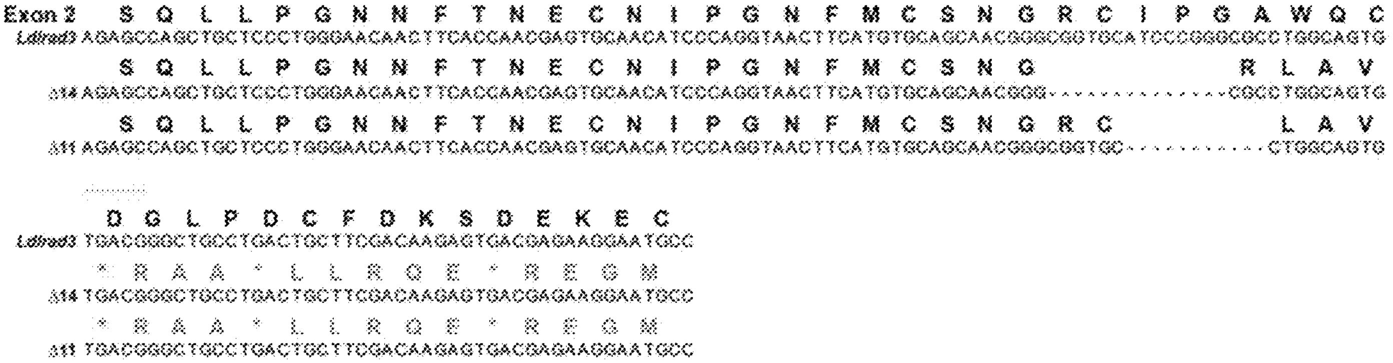
Figure 13C:
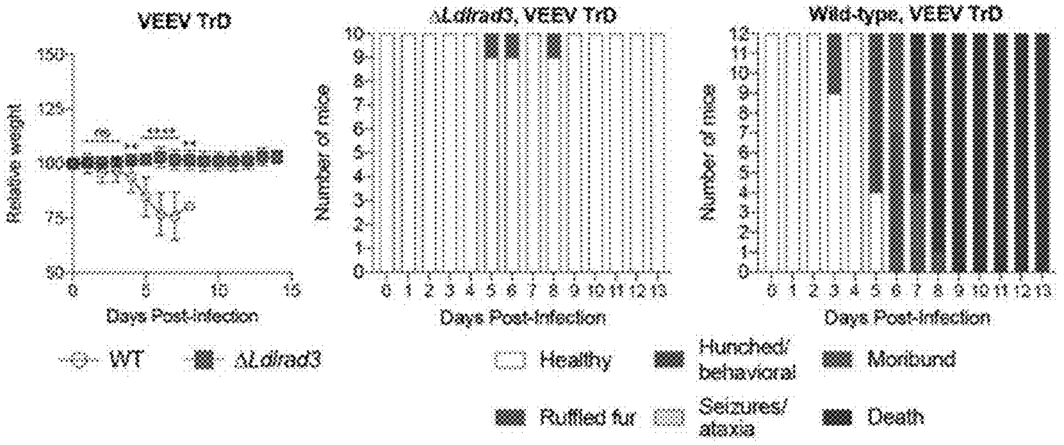
Figure 13D:
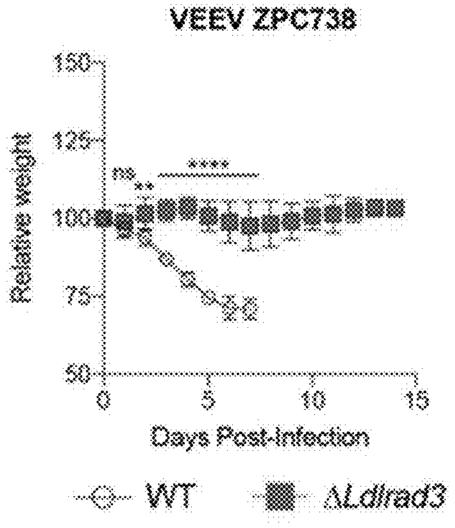

To corroborate these findings, C57BL/6J mice with deletions in Ldlrad3 were generated by gene editing. sgRNA were designed to target a region of Ldlrad3 corresponding to D1 (FIG. 13A). One sgRNA gave rise to two out-of-frame deletion variants (Δ11 and Δ14 nucleotides) (FIG. 13B). Founder mice were bred as compound heterozygotes or homozygotes for experimentation. All mice with Ldlrad3 gene deletions were resistant to challenge with VEEV TrD or ZPC738 and showed virtually no weight loss, mortality, or clinical disease whereas control mice succumbed to infection (FIGS. 10I-10J and FIGS. 13C-13D).

Figure 14A:
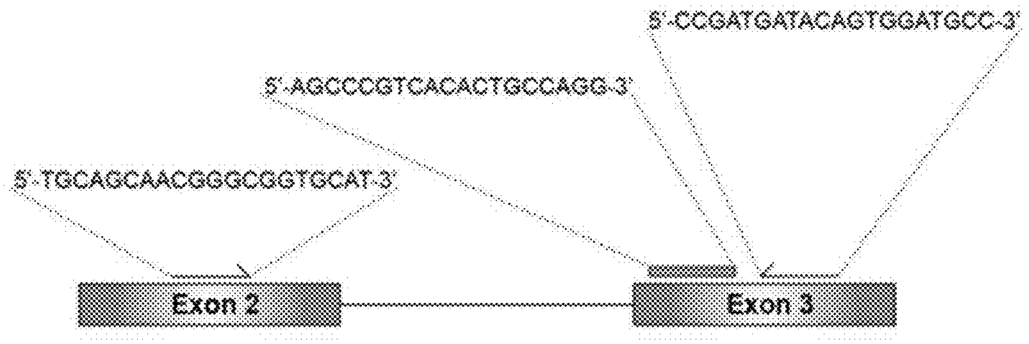
Figure 14B:
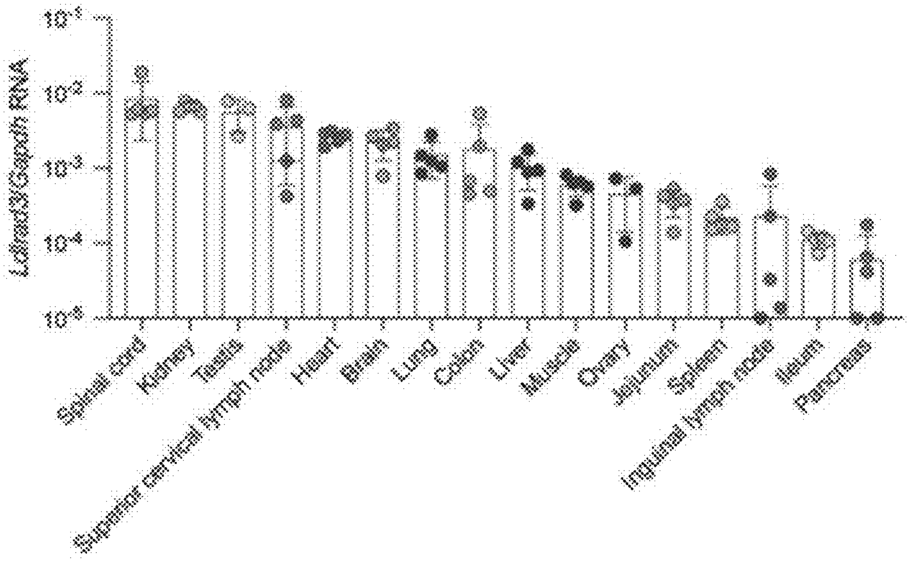
FIG. 14B shows the profile of Ldlrad3 mRNA expression in different mice tissues.
Figure 14C:
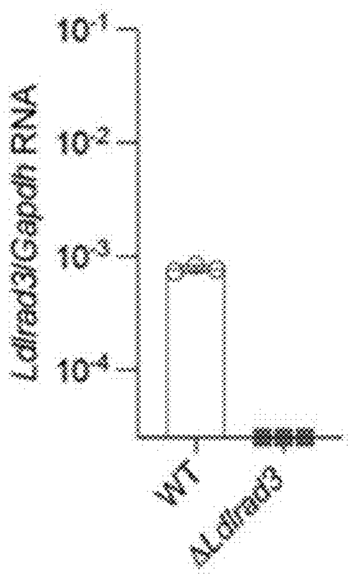
FIG. 14C shows the profile of Ldlrad3 mRNA expression in the brains of wild-type and Ldlrad3-deficient mice. Data are the mean±s.d. of one experiment (b, spinal cord, kidney, superior cervical lymph node, heart, brain, lung, colon, liver, muscle, jejunum, spleen, inguinal lymph node, ileum and pancreas, n=5; testis and ovary, n=3; c, n=3).
Figure 14D:
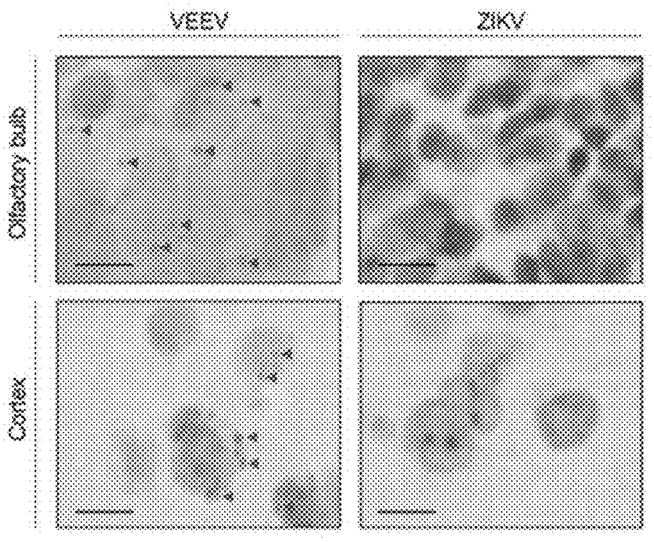
FIG. 14D shows in situ hybridization (brown) of Ldlrad3 (olfactory bulb, cortex, thalamus, and hippocampus) from wild-type mice (left). Ldlrad3 RNA puncta are indicated by left-pointing red arrows. A Zika virus (ZIKV) RNA in situ hybridization probe was used as a negative control (right). Slides were counterstained with Gill's haematoxylin. Representative high-power (63×) magnification images from n=5 per group are shown. Scale bar, 10 μm.
Figure 15A:
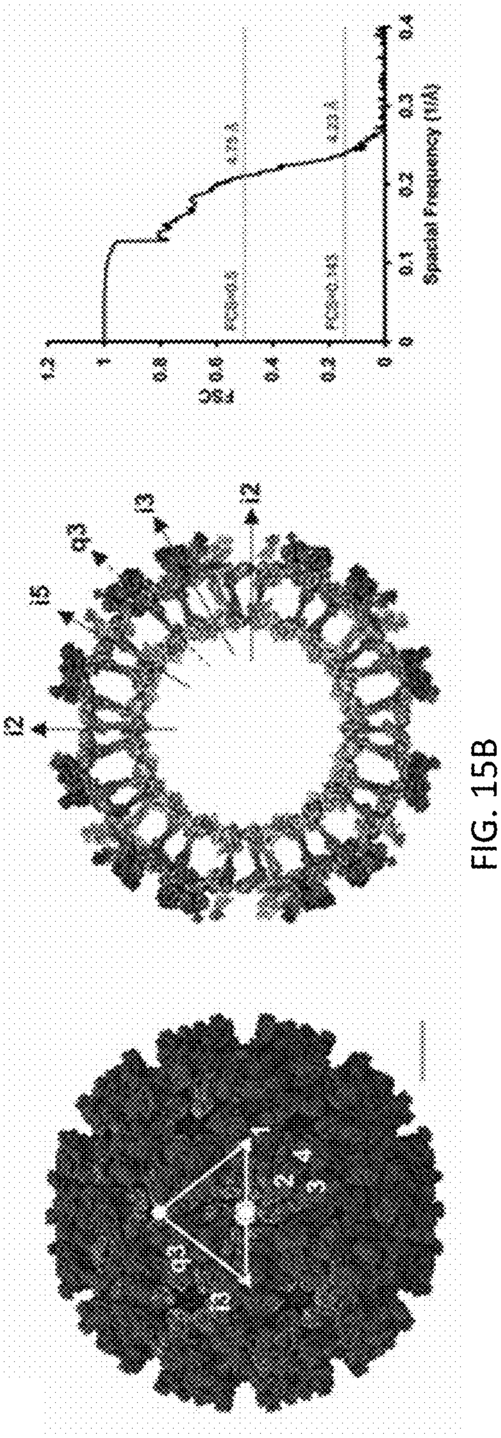
FIG. 15A-15B show Cryo-EM reconstructions of VEEV VLP with and without LDLRAD3 D1. Colored surface representations (left), equatorial cross-sections (middle) and Fourier shell correlation (FSC) plots versus resolution (right) for VEEV VLP alone and with complexed LDLRAD3 D1.
Figure 15B:
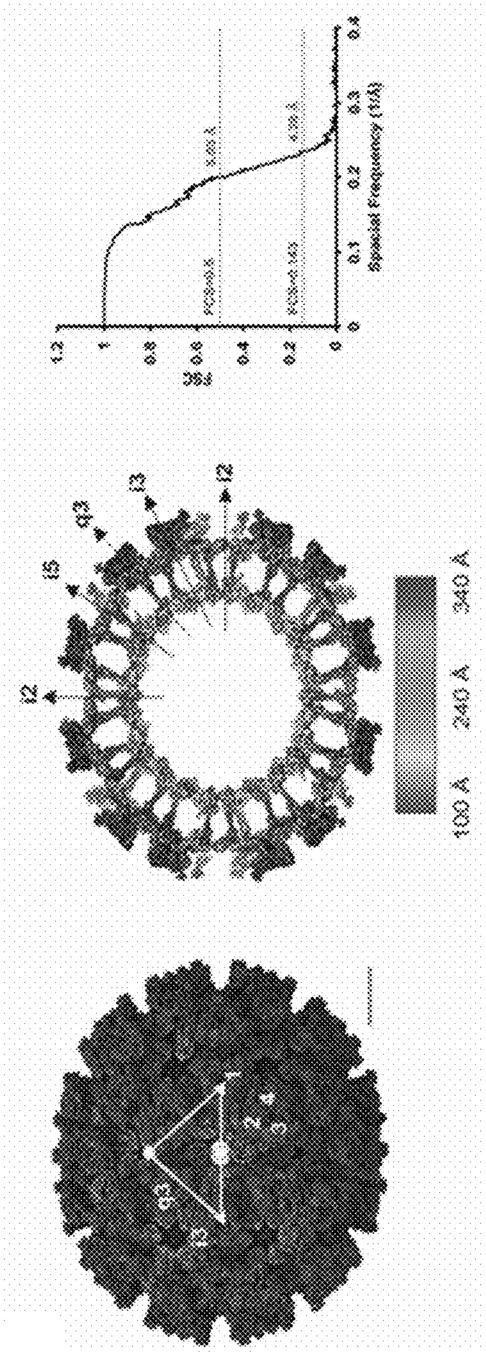
Figure 16:
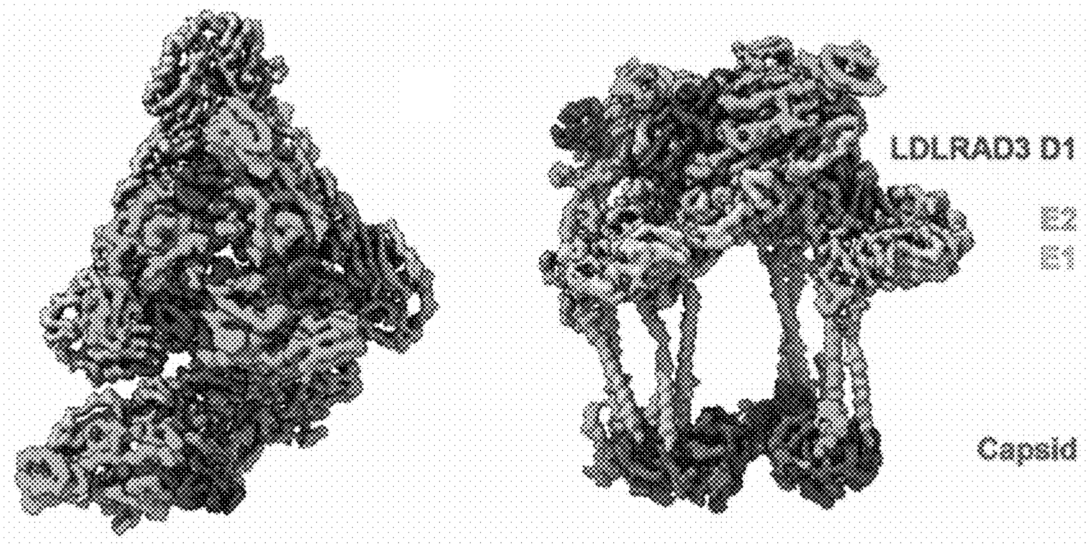
FIG. 16 shows Cryo-EM reconstruction of LDLRAD3 D1 bound to VEEV. Electron density of one asymmetric unit of the virus and receptor complex containing four unique copies of E1 (grey), E2 (cyan), capsid (forest green), and LDLRAD3 D1 (purple).
Figure 17:
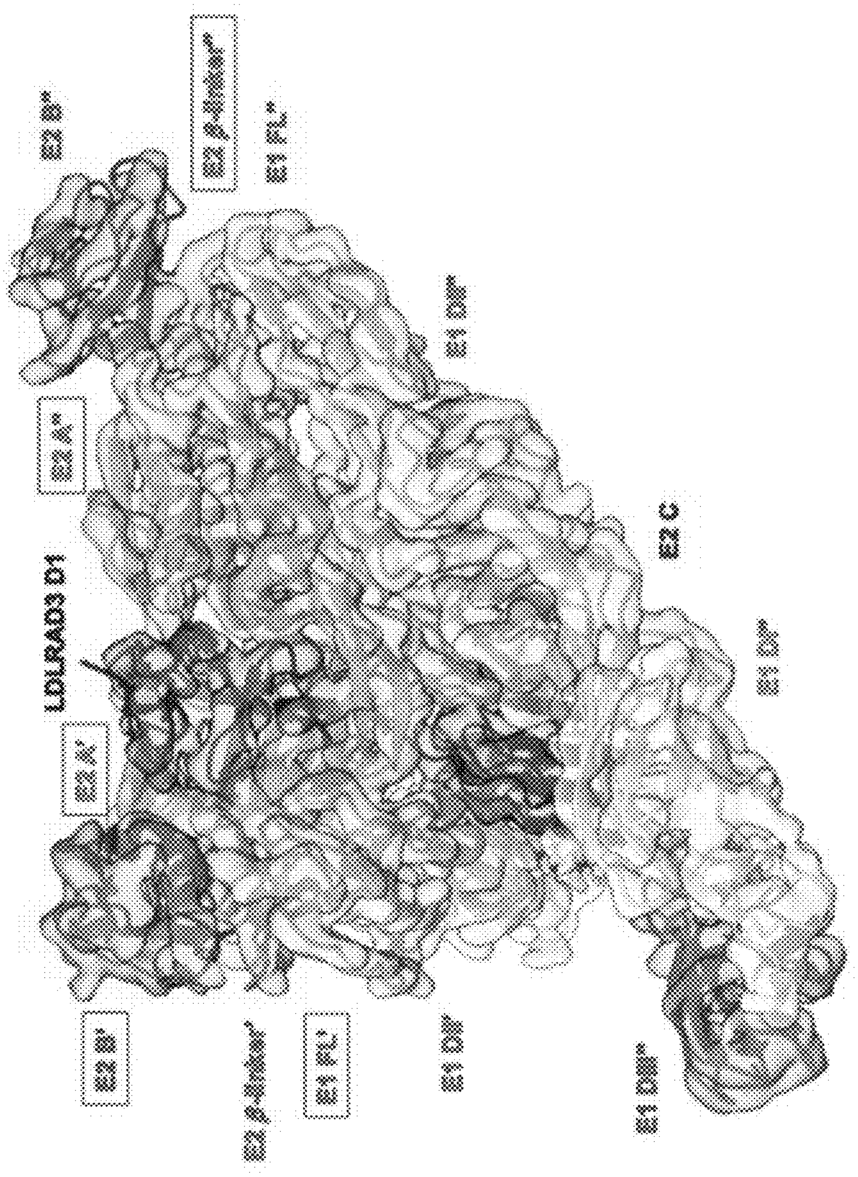
FIG. 17 shows an atomic Model of LDLRAD3 D1 Interaction with VEEV. Individual E2-E1 ectodomains at the binding interface of LDLRAD3 D1, colored by domain. 'and" denotes domains with the wrapped and intraspike heterodimers, respectively. LDLRAD3 D1 and VEEV E2-E1 are colored by domain. LDLRAD3 D1: purple. E1: DI, light grey; DII, medium grey; DIII, dark grey; fusion loop (FL), orange. E2: A domain, cyan; b-linker, medium blue; B domain, dark cyan; C domain, blue. N-linked glycans are depicted as balls and sticks and colored by heteroatom.
Figure 18:
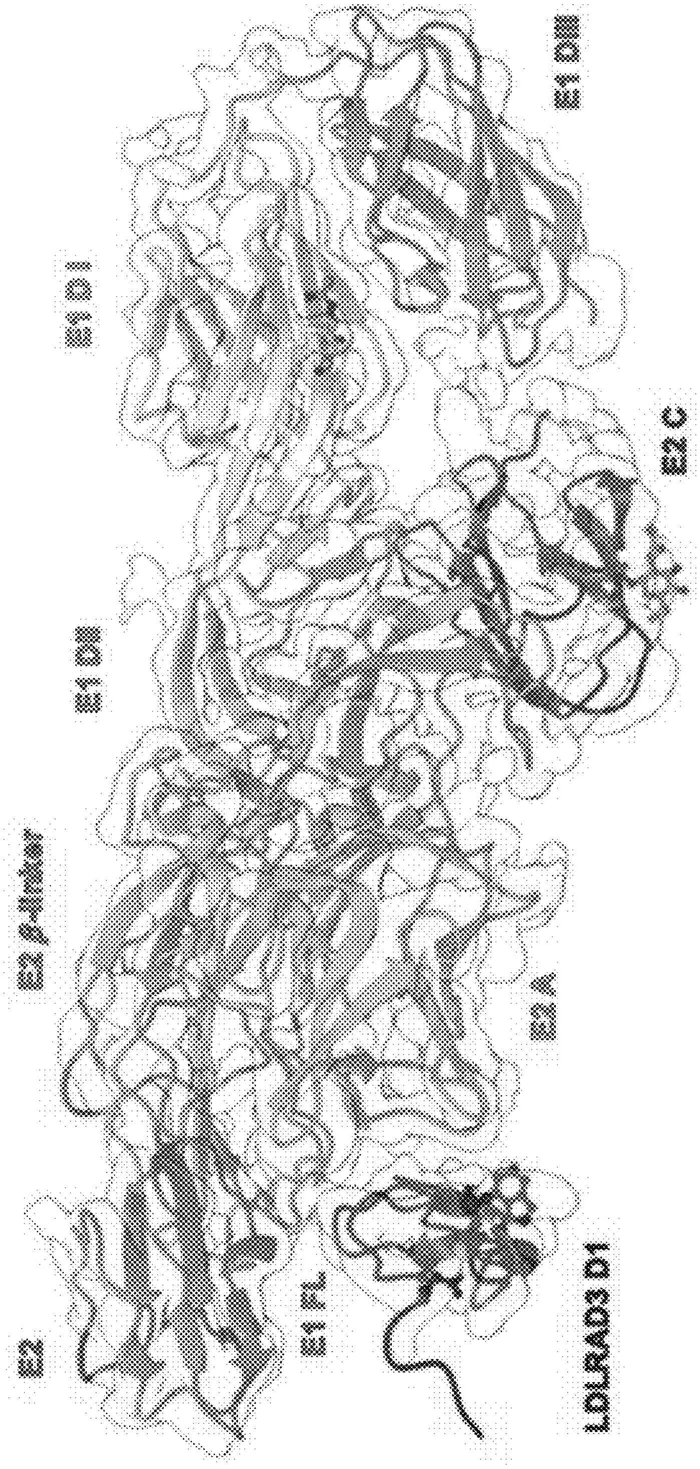
FIG. 18 shows an atomic Model of LDLRAD3 D1 and the wrapped VEEV E2-E1 heterodimer. Isolated view of LDLRAD3 D1 and its wrapped heterodimer. "Wrapped" refers to the E2-E1 heterodimer whose fusion loop is covered by LDLRAD3. Naming convention consistent with previous alphavirus-receptor structural studies (Basore et al., 2019). LDLRAD3 D1 and VEEV E2-E1 are colored by domain. LDLRAD3 D1: purple. E1: DI, light grey; DII, medium grey; DIII, dark grey; fusion loop (FL), orange. E2: A domain, cyan; b-linker, medium blue; B domain, dark cyan; C domain, blue. N-linked glycans are depicted as balls and sticks and colored by heteroatom.
Figure 19:
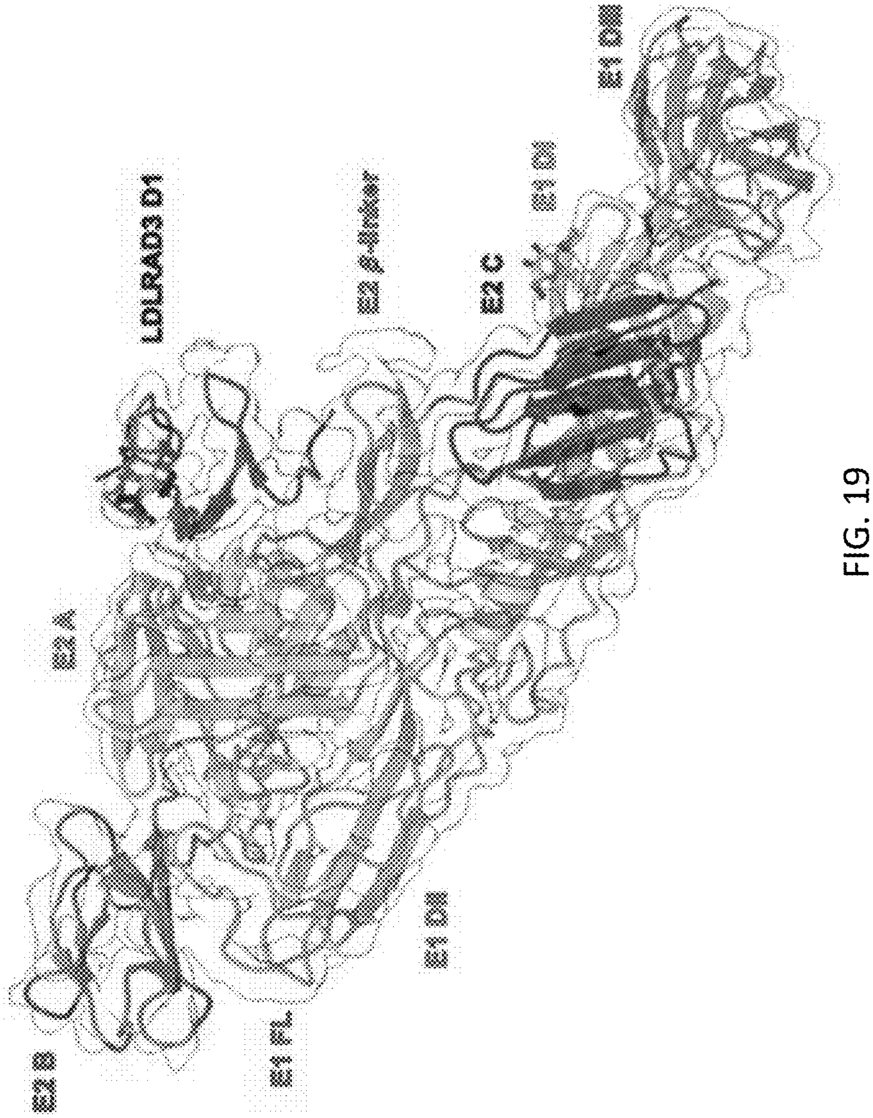
FIG. 19 shows an atomic Model of LDLRAD3 D1 and the intraspike VEEV E2-E1 heterodimer. Isolated view of LDLRAD3 D1 and its intraspike heterodimer. "Intraspike" refers to heterodimer adjacent to the wrapped heterodimer but within the same trimeric spike. Naming convention consistent with previous alphavirus-receptor structural studies (Basore et al., 2019). LDLRAD3 D1 and VEEV E2-E1 are colored by domain. LDLRAD3 D1: purple. E1: DI, light grey; DII, medium grey; DIII, dark grey; fusion loop (FL), orange. E2: A domain, cyan; b-linker, medium blue; B domain, dark cyan; C domain, blue. N-linked glycans are depicted as balls and sticks and colored by heteroatom.

Available transcriptomics data suggest that LDLRAD3 expression occurs in neurons of the brain, which is a site of VEEV infection and pathogenesis. Because LDLRAD3 mRNA has also been reported to be expressed in epithelial, muscle and myeloid cells, it could have additional roles in VEEV tropism. To evaluate the tissue expression of LDLRAD3 and confirm deletion of LDLRAD3 in the gene-edited mice, a TaqMan primer set was generated that spanned the deletion region in exons 2 and 3 (FIG. 14A). Ldlrad3 mRNA was detected in many tissues in wild-type mice, whereas no signal was detected in the brains of ΔLdlrad3 mice by quantitative PCR with reverse transcription (qRT-PCR) (FIG. 14B-14C). In situ hybridization of Ldlrad3 mRNA in the brain of wild-type mice showed punctate staining of neurons (FIG. 14D).

Low levels of residual VEEV infection were observed in the absence of LDLRAD3 expression in N2a or SH-SY5Y cells, which suggests that additional factors might contribute to cell entry. Whether this is due to interaction with laminin-binding proteins or other host factors is undetermined. Mosquitoes—a natural host for VEEV—lack an apparent LDLRAD3 orthologue and thus must have separate entry receptors. Moreover, as EEEV and WEEV do not require LDLRAD3 for infection, additional receptors for this virus family probably exist.

The experiments in genetically engineered mice with deletions in D1 of Ldlrad3 showed markedly diminished morbidity and mortality. Given the protective activity of LDLRAD3(D1)-Fc even in the setting of direct intracranial inoculation with the pathogenic VEEV TrD strain, variants of this fusion protein that have been optimized for effector function and half-life have potential as treatments for VEEV infections in humans and other susceptible animals.

Methods

Cells and viruses: N2a (ATCC CCL-131) and BV-2 (obtained from H. Virgin) cells were cultured at 37° C. in Dulbecco's modified Eagle medium (DMEM) with 10% fetal bovine serum (FBS), 10 mM HEPES, 100 U/ml penicillin and 100 U/ml streptomycin. SH-SY5Y cells (ATCC CRL-2266) were maintained at 37° C. in DMEM:F12 medium supplemented with 10% FBS, 10 mM HEPES, 100 U/ml penicillin and 100 U/ml streptomycin. For N2a, BV2 and SH-SY5Y cells, selection was maintained using the following antibiotics: puromycin (2.5 μg/ml, InvivoGen), blasticidin (4 μg/ml, InvivoGen) or hygromycin (200 μg/ml, InvivoGen). Cell viability and cytotoxicity assays were conducted using CellTiter-Glo (Promega) as per the manufacturer's instructions. Luminescence was read on a Synergy H1 Hybrid Multi-Mode Reader (BioTek) at room temperature with 0.5 s integration time per well. 293T (ATCC CRL-3216), NIH/3T3 (ATCC CRL-1658), HeLa (ATCC CCL-1) and Huh7.5 (obtained from C. Rice) cells were maintained in DMEM with 10% FBS, 10 mM HEPES, 100 U/ml penicillin and 100 U/ml streptomycin. A549 (ATCC CCL-185) cells were cultured in F-12K medium with 10% FBS, 10 mM HEPES, 100 U/ml penicillin and 100 U/ml streptomycin. HAP1 (ATCC CRL-2815) and K562 (ATCC CCL-243) cells were propagated in Iscove's modified Dulbecco's medium with 10% FBS, 10 mM HEPES, 100 U/ml penicillin and 100 U/ml streptomycin. HeLa (ATCC CCL-1), HT-1080 (ATCC CCL-121), LADMAC (ATCC CRL-2420) and MRC-5 (ATCC CCL-171) cells were maintained in Eagle's minimum essential medium with 10% FBS, 10 mM HEPES, 100 U/ml penicillin and 100 U/ml streptomycin. hCMEC/D3 cells (Millipore Sigma) were maintained in EndoGRO-MV complete culture medium (Millipore Sigma) supplemented with 1 ng/ml FGF-2 (Millipore Sigma). Raji (ATCC CCL-86) and Jurkat (ATCC TIB-152) cells were grown in RPMI-1640 with 10% FBS, 100 U/ml penicillin, 100 U/ml streptomycin and 0.05 mM 2-mercaptoethanol. U2OS cells (ATCC HTB-96) were maintained in McCoy's 5a medium modified, 10% FBS, 10 mM HEPES, 100 U/ml penicillin and 100 U/ml streptomycin. Human dermal microvascular endothelial cells (CADMEC, Cell Applications no. 100K-05a), human dermal fibroblasts (HDF, Cell Applications no. 106K-05a), human peripheral blood monocytes (HPBM, Cell Applications no. 6906K-50a), and human peripheral blood T cells (HPBT, Cell Applications no. 6902K-50a) were maintained in cell-type specific medium as per the manufacturer's instructions. All cell lines were tested routinely for mycoplasma infection and found negative.

The following viruses were used: SINV-VEEV (subtype IAB strains TrD or TrD-GFP20, IC strain INH9813 and ID strain ZPC738), VEEV (IAB strain TrD21, TrD-GFP20, IAB strain TC-8322 and ID strain ZPC73823), SINV-EEEV (FL93-939), EEEV (FL93-939 or FL93-939-GFP), SINV-WEEV (CBA87), SINV (strains AR86, TR339, Toto1101 and Girdwood), MAW (BeH407), VSV-GFP (Indiana) and WNV (Kunjin). Replication-competent SINV chimeric viruses were generated by replacing the SINV TR339 structural proteins with VEEV, EEEV or WEEV structural proteins 24. All viruses were propagated in Vero cells and titrated by focus-forming or plaque assay.

CRISPR-Cas9 screen and data analysis: The CRISPR screen was performed using a clonal heparan-sulfate-deficient ΔB4galt7 N2a cell line. N2a cells was first transduced with lentiCas9-Blast (Addgene no. 52962), and single clones were generated by limiting dilution. An Alt-R CRISPR-Cas9 tracrRNA and two synthesized crRNAs (crRNA-1: /AltR1/rCrU rCrCrU rCrArA rArGrC rGrCrU rCrArC rGrArA rGrUrU rUrUrA rGrArG rCrUrA rUrGrC rU/AltR2/; and crRNA-2: /AltR1/rCrG rGrGrC rArGrC rArCrU rCrArU rCrArA rUrGrU rGrUrU rUrUrA rGrArG rCrUrA rUrGrC rU/AltR2/) (Integrated DNA Technologies) were introduced into Cas9-expressing N2a cells using Lipofectamine RNAiMAX reagent (Thermo Fisher). Single clones were isolated using limiting dilution, stained with biotinylated R1725, and screened for the absence of cell-surface heparan-sulfate expression by flow cytometry.

A genome-wide CRISPR-Cas9 screen was performed using the mouse GeCKO v.2 CRISPR knockout pooled library26 (Addgene no. 1000000053) containing 130,209 sgRNAs targeting 20,611 genes. The sgRNA library was divided in half (A and B), packaged in HEK-293 cells with psPAX2 (Addgene no. 12260) and pMD2.G (Addgene no. 12259) using FugeneHD (Promega), and used for two independent screens. Supernatant was collected 48 h post-transfection, centrifuged to clear cell debris and stored at −80° C. until use. Approximately $3\times10^8$ ΔB4galt7 N2a cells were transduced at a multiplicity of infection (MOI) of about 0.1 for each sublibrary and then selected with puromycin for 7 to 10 days. For each half-library, $1\times10^8$ sgRNA-containing cells were seeded into ten 175-$cm^2$ tissue culture flasks, cultured for 20 h and inoculated (MOI of 1) with SINV-VEEV-GFP (TrD) for 18 h. Cells lacking GFP expression were sorted using a Sony Synergy sorter, and GFP-negative cells were expanded in DMEM supplemented with 10% FBS and a cocktail (2 μg/ml) of anti-VEEV monoclonal antibodies (VEEV-57, VEEV-67 and VEEV-68) (N.M.K. and M.S.D., unpublished). Expanded cells were re-inoculated with SINV-VEEV-GFP (TrD) and sorted for GFP-negative cells for two additional rounds. Three and four independent repeats were performed with sublibraries A and B, respectively.

Genomic DNA was extracted from uninfected control cells ($3\times10^7$ per sublibrary) and sorted cells ($1\times10^7$ per repeat). The sgRNAs were enriched, amplified and sequenced using an Illumina HiSeq 2500 (Genome Technology Access Center of Washington University). The sgRNA sequences against specific genes were obtained after removal of the tag sequences using the FASTX-Toolkit (hannonlab.cshl.edu/fastx_toolkit/) and cutadapt (version 1.8.1). sgRNA sequences were analysed using a published computational tool (MAGeCK).

Gene validation: LDLRAD3 was validated using two sgRNAs to the Ldlrad3 gene (Ldlrad3 sgRNA-1: ACCAACGAGTGCAACATCCC (SEQ ID NO: 41; Ldlrad3 sgRNA-2: AGCATCACGTACGCCATCAT (SEQ ID NO: 42). A sgRNA (control sgRNA: GAAGTTCGAGGGCGACACCC (SEQ ID NO: 43) that targets neither the mouse nor human genome was included as a negative control. The sgRNAs were cloned into lentiCRISPR v.2 (Addgene no. 52961) and packaged in HEK-293 cells with psPAX2 (Addgene no. 12260) and pMD2.G (Addgene no. 12259) using Lipofectamine 3000 (Thermo Fisher). ΔB4galt7 and parental N2a cells were transduced with lentiviruses containing Ldlrad3 sgRNAs and selected for 7 days in the presence of puromycin. Clonal LDLRAD3-deficient cell lines were obtained by limiting dilution. Ldlrad3 gene editing was validated by next generation sequencing on an Illumina HiSeq 2500 platform (Genome Technology Access Center of Washington University) with 300-base-pair paired-end sequencing. Ldlrad3 was edited in BV2 cells in the same way as in N2a cells. Clonal lines were generated by limiting dilution. Gene editing was confirmed with next-generation sequencing. BV2 cells deficient in both Ldlrad3 and B4galt7 genes were generated by sequential CRISPR-Cas9 gene editing. The B4galt7 gene was edited by an sgRNA (B4galt7 sgRNA: ATCTATGTGCTCAACCAGGTGG (SEQ ID NO: 44)) using lentiCRISPR v.2-Puro, selected with puromycin and cloned by limiting dilution. B4galt7 gene editing was confirmed by next-generation sequencing and flow cytometry analysis of glycosaminoglycan surface expression using biotinylated R1725 protein. Subsequently, Ldlrad3 was edited using the two Ldlrad3 sgR-NAs mentioned for in N2a cells, but with lentiCRISPR v.2-Blast (Addgene no. 83480), selected with blasticidin and cloned by limiting dilution. Editing of Ldlrad3 was confirmed by next-generation sequencing. The human gene orthologue LDLRAD3 was edited in SH-SY5Y cells. Two sgRNAs targeting LDLRAD3 (LDLRAD3 sgRNA-1: GCCAAGGCTAAGTCGAAATG (SEQ ID NO: 45) and LDLRAD3 sgRNA-2: TGAAGCTCTTGTCAATACAG (SEQ ID NO: 46)) were cloned into lentiCRISPR v.2, packaged as lentivirus and introduced into cells as described for N2a cells. Clonal lines were generated by limiting dilution. LDLRAD3-gene-edited SH-SY5Y cells were confirmed by next-generation sequencing.

Complementation experiments: The mouse Ldlrad3 gene (NM_178886.3), the Ldlrad3 isoform 2 (which encodes a protein that lacks 32 residues near the N terminus (XM_006499481.4)) and human LDLRAD3 (NM_174902.4) were codon-optimized and synthesized (GeneWiz), and then inserted into the lentivirus vector pLV-EF1a-IRES-Hygro (Addgene no. 85134) between the BamHI and MluI restriction enzyme sites using In-Fusion HD Cloning (Takara). The Ldlrad3 sgRNA target sequence was mutated synonymously (sgRNA-1: ACAAATGAATGTAATATTCC (SEQ ID NO: 47); sgRNA-2: TCTATTACTTATGCTATTAT SEQ ID NO:48)) to prevent editing of the re-introduced gene. Ldlrad3 cDNA fragments containing an N-terminal Flag tag downstream of the signal sequence to monitor cell surface expression were codon-optimized, synthesized and inserted into the lentivirus vector pLV-EF1a-IRES-Hygro as described. The following Ldlrad3 constructs were generated: full-length (NM_178886.3), D1+stalk+transmembrane (TM)+cytoplasmic (cyt) domains (residues 18-70 and 154-345), D1+D2+stalk+TM+cyt (residues 18-112 and 154-345), D2+D3+stalk+TM+cyt (residues 71-345), Ldlrad3 lacking the TM and cyt domain (clone 1: residues 18-163 and clone 2: residues 18-173) fused to the human placental alkaline phosphatase glycophosphatidylinositol (GPI) anchor (GPI sequence: CTGGCGCCCCCCGCCGGCAC-CACCGACGCCGCGCACCCGGGGCGGTCCGTGGT CCCCGCGTTGCTTCCTCTGCTGGCCGGGACCCTGC TGCTGCTGGAGACGGCCAC TGCTCCC (SEQ ID NO: 49)). Ldlrad3-encoding vectors were packaged as lentiviruses and cells were transduced. Complemented cells were selected with hygromyci (200 μg/ml) for at least 5 days before use. Complemented cells were assessed for LDLRAD3 surface expression using an anti-Flag antibody (Cell Signaling Technology, no. 14793) and Alexa Fluor 647-conjugated goat anti-rabbit IgG (Thermo Fisher, A27040) or mouse anti-LDLRAD3 serum (1:2,000) and Alexa Fluor 647-conjugated goat anti-mouse IgG (Thermo Fisher, A21236). Stained cells were analysed on a MACSQuant Analyzer 10 (Miltenyi Biotec).

Infectivity assays: ΔB4galt7, ΔB4galt7 ΔLdlrad3, and Ldlrad3- or LDLRAD3-complemented N2a cells were inoculated with the following viruses: SINV-VEEV-GFP IAB TrD (MOI 20, 7.5 h), SINV-VEEV IC INH9813 (MOI 5, 8 h), SINV-VEEV ID ZPC738 (MOI 5, 10 h), VEEV TC-83 (MOI 20, 7.5 h), SINV-EEEV (MOI 40, 12 h), SINV-WEEV (MOI 30, 12 h), SINV AR86 (MOI 5, 12 h), SINV-GFP TR339 (MOI 5, 10 h), SINV Toto1101 (MOI 20, 12 h), SINV-GFP Girdwood (MOI 20, 10 h), MAW (MOI 5, 8 h), VEEV TrD-GFP (MOI 5, 15 h), EEEV FL93-939-GFP (MOI 10, 15 h) and VSV-GFP (MOI 3, 6 h). Ldlrad3 gene-edited BV2 cells were inoculated with SINV-VEEV-GFP IAB TrD (MOI 20, 7.5 h). At indicated time points, cells were collected using trypsin and fixed with 1% or 2% paraformaldehyde (PFA) in PBS for 15 min at room temperature. Cells inoculated with GFP-containing viruses were analysed either on a MACSQuant Analyzer 10 (Miltenyi Biotec) or an LSR-II Analyzer (Beckton-Dickinson). Cells infected with non-GFP-expressing viruses were permeabilized in Hank's Balanced Salt Solution (HBSS) supplemented with 10 mM HEPES, 0.1% (w/v) saponin and 2% FBS for 10 min at room temperature. The following virus-specific antibodies (1 μg/ml or 1:1,000 dilution) were used to stain cells for 30 min at 4° C.: VEEV (mouse 3B4C-4), EEEV (mouse EEEV-10), WEEV (mouse WEEV-209), SINV (mouse ascites fluid, ATCC no. VR-1248AF) and MAYV (mouse CHK-265). Cells were washed and incubated with 1 μg ml-1 of Alexa Fluor 647-conjugated goat anti-mouse IgG (Thermo Fisher) for 30 min at 4° C. After washing, cells were analysed on a MACSQuant Analyzer 10 (Miltenyi Biotec). All flow cytometry data were processed using FlowJo (FlowJo).

For multistep virus growth curves, ΔB4galt7, ΔB4galt7 ΔLdlrad3 or LDLRAD3-complemented ΔB4galt7 ΔLdlrad3 cells were inoculated with SINV-VEEV-GFP IAB TrD (MOI 0.001), SINV-VEEV IC INH9813 (MOI 0.001), SINV-VEEV ID ZPC738 (MOI 0.001) or WNV Kunjin (MOI 0.05) in DMEM supplemented with 2% FBS. Supernatants were collected at indicated time points, and viral yield was determined by focus-forming assay. Cells were fixed, permeabilized and stained with 3B4C-4 (VEEV) or E16 (WNV) monoclonal antibodies (1 μg ml-1), and horseradish-peroxidase-conjugated goat anti-mouse IgG (Sigma, 1:1,000 dilution). Infected foci were visualized using TrueBlue peroxidase substrate (KPL) and quantified on an ImmunoSpot 5.0.37 Macroanalyzer (Cellular Technologies).

Virus binding and internalization assays: For virus-binding assays, SINV-VEEV TrD virions (MOI of 0.1) were added to $5\times10^5$ cells in a 12-well plate and incubated on ice for 30 min. To remove unbound virions, cells were washed 6 times with ice-cold PBS supplemented with 2% bovine serum albumin. Cells were collected, lysed in RLT buffer (Qiagen) and RNA extraction was performed using an RNeasy Mini Kit (Qiagen). For internalization assays, SINV-VEEV TrD virions (MOI of 0.1) were added to $5\times10^5$ cells in a 12-well plate and incubated at 4° C. for 30 min. After 6 washes with ice-cold PBS and 2% BSA, pre-warmed 37° C. medium supplemented with 2% FBS and 15 mM NH4Cl was added to cells. Cells were incubated at 37° C. for 1 h to allow virus internalization. Cells were then chilled on ice and incubated with 500 ng $ml^{-1}$ proteinase K in PBS at 4° C. for 2 h to remove residual plasma-membrane-bound virions. After 6 additional washes with ice-cold PBS and 2% bovine serum albumin (BSA), cells were lysed in RLT buffer and RNA was extracted. The qRT-PCR was performed using a TaqMan RNA-to-CT 1-Step Kit (Thermo Fisher) with Gapdh as an internal control. Primers and probes used are as follows: SINV-VEEV forward: 5'-AAGATCATCGACGCAGTCATC-3' (SEQ ID NO: 50); SINV-VEEV reverse: 5'-GCTGTGGAAGTAACCGAATCT-3' (SEQ ID NO: 51); Gapdh forward: 5'-GCCCAGAACATCATCCCTGC-3' (SEQ ID NO: 52); Gapdh reverse: 5'-CCGTTCAGCTCTGGGATGACC-3' (SEQ ID NO: 53).

P1-PLC experiments: N2a cells expressing LDLRAD3 or LDLRAD3-GPI ($3\times10^4$ cells per well) were seeded in a 96-well plate 16 h before the assay. Cells were washed with PBS supplemented with $Ca^{2+}$ (0.9 mM) and $Mg^{2+}$ (0.5 mM) and incubated with different concentrations (0, 0.1 or 1 U ml-1) of PI-PLC (Thermo Fisher, P6466) in 50 μl PBS with $Ca^{2+}$ and $Mg^{2+}$ at 37° C. for 1 h. Cells were washed twice with ice-cold medium, inoculated with SINV-VEEV-GFP (MOI 10) and incubated for 1 h at 4° C. Cells were washed four times with ice-cold medium to remove unbound virions. After allowing infection to proceed for 7 h at 37° C., cells were fixed with 2% PFA for 15 min at room temperature. LDLRAD3 expression was assessed by staining of the N-terminal Flag tag using a rabbit anti-Flag tag antibody (Cell Signal Technology, clone D6W5B) for 1 h at 4° C. and Alexa Fluor 647-conjugated goat anti-rabbit IgG (1:2,000 dilution, Thermo Fisher) for 30 min at 4° C. VEEV infection levels were assessed by GFP expression levels. Cells were fixed and directly analysed on a MACSQuant Analyzer 10 (Miltenyi Biotec).

Recombinant LDLRAD3 proteins: To achieve robust expression in human HEK293 cells, we cotransfected the human receptor-associated protein (RAP), a chaperone that promotes passage of LDL-receptor family proteins through the secretory pathway and enhances their cell-surface expression. Gene fragments (D1, residues 18-70; D2, residues 69-112; and D1+D2, residues 18-112) encoding the Ldlrad3 gene (GenBank NM_001290784) were codon-optimized, synthesized (Integrated DNA Technologies) and inserted into the pCDNA3.4 vector (Thermo Fisher) with the native signal peptide sequence and the mouse IgG2b Fc region. HRV 3C cleavable constructs contained the cleavage site (LEVLFQGP) immediately downstream of the LDLRAD3 coding sequence. To generate the human LDLRAD3 (D1) human IgG1 fusion protein, LDLRAD3 D1 (residues 18-70) was codon-optimized, synthesized (Integrated DNA Technologies) and inserted into the pHLSEC vector with the native signal peptide sequence, [SSG]3 linker, and the human IgG1 Fc region. To generate the RAP chaperone protein, a cDNA fragment encoding residues 1-357 (GenBank NM_002337) was codon-optimized, synthesized and inserted into the pCDNA3.4 vector. All constructs were confirmed by Sanger sequencing. Expi293 cells (50 ml) were seeded at $1.5\times10^6$ cells per ml on the day of transfection. LDLRAD3-Fc (50 μg) and RAP (10 μg) plasmids were diluted in Opti-MEM, complexed with ExpiFectamine 293 transfection reagent (Thermo Fisher) and added to cells. One day after transfection, cells were supplemented with ExpiFectamine 293 transfection enhancers 1 and 2 to boost transfection levels. Supernatant was collected 4 days after transfection, centrifuged at 3,000 g for 20 min and purified using protein A sepharose 4B (Thermo Fisher). After elution, the purified protein was dialysed into 1×PBS with 1 mM $CaCl_2$) and EDTA-free protease inhibitors (Roche). Protein purity was confirmed by SDS-PAGE. To generate LDLRAD3 proteins that are cleaved from the IgG backbone, purified LDLRAD3-Fc proteins were incubated with HRV 3C protease (Thermo Fisher) at a 1:10 (w/w) ratio overnight at 4° C. The cleaved Fc fragments were depleted using sequential Protein A Sepharose 4B and Superdex 75 size-exclusion chromatography and analysed by SDS-PAGE.

Recombinant VEEV p62-E1 protein: A cDNA fragment encoding VEEV (TrD strain, GenBank AAC19322) p62-E1 (E3 residues Ser1-Arg59, E2 residues Ser1-Glu342, $(GGGGS)_4$ (SEQ ID NO: 54) linker and E1 residues Tyr1-Ser412) and a C-terminal hexa-histidine tag was inserted into the baculovirus expression transfer vector pOET1 (Oxford Expression Technologies) under the control of the AcMNPV polyhedrin (polh) promoter. Transfection and baculovirus amplification were conducted with Sf9 cells, and the recombinant protein was expressed in High Five cells for 3 days. Soluble p62-E1 protein was purified by nickel affinity (GoldBio) and HiLoad 16/600 Superdex 200 size-exclusion (GE Healthcare) chromatography in 20 mM HEPES pH 7.4, 150 mM NaCl and 0.01% $NaN_3$.

ELISA binding assays: Nunc MaxiSorp ELISA plates (Thermo Fisher) were coated with anti-alphavirus E1 or E2 monoclonal antibodies (DC2.112 and DC2.315 (2 μg $ml^{-1}$), $1A4A^{-1}$ (2 μg $ml^{-1}$) or CHK-152 and CHK-166 (2 μg $ml^{-1}$)) overnight in sodium bicarbonate buffer, pH 9.3. Plates were washed with PBS and blocked with PBS containing 4% (w/v) BSA for 1 h at room temperature. VEEV VLPs28 or CHIKV VLPs5 (1 μg $ml^{-1}$) were diluted in PBS containing 2% BSA and added to wells for 1 h at room temperature. LDLRAD3-Fc proteins, positive (anti-VEEV, 3B4C-4 and anti-CHIKV, CHK-152) and negative (anti-hepatitis C virus (HCV), H77.39 and anti-WNV, E16) controls were diluted in 2% BSA and incubated for 1 h at room temperature. Plates were washed with PBS and incubated with horseradish-peroxide-conjugated goat anti-mouse IgG (H+L) or horse-radish-peroxide-conjugated goat anti-human IgG (1:2,000 dilution, Jackson ImmunoResearch) for 1 h at room temperature. Plate were developed 3,3'-5,5'-tetramethylbenzidine substrate (Thermo Fisher), stopped with 2N $H_2SO_4$ and read at 450 nM using a TriStar Microplate Reader (Berthold). For antibody competition assays, 10 μg $ml^{-1}$ of indicated anti-VEEV monoclonal antibodies 1A4A-1, 3B4C-4 or anti-HCV H77.39 isotype control were incubated with VEEV VLPs28 for 30 min before addition of biotinylated LDLRAD3(D1)-Fc protein. Plates were incubated with horseradish-peroxide-conjugated streptavidin (1:2,000 dilution, Vector Laboratories) for 1 h at room temperature and developed as described above.

LDLRAD3-Fc inhibition assays: SINV-VEEV-GFP TrD or SINV-EEEV-GFP FL93-939 (MOI of 20) was pre-incubated at 37° C. with LDLRAD3(D1)-Fc, LDLRAD3(D1-HRV)-Fc, LDLRAD3(D2)-Fc or LDLRAD3(D1+D2)-Fc (0-100 μg ml-1, tenfold dilutions) in DMEM supplemented with 10% FBS. Anti-HCV monoclonal antibody H77.39 was included as a negative isotype control. The complexes were added to either N2a or ΔB4galt7 N2a cells for 7.5 h. Cells were analysed for GFP expression by flow cytometry using a MACSQuant Analyzer 10 (Miltenyi Biotec).

Anti-LDLRAD3 antibodies: $Ldlrad3^{-/-}$ mice were immunized via intraperitoneal route with 25 μg of purified LDLRAD3 protein and complete Freund's adjuvant. After two boosts with LDLRAD3(D1)-Fc protein in incomplete Freund's adjuvant, mice were euthanized and a terminal bleed was performed. Serum was isolated and heat-inactivated at 56° C. for 30 min before use.

Anti-LDLRAD3 antibody inhibition assays: ΔB4galt7 N2a cells ($2\times10^4$ cells per well in a 96-well plate) were incubated with serial dilutions of anti-LDLRAD3 polyclonal or naive serum for 30 min at 37° C. After incubation, cells were inoculated with SINV-VEEV-GFP (MOI 20, 7.5 h) or SINV-EEEV-GFP (MOI 10, 17 h). Cells were collected, fixed and analysed for GFP expression by flow cytometry using a MACSQuant Analyzer 10 (Miltenyi Biotec).

Surface plasmon resonance: Binding affinity of LDLRAD3 to VEEV was assessed using a Biacore T200 system (GE Healthcare). All experiments were performed with 10 mM HEPES pH 7.4, 150 mM NaCl, 1 mM $CaCl_2$), 0.005% (v/v) surfactant P20 as running buffer. VEEV p62-E1 or CHIKV p62-E129 was immobilized onto a CM5 sensor chip (GE Healthcare) using standard amine coupling chemistry. HRV-cleaved LDLRAD3(D1) was injected at 30 μl min-1 at 25° C. over a range of concentrations (2,000 nM to 16 nM) for 10 min followed by a dissociation period of 30 min. Immobilized CHIKV p62-E1 served as a reference surface to correct for bulk refractive index changes. Kinetic profiles and steady-state equilibrium concentration curves were fitted with a global 1:1 binding algorithm with drifting baseline using BIAevaluation 3.1 (GE Healthcare).

Generation of mice with deletions in Ldlrad3: Gene-edited mice were generated with support from the Genome Engineering and iPSC Center and Department of Pathology Micro-Injection Core (Washington University School of Medicine). Two sgRNAs targeting Ldlrad3 exon 2 were selected on the basis of minimal off-target profile and the distance to the target site: sgRNA-1: 5'-CAGCAACGGGCGGTGCATCCNGG-3' (SEQ ID NO: 55) and sgRNA-2: 5'-CGTCACACTGCCAGGCGCCCNGG-3' (SEQ ID NO: 56). The sgRNAs were synthesized (Integrated DNA Technologies) and after screening guide sequences for minimal off-target effects in silico, each sgRNA was complexed with Cas9 protein and introduced into half-day-old C57BL/6J embryos (embryonic day 0.5) via electroporation. Founder lines (Δ11 and Δ14 nucleotides) were confirmed and genotyped by next-generation sequencing.

Mouse experiments: All experiments were conducted with approval of the Institutional Animal Care and Use Committee at Washington University School of Medicine (assurance number A3381-01) or University of Pittsburgh. In vivo studies were not blinded, and mice were randomly assigned to treatment groups. No sample-size calculations were performed to power each study. Instead, sample sizes were determined on the basis of previous in vivo virus challenge experiments.

For LDLRAD3(D1)-Fc studies, depending on availability, experiments were performed using either LDLRAD3(D1)-Fc or LDLRAD3(D1-HRV)-Fc, which have equivalent VEEV binding and neutralizing activity. For SINV-VEEV TrD infections, four-week-old male C57BL/6J mice (Jackson Laboratories) were administered 750 μg of anti-IFNAR1 monoclonal antibody (Leinco Technologies, clone MAR1-5A3) by intraperitoneal injection 24 h before virus inoculation. Either 6 h before (prophylaxis) or 24 h after (therapy) virus inoculation, mice were injected via the intraperitoneal route with 250 μg of LDLRAD3(D1)-Fc or isotype control mouse antibody JEV-13. Mice were then inoculated intraperitoneally with 105 focus-forming units (FFU) of SINV-VEEV TrD. Survival was monitored, and body weight was measured before infection and daily thereafter for 14 days. At 4 dpi, a subset of mice was extensively perfused, and serum, spleen, brain and peripheral blood leukocytes (PBLs) were collected. Viral RNA was extracted using the MagMax-96 Viral RNA isolation kit (Thermo Fisher) and the KingFisher Flex system (Thermo Fisher). PBLs were processed by mixing 100-200 μl of blood with 30 μl of 0.5 M EDTA and then incubating with 10 ml of red blood cell (RBC) lysing buffer Hybri-Max (Sigma) for 3 min. Cells were washed with 30 ml of PBS and centrifuged at 1,500 rpm for 5 min at 4° C. PBLs were washed twice in 10 ml of FACS buffer (5% fetal bovine serum, 5 mM EDTA in 1×PBS) at 4° C., and viral RNA was isolated using Viral RNeasy Mini Kit (Qiagen). Viral RNA was extracted using the Qiagen RNeasy viral RNA kit and quantified by qRT-PCR using a TaqMan RNA-to-CT 1-Step Kit (Thermo Fisher). A standard curve was generated using serial tenfold dilutions of SINV-VEEV TrD RNA extracted from a viral stock of known titre. Serum, spleen and brain viral RNA burden were expressed on a log 10 scale as FFU equivalents per ml of serum or gram of tissue. PBL viral RNA levels were normalized to mouse Gapdh levels.

For VEEV infections, immunocompetent female CD-1 mice were injected via the intraperitoneal route with 200 μg of LDLRAD3(D1)-Fc or isotype control monoclonal antibody (JEV-13) 6 h before subcutaneous inoculation in the left rear footpad with $10^3$ plaque-forming units (PFU) of VEEV TrD or intracranial inoculation with $10^3$ PFU of VEEV TrD nanoLuc TaV20. Six-week-old male C57BL/6J mice were injected via intraperitoneal route with 250 μg of LDLRAD3(D1)-Fc or isotype control monoclonal antibody (JEV-13) 6 h before subcutaneous inoculation in the left rear footpad with 102 FFU of VEEV ZPC738. Survival was monitored, and body weight was measured before infection and daily thereafter for 14 days. In some cohorts, serum, spleen, brain and PBLs were collected at 6 dpi and processed as described in in the preceding paragraph. A standard curve was generated using serial tenfold dilutions of VEEV ZPC738 RNA extracted from a viral stock of known titre. The following primers and probes were used to quantify VEEV ZPC738 RNA levels: VEEV ZPC738 nsP3 forward: 5'-CAAGTCGAGGCAGACATTCA-3' (SEQ ID NO: 57); VEEV ZPC738 nsP3 reverse: 5'-CAGGGTGT-CAAGGATGGATAAA-3' (SEQ ID NO: 58); and *M. musculus* Gapdh (Mm.PT.39a.1 predesigned set, Integrated DNA Technologies). For VEEV infections with Ldlrad3−/− mice, seven-week-old Ldlrad3−/− or wild-type male and female C57BL/6J mice were inoculated subcutaneously in the left rear footpad with 103 PFU of VEEV TrD or 102 FFU VEEV ZPC738. Mice were monitored daily for survival, body weight and clinical signs of disease. To quantify Ldlrad3 mRNA expression levels, total RNA was isolated from tissues using the MagMax-96 Viral RNA isolation kit (Thermo Fisher) and the KingFisher Flex system (Thermo Fisher) and DNase-treated (TURBO DNase, Thermo Fisher). Ldlrad3 mRNA expression levels were normalized to mouse Gapdh levels. The following primers and probes were used to quantify Ldlrad3 RNA levels: Ldlrad3 forward: 5'-TGCAGCAACGGGCGGTGCAT-3' (SEQ ID NO: 59); Ldlrad3 reverse: 5'-CCGATGATACAGTGGATGCC-3' (SEQ ID NO: 60); and *Mus musculus* Gapdh as described in the preceding paragraphs of this section.

In vivo imaging system analysis: Female CD-1 mice treated with LDLRAD3(D1)-Fc or isotype control monoclonal antibody (JEV-13) and inoculated via intracranial route with $10^3$ PFU of VEEV TrD nanoLuc TaV were anaesthetized with isoflurane and injected intraperitoneally with 500 μl 1% (v/v) NanoGlo reagent (Promega) in DPBS. After a 4-min incubation, the dorsal cranium was imaged using an IVIS SpectrumCT In Vivo Imaging System (Perkin Elmer) at 405 nm. False-colour ranged luminescence was superimposed over bright-field images. Equal-sized areas of interest were selected, and total flux (photons s-1) was measured using Living Image software (Perkin Elmer) and plotted on a log scale.

Histology and in situ viral RNA hybridization: Mice were euthanized and perfused with 15 ml PBS and 15 ml 10% neutral buffered formalin (NBF) for fixation. Whole brain and spinal cord were removed and drop-fixed in 40 ml of 10% NBF for 24 h before processing and sectioning. A subset of slides was stained with haematoxylin and eosin. Paraffin-embedded tissue sections were subsequently deparaffinized at 60° C. for 1 h, and endogenous peroxidases were quenched with $H_2O_2$ for 10 min at room temperature. Slides then were boiled for 15 min in RNAscope Target Retrieval Reagents and incubated for 30 min in RNAscope Protease Plus reagent before hybridization with the VEEV ZPC738 (Advanced Cell Diagnostics no. NPR-0008615) or Ldlrad3 RNA probe (Advanced Cell Diagnostics no. NPR-0008187) and signal amplification. A ZIKV RNA probe (Advanced Cell Diagnostics no. 467771) was used as a negative control. Sections were counterstained with Gill's haematoxylin, mounted using Cytoseal Mounting Medium (Thermo Scientific), and allowed to dry for 24 h before imaging. Full slides were scanned using a NanoZoomer slide scanning system (Hamamatsu Photonics) and imaged using the NanoZoomer Digital Pathology digital slide viewer program.

Statistical analysis: Statistical significance was assigned when P values were <0.05 using Prism (Version 8, GraphPad); P values are indicated in each of the figure legends. Cell culture experiments were analysed by one-way or two-way ANOVA with a multiple comparison corrections. Analysis of survival, weight change and viral burden in vivo were determined by log-rank, two-way ANOVA and Mann-Whitney tests, respectively.

Example 2: Cryo-EM Identifies Residues of VEEV E2-E1 and Ldlrad3 D1 Binding Interface Cryo-EM sample preparation, data collection, and single particle reconstruction: VEEV VLPs with and without cleaved LDLRAD3 D1 or LDLRAD3 D1+D2 in molar excess were flash cooled on lacey carbon grids in liquid ethane using an FEI Vitrobot (ThermoFischer). Movies of the VEEV VLP alone and with LDLRAD3 D1 samples were recorded with the software EPU (ThermoFisher) using a K2 Summit electron detector (Gatan) mounted on a Bioquantum 968 GIF Energy Filter (Gatan) attached to a Titan Krios microscope operating at 300 keV with an electron dose of 35 e−/Å2 and a magnification of 105,000×. Movies of VEEV VLP with cleaved LDLRAD3 D1+D2 were recorded using a Falcon 4 Direct Electron Detector with a magnification of 59,000×. Movies from all samples were corrected for beam-induced motion using MotionCor2. Contrast transfer function parameters of the electron micrographs were estimated using Gctf and particles were auto-picked using crYOLO. Single-particle analysis, specifically reference-free 2D classification, 3D refinement, Movie refinement, Bayesian polishing, post-processing and local resolution estimation were performed in RELION-3.1. Post-processing of maps was also done using DeepEMhancer for improved atomic model building and refinement. Structural visualization of the electron maps was performed using ChimeraX.

TABLE 1

Summary of Cryo-EM data collection

| Sample | VLP alone | VLP + LDLRAD3 D1 |
|---|---|---|
| # of Micrographs | 2237 | 8979 |
| # of particles picked | 19516 | 30242 |
| # of particles after 2D classification | 9816 | 14648 |
| # of particles after 3D classification | 7993 | 12216 |
| $Resolution_{FSC=0.5}$ (Å) | 4.75 | 5.03 |
| $Resolution_{FCS=0.143}$ (Å) | 4.23 | 4.28 |

The microscope settings for image collection were: Dose: 35 $e^-/Å^2$; Magnification: 105,000x; Pixel size: 1.1; and Voltage: 300 keV.

TABLE 2

| Refinement and model statistics | | | |
|---|---|---|---|
| Asymmetric Unit Model | | VLP alone | VLP + LDLRAD3 D1 |
| # of chains | | 12 | 16 |
| # of residues | | 4108 | 4264 |
| # of carbohydrates | | 8 | 8 |
| # of CA ions | | 0 | 4 |
| Resolution (Å) | | 4.2 | 4.3 |
| MolProbity score | | 1.84 | 1.94 |
| All-atom clash score | | 7.38 | 9.31 |
| Rotamer outliers (%) | | 0.00 | 0.00 |
| Cβ outliers (%) | | 0.00 | 0.00 |
| Ramachandran | Favored (%) | 93.34 | 93.10 |
| Plot values | Allowed (%) | 5.39 | 5.67 |
| | Outliers (%) | 1.27 | 1.23 |
| R.M.S. | Bond lengths (Å) | 0.002 | 0.003 |
| Deviations | Bond angles (°) | 0.667 | 0.734 |

TABLE 3

List of contact residues of VEEV E2-E1 and LDLRAD3 D1 binding interface

| E2-E1 heterodimer | E2-E1 domain | E2-E1 residues | LDLRAD3 D1 residues |
|---|---|---|---|
| wrapped | Domain A of E2 | V24, G25, S26, C27, H28, M70, H71, K116, S118, V119 | C12, N17, N22, R24, C25, I26, P27, W30, L35, D37, F39 |
| | Domain B of E2 | S176, S177, K223 | S21, D40, K45 |
| | Fusion loop of E1 | Y85, F87, M88, W89, G90, G91, A92 | M19, S21, N22, G23, R24, C38, F39, D40 |
| intraspike | Domain A of E2 | L5, G63, R64, L79, I92, V93, D94, G95 | C25, I26, P27, G28, A29, W30, D33, G24, L35 |
| | β-linker of E2 | E148, V153, Y154, A155, H156, D157, A158, Q159, A262, D263, G264, K265, C266, T267 | E11, C12, N13, I14, P15, G16, N17 |

Contact residues were identified using PDBePISA. "Wrapped" denotes contacts to the wrapped E2-E1 heterodimer whose fusion loop is covered by LDLRAD3 D1. "Intraspike" refers to the intraspike heterodimer, which is adjacent to the wrapped heterodimer but within the same trimeric spike.

Homology modeling of LDLRAD3 D1. LDLRAD3 D1 was identified as an LDL receptor type A (LA) domain by the Pfam database (Finn et al., 2014). LA domains are about 40 amino acids in length and contain six disulfide-bound cysteines and a cluster of highly conserved acidic residues which coordinate a calcium ion. The domain architecture has been well characterized with over 200 instances of it found in the PDB, revealing a well conserved fold. The initial model of LDLRAD3 D1 was built from its primary amino acid sequence by homology modelling using the SWISS-MODEL server (Waterhouse et al., 2018) with multiple high-resolution crystal structures of homologous LDL receptors as templates. This model docked well into the electron density of VEEV VLP with LDLRAD3 D1 cryo-EM map, with the N-terminus proximal to the core of the virus particle.

Model building and refinement. The initial models of the VEEV structural proteins (E1, E2, TM regions, and Capsid) with or without LDLRAD3 were constructed by docking coordinates of the previously built model of VEEV strain TC-83 (PDB 3J0C; Zhang et al., 2011) and the predicted model of LDLRAD3 D1 into the electron density of the asymmetric units of the cryo-EM maps using the fitmap command in Chimera. N-linked glycans and coordinated calcium ions were built manually using COOT (Emsley et al., 2010). The model then underwent real-space refinement in PHENIX (Afonine et al, 2012) using default parameters plus Morphing and secondary-structure, rotamer, and torsion restraints with the initial model as the reference. Bond and angle restraints were also applied for the modeled N-linked glycans and calcium ions. After optimization, coordinates of the asymmetric units were checked by MolProbity. Contact residues were identified using PDBePISA (ebi.ac.uk/pdbe/pisa/).

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All references, patents and patent applications disclosed herein are incorporated by reference with respect to the subject matter for which each is cited, which in some cases may encompass the entirety of the document.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Unless otherwise defined, all technical terms used herein have the same meaning as commonly understood by one of ordinary skill in the art to which this invention belongs. As used in this specification and the appended claims, the singular forms "a," "an," and "the" include plural references unless the context clearly dictates otherwise. Any reference to "or" herein is intended to encompass "and/or" unless otherwise stated.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," "less than or equal to," or "at most" precedes the first numerical value in a series of two or more numerical values, the term "no more than," "less than" or "less than or equal to," or "at most" applies to each of the numerical values in that series of numerical values. For example, less than or equal to 3, 2, or 1 is equivalent to less than or equal to 3, less than or equal to 2, or less than or equal to 1.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

What is claimed is:

1. A method of reducing or treating a viral infection in a subject having, suspected of having, or at risk for contracting a virus, the method comprising:

administering to the subject an effective amount of a composition comprising at least one pharmaceutically acceptable excipient and a Low-density lipoprotein receptor class A domain-containing protein 3 (LDLRAD3) viral decoy receptor.

2. The method of claim 1, wherein the LDLRAD3 viral decoy receptor comprises an LDL-receptor class A domain 1.

3. The method of 1, wherein the LDLRAD3 viral decoy receptor comprises:

(a) an amino acid sequence set forth in SEQ ID NO: 3;

(b) an amino acid sequence set forth in SEQ ID NO: 77;

(c) an amino acid sequence with 80% sequence identity, 81% sequence identity, 82% sequence identity, 83% sequence identity, 84% sequence identity, 85% sequence identity, 86% sequence identity, 87% sequence identity, 88% sequence identity, 89% sequence identity, 90% sequence identity, 91% sequence identity, 92% sequence identity, 93% sequence identity, 94% sequence identity, 95% sequence identity, 96% sequence identity, 97% sequence identity, 98% sequence identity, 99% sequence identity to SEQ ID NO: 1, 2, 4, 5, 6, 7, 8, or 78; or (d) a fusion protein.

4. The method of claim 3, wherein the LDLRAD3 viral decoy receptor-fusion protein comprises a LDLRAD3 viral decoy receptor linked to an Fc region.

5. The method of claim 4, wherein the Fc region comprises the heavy chain constant region of an antibody.

6. The method of claim 5, wherein the Fc region is an IgG Fc fragment.

7. The method of claim 6, wherein Fc region is Fc region an IgG2b Fc domain.

8. The method of claim 2, wherein the viral recognition site inhibiting agent is a LDLRAD3-D1 human IgG1 fusion viral decoy receptor.

9. The method of claim 1, wherein the viral infection is an alphavirus infection.

10. The method of claim 9, wherein:

(a) the alphavirus infection is from an alphavirus capable of binding a LDLRAD3 receptor on a cell;

(b) the alphavirus is a virus capable of binding domain 1 (D1) of LDLRAD;

(c) the alphavirus infection is a neurotropic alphavirus infection; or (d) the alphavirus infection is an encephalitic alphavirus infection.

11. An isolated viral decoy receptor peptide comprising an LDLRAD3 ectodomain.

12. The viral decoy receptor of claim 11, wherein:

(a) the LDLRAD3 ectodomain comprises the amino acid sequence of SEQ ID NO: 3;

(b) the LDLRAD3 ectodomain comprises LDLRAD3 D1;

(c) the LDLRAD3 ectodomain comprises the amino acid sequence of SEQ ID NO: 77; or (d) the viral decoy receptor is a fusion protein linked to an Fc region.

* * * * *